US006878817B2

(12) United States Patent
Lees et al.

(10) Patent No.: US 6,878,817 B2
(45) Date of Patent: Apr. 12, 2005

(54) LOW DENSITY LIPOPROTEIN BINDING PROTEINS AND THEIR USE IN DIAGNOSING AND TREATING ATHEROSCLEROSIS

(75) Inventors: Ann M. Lees, Brookline, MA (US); Robert S. Lees, Brookline, MA (US); Simon W. Law, Lexington, MA (US); Anibal A. Arjona, Boston, MA (US)

(73) Assignee: Boston Heart Foundation, Inc., Cambridge, MA (US)

( * ) Notice: Subject to any disclaimer, the term of this patent is extended or adjusted under 35 U.S.C. 154(b) by 422 days.

(21) Appl. No.: 09/976,740

(22) Filed: Oct. 12, 2001

(65) Prior Publication Data

US 2002/0194633 A1 Dec. 19, 2002

Related U.S. Application Data

(60) Division of application No. 09/616,289, filed on Jul. 14, 2000, now Pat. No. 6,632,923, which is a continuation-in-part of application No. 09/517,849, filed on Mar. 2, 2000, now Pat. No. 6,605,588, which is a continuation-in-part of application No. 08/979,608, filed on Nov. 26, 1997, now Pat. No. 6,355,451

(60) Provisional application No. 60/031,930, filed on Nov. 27, 1996, and provisional application No. 60/048,547, filed on Jun. 3, 1997.

(51) Int. Cl.[7] .......................... C07H 21/04; C07K 1/00; A61K 38/00; C12N 15/00

(52) U.S. Cl. ..................... 536/23.5; 536/23.1; 530/300; 530/350; 530/359; 435/440; 435/441

(58) Field of Search .............................. 536/23.1, 23.5; 530/300, 350, 353; 435/440, 441

(56) References Cited

U.S. PATENT DOCUMENTS

| | | | | |
|---|---|---|---|---|
| 4,660,563 A | | 4/1987 | Lees | 128/654 |
| 4,877,599 A | | 10/1989 | Lees | 424/1.1 |
| 5,196,324 A | | 3/1993 | Bumol et al. | 435/70.21 |
| 5,661,015 A | | 8/1997 | Binger et al. | 435/172.3 |
| 5,665,872 A | | 9/1997 | Saito et al. | 536/23.5 |
| 5,726,153 A | | 3/1998 | Lees et al. | 514/12 |
| 6,177,614 B1 | * | 1/2001 | Colasanti et al. | 800/290 |

FOREIGN PATENT DOCUMENTS

| | | |
|---|---|---|
| EP | 0 586 094 A1 | 3/1994 |
| EP | 0773290 A2 | 5/1997 |
| WO | WO 91/06011 | 5/1991 |
| WO | WO 91/16919 | 11/1991 |
| WO | WO 94/16074 | 7/1994 |
| WO | WO 96/12811 | 5/1996 |
| WO | WO 98/23282 | 6/1998 |

OTHER PUBLICATIONS

Colasanti et al "Control of floral induction in plants", Database: Issued_Patents_AA, Accession NO: 09–056–226–2, earlier filing date: Mar. 16, 1995, alignment result 41.*

Altenburger et al., Database: A_Geneseq_0601, Accession No.: AAW33626 (May 21, 1998).

Daikin Kogyo KK, Database: A_Geneseq_0601, Accession No.: AAR30641 (May 6, 1996).

Gottschling et al., Database: A_Geneseq_0601, Accession No.: AAR95607 (Oct. 12, 1996).

Miki et al., Database: SPTREMBL_16, Accession No.: Q95107 (Feb. 1, 1997).

Miki et al., "N–WASP, a novel actin–depolymerizing protein, regulates the cortical cytoskeletal rearrangement in a PIP2–dependent manner downstream of tyrosine kinases," The EMBO Journal, vol. 15(19):5326–5335 (1996).

Accession AF006088, GenBank, Dec. 15, 1999.

Accession AF017807, GenBank, Sep. 18, 1997.

Accession AL022098, GenBank, Nov. 23, 1999.

Accession AL049795, GenBank, Feb. 18, 2000.

Accession AL137800, GenBank, Jun. 20, 2000.

Accession L15344, GenBank, May 25, 1995.

Accession NM005717, GenBank, Jun. 9, 1999.

GenBank™ Accession No. AA287095 (Aug. 14, 1997).

GenBank™ Accession No. R76498 (Jun. 6, 1995).

GenBank™ Accession No. W07246 (Apr. 25, 1996).

Camejo et al., "Characterization and Properties of a Lipoprotein–Complexing Proteoglycan from Human Aorta," Atherosclerosis, 35:307–320, (1980).

Chang et al., "Low–Density Lipoprotein Modification and Arterial Wall accumulation In a Rabbit Model of Atherosclerosis," Biochemistry, 32(33):8518–8524, (1993).

Chang et al., "Time Course of $^{123}$I–Labeled LDL Accumulation in the Healing, Balloon–Deendothelialized Rabbit Aorta," Arteriosclerosis and Thrombosis, 12(9):1088–1098, (Sep. 1992).

Davies, "Flow–Mediated Endothelial Mechanotransduction," Physiological Reviews, 75(3):519–560, (Jul. 1995).

de Rijke et al., "Rat Liver Kupffer and Endothelial Cells Express Different Binding Proteins for Modified Low Density Lipoproteins," The Journal of Biological Chemistry, 269(2):824–827, (Jan. 14, 1994).

DePaola et al., "Vascular Endothelium Responds to Fluid Shear Stress Gradients," Arteriosclerosis and Thrombosis, 12(11):1254–1257, (Nov. 1992).

(Continued)

*Primary Examiner*—Jon Weber
*Assistant Examiner*—Rita Mitra
(74) *Attorney, Agent, or Firm*—Fish & Richardson PC

(57) ABSTRACT

Isolated polynucleotides encoding novel polypeptides which are capable of binding to native and methylated LDL (low density lipoprotein), the isolated polypeptides, called LBPs (LDL binding proteins), and biologically active fragments and analogs thereof, are described. Also described are methods for determining if an animal is at risk for atherosclerosis, methods for evaluating an agent for use in treating atherosclerosis, methods for treating atherosclerosis, and methods for treating a cell having an abnormality in structure or metabolism of LBP. Pharmaceutical compositions and vaccine compositions are also provided.

24 Claims, 67 Drawing Sheets

OTHER PUBLICATIONS

Esterbauer et al., "The Role of Lipid Peroxidation and Antioxidants In Oxidative Modification of LDL," Free Radical Biology & Medicine, 13:341–390, (1992).

Fischman et al., "Accumulation of Native and Methylated Low Density Lipoproteins by Healing Rabbit Arterial Wall," Arteriosclerosis, 7(4):361–366, (Jul./Aug. 1987).

Gimbrone, Jr. et al., "Vascular Endothelium An Integrator of Pathophysiological Stimuli in Atherogenesis," Annals New York Academy of Sciences, 748:122–131, (1995).

Gofman et al., "Blood Lipids and Human Atherosclerosis," The Journal of the American Heart Association, II(2):161–178, (Aug. 1950).

Hoff et al., "Apolipoprotein B Retention in the Grossly Normal and Atherosclerotic Human Aorta," Circulation Research, 41(5):684–690, (Nov. 1977).

Hoff et al., "Detergent Extraction of Tightly–Bound apoB from Extracts of Normal Aortic Intima and Plaques," Experimental and Molecular Pathology, 28:290–300, (1978).

Kuzmenko et al., "Characteristics of Smooth Muscle Cell Lipoprotein Binding Proteins (p105/p130) as T–Cadherin and Regulation by Positive and Negative Growth Regulators," Biochemical and Biophysical Research Communications, 246:489–494, (1998).

Lee et al., "Nucleotide sequence of the rat low density lipoprotein receptor cDNA," Nucleic Acids Res. 17(3):1259–1260 (1989).

Lees et al., "$^{99m}$ Technetium–labeled low density lipoprotein: receptor recognition and intracellular sequestration of radiolabel," Journal of Lipid Research, 32(1):1–8 (1991).

Lees et al.,. "Imaging Human Atherosclerosis with $^{99m}$Tc–labeled Low Density Lipoprotiens," Arteriosclerosis, 8(5):461–470, (Sep./Oct. 1988).

Minick et al., "Role of Endothelium and Hypercholesterolemia in Intimal Thickening and Lipid Accumulation," American Journal of Pathology, 95(1):131–151, Figs. 1–7, (Apr. 1979).

Morel et al., "Endothelial and Smooth Muscle Cells Alter Low Density Lipoprotein In Vitro by Free Radical Oxidation," Arteriosclerosis, 4(4):357–364, (Jul./Aug. 1984).

Nielsen, "Transfer of Low Density Lipoprotein Into the Arterial Wall and Risk of Atherosclerosis," Atherosclerosis, 123:1–15, (1996).

Nievelstein et al., "Lipid Accumulation in Rabbit Aortic Intima 2 Hours Aftger Bolus Infusion of Low Density Lipoprotein," Arteriosclerosis and Thrombosis, 11(6):1795–1805, (Nov./Dec. 1991).

Ramprasad et al., "Cell Surface Expression of Mouse Macrosialin and Human CD68 and Their Role As Macrophage Receptors for Oxidized Low Density Lipoprotein," Proc. Natl. Acad. Sci. USA, 93:14833–14838, (Dec. 1996).

Roberts et al., "Selective Accumulation of Low Density Lipoproteins In Damaged Arterial Wall," Journal of Lipid Research, 24:1160–1167, (1983).

Scandinavian Simvastatin Survival Study Group, Randomised Trial of Cholesterol Lowering in 4444 Patients with Coronary Heart Disease: the Scandinavian Simvastatin Survival Study (4S), The Lancet, 344:1383–1389, (Nov. 19, 1994).

Schwenke et al., "Initiation of Atherosclerotic Lesions in Cholesterol–fed Rabbits," Arteriosclerosis, 9(6):895–907, (Nov./Dec. 1989).

Schwenke et al., "Initiation of Atherosclerotic Lesions in Cholesterol–fed Rabbits," Arteriosclerosis, 9(6):908–918, (Nov./Dec. 1989).

Shepherd et al., "Prevention of Coronary Heart Disease with Pravastatin In Men with Hypercholesterolemia," The New England Journal of Medicine, 333(20):1301–1307, (Nov. 16, 1995).

Shih, "Focal Accumulation of An Apolipoprotein B–based Synthetic Oligopeptide in the Healing Rabbit Arterial Wall," Proc. Natl. Acad. Sci. USA, 87:1436–1440, (Feb. 1990).

Sigma Chemical Company, Biochemicals Organic Compounds for Research and Diagnostic Reagents, p. 1906 (1995).

Smith, "The Relationship Between Plasma and Tissue Lipids in Human Atherosclerosis," Adv. Lipid Res., 12:1–49, (1974).

Srinivasan et al., "Isolation of Lipoprotein–Acid Mucopolysaccharide Complexes from Fatty Streaks of Human Aortas," Atherosclerosis, 16:95–104, (1972).

Stamler et al., "Is Relationship Between Serum Cholesterol and Risk of Premature Death From Coronary Heart Disease Continuous and Graded?," JAMA, 256(20):2823–2828, (Nov. 28, 1986).

Stampfer et al., "A Prospective Study of Cholesterol, Apolipoproteins, and the Risk of Myocardial Infarction," New England Journal of Medicine, 325:373–381, (Aug. 8, 1991).

Stary et al., "A Definition of Initial, Fatth Streak, and Intermediate Lesions of Atherosclerosis," Arteriosclerosis and Thrombosis, 14(5):840–856 (May 1994).

Steingerg et al., "Beyond Cholesterol Modifications of Low–Density Lipoprotein That Increase Its Atherogenicity," The New England Journal of Medicine, 320(14):915–924, (Apr. 6, 1989).

Steinbrecher et al., "Modification of Low Density Lipoprotein By Endothelial Cells Involves Lipid Peroxidation and Degradation of Low Density Lipoprotein Phospholipids," Proc. Natl. Acad. Sci. USA, 81:3883–3887, (Jun. 1984).

Tkachuk, "Identification of an atypical lipoprotein–binding protein from human aortic smooth muscle as T–cadherin," Federation of European Biochemical Societies, 421:208–212, (1998).

Weisgraber et al., "Role of the Lysine Residues of Plasma Lipoproteins in High Affinity Binding to Cell Surface Receptors on Human Fibroblasts," The Journal of Biological Chemistry, 253:9053–9062, (1978).

Welch et al., "Actin Polymerization is Induced by Arp2/3 Protein Complex at the Surface of Listeria Monocytogenes," Nature, 385:265–269, (Jan. 16, 1997).

Welch et al., "The Human Arp2/3 Complex Is Composed of Evolutionarily Conserved Subunits and Is Localized to Cellular Regions of Dynamic Actin Filament Assembly," The Journal of Cell Biology, 138(2):375–384, (Jul. 28, 1997).

Williams, "The Response–to Retention Hypothesis of Early Atherogenesis," Arteriosclerosis, Thrombosis, and Vascular Biology, 15(5):551–561, (May 1995).

Yang et al., "Protein farnesyltransferase in plants. Molecular cloning and expression of a homolog of the beta subunit from the garden pea," Plant Physiol. 101:667–674 (1993).

* cited by examiner

Fig. 1 met ser lys asn thr
val ser ser ala arg phe arg lys val asp val asp
glu tyr asp glu asn lys phe val asp glu glu asp
gly gly asp gly gln ala gly pro asp glu gly glu
val asp ser cys leu arg gln gly asn met thr ala
ala leu gln ala ala leu lys asn pro pro ile asn
thr arg ser gln ala val lys asp arg ala gly ser
ile val leu lys val leu ile ser phe lys ala gly
asp ile glu lys ala val gln ser leu asp arg asn
gly val asp leu leu met lys tyr ile tyr lys gly
phe glu ser pro ser asp asn ser ser ala val leu
leu gln trp his glu lys ala leu ala ala gly gly
val gly ser ile val arg val leu thr ala arg lys
thr val

Fig. 2A (1/3)

```
ggtctgtgtg tgcgtgcgtg cgagtgagtg agtgtgtgca tatttttttt tctcttttct    60
ttctctctct tttttttttt tttgcaaaga aacagcagcg ccgccgccgc tccgccgagg   120
cgctgcgccc cccggggggg ggaggcggag gaggcgggca gcggcggagg gaggggagcc   180
ggggaggggg gcgccgcgct gggagggagg cagcgcgcac ggtgcagccg ggccgggcgg   240
gaggc atg gcg ggg ccc ccg gcc cta ccc ccg ccg gag acg gcg gcg gcc   290
      Met Ala Gly Pro Pro Ala Leu Pro Pro Pro Glu Thr Ala Ala Ala
       1               5                  10                  15

gcc acc acg gcc gcg gcc gcc gcc tcg tcg tcc gcc gct tcc ccg cac      338
Ala Thr Thr Ala Ala Ala Ala Ala Ser Ser Ser Ala Ala Ser Pro His
                20                  25                  30

tac caa gag tgg att ctg gac acc atc gac tcg ctg cgc tcg cgc aag      386
Tyr Gln Glu Trp Ile Leu Asp Thr Ile Asp Ser Leu Arg Ser Arg Lys
            35                  40                  45

gcg cgg ccg gac ctg gag cgc atc tgc cgg atg gtg cgg cgg cgg cac      434
Ala Arg Pro Asp Leu Glu Arg Ile Cys Arg Met Val Arg Arg Arg His
        50                  55                  60

ggc ccg gag ccg gag cgc acg cgc gcc gag ctc gag aaa ctg atc cag      482
Gly Pro Glu Pro Glu Arg Thr Arg Ala Glu Leu Glu Lys Leu Ile Gln
    65                  70                  75

cag cgc gcc gtg ctc cgg gtc agc tac aag ggg agc atc tcg tac cgc      530
Gln Arg Ala Val Leu Arg Val Ser Tyr Lys Gly Ser Ile Ser Tyr Arg
80                  85                  90                  95

aac gcg gcg cgc gtc cag ccg ccc cgg cgc gga gcc acc ccg ccg gcc      578
Asn Ala Ala Arg Val Gln Pro Pro Arg Arg Gly Ala Thr Pro Pro Ala
                100                 105                 110

ccg ccg cgc gcc ccc cgc ggg ggc ccc gcc gcc gcc gcc gcg ccg ccg      626
Pro Pro Arg Ala Pro Arg Gly Gly Pro Ala Ala Ala Ala Ala Pro Pro
            115                 120                 125

ccc acg ccc gcc ccg ccg ccg ccg ccc gcg ccc gtc gcc gcc gcc gcc      674
Pro Thr Pro Ala Pro Pro Pro Pro Pro Ala Pro Val Ala Ala Ala Ala
        130                 135                 140

gcc ccg gcc cgg gcg ccc cgc gcg gcc gcc gcc gcc gct gcc gcc aca      722
Ala Pro Ala Arg Ala Pro Arg Ala Ala Ala Ala Ala Ala Ala Ala Thr
    145                 150                 155

gcg ccc ccc tcg ccc ggc ccc gcg cag ccg ggc ccc cgc gcg cag cgg      770
Ala Pro Pro Ser Pro Gly Pro Ala Gln Pro Gly Pro Arg Ala Gln Arg
160                 165                 170                 175

gcc gcg ccc ctg gcc gcg ccg ccg ccc gcg ccc gcc gct ccc ccg gcg      818
Ala Ala Pro Leu Ala Ala Pro Pro Pro Ala Pro Ala Ala Pro Pro Ala
                180                 185                 190
```

Fig. 2A (continued 2/3)

gcg gcg ccc ccg gcc ggc ccg cgc cgc gcc ccc ccg ccc gcc gcc gcc 866
Ala Ala Pro Pro Ala Gly Pro Arg Arg Ala Pro Pro Pro Ala Ala Ala
195 200 205 gtc gcc gcc cgg gag tcg ccg ctg ccg ccg ccg cca cag ccg ccg gcg 914
Val Ala Ala Arg Glu Ser Pro Leu Pro Pro Pro Pro Gln Pro Pro Ala
210 215 220 ccg cca cag cag cag cag cag ccg ccg ccg cca ccg ccg ccg cag cag 962
Pro Pro Gln Gln Gln Gln Gln Pro Pro Pro Pro Pro Pro Pro Gln Gln
225 230 235 cca cag ccg ccg ccg gag ggg ggc gcg gcg cgg gcc ggc ggc ccg gcg 1010
Pro Gln Pro Pro Pro Glu Gly Gly Ala Ala Arg Ala Gly Gly Pro Ala
240 245 250 255 cgg ccc gtg agc ctg cgg gaa gtc gtg cgc tac ctc ggg ggt agc agc 1058
Arg Pro Val Ser Leu Arg Glu Val Val Arg Tyr Leu Gly Gly Ser Ser
260 265 270 ggc gct ggc ggc cgc ctg acc cgc ggc cgc gtg cag ggt ctg ctg gaa 1106
Gly Ala Gly Gly Arg Leu Thr Arg Gly Arg Val Gln Gly Leu Leu Glu
275 280 285 gag gag gcg gcg gcg cgg ggc cgc ctg gag cgc acc cgt ctc gga gcg 1154
Glu Glu Ala Ala Ala Arg Gly Arg Leu Glu Arg Thr Arg Leu Gly Ala
290 295 300 ctt gcg ctg ccc cgc ggg gac agg ccc gga cgg gcg cca ccg gcc gcc 1202
Leu Ala Leu Pro Arg Gly Asp Arg Pro Gly Arg Ala Pro Pro Ala Ala
305 310 315 agc gcc cgc gcg gcg cgg aac aag aga gct ggc gag gag cga gtg ctt 1250
Ser Ala Arg Ala Ala Arg Asn Lys Arg Ala Gly Glu Glu Arg Val Leu
320 325 330 335 gaa aag gag gag gag gag gag gag gag gaa gac gac gag gac gac gac 1298
Glu Lys Glu Glu Glu Glu Glu Glu Glu Glu Asp Asp Glu Asp Asp Asp
340 345 350 gac gac gtc gtg tcc gag ggc tcg gag gtg ccc gag agc gat cgt ccc 1346
Asp Asp Val Val Ser Glu Gly Ser Glu Val Pro Glu Ser Asp Arg Pro
355 360 365 gcg ggt gcg cag cat cac cag ctg aat ggc ggc gag cgc ggc ccg cag 1394
Ala Gly Ala Gln His His Gln Leu Asn Gly Gly Glu Arg Gly Pro Gln
370 375 380 acc gcc aag gag cgg gcc aag gag tgg tcg ctg tgt ggc ccc cac cct 1442
Thr Ala Lys Glu Arg Ala Lys Glu Trp Ser Leu Cys Gly Pro His Pro
385 390 395 ggc cag gag gaa ggg cgg ggg ccg gcc gcg ggc agt ggc acc cgc cag 1490
Gly Gln Glu Glu Gly Arg Gly Pro Ala Ala Gly Ser Gly Thr Arg Gln
400 405 410 415

Fig. 2A (continued 3/3)

```
gtg ttc tcc atg gcg gcc ttg agt aag gag ggg gga tca gcc tct tcg      1538
Val Phe Ser Met Ala Ala Leu Ser Lys Glu Gly Gly Ser Ala Ser Ser
                420                 425                 430

acg acc ggg cct gac tcc ccg tcc ccg gtg cct ttg ccc ccc ggg aag      1586
Thr Thr Gly Pro Asp Ser Pro Ser Pro Val Pro Leu Pro Pro Gly Lys
            435                 440                 445

cca gcc ctc cca gga gcc gat ggg acc ccc ttt ggc tgc cct gcc ggg      1634
Pro Ala Leu Pro Gly Ala Asp Gly Thr Pro Phe Gly Cys Pro Ala Gly
        450                 455                 460

cgc aaa gag aag ccg gca gac ccc gtg gag tgg aca gtc atg gac gtc      1682
Arg Lys Glu Lys Pro Ala Asp Pro Val Glu Trp Thr Val Met Asp Val
    465                 470                 475

gtg gag tac ttc acc gag gcg ggc ttc cct gag caa gcc acg gct ttc      1730
Val Glu Tyr Phe Thr Glu Ala Gly Phe Pro Glu Gln Ala Thr Ala Phe
480                 485                 490                 495

cag gag cag gag atc gac ggc aag tcc ctg ctg ctc atg cag cgc acc      1778
Gln Glu Gln Glu Ile Asp Gly Lys Ser Leu Leu Leu Met Gln Arg Thr
                500                 505                 510

gat gtc ctc acc ggc ctg tcc atc cgc ctg ggg cca gcg ttg aaa atc      1826
Asp Val Leu Thr Gly Leu Ser Ile Arg Leu Gly Pro Ala Leu Lys Ile
            515                 520                 525

tat gag cac cat atc aag gtg ctg cag cag ggt cac ttc gag gac gat      1874
Tyr Glu His His Ile Lys Val Leu Gln Gln Gly His Phe Glu Asp Asp
        530                 535                 540

gac ccg gaa ggc ttc ctg gga t gagcacagag ccgccgcgcc ccttgtcccc      1926
Asp Pro Glu Gly Phe Leu Gly
    545                 550

acccccaccc cgcctggacc cattcctgcc tccatgtcac ccaaggtgtc ccagaggcca   1986
ggagctggac tgggcaggcg aggggtgcgg acctaccctg attctggtag ggggcggggc   2046
cttgctgtgc tcattgctac ccccccaccc cgtgtgtgtc tctgcacctg cccccagcac   2106
acccctcccg gagcctggat gtcgcctggg actctggcct gctcatttg cccccagatc   2166
agcccccctcc ctccctcctg tcccaggaca ttttttaaaa gaaaaaaagg aaaaaaaaaa   2226
attggggagg gggctgggaa ggtgccccaa gatcctcctc ggcccaacca ggtgtttatt   2286
cctatatata tatatatatg ttttgttctg cctgttttc gtttttggt gcgtggcctt     2346
tcttccctcc caccaccact catggcccca gccctgctcg ccctgtcggc gggagcagct   2406
gggaatggga ggagggtggg accttgggtc tgtctcccac cctctctccc gttggttctg   2466
ttgtcgctcc agctggctgt attgcttttt aatattgcac cgaagggttg ttttttttt    2526
tttaaataaa attttaaaaa aaggaaaaaa aaaaa                              2561
```

Fig. 2B asp cys arg ser ser ser asn asn arg Xaa pro lys
gly gly ala ala arg ala gly gly pro ala arg pro
val ser leu arg glu val val arg tyr leu gly gly
ser ser gly ala gly gly arg leu thr arg gly arg
val gln gly leu leu glu glu glu ala ala ala arg
gly arg leu glu arg thr arg leu gly ala leu ala
leu pro arg gly asp arg pro gly arg ala pro pro
ala ala ser ala arg ala ala arg asn lys arg ala
gly glu glu arg val leu glu lys glu glu glu glu
glu glu glu glu asp asp glu asp asp asp asp asp
val val ser glu gly ser glu val pro glu ser asp
arg pro ala gly ala gln his his gln leu asn gly
gly glu arg gly pro gln thr ala lys glu arg ala
lys glu trp ser leu cys gly pro his pro gly gln
glu glu gly arg gly pro ala ala gly ser gly thr
arg gln val phe ser met ala ala leu ser lys glu
gly gly ser ala ser ser thr thr gly pro asp ser
pro ser pro val pro leu pro pro gly lys pro ala
leu pro gly ala asp gly thr pro phe gly cys pro
ala gly arg lys glu lys pro ala asp pro val glu
trp thr val met asp val val glu tyr phe thr glu
ala gly phe pro glu gln ala thr ala phe gln glu
gln glu ile asp gly lys ser leu leu leu met gln
arg thr asp val leu thr gly leu ser ile arg leu
gly pro ala leu lys ile tyr glu his his ile lys
val leu gln gln gly his phe glu asp asp asp pro
glu gly phe leu gly

Fig. 3 ala ser ala arg ala ala arg asn lys arg ala gly glu glu arg val leu glu lys glu glu glu glu glu glu glu glu asp asp glu asp asp asp asp asp val val ser glu gly ser glu val pro glu ser asp arg pro ala gly ala gln his his gln leu asn gly gly glu arg gly pro gln thr ala lys glu arg ala lys glu trp ser leu cys gly pro his pro gly gln glu glu gly arg gly pro ala ala gly ser gly thr arg gln val phe ser met ala ala leu ser lys glu gly gly ser ala ser ser thr thr gly pro asp ser pro ser pro val pro leu pro pro gly lys pro ala leu pro gly ala asp gly thr pro phe gly cys pro ala gly arg lys glu lys pro ala asp pro val glu trp thr val met asp val val glu tyr phe thr glu ala gly phe pro glu gln ala thr ala phe gln glu gln glu ile asp gly lys ser leu leu leu met gln arg thr asp val leu thr gly leu ser ile arg leu gly pro ala leu lys ile tyr glu his his ile lys val leu gln gln gly his phe glu asp asp asp pro glu gly phe leu gly

Fig. 4 thr arg leu gly ala leu ala leu pro arg gly asp arg pro gly arg ala pro pro ala ala ser ala arg ala ala arg asn lys arg ala gly glu glu arg val leu glu lys glu glu glu glu glu glu glu glu asp asp glu asp asp asp asp asp val val ser glu gly ser glu val pro glu ser asp arg pro ala gly ala gln his his gln leu asn gly gly glu arg gly pro gln thr ala lys glu arg ala lys glu trp ser leu cys gly pro his pro gly gln glu glu gly arg gly pro ala ala gly ser gly thr arg gln val phe ser met ala ala leu ser lys glu gly gly ser ala ser ser thr thr gly pro asp ser pro ser pro val pro leu pro pro gly lys pro ala leu pro gly ala asp gly thr pro phe gly cys pro ala gly arg lys glu lys pro ala asp pro val glu trp thr val met asp val val glu tyr phe thr glu ala gly phe pro glu gln ala thr ala phe gln glu gln glu ile asp gly lys ser leu leu leu met gln arg thr asp val leu thr gly leu ser ile arg leu gly pro ala leu lys ile tyr glu his his ile lys val leu gln gln gly his phe glu asp asp asp pro glu gly phe leu gly

Fig. 5 met lys asn gln
asp lys lys asn gly ala ala lys gln pro asn pro
lys ser ser pro gly gln pro glu ala gly ala glu
gly ala gln gly arg pro gly arg pro ala pro ala
arg glu ala glu gly ala ser ser gln ala pro gly
arg pro glu gly ala gln ala lys thr ala gln pro
gly ala leu cys asp val ser glu glu leu ser arg
gln leu glu asp ile leu ser thr tyr cys val asp
asn asn gln gly ala pro gly glu asp gly val gln
gly glu pro pro glu pro glu asp ala glu lys ser
arg ala tyr val ala arg asn gly glu pro glu pro
gly thr pro val val asn gly glu lys glu thr ser
lys ala glu pro gly thr glu glu ile arg thr ser
asp glu val gly asp arg asp his arg arg pro gln
glu lys lys lys ala lys gly leu gly lys glu ile
thr leu leu met gln thr leu asn thr leu ser thr
pro glu glu lys leu ala ala leu cys lys lys tyr
ala glu leu leu glu glu his arg asn ser gln lys
gln met lys leu leu gln lys lys gln ser gln leu
val gln glu lys asp his leu arg gly glu his ser
lys ala ile leu ala arg ser lys leu glu ser leu
cys arg glu leu gln arg his asn arg ser leu lys
glu glu gly val gln arg ala arg glu glu glu glu
lys arg lys glu val thr ser his phe gln met thr
leu asn asp ile gln leu gln met glu gln his asn
glu arg asn ser lys leu arg gln glu asn met glu

Fig. 5 (continued)

leu ala glu arg leu lys lys leu ile glu gln tyr
glu leu arg glu glu his ile asp lys val phe lys
his lys asp leu gln gln gln leu val asp ala lys
leu gln gln ala gln glu met leu lys glu ala glu
glu arg his gln arg glu lys asp phe leu leu lys
glu ala val glu ser gln arg met cys glu leu met
lys gln gln glu thr his leu lys gln gln leu ala
leu tyr thr glu lys phe glu glu phe gln asn thr
leu ser lys ser ser glu val phe thr thr phe lys
gln glu met glu lys met thr lys lys ile lys lys
leu glu lys glu thr thr met tyr arg ser arg trp
glu ser ser asn lys ala leu leu glu met ala glu
glu lys thr leu arg asp lys glu leu glu gly leu
gln val lys ile gln arg leu glu lys leu cys arg
ala leu gln thr glu arg asn asp leu asn lys arg
val gln asp leu ser ala gly gly gln gly pro val
ser asp ser gly pro glu arg arg pro glu pro ala
thr thr ser lys glu gln gly val glu gly pro gly
ala gln val pro asn ser pro arg ala thr asp ala
ser cys cys ala gly ala pro ser thr glu ala ser
gly gln thr gly pro gln glu pro thr thr ala thr
ala

Fig. 6 met ser lys asn thr val ser ser ala arg phe arg lys val asp val asp glu tyr asp glu asn lys phe val asp glu glu asp gly gly asp gly gln ala gly pro asp glu gly glu val asp ser cys leu arg gln gly asn met thr ala ala leu gln ala ala leu lys asn pro pro ile asn thr lys ser gln ala val lys asp arg ala gly ser ile val leu lys val leu ile ser phe lys ala asn asp ile glu lys ala val gln ser leu asp lys asn gly val asp leu leu met lys tyr ile tyr lys gly phe glu ser pro ser asp asn ser ser ala met leu leu gln trp his glu lys ala leu ala ala gly gly val gly ser ile val arg val leu thr ala arg lys thr val

Fig. 7A (1/3)

```
atg gcg ggg ccc ccg gcc cta ccc ccg ccg gag acg gcg gcg gcc gcc     48
Met Ala Gly Pro Pro Ala Leu Pro Pro Pro Glu Thr Ala Ala Ala Ala
 1               5                  10                  15

acc acg gcg gcc gcc gcc tcg tcg tcc gcc gct tcc ccg cac tac caa     96
Thr Thr Ala Ala Ala Ala Ser Ser Ser Ala Ala Ser Pro His Tyr Gln
            20                  25                  30

gag tgg atc ctg gac acc atc gac tcg ctg cgc tcg cgc aag gcg cgg    144
Glu Trp Ile Leu Asp Thr Ile Asp Ser Leu Arg Ser Arg Lys Ala Arg
        35                  40                  45

ccg gac ctg gag cgc atc tgc cgg atg gtg cgg cgg cgg cac ggc ccg    192
Pro Asp Leu Glu Arg Ile Cys Arg Met Val Arg Arg Arg His Gly Pro
    50                  55                  60

gag ccg gag cgc acg cgc gcc gag ctc gag aaa ctg atc cag cag cgc    240
Glu Pro Glu Arg Thr Arg Ala Glu Leu Glu Lys Leu Ile Gln Gln Arg
65                  70                  75                  80

gcc gtg ctc cgg gtc agc tac aag ggg agc atc tcg tac cgc aac gcg    288
Ala Val Leu Arg Val Ser Tyr Lys Gly Ser Ile Ser Tyr Arg Asn Ala
                85                  90                  95

gcg cgc gtc cag ccg ccc cgg cgc gga gcc acc ccg ccg gcc ccg ccg    336
Ala Arg Val Gln Pro Pro Arg Arg Gly Ala Thr Pro Pro Ala Pro Pro
            100                 105                 110

cgc gcc ccc cgc ggg gcc ccc gcc gcc gcc gcc gcc gcc gcg ccg ccg    384
Arg Ala Pro Arg Gly Ala Pro Ala Ala Ala Ala Ala Ala Ala Pro Pro
        115                 120                 125

ccc acg ccc gcc ccg ccg cca ccg ccc gcg ccc gtc gcc gcc gcc gcc    432
Pro Thr Pro Ala Pro Pro Pro Pro Pro Ala Pro Val Ala Ala Ala Ala
    130                 135                 140

ccg gcc cgg gcg ccc cgc gcg gcc gcc gcc gcc gcc aca gcg ccc ccc    480
Pro Ala Arg Ala Pro Arg Ala Ala Ala Ala Ala Ala Thr Ala Pro Pro
145                 150                 155                 160

tcg cct ggc ccc gcg cag ccg ggc ccc cgc gcg cag cgg gcc gcg ccc    528
Ser Pro Gly Pro Ala Gln Pro Gly Pro Arg Ala Gln Arg Ala Ala Pro
                165                 170                 175

ctg gcc gcg ccg ccg ccc gcg cca gcc gct ccc ccg gcg gtg gcg ccc    576
Leu Ala Ala Pro Pro Pro Ala Pro Ala Ala Pro Pro Ala Val Ala Pro
            180                 185                 190

ccg gcc ggc ccg cgc cgc gcc ccc ccg ccc gcc gtc gcc gcc cgg gag    624
Pro Ala Gly Pro Arg Arg Ala Pro Pro Pro Ala Val Ala Ala Arg Glu
        195                 200                 205

ccg ccg ctg ccg ccg ccg cca cag ccg ccg gcg ccg cca cag cag cag    672
Pro Pro Leu Pro Pro Pro Pro Gln Pro Pro Ala Pro Pro Gln Gln Gln
    210                 215                 220
```

Fig. 7A (continued; 2/3)

```
cag ccg ccg ccg ccg cag cca cag ccg ccg ccg gag ggg ggc gcg gtg      720
Gln Pro Pro Pro Pro Gln Pro Gln Pro Pro Pro Glu Gly Gly Ala Val
225                 230                 235                 240

cgg gcc ggc ggc gcg gcg cgg ccc gtg agc ctg cgg gaa gtc gtg cgc      768
Arg Ala Gly Gly Ala Ala Arg Pro Val Ser Leu Arg Glu Val Val Arg
                245                 250                 255

tac ctc ggg ggc agc ggc ggc gcc ggc ggt cgc cta acc cgc ggc cgc      816
Tyr Leu Gly Gly Ser Gly Gly Ala Gly Gly Arg Leu Thr Arg Gly Arg
            260                 265                 270

gtg cag ggg ctg ctg gag gag gag gcg gcg gct cga ggc cgt ctg gag      864
Val Gln Gly Leu Leu Glu Glu Glu Ala Ala Ala Arg Gly Arg Leu Glu
        275                 280                 285

cgc acc cgt ctc gga gcg ctt gcg ctg ccc cgc ggg gac agg ccc gga      912
Arg Thr Arg Leu Gly Ala Leu Ala Leu Pro Arg Gly Asp Arg Pro Gly
    290                 295                 300

cgg gcg ccg ccg gcc gcc agc gcc cgc ccg tct cgc agc aag aga ggt      960
Arg Ala Pro Pro Ala Ala Ser Ala Arg Pro Ser Arg Ser Lys Arg Gly
305                 310                 315                 320

gga gaa gag cga gta ctt gag aaa gaa gag gaa gaa gat gat gat gaa     1008
Gly Glu Glu Arg Val Leu Glu Lys Glu Glu Glu Glu Asp Asp Asp Glu
                325                 330                 335

gat gaa gat gaa gaa gat gat gtg tca gag ggc tct gaa gtg ccc gag     1056
Asp Glu Asp Glu Glu Asp Asp Val Ser Glu Gly Ser Glu Val Pro Glu
            340                 345                 350

agt gac cgt cct gca ggt gcc cag cac cac cag ctt aac ggc gag cgg     1104
Ser Asp Arg Pro Ala Gly Ala Gln His His Gln Leu Asn Gly Glu Arg
        355                 360                 365

gga cct cag agt gcc aag gag agg gtc aag gag tgg acc ccc tgc gga     1152
Gly Pro Gln Ser Ala Lys Glu Arg Val Lys Glu Trp Thr Pro Cys Gly
    370                 375                 380

ccg cac cag ggc cag gat gaa ggg cgg ggg cca gcc ccg ggc agc ggc     1200
Pro His Gln Gly Gln Asp Glu Gly Arg Gly Pro Ala Pro Gly Ser Gly
385                 390                 395                 400

acc cgc cag gtg ttc tcc atg gca gcc atg aac aag gaa ggg gga aca     1248
Thr Arg Gln Val Phe Ser Met Ala Ala Met Asn Lys Glu Gly Gly Thr
                405                 410                 415

gct tct gtt gcc acc ggg cca gac tcc ccg tcc ccc gtg cct ttg ccc     1296
Ala Ser Val Ala Thr Gly Pro Asp Ser Pro Ser Pro Val Pro Leu Pro
            420                 425                 430

cca ggc aaa cca gcc cta cct ggg gcc gac ggg acc ccc ttt ggc tgt     1344
Pro Gly Lys Pro Ala Leu Pro Gly Ala Asp Gly Thr Pro Phe Gly Cys
        435                 440                 445
```

Fig. 7A (continued; 3/3)

ccg ccc ggg cgc aaa gag aag cca tct gat ccc gtc gag tgg acc gtg 1392
Pro Pro Gly Arg Lys Glu Lys Pro Ser Asp Pro Val Glu Trp Thr Val
450 455 460 atg gat gtc gtc gaa tat ttt act gag gct gga ttc ccg gag cag gcg 1440
Met Asp Val Val Glu Tyr Phe Thr Glu Ala Gly Phe Pro Glu Gln Ala
465 470 475 480 aca gct ttc caa gag cag gaa att gat ggc aaa tct ttg ctg ctc atg 1488
Thr Ala Phe Gln Glu Gln Glu Ile Asp Gly Lys Ser Leu Leu Leu Met
485 490 495 cag cgc aca gat gtg ctc acc ggc ctg tcc atc cgc ctc ggg cca gcc 1536
Gln Arg Thr Asp Val Leu Thr Gly Leu Ser Ile Arg Leu Gly Pro Ala
500 505 510 ctg aaa atc tac gag cac cac atc aag gtg ctt cag caa ggc cac ttt 1584
Leu Lys Ile Tyr Glu His His Ile Lys Val Leu Gln Gln Gly His Phe
515 520 525 gag gat gat gac ccc gat ggc ttc tta ggc 1614
Glu Asp Asp Asp Pro Asp Gly Phe Leu Gly
530 535

Fig. 7B glu glu arg val leu glu lys glu glu glu glu asp asp asp glu asp glu asp glu glu asp asp val ser glu gly ser glu val pro glu ser asp arg pro ala gly ala gln his his gln leu asn gly glu arg gly pro gln ser ala lys glu arg val lys glu trp thr pro cys gly pro his gln gly gln asp glu gly arg gly pro ala pro gly ser gly thr arg gln val phe ser met ala ala met asn lys glu gly gly thr ala ser val ala thr gly pro asp ser pro ser pro val pro leu pro pro gly lys pro ala leu pro gly ala asp gly thr pro phe gly cys pro pro gly arg lys glu lys pro ser asp pro val glu trp thr val met asp val val glu tyr phe thr glu ala gly phe pro glu gln ala thr ala phe gln glu gln glu ile asp gly lys ser leu leu leu met gln arg thr asp val leu thr gly leu ser ile arg leu gly pro ala leu lys ile tyr glu his his ile lys val leu gln gln gly his phe glu asp asp asp pro asp gly phe leu gly

Fig. 8A (1/3)

```
atg aag aac caa gac aaa aag aac ggg gct gcc aaa caa tcc aat cca     48
Met Lys Asn Gln Asp Lys Lys Asn Gly Ala Ala Lys Gln Ser Asn Pro
 1               5                  10                  15

aaa agc agc cca gga caa ccg gaa gca gga ccc gag gga gcc cag gag     96
Lys Ser Ser Pro Gly Gln Pro Glu Ala Gly Pro Glu Gly Ala Gln Glu
            20                  25                  30

cgg ccc agc cag gcg gct cct gca gta gaa gca gaa ggt ccc ggc agc    144
Arg Pro Ser Gln Ala Ala Pro Ala Val Glu Ala Glu Gly Pro Gly Ser
        35                  40                  45

agc cag gct cct cgg aag ccg gag ggt gct caa gcc aga acg gct cag    192
Ser Gln Ala Pro Arg Lys Pro Glu Gly Ala Gln Ala Arg Thr Ala Gln
    50                  55                  60

tct ggg gcc ctt cgt gat gtc tct gag gag ctg agc cgc caa ctg gaa    240
Ser Gly Ala Leu Arg Asp Val Ser Glu Glu Leu Ser Arg Gln Leu Glu
65                  70                  75                  80

gac ata ctg agc aca tac tgt gtg gac aat aac cag ggg ggc ccc ggc    288
Asp Ile Leu Ser Thr Tyr Cys Val Asp Asn Asn Gln Gly Gly Pro Gly
                85                  90                  95

gag gat ggg gca cag ggt gag ccg gct gaa ccc gaa gat gca gag aag    336
Glu Asp Gly Ala Gln Gly Glu Pro Ala Glu Pro Glu Asp Ala Glu Lys
            100                 105                 110

tcc cgg acc tat gtg gca agg aat ggg gag cct gaa cca act cca gta    384
Ser Arg Thr Tyr Val Ala Arg Asn Gly Glu Pro Glu Pro Thr Pro Val
        115                 120                 125

gtc aat gga gag aag gaa ccc tcc aag ggg gat cca aac aca gaa gag    432
Val Asn Gly Glu Lys Glu Pro Ser Lys Gly Asp Pro Asn Thr Glu Glu
    130                 135                 140

atc cgg cag agt gac gag gtc gga gac cga gac cat cga agg cca cag    480
Ile Arg Gln Ser Asp Glu Val Gly Asp Arg Asp His Arg Arg Pro Gln
145                 150                 155                 160

gag aag aaa aaa gcc aag ggt ttg ggt aag gag atc acg ttg ctg atg    528
Glu Lys Lys Lys Ala Lys Gly Leu Gly Lys Glu Ile Thr Leu Leu Met
                165                 170                 175

cag aca ttg aat act ctg agt acc cca gag gag aag ctg gct gct ctg    576
Gln Thr Leu Asn Thr Leu Ser Thr Pro Glu Glu Lys Leu Ala Ala Leu
            180                 185                 190

tgc aag aag tat gct gaa ctg ctg gag gag cac cgg aat tca cag aag    624
Cys Lys Lys Tyr Ala Glu Leu Leu Glu Glu His Arg Asn Ser Gln Lys
        195                 200                 205
```

Fig. 8A (continued; 2/3)

cag atg aag ctc cta cag aaa aag cag agc cag ctg gtg caa gag aag 672
Gln Met Lys Leu Leu Gln Lys Lys Gln Ser Gln Leu Val Gln Glu Lys
210 215 220 gac cac ctg cgc ggt gag cac agc aag gcc gtc ctg gcc cgc agc aag 720
Asp His Leu Arg Gly Glu His Ser Lys Ala Val Leu Ala Arg Ser Lys
225 230 235 240 ctt gag agc cta tgc cgt gag ctg cag cgg cac aac cgc tcc ctc aag 768
Leu Glu Ser Leu Cys Arg Glu Leu Gln Arg His Asn Arg Ser Leu Lys
245 250 255 gaa gaa ggt gtg cag cgg gcc cgg gag gag gag gag aag cgc aag gag 816
Glu Glu Gly Val Gln Arg Ala Arg Glu Glu Glu Glu Lys Arg Lys Glu
260 265 270 gtg acc tcg cac ttc cag gtg aca ctg aat gac att cag ctg cag atg 864
Val Thr Ser His Phe Gln Val Thr Leu Asn Asp Ile Gln Leu Gln Met
275 280 285 gaa cag cac aat gag cgc aac tcc aag ctg cgc caa gag aac atg gag 912
Glu Gln His Asn Glu Arg Asn Ser Lys Leu Arg Gln Glu Asn Met Glu
290 295 300 ctg gct gag agg ctc aag aag ctg att gag cag tat gag ctg cgc gag 960
Leu Ala Glu Arg Leu Lys Lys Leu Ile Glu Gln Tyr Glu Leu Arg Glu
305 310 315 320 gag cat atc gac aaa gtc ttc aaa cac aag gac cta caa cag cag ctg 1008
Glu His Ile Asp Lys Val Phe Lys His Lys Asp Leu Gln Gln Gln Leu
325 330 335 gtg gat gcc aag ctc cag cag gcc cag gag atg cta aag gag gca gaa 1056
Val Asp Ala Lys Leu Gln Gln Ala Gln Glu Met Leu Lys Glu Ala Glu
340 345 350 gag cgg cac cag cgg gag aag gat ttt ctc ctg aaa gag gca gta gag 1104
Glu Arg His Gln Arg Glu Lys Asp Phe Leu Leu Lys Glu Ala Val Glu
355 360 365 tcc cag agg atg tgt gag ctg atg aag cag caa gag acc cac ctg aag 1152
Ser Gln Arg Met Cys Glu Leu Met Lys Gln Gln Glu Thr His Leu Lys
370 375 380 caa cag ctt gcc cta tac aca gag aag ttt gag gag ttc cag aac aca 1200
Gln Gln Leu Ala Leu Tyr Thr Glu Lys Phe Glu Glu Phe Gln Asn Thr
385 390 395 400 ctt tcc aaa agc agc gag gta ttc acc aca ttc aag cag gag atg gaa 1248
Leu Ser Lys Ser Ser Glu Val Phe Thr Thr Phe Lys Gln Glu Met Glu
405 410 415

Fig. 8A (continued; 3/3)

```
aag atg act aag aag atc aag aag ctg gag aaa gaa acc acc atg tac     1296
Lys Met Thr Lys Lys Ile Lys Lys Leu Glu Lys Glu Thr Thr Met Tyr
            420                 425                 430

cgg tcc cgg tgg gag agc agc aac aag gcc ctg ctt gag atg gct gag     1344
Arg Ser Arg Trp Glu Ser Ser Asn Lys Ala Leu Leu Glu Met Ala Glu
        435                 440                 445

gag aaa aca gtc cgg gat aaa gaa ctg gag ggc ctg cag gta aaa atc     1392
Glu Lys Thr Val Arg Asp Lys Glu Leu Glu Gly Leu Gln Val Lys Ile
    450                 455                 460

caa cgg ctg gag aag ctg tgc cgg gca ctg cag aca gag cgc aat gac     1440
Gln Arg Leu Glu Lys Leu Cys Arg Ala Leu Gln Thr Glu Arg Asn Asp
465                 470                 475                 480

ctg aac aag agg gta cag gac ctg agt gct ggt ggc cag ggc tcc ctc     1488
Leu Asn Lys Arg Val Gln Asp Leu Ser Ala Gly Gly Gln Gly Ser Leu
                485                 490                 495

act gac agt ggc cct gag agg agg cca gag ggg cct ggg gct caa gca     1536
Thr Asp Ser Gly Pro Glu Arg Arg Pro Glu Gly Pro Gly Ala Gln Ala
            500                 505                 510

ccc agc tcc ccc agg gtc aca gaa gcg cct tgc tac cca gga gca ccg     1584
Pro Ser Ser Pro Arg Val Thr Glu Ala Pro Cys Tyr Pro Gly Ala Pro
        515                 520                 525

agc aca gaa gca tca ggc cag act ggg cct caa gag ccc acc tcc gcc     1632
Ser Thr Glu Ala Ser Gly Gln Thr Gly Pro Gln Glu Pro Thr Ser Ala
    530                 535                 540

agg gcc                                                             1638
Arg Ala
545
```

Fig. 8 B lys ser ser pro gly gln pro glu ala gly pro glu gly ala
gln glu arg pro ser gln ala ala pro ala val glu ala glu gly
pro gly ser ser gln ala pro arg lys pro glu gly ala gln ala
arg thr ala gln ser gly ala leu arg asp val ser glu glu leu
ser arg gln leu glu asp ile leu ser thr tyr cys val asp asn
asn gln gly gly pro gly glu asp gly ala gln gly glu pro ala
glu pro glu asp ala glu lys ser arg thr tyr val ala arg asn
gly glu pro glu pro thr pro val val tyr gly glu lys glu pro
ser lys gly asp pro asn thr glu glu ile arg gln ser asp glu
val gly asp arg asp his arg arg pro gln glu lys lys lys ala
lys gly leu gly lys glu ile thr leu leu met gln thr leu asn
thr leu ser thr pro glu glu lys leu ala ala leu cys lys lys
tyr ala glu leu leu glu glu his arg asn ser gln lys gln met
lys leu leu gln lys lys gln ser gln leu val gln glu lys asp
his leu arg gly glu his ser lys ala val leu ala arg ser lys
leu glu ser leu cys arg glu leu gln arg his asn arg ser leu
lys glu glu gly val gln arg ala arg glu glu glu glu lys arg
lys glu val thr ser his phe gln val thr leu asn asp ile gln
leu gln met glu gln his asn glu arg asn ser lys leu arg gln
glu asn met glu leu ala glu arg leu lys lys leu ile glu gln
tyr glu leu arg glu glu his ile asp lys val phe lys his lys
asp leu gln gln gln leu val asp ala lys leu gln gln ala gln
glu met leu lys glu ala glu glu arg his gln arg glu lys asp
phe leu leu lys glu ala val glu ser gln arg met cys glu leu
met lys gln gln glu thr his leu lys gln gln leu ala leu tyr
thr glu lys phe glu glu phe gln asn thr leu ser lys ser ser Fig. 8 B(continued)

glu val phe thr thr phe lys gln glu met glu lys met thr lys
lys ile lys lys leu glu lys glu thr thr met tyr arg ser arg
trp glu ser ser asn lys ala leu leu glu met ala glu glu lys
thr val arg asp lys glu leu glu gly leu gln val lys ile gln
arg leu glu lys leu cys arg ala leu gln thr glu arg asn asp
leu asn lys arg val gln asp leu ser ala gly gly gln gly ser
leu thr asp ser gly pro glu arg arg pro glu gly pro gly ala
gln ala pro ser ser pro arg val thr glu ala pro cys tyr pro
gly ala pro ser thr glu ala ser gly gln thr gly pro gln glu
pro thr ser ala arg ala ***

Fig. 9 val asp val asp glu tyr asp glu asn lys phe val asp glu glu asp gly gly asp gly

Fig. 10

| | | | | | | | | | | | | |
|---|---|---|---|---|---|---|---|---|---|---|---|---|
| 1 | AAG | CCT | CGC | AGC | GGT | CGG | GGC | GGC | GCC | GCG | GAG | GCT |
| 37 | CGA | GGG | CGG | CGG | GCG | GCG | GCG | ATG | TCG | AAG | AAC | ACG |
| | | | | | | | | met | ser | lys | asn | thr |
| 73 | GTG | TCG | TCG | GCG | CGG | TTC | CGG | AAG | GTG | GAC | GTG | GAT |
| | val | ser | ser | ala | arg | phe | arg | lys | val | asp | val | asp |
| 109 | GAG | TAC | GAC | GAG | AAC | AAG | TTC | GTG | GAC | GAG | GAA | GAC |
| | glu | tyr | asp | glu | asn | lys | phe | val | asp | glu | glu | asp |
| 145 | GGC | GGC | GAC | GGC | CAG | GCG | GGG | CCG | GAC | GAG | GGC | GAG |
| | gly | gly | asp | gly | gln | ala | gly | pro | asp | glu | gly | glu |
| 181 | GTG | GAC | TCG | TGC | CTG | CGG | CAA | GGG | AAC | ATG | ACA | GCC |
| | val | asp | ser | cys | leu | arg | gln | gly | asn | met | thr | ala |
| 217 | GCC | CTG | CAG | GCG | GCG | CTG | AAG | AAC | CCT | CCC | ATC | AAC |
| | ala | leu | gln | ala | ala | leu | lys | asn | pro | pro | ile | asn |
| 253 | ACC | AGG | AGC | CAG | GCG | GTG | AAG | GAC | CGG | GCA | GGC | AGC |
| | thr | **arg** | ser | gln | ala | val | lys | asp | arg | ala | gly | ser |
| 289 | ATC | GTG | CTG | AAG | GTG | CTC | ATC | TCC | TTC | AAG | GCC | GGC |
| | ile | val | leu | lys | val | leu | ile | ser | phe | lys | ala | **gly** |
| 325 | GAC | ATA | GAA | AAG | GCC | GTG | CAG | TCC | CTG | GAC | AGG | AAC |
| | asp | ile | glu | lys | ala | val | gln | ser | leu | asp | **arg** | asn |
| 361 | GGC | GTG | GAC | CTG | CTC | ATG | AAG | TAC | ATC | TAC | AAG | GGC |
| | gly | val | asp | leu | leu | met | lys | tyr | ile | tyr | lys | gly |
| 397 | TTC | GAG | AGC | CCC | TCC | GAC | AAC | AGC | AGC | GCC | GTG | CTC |
| | phe | glu | ser | pro | ser | asp | asn | ser | ser | ala | **val** | leu |
| 433 | CTG | CAG | TGG | CAC | GAG | AAG | GCG | CTG | GCT | GCA | GGA | GGA |
| | leu | gln | trp | his | glu | lys | ala | leu | ala | ala | gly | gly |
| 469 | GTG | GGC | TCC | ATC | GTC | CGT | GTC | CTG | ACT | GCA | AGG | AAA |
| | val | gly | ser | ile | val | arg | val | leu | thr | ala | arg | lys |
| 505 | ACC | GTG | TAG | CCT | GGC | AGG | AAC | GGG | TGC | CTG | CCG | GGG |
| | thr | val | | | | | | | | | | |

Fig. 10 (continued)

541 AGC GGG AGC TGC CGG TAC AAA GAC CAA AAC GCC CAG
577 ATG CCG CCG CTG CCC TGT GGG CGG CGT CTG TTC CCA
613 GCT TCG CTT TTT CCC TTT CCC GTG TCT GTC AGG ATT
649 ACA TAA GGT TTC CCT TCG TGA GAA TCG GAG TGG CGC
685 AGA GGG TCC TGT TCA TAC GCG CCG TGC GTC CGG CTG
721 TGT AAG ACC CCT GCC TTC AGT GTC CTT GAG CAA CGG
757 TAG CGT GTC GCC GGC TGG GTT TGG TTT TGT CGT GGA
793 GGG ATC TGG TCA GAA TTT GAG GCC AGT TTC CTA ACT
829 CAT TGC TGG TCA GGA AAT GAT CTT CAT TTA AAA AAA
865 AAA AAA AGA CTG GCA GCT ATT ATG CAA AAC TGG ACC
901 CTC TTC CCT TAT TTA AGC AGA GTG AGT TTC TGG AAC
937 CAG TGG TGC CCC CCC CCC CGC CCC GGC CGC CGT CCT
973 GCT CAA GGG AAG CCT CCC TGC AGA GCA GCA GAG CCC
1009 CTG GGC AGG AGC GCC GCG TCC CGC TCC CAG GAG ACA
1045 GCA TGC GCG GTC ACG CGG CAC TTC CTG TGC CTC CCA
1081 GCC CCA GTG CCC CGG AGT TCT TCA GGG CGA CAG GGA
1117 CCT CAG AAG ACT GGA TCC GAT CCA GAC AGA CGC CCA
1153 TTC TTG GTT CAG CTC AGT GTT TTC AAA AGG AAC GTG
1189 CTA CCG TGG GTA GAG CAC ACT GGT TCT CAG AAC ACG
1225 GCC GGC GCT TGA CGG TTG TCA CAG CTC CAG AAC AAA
1261 TCC TGG GAG ACA GGC GAG CGC GAG TCG CCG GGC AGG
1297 AAT TCC ACA CAC TCG TGC TGT TTT TGA TAC CTG CTT
1333 TTT GTT TTG TTT TGT AAA AAT GAT GCA CTT GAG AAA
1369 ATA AAA CGT CAG TGT TGA CAA AAA AAA AAA AAA AAA

Fig. 11

```
1    GAC TGC CGC AGC AGC AGC AAC AAC CGC TAG CCG AAG
     asp cys arg ser ser ser asn asn arg Xaa pro lys

37   GGT GGC GCG GCG CGG GCC GGC GGC CCG GCG CGG CCC
     gly gly ala ala arg ala gly gly pro ala arg pro

73   GTG AGC CTG CGG GAA GTC GTG CGC TAC CTC GGG GGT
     val ser leu arg glu val val arg tyr leu gly gly

109  AGC AGC GGC GCT GGC GGC CGC CTG ACC CGC GGC CGC
     ser ser gly ala gly gly arg leu thr arg gly arg

145  GTG CAG GGT CTG CTG GAA GAG GAG GCG GCG GCG CGG
     val gln gly leu leu glu glu glu ala ala ala arg

181  GGC CGC CTG GAG CGC ACC CGT CTC GGA GCG CTT GCG
     gly arg leu glu arg thr arg leu gly ala leu ala

217  CTG CCC CGC GGG GAC AGG CCC GGA CGG GCG CCA CCG
     leu pro arg gly asp arg pro gly arg ala pro pro

253  GCC GCC AGC GCC CGC GCG GCG CGG AAC AAG AGA GCT
     ala ala ser ala arg ala ala arg asn lys arg ala

289  GGC GAG GAG CGA GTG CTT GAA AAG GAG GAG GAG GAG
     gly glu glu arg val leu glu lys glu glu glu glu

325  GAG GAG GAG GAA GAC GAC GAG GAC GAC GAC GAC GAC
     glu glu glu glu asp asp glu asp asp asp asp asp

361  GTC GTG TCC GAG GGC TCG GAG GTG CCC GAG AGC GAT
     val val ser glu gly ser glu val pro glu ser asp

397  CGT CCC GCG GGT GCG CAG CAT CAC CAG CTG AAT GGC
     arg pro ala gly ala gln his his gln leu asn gly

433  GGC GAG CGC GGC CCG CAG ACC GCC AAG GAG CGG GCC
     gly glu arg gly pro gln thr ala lys glu arg ala

469  AAG GAG TGG TCG CTG TGT GGC CCC CAC CCT GGC CAG
     lys glu trp ser leu cys gly pro his pro gly gln
```

Fig. 11 (continued)

```
505   GAG GAA GGG CGG GGG CCG GCC GCG GGC AGT GGC ACC
      glu glu gly arg gly pro ala ala gly ser gly thr

541   CGC CAG GTG TTC TCC ATG GCG GCC TTG AGT AAG GAG
      arg gln val phe ser met ala ala leu ser lys glu

577   GGG GGA TCA GCC TCT TCG ACC ACC GGG CCT GAC TCC
      gly gly ser ala ser ser thr thr gly pro asp ser

613   CCG TCC CCG GTG CCT TTG CCC CCC GGG AAG CCA GCC
      pro ser pro val pro leu pro pro gly lys pro ala

649   CTC CCA GGA GCC GAT GGG ACC CCC TTT GGC TGC CCT
      leu pro gly ala asp gly thr pro phe gly cys pro

685   GCC GGG CGC AAA GAG AAG CCG GCA GAC CCC GTG GAG
      ala gly arg lys glu lys pro ala asp pro val glu

721   TGG ACA GTC ATG GAC GTC GTG GAG TAC TTC ACC GAG
      trp thr val met asp val val glu tyr phe thr glu

757   GCG GGC TTC CCT GAG CAA GCC ACG GCT TTC CAG GAG
      ala gly phe pro glu gln ala thr ala phe gln glu

793   CAG GAG ATC GAC GGC AAG TCC CTG CTG CTC ATG CAG
      gln glu ile asp gly lys ser leu leu leu met gln

829   CGC ACC GAT GTC CTC ACC GGC CTG TCC ATC CGC CTG
      arg thr asp val leu thr gly leu ser ile arg leu

865   GGG CCA GCG TTG AAA ATC TAT GAG CAC CAT ATC AAG
      gly pro ala leu lys ile tyr glu his his ile lys

901   GTG CTG CAG CAG GGT CAC TTC GAG GAC GAT GAC CCG
      val leu gln gln gly his phe glu asp asp asp pro

937   GAA GGC TTC CTG GGA TGA GCA CAG AGC CGC CGC GCC
      glu gly phe leu gly

973   CCT TGT CCC CAC CCC CAC CCC GCC TGG ACC CAT TCC
1009  TGC CTC CAT GTC ACC CAA GGT GTC CCA GAG GCC AGG
1045  AGC TGG ACT GGG CAG GCG AGG GGT GCG GAC CTA CCC
1081  TGA TTC TGG TAG GGG GCG GGG CCT TGC TGT GCT CAT
```

Fig. 11 (continued)

| | | | | | | | | | | | | |
|---|---|---|---|---|---|---|---|---|---|---|---|---|
| 1117 | TGC | TAC | CCC | CCC | ACC | CCG | TGT | GTG | TCT | CTG | CAC | CTG |
| 1153 | CCC | CCA | GCA | CAC | CCC | TCC | CGG | AGC | CTG | GAT | GTC | GCC |
| 1189 | TGG | GAC | TCT | GGC | CTG | CTC | ATT | TTG | CCC | CCA | GAT | CAG |
| 1225 | CCC | CCT | CCC | TCC | CTC | CTG | TCC | CAG | GAC | ATT | TTT | TAA |
| 1261 | AAG | AAA | AAA | AGG | AAA | AAA | AAA | AAT | TGG | GGA | GGG | GGC |
| 1297 | TGG | GAA | GGT | GCC | CCA | AGA | TCC | TCC | TCG | GCC | CAA | CCA |
| 1333 | GGT | GTT | TAT | TCC | TAT | ATA | TAT | ATA | TAT | ATG | TTT | TGT |
| 1369 | TCT | GCC | TGT | TTT | TCG | TTT | TTT | GGT | GCG | TGG | CCT | TTC |
| 1405 | TTC | CCT | CCC | ACC | ACC | ACT | CAT | GGC | CCC | AGC | CCT | GCT |
| 1441 | CGC | CCT | GTC | GGC | GGG | AGC | AGC | TGG | GAA | TGG | GAG | GAG |
| 1477 | GGT | GGG | ACC | TTG | GGT | CTG | TCT | CCC | ACC | CTC | TCT | CCC |
| 1513 | GTT | GGT | TCT | GTT | GTC | GCT | CCA | GCT | GGC | TGT | ATT | GCT |
| 1549 | TTT | TAA | TAT | TGC | ACC | GAA | GGG | TTG | TTT | TTT | TTT | TTT |
| 1585 | TAA | ATA | AAA | TTT | TAA | AAA | AAG | GAA | AAA | AAA | AAA | |

Fig. 12

| | | | | | | | | | | | | |
|---|---|---|---|---|---|---|---|---|---|---|---|---|
| 256 | | GCC | AGC | GCC | CGC | GCG | GCG | CGG | AAC | AAG | AGA | GCT |
| | | ala | ser | ala | arg | ala | ala | arg | asn | lys | arg | ala |
| 289 | GGC | GAG | GAG | CGA | GTG | CTT | GAA | AAG | GAG | GAG | GAG | GAG |
| | gly | glu | glu | arg | val | leu | glu | lys | glu | glu | glu | glu |
| 325 | GAG | GAG | GAG | GAA | GAC | GAC | GAG | GAC | GAC | GAC | GAC | GAC |
| | **glu** | **glu** | **glu** | glu | asp | **asp** | **glu** | **asp** | **asp** | asp | asp | **asp** |
| 361 | GTC | GTG | TCC | GAG | GGC | TCG | GAG | GTG | CCC | GAG | AGC | GAT |
| | **val** | val | ser | glu | gly | ser | glu | val | pro | glu | ser | asp |
| 397 | CGT | CCC | GCG | GGT | GCG | CAG | CAT | CAC | CAG | CTG | AAT | GGC |
| | arg | pro | ala | gly | ala | gln | his | his | gln | leu | asn | **gly** |
| 433 | GGC | GAG | CGC | GGC | CCG | CAG | ACC | GCC | AAG | GAG | CGG | GCC |
| | gly | glu | arg | gly | pro | gln | **thr** | ala | lys | glu | arg | **ala** |
| 469 | AAG | GAG | TGG | TCG | CTG | TGT | GGC | CCC | CAC | CCT | GGC | CAG |
| | lys | glu | trp | **ser** | **leu** | cys | gly | pro | his | **pro** | gly | gln |
| 505 | GAG | GAA | GGG | CGG | GGG | CCG | GCC | GCG | GGC | AGT | GGC | ACC |
| | **glu** | glu | gly | arg | gly | pro | ala | **ala** | gly | ser | gly | thr |
| 541 | CGC | CAG | GTG | TTC | TCC | ATG | GCG | GCC | TTG | AGT | AAG | GAG |
| | **arg** | gln | val | phe | ser | met | ala | ala | **leu** | **ser** | lys | glu |
| 577 | GGG | GGA | TCA | GCC | TCT | TCG | ACC | ACC | GGG | CCT | GAC | TCC |
| | gly | gly | **ser** | ala | ser | **ser** | **thr** | thr | gly | pro | asp | ser |
| 613 | CCG | TCC | CCG | GTG | CCT | TTG | CCC | CCC | GGG | AAG | CCA | GCC |
| | **pro** | ser | pro | val | pro | leu | **pro** | **pro** | gly | lys | **pro** | ala |
| 649 | CTC | CCA | GGA | GCC | GAT | GGG | ACC | CCC | TTT | GGC | TGC | CCT |
| | **leu** | pro | gly | ala | asp | gly | thr | pro | phe | gly | cys | **pro** |
| 685 | GCC | GGG | CGC | AAA | GAG | AAG | CCG | GCA | GAC | CCC | GTG | GAG |
| | **ala** | gly | arg | lys | glu | lys | pro | **ala** | asp | pro | val | glu |
| 721 | TGG | ACA | GTC | ATG | GAC | GTC | GTG | GAG | TAC | TTC | ACC | GAG |
| | **trp** | thr | val | met | asp | val | val | glu | tyr | phe | thr | glu |

Fig. 12 (continued)

```
757   GCG GGC TTC CCT GAG CAA GCC ACG GCT TTC CAG GAG
      ala gly phe pro glu gln ala thr ala phe gln glu

793   CAG GAG ATC GAC GGC AAG TCC CTG CTG CTC ATG CAG
      gln glu ile asp gly lys ser leu leu leu met gln

829   CGC ACC GAT GTC CTC ACC GGC CTG TCC ATC CGC CTG
      arg thr asp val leu thr gly leu ser ile arg leu

865   GGG CCA GCG TTG AAA ATC TAT GAG CAC CAT ATC AAG
      gly pro ala leu lys ile tyr glu his his ile lys

901   GTG CTG CAG CAG GGT CAC TTC GAG GAC GAT GAC CCG
      val leu gln gln gly his phe glu asp asp asp pro

937   GAA GGC TTC CTG GGA TGA GCA CAG AGC CGC CGC GCC
      glu gly phe leu gly

973   CCT TGT CCC CAC CCC CAC CCC GCC TGG ACC CAT TCC
1009  TGC CTC CAT GTC ACC CAA GGT GTC CCA GAG GCC AGG
1045  AGC TGG ACT GGG CAG GCG AGG GGT GCG GAC CTA CCC
1081  TGA TTC TGG TAG GGG GCG GGG CCT TGC TGT GCT CAT
1117  TGC TAC CCC CCC ACC CCG TGT GTG TCT CTG CAC CTG
1153  CCC CCA GCA CAC CCC TCC CGG AGC CTG GAT GTC GCC
1189  TGG GAC TCT GGC CTG CTC ATT TTG CCC CCA GAT CAG
1225  CCC CCT CCC TCC CTC CTG TCC CAG GAC ATT TTT TAA
1261  AAG AAA AAA AGG AAA AAA AAA AAT TGG GGA GGG GGC
1297  TGG GAA GGT GCC CCA AGA TCC TCC TCG GCC CAA CCA
1333  GGT GTT TAT TCC TAT ATA TAT ATA TAT ATG TTT TGT
1369  TCT GCC TGT TTT TCG TTT TTT GGT GCG TGG CCT TTC
1405  TTC CCT CCC ACC ACC ACT CAT GGC CCC AGC CCT GCT
1441  CGC CCT GTC GGC GGG AGC AGC TGG GAA TGG GAG GAG
1477  GGT GGG ACC TTG GGT CTG TCT CCC ACC CTC TCT CCC
1513  GTT GGT TCT GTT GTC GCT CCA GCT GGC TGT ATT GCT
1549  TTT TAA TAT TGC ACC GAA GGG TTG TTT TTT TTT TTT
1585  TAA ATA AAA TTT TAA AAA AAG GAA AAA AAA AAA
```

Fig. 13

| | | | | | | | | | | | | |
|---|---|---|---|---|---|---|---|---|---|---|---|---|
| 196 | | | | | | ACC | CGT | CTC | GGA | GCG | CTT | GCG |
| | | | | | | thr | arg | leu | gly | ala | leu | ala |
| 217 | CTG | CCC | CGC | GGG | GAC | AGG | CCC | GGA | CGG | GCG | CCA | CCG |
| | leu | pro | arg | gly | asp | arg | pro | gly | arg | ala | pro | pro |
| 253 | GCC | GCC | AGC | GCC | CGC | GCG | GCG | CGG | AAC | AAG | AGA | GCT |
| | ala | ala | ser | ala | arg | ala | ala | arg | asn | lys | arg | ala |
| 289 | GGC | GAG | GAG | CGA | GTG | CTT | GAA | AAG | GAG | GAG | GAG | GAG |
| | gly | glu | glu | arg | val | leu | glu | lys | glu | glu | glu | glu |
| 325 | GAG | GAG | GAG | GAA | GAC | GAC | GAG | GAC | GAC | GAC | GAC | GAC |
| | **glu** | **glu** | **glu** | glu | asp | **asp** | **glu** | **asp** | **asp** | asp | asp | **asp** |
| 361 | GTC | GTG | TCC | GAG | GGC | TCG | GAG | GTG | CCC | GAG | AGC | GAT |
| | **val** | val | ser | glu | gly | ser | glu | val | pro | glu | ser | asp |
| 397 | CGT | CCC | GCG | GGT | GCG | CAG | CAT | CAC | CAG | CTG | AAT | GGC |
| | arg | pro | ala | gly | ala | gln | his | his | gln | leu | asn | **gly** |
| 433 | GGC | GAG | CGC | GGC | CCG | CAG | ACC | GCC | AAG | GAG | CGG | GCC |
| | gly | glu | arg | gly | pro | gln | **thr** | ala | lys | glu | arg | **ala** |
| 469 | AAG | GAG | TGG | TCG | CTG | TGT | GGC | CCC | CAC | CCT | GGC | CAG |
| | lys | glu | trp | **ser** | **leu** | cys | gly | pro | his | **pro** | gly | gln |
| 505 | GAG | GAA | GGG | CGG | GGG | CCG | GCC | GCG | GGC | AGT | GGC | ACC |
| | **glu** | glu | gly | arg | gly | pro | ala | **ala** | gly | ser | gly | thr |
| 541 | CGC | CAG | GTG | TTC | TCC | ATG | GCG | GCC | TTG | AGT | AAG | GAG |
| | **arg** | gln | val | phe | ser | met | ala | ala | **leu** | **ser** | lys | glu |
| 577 | GGG | GGA | TCA | GCC | TCT | TCG | ACC | ACC | GGG | CCT | GAC | TCC |
| | gly | gly | **ser** | ala | ser | **ser** | **thr** | thr | gly | pro | asp | ser |
| 613 | CCG | TCC | CCG | GTG | CCT | TTG | CCC | CCC | GGG | AAG | CCA | GCC |
| | pro | ser | pro | val | pro | leu | pro | pro | gly | lys | pro | ala |
| 649 | CTC | CCA | GGA | GCC | GAT | GGG | ACC | CCC | TTT | GGC | TGC | CCT |
| | leu | pro | gly | ala | asp | gly | thr | pro | phe | gly | cys | pro |

Fig. 13 (continued)

685 GCC GGG CGC AAA GAG AAG CCG GCA GAC CCC GTG GAG
ala gly arg lys glu lys pro ala asp pro val glu 721 TGG ACA GTC ATG GAC GTC GTG GAG TAC TTC ACC GAG
trp thr val met asp val val glu tyr phe thr glu 757 GCG GGC TTC CCT GAG CAA GCC ACG GCT TTC CAG GAG
ala gly phe pro glu gln ala thr ala phe gln glu 793 CAG GAG ATC GAC GGC AAG TCC CTG CTG CTC ATG CAG
gln glu ile asp gly lys ser leu leu leu met gln 829 CGC ACC GAT GTC CTC ACC GGC CTG TCC ATC CGC CTG
arg thr asp val leu thr gly leu ser ile arg leu 865 GGG CCA GCG TTG AAA ATC TAT GAG CAC CAT ATC AAG
gly pro ala leu lys ile tyr glu his his ile lys 901 GTG CTG CAG CAG GGT CAC TTC GAG GAC GAT GAC CCG
val leu gln gln gly his phe glu asp asp asp pro 937 GAA GGC TTC CTG GGA TGA GCA CAG AGC CGC CGC GCC
glu gly phe leu gly 973 CCT TGT CCC CAC CCC CAC CCC GCC TGG ACC CAT TCC
1009 TGC CTC CAT GTC ACC CAA GGT GTC CCA GAG GCC AGG
1045 AGC TGG ACT GGG CAG GCG AGG GGT GCG GAC CTA CCC
1081 TGA TTC TGG TAG GGG GCG GGG CCT TGC TGT GCT CAT
1117 TGC TAC CCC CCC ACC CCG TGT GTG TCT CTG CAC CTG
1153 CCC CCA GCA CAC CCC TCC CGG AGC CTG GAT GTC GCC
1189 TGG GAC TCT GGC CTG CTC ATT TTG CCC CCA GAT CAG
1225 CCC CCT CCC TCC CTC CTG TCC CAG GAC ATT TTT TAA
1261 AAG AAA AAA AGG AAA AAA AAA AAT TGG GGA GGG GGC
1297 TGG GAA GGT GCC CCA AGA TCC TCC TCG GCC CAA CCA
1333 GGT GTT TAT TCC TAT ATA TAT ATA TAT ATG TTT TGT
1369 TCT GCC TGT TTT TCG TTT TTT GGT GCG TGG CCT TTC
1405 TTC CCT CCC ACC ACC ACT CAT GGC CCC AGC CCT GCT
1441 CGC CCT GTC GGC GGG AGC AGC TGG GAA TGG GAG GAG
1477 GGT GGG ACC TTG GGT CTG TCT CCC ACC CTC TCT CCC
1513 GTT GGT TCT GTT GTC GCT CCA GCT GGC TGT ATT GCT
1549 TTT TAA TAT TGC ACC GAA GGG TTG TTT TTT TTT TTT
1585 TAA ATA AAA TTT TAA AAA AAG GAA AAA AAA AAA

Fig. 14

1 GTG GAA AAT AGC AAC TGT GTT TCT CAA GGA TCC AAT

37 CCC AAC CTA AGG TGG CAG CGC ACA ATG AAG AAT CAA met lys asn gln

73 GAC AAA AAG AAC GGG GCT GCC AAA CAG CCC AAC CCC asp lys lys asn gly ala ala lys gln pro asn pro

109 AAA AGC AGC CCG GGA CAG CCG GAA GCA GGA GCG GAG lys ser ser pro gly gln pro glu ala gly ala glu

145 GGA GCC CAG GGG CGG CCC GGC CGG CCG GCC CCC GCC gly ala gln gly arg pro gly arg pro ala pro ala

181 CGA GAA GCC GAA GGT GCC AGC AGC CAG GCT CCC GGG arg glu ala glu gly ala ser ser gln ala pro gly

217 AGG CCG GAG GGG GCT CAA GCC AAA ACT GCT CAG CCT arg pro glu gly ala gln ala lys thr ala gln pro

253 GGG GCG CTC TGT GAT GTC TCT GAG GAG CTG AGC CGC gly ala leu cys asp val ser glu glu leu ser arg

289 CAG TTG GAA GAC ATA CTC AGT ACA TAC TGT GTG GAC gln leu glu asp ile leu ser thr tyr cys val asp

325 AAC AAC CAG GGG GCC CCG GGT GAG GAT GGG GTC CAG asn asn gln gly ala pro gly glu asp gly val gln

361 GGT GAG CCC CCT GAA CCT GAA GAT GCA GAG AAG TCT gly glu pro pro glu pro glu asp ala glu lys ser

397 CGC GCC TAT GTG GCA AGG AAT GGG GAG CCG GAG CCG arg ala tyr val ala arg asn gly glu pro glu pro

433 GGC ACC CCA GTA GTC AAT GGC GAG AAG GAG ACC TCC gly thr pro val val asn gly glu lys glu thr ser

469 AAG GCA GAG CCG GGC ACG GAA GAG ATC CGG ACG AGC lys ala glu pro gly thr glu glu ile arg thr ser

505 GAT GAG GTC GGA GAC CGA GAC CAC CGG AGG CCA CAG asp glu val gly asp arg asp his arg arg pro gln

Fig. 14 (continued)

```
541  GAA AAG AAG AAG GCC AAG GGT CTG GGA AAG GAG ATC
     glu lys lys lys ala lys gly leu gly lys glu ile

577  ACG CTG CTG ATG CAG ACA CTG AAC ACG CTG AGC ACC
     thr leu leu met gln thr leu asn thr leu ser thr

613  CCA GAG GAG AAG CTG GCG GCT CTG TGC AAG AAG TAT
     pro glu glu lys leu ala ala leu cys lys lys tyr

649  GCG GAA CTG CTC GAG GAG CAC CGG AAC TCG CAG AAG
     ala glu leu leu glu glu his arg asn ser gln lys

685  CAG ATG AAG CTG CTG CAG AAG AAG CAG AGC CAG CTG
     gln met lys leu leu gln lys lys gln ser gln leu

721  GTG CAG GAG AAG GAC CAC CTG CGT GGC GAG CAC AGC
     val gln glu lys asp his leu arg gly glu his ser

757  AAG GCC ATC CTG GCC CGC AGC AAG CTC GAG AGC CTG
     lys ala ile leu ala arg ser lys leu glu ser leu

793  TGC CGG GAG CTG CAG CGG CAC AAC CGC TCG CTC AAG
     cys arg glu leu gln arg his asn arg ser leu lys

829  GAA GAA GGT GTG CAG CGA GCC CGA GAG GAG GAG GAG
     glu glu gly val gln arg ala arg glu glu glu glu

865  AAG CGC AAG GAG GTG ACG TCA CAC TTC CAG ATG ACG
     lys arg lys glu val thr ser his phe gln met thr

901  CTC AAC GAC ATT CAG CTG CAG ATG GAG CAG CAC AAC
     leu asn asp ile gln leu gln met glu gln his asn

937  GAG CGC AAC TCC AAG CTG CGC CAG GAG AAC ATG GAG
     glu arg asn ser lys leu arg gln glu asn met glu

973  CTG GCC GAG CGG CTC AAG AAG CTG ATT GAG CAG TAC
     leu ala glu arg leu lys lys leu ile glu gln tyr

1009 GAG CTG CGA GAA GAG CAC ATC GAC AAA GTC TTC AAA
     glu leu arg glu glu his ile asp lys val phe lys
```

Fig. 14 (continued)

| | |
|---|---|
| 1045 | CAC AAG GAT CTG CAG CAG CAG CTG GTG GAC GCC AAG<br>his lys asp leu gln gln gln leu val asp ala lys |
| 1081 | CTC CAG CAG GCC CAG GAG ATG CTG AAG GAG GCA GAG<br>leu gln gln ala gln glu met leu lys glu ala glu |
| 1117 | GAG CGG CAC CAG CGG GAG AAG GAC TTT CTC CTG AAG<br>glu arg his gln arg glu lys asp phe leu leu lys |
| 1153 | GAG GCC GTG GAG TCC CAG AGG ATG TGC GAG CTG ATG<br>glu ala val glu ser gln arg met cys glu leu met |
| 1189 | AAG CAA CAG GAG ACC CAC CTG AAG CAG CAG CTT GCC<br>lys gln gln glu thr his leu lys gln gln leu ala |
| 1225 | CTA TAC ACA GAG AAG TTT GAG GAG TTC CAG AAC ACT<br>leu tyr thr glu lys phe glu glu phe gln asn thr |
| 1261 | CTT TCC AAA AGC AGC GAG GTG TTC ACC ACA TTC AAA<br>leu ser lys ser ser glu val phe thr thr phe lys |
| 1297 | CAG GAA ATG GAA AAG ATG ACA AAG AAG ATC AAG AAG<br>gln glu met glu lys met thr lys lys ile lys lys |
| 1333 | CTG GAG AAA GAG ACC ACC ATG TAC CGT TCC CGG TGG<br>leu glu lys glu thr thr met tyr arg ser arg trp |
| 1369 | GAG AGC AGC AAC AAG GCC CTG CTT GAG ATG GCT GAG<br>glu ser ser asn lys ala leu leu glu met ala glu |
| 1405 | GAG AAA ACA CTC CGG GAC AAA GAG CTG GAA GGC CTG<br>glu lys thr leu arg asp lys glu leu glu gly leu |
| 1441 | CAG GTG AAA ATC CAG CGG CTG GAG AAG CTG TGC CGG<br>gln val lys ile gln arg leu glu lys leu cys arg |
| 1477 | GCA CTG CAG ACA GAG CGC AAT GAC CTG AAC AAG AGG<br>ala leu gln thr glu arg asn asp leu asn lys arg |
| 1513 | GTG CAG GAC CTG AGT GCC GGT GGC CAG GGC CCC GTC<br>val gln asp leu ser ala gly gly gln gly pro val |

Fig. 14 (continued)

1549 TCC GAC AGC GGT CCT GAG CGG AGG CCA GAG CCC GCC
ser asp ser gly pro glu arg arg pro glu pro ala

1585 ACC ACC TCC AAG GAG CAG GGT GTC GAG GGC CCC GGG
thr thr ser lys glu gln gly val glu gly pro gly 1621 GCT CAA GTA CCC AAC TCT CCA AGG GCC ACA GAC GCT
ala gln val pro asn ser pro arg ala thr asp ala 1657 TCC TGC TGC GCA GGT GCA CCC AGC ACA GAG GCA TCA
ser cys cys ala gly ala pro ser thr glu ala ser 1693 GGC CAG ACA GGG CCC CAG GAG CCC ACC ACT GCC ACT
gly gln thr gly pro gln glu pro thr thr ala thr

1729 GCC TAG AGA GCT TGG TGC TGG GGT GTG CCA GGA AGG
ala

1765 GAG CAG GCA GCC CAG CCA GGC CTG GCC CAG CCC AGG
1801 CTC CCA TGC TAA GCA GTC CGG TGC TGA GGC CAG GAT
1837 GTT CTG ACC TGG CTG GCA CCT GAC CCT CTG CAG TCT
1873 TGG ATT TTG TGG GTC AGT TTT ACA TGC ATA TGG CAC
1909 ACA TGC AAG GCC TCA CAC ATT TGT GTC TCT AAG TGT
1945 ACT GTG GGC TTG CAT CGG GGG TGA CGA TGG ACA GAT
1981 GAA GCC AGC GGC TCC CTT GTG AGC TGA AGT CTT ACG
2017 GAG GAG ACG GCG TCT GCA CTG CCA TCG CAG TGA CCT
2053 GCA GGA CGA GTT CCT TGA GCT TTC CCT GCC TGC TTT
2089 GAG GCT GAG ACC CCT CCC GGC CCT TCA GAG CTC CTG
2125 ACA GGT GAT ACA CAC CCA GCC TTG ACC GCA CTT CTC
2161 TTG GGT AGC TGG GCT CTC CTA GCC TCC CCC AGA GGC
2197 GCC ATT GCT TCT CTT GAC TTG GAG AGG GGA TGC CCA
2233 GGC GTG GCC TTG GCA GGC ACT GGG AGC TAG TGA TTG
2269 GGC TGC TCT CCT GCC TCG AGC AGG GGC AGG AGT GTT
2305 TCT GGT GGG ATG ATG CGC TCG CTG GTC AGG AGC CCC
2341 GTG GGC GCT GCT TCC CCC GCC CTC TGG TGA TGC CAG
2377 GAC CAG GCC AGT GAT GCT TCT CAG TAG CCT TAC CAT
2413 TCA CAG GTG CCT CTC CAG CCC GCA CAG TGA GTG ACA
2449 AGA TCA TCC AAA GGA TTC CTT CTG AAG GTG TTC GTT
2485 TCG TTT TGT TTT GTT GCA CGT GAC GGT TTG TAT TGA
2521 GGA CCC TCT GAG GAA GAG GGG TGC TGT AGC AGT GGT
2557 CCC TGC GTG CCT GGC TCC AGT GTC CTG CCC TCC CCC
2593 CCC TCG CCA TGG CTC CTC GGC CGC CTT GGT GCT GAG
2629 GTT TCT GTT TGG TGA GAT CAG GTT GTC TGT TCA GAG

Fig. 14 (continued)

| | | | | | | | | | | | | |
|---|---|---|---|---|---|---|---|---|---|---|---|---|
| 2665 | AGA | AGA | GGC | GTC | TGA | TGG | CTT | TGC | CGC | CAG | CTT | GCC |
| 2701 | TGC | GGG | CCT | CAA | TCC | CGG | GAG | GCC | GCC | CGG | TTC | CCG |
| 2737 | TCA | CTG | TTG | TCC | CCG | TGC | AGT | GCG | TTG | CTG | GTC | CCC |
| 2773 | AGG | ACC | AGC | TGC | TCG | TTT | GCT | GTA | TGG | GTC | AGT | TTC |
| 2809 | TGC | TTC | CTG | CCC | CCC | ACT | CCA | CCT | AAC | TGC | AAT | CCT |
| 2845 | TGG | GGT | TTC | CCT | GGT | TCT | CGT | CCC | TGG | TAC | CTC | TGT |
| 2881 | GCC | CAA | GAA | GTA | GCC | TTC | TTT | GGG | ATT | CTT | GTT | CTG |
| 2917 | CCC | ATG | CGG | GAG | CTG | CTG | CTG | TCT | GAC | AGG | TGA | GGC |
| 2953 | CTG | AGA | CTC | AGC | GGC | TGA | CAG | AGC | TGC | AGA | GCT | CTG |
| 2989 | CAC | GGT | GGC | TCC | CGG | GGC | GGC | CTC | TGT | GTG | CTG | CAC |
| 3025 | ACC | GCT | GCT | CTG | CTG | GCA | CTG | GCC | AGT | CTG | TGC | AGA |
| 3061 | GCA | TTT | GAG | TAC | TGG | CTC | AGG | AGG | GAG | GGC | TCT | GCT |
| 3097 | GGC | CTC | GAG | GGA | CAG | CGC | CAC | GTC | TCC | AGC | TGG | GCT |
| 3133 | CAG | GGA | GAG | CCC | CAG | ACT | GGC | TGC | GTA | GGG | TGC | TTG |
| 3169 | GGG | TTT | GCT | TCT | TGC | AGT | ATT | TCT | TGG | AAG | CTG | TTT |
| 3205 | TGT | TGT | CCT | GCT | ATT | CCT | TCA | TCT | TCC | ACA | GTC | CAC |
| 3241 | GCT | CAG | CCT | TTA | ACT | TGG | ATC | CCT | CAC | ATA | ACA | GGG |
| 3277 | TTC | ATG | AGA | CCC | GCA | AGT | ACG | CCC | AAG | CTA | CGT | ATG |
| 3313 | GCT | GAG | GCC | AGC | TGG | CAG | GTG | AAT | GGC | ACG | CCA | TTG |
| 3349 | CTG | CTG | CTA | ATC | CCT | GGC | ATA | TCT | TTA | GTT | CAC | CTC |
| 3385 | GAA | ATG | CCC | CCG | CCA | CAG | TGC | AAG | CAG | TGA | GTC | CAC |
| 3421 | GTG | CCA | CCC | TGG | GCT | GAA | TCC | CAC | CCC | CTG | TGA | GTG |
| 3457 | TTG | CCC | GAG | ATT | GTG | TCT | CTT | CTG | AAT | GCC | TTC | ACT |
| 3493 | GGG | AAT | GGC | CTC | TGC | CGC | CTC | CTG | CTC | AGG | GAG | GCT |
| 3529 | TTC | CCC | TTC | CCT | CAG | CCC | CTG | TGC | CAG | ACT | GAG | GTA |
| 3565 | CAA | GAA | CCG | CCA | AGC | CCA | TGC | AAG | GTG | TGG | CTA | GGC |
| 3601 | GCC | AGG | GTG | CAG | GAA | GGA | GGC | AGG | TAG | CTG | CCT | GCA |
| 3637 | CCC | TTG | AAA | GCC | AAG | AGG | CCT | ACG | GTG | GCC | TCC | ATC |
| 3673 | CTG | GCT | TGC | CTC | ACT | TCA | GCT | ACC | TCG | CAT | AGC | CCA |
| 3709 | GGG | GTG | GGG | CTA | TTG | GAT | TCC | AGG | GTG | GGG | GGA | TGG |
| 3745 | GAA | GCT | GCA | GGG | GGC | AGG | TGG | CTC | TCA | CTA | GGC | TTC |
| 3781 | CCA | GCT | CAG | GAA | TGT | GGG | CCT | CAG | GTA | GGG | GAG | AGC |
| 3817 | CTT | TGC | TCC | ACT | CCA | CCC | ATT | TGC | AGG | CAT | CTA | GGC |
| 3853 | CAG | TCT | AGA | TGG | CGA | CCC | CTT | CTC | TTC | CTC | TCC | ATT |
| 3889 | GAC | CAA | ATC | GTA | CCT | GTC | TCT | CCA | GCT | GCT | CGC | TTG |
| 3925 | CTC | TGC | TTT | CCA | AAG | TCA | GCC | CAG | GTA | CCC | AGG | TGC |
| 3961 | CGC | CCA | CAT | TGG | CCT | GGA | ACC | TGG | ACC | AGA | GGC | AAG |
| 3997 | GGA | GGT | GGC | CTA | TCC | TTG | AGT | GAT | AGC | CAG | TGC | CTT |
| 4033 | CCT | CAC | CCG | GTG | GCT | TCC | ATG | CCT | GTG | ACC | TCA | GAT |
| 4069 | TTA | GGA | CCA | AGA | GCT | GTG | TTG | GTT | TCT | TAC | GTT | GTG |
| 4105 | AGC | TTT | CCC | TCC | AGG | GGA | CCA | CAG | CAG | GTG | AGG | CTC |
| 4141 | GGA | GCC | CAG | AGC | CCT | TGG | CGC | CGC | CAG | CAG | TAA | CTT |
| 4177 | GTG | TCC | GGA | CCT | TGT | CCA | GCT | GAG | CGC | TTC | GTG | TAT |

Fig. 14 (continued)

4213 GAC TCA GCT TCG TGT GTG AGT CCA GCG GAG TGC GTC
4249 ACG TGA CCT AGA CTC AGC GGT GTC AGC CGC ACT TTG
4285 ATT TGT TTG TTT TCC ATG AGG TTT TTG GAC CAT GGG
4321 CTT AGC TCA GGC AAC TTT TCT GTA AGG AGA ATG TTA
4357 ACT TTC TGT AAA GAT GCT TAT TTA ACT AAC GCC TGC
4393 TTC CCC CAC TCC CAA CCA GGT GGC CAC CGA GAG CTC
4429 ACC AGG AGG CCA ATA GAG CTG CTC CAG CTC TCC CAT
4465 CTT GCA CCG CAC AAA GGT GGC CGC CCC AGG GAC AGC
4501 CAG GCA CCT GCC TGG GGG AGG GGC TTC TCT TCC TTA
4537 TGG CCT GGC CAT CTA GAT TGT TTA AAG TTG TGC TGA
4573 CAG CTT TTT TTG GTT TTT TGG TTT TTG TTT TTG TTT
4609 TTG TTT TTG TTT TTG TCT ACT TTT GGT ATT CAC AAC
4645 AGC CAG GGA CTT GAT TTT GAT GTA TTT TAA GCC ACA
4681 TTA AAT AAA GAG TCT GTT GCC TTA AAA AAA AAA AAA
4717 AAA AAA

Fig. 15

```
  1  GAC GCC TCA GAG CGG AAC AGG GAA GTG AAT CAG GCG
 37  CCG GGT AGT GGG TTG CTG GGC TGG GCT TGC TGA GGT
 73  AGA GGC AGC GCC AAG AAG AGG CCT TTG CCG CTG GTC
109  GGG ATT GGG ATG TCG AAG AAC ACA GTG TCG TCG GCC
                 met ser lys asn thr val ser ser ala

145  CGC TTC CGG AAG GTG GAC GTG GAT GAA TAT GAC GAG
     arg phe arg lys val asp val asp glu tyr asp glu

181  AAC AAG TTC GTG GAC GAA GAA GAT GGG GGC GAC GGC
     asn lys phe val asp glu glu asp gly gly asp gly

217  CAG GCC GGG CCC GAC GAG GGC GAG GTG GAC TCC TGC
     gln ala gly pro asp glu gly glu val asp ser cys

253  CTG CGG CAA GGA AAC ATG ACA GCT GCC CTA CAG GCA
     leu arg gln gly asn met thr ala ala leu gln ala

289  GCT CTG AAG AAC CCC CCT ATC AAC ACC AAG AGT CAG
     ala leu lys asn pro pro ile asn thr lys ser gln

325  GCA GTG AAG GAC CGG GCA GGC AGC ATT GTC TTG AAG
     ala val lys asp arg ala gly ser ile val leu lys

361  GTG CTC ATC TCT TTT AAA GCT AAT GAT ATA GAA AAG
     val leu ile ser phe lys ala asn asp ile glu lys

397  GCA GTT CAA TCT CTG GAC AAG AAT GGT GTG GAT CTC
     ala val gln ser leu asp lys asn gly val asp leu

433  CTA ATG AAG TAT ATT TAT AAA GGA TTT GAG AGC CCG
     leu met lys tyr ile tyr lys gly phe glu ser pro

469  TCT GAC AAT AGC AGT GCT ATG TTA CTG CAA TGG CAT
     ser asp asn ser ser ala met leu leu gln trp his

505  GAA AAG GCA CTT GCT GCT GGA GGA GTA GGG TCC ATT
     glu lys ala leu ala ala gly gly val gly ser ile

541  GTT CGT GTC TTG ACT GCA AGA AAA ACT GTG TAG TCT
     val arg val leu thr ala arg lys thr val
```

Fig. 15 (continued)

577 GGC AGG AAG TGG ATT ATC TGC CTC GGG AGT GGG AAT
613 TGC TGG TAC AAA GAC CAA AAC AAC CAA ATG CCA CCG
649 CTG CCC TGT GGG TAG CAT CTG TTT CTC TCA GCT TTG
685 CCT TCT TGC TTT TTC ATA TCT GTA AAG AAA AAA ATT
721 ACA TAT CAG TTG TCC CTT TAA TGA AAA TTG GGA TAA
757 TAT AGA AGA AAT TGT GTT AAA ATA GAA GTG TTT CAT
793 CCT TTC AAA ACC ATT TCA GTG ATG TTT ATA CCA ATC
829 TGT ATA TAG TAT AAT TTA CAT TCA AGT TTT AAT TGT
865 GCA ACT TTT AAC CCT GTT GGC TGG TTT TTG GTT CTG
901 TTT GGT TTT GTA TTA TTT TTA ACT AAT ACT GAA AAA
937 TTT GGT CAG AAT TTG AGG CCA GTT TCC TAG CTC ATT
973 GCT AGT CAG GAA ATG ATA TTT ATA AAA AAT ATG AGA
1009 GAC TGG CAG CTA TTA ACA TTG CAA AAC TGG ACC ATA
1045 TTT CCC TTA TTT AAT AAG CAA AAT ATG TTT TTG GAA
1081 TAA GTG GTG GGT GAA TAC CAC TGC TAA GTT ATA GCT
1117 TTG TTT TTG CTT GCC TCC TCA TTA TCT GTA CTG TGG
1153 GTT TAA GTA TGC TAC TTT CTC TCA GCA TCC AAT AAT
1189 CAT GGC CCC TCA ATT TAT TTG TGG TCA CGC AGG GTT
1225 CAG AGC AAG AAG TCT TGC TTT ATA CAA ATG TAT CCA
1261 TAA AAT ATC AGA GCT TGT TGG GCA TGA ACA TCA AAC
1297 TTT TGT TCC ACT AAT ATG GCT CTG TTT GGA AAA AAC
1333 TGC AAA TCA GAA AGA ATG ATT TGC AGA AAG AAA GAA
1369 AAA CTA TGG TGT AAT TTA AAC TCT GGG CAG CCT CTG
1405 AAT GAA ATG CTA CTT TCT TTA GAA ATA TAA TAG CTG
1441 CCT TAG ACA TTA TGA GGT ATA CAA CTA GTA TTT AAG
1477 ATA CCA TTT AAT ATG CCC CGT AAA TGT CTT CAG TGT
1513 TCT TCA GGG TAG TTG GGA TCT CAA AAG ATT TGG TTC
1549 AGA TCC AAA CAA ATA CAC ATT CTG TGT TTT AGC TCA
1585 GTG TTT TCT AAA AAA AGA AAC TGC CAC ACA GCA AAA
1621 AAT TGT TTA CTT TGT TGG ACA AAC CAA ATC AGT TCT
1657 CAA AAA ATG ACC GGT GCT TAT AAA AAG TTA TAA ATA
1693 TCG AGT AGC TCT AAA ACA AAC CAC CTG ACC AAG AGG
1729 GAA GTG AGC TTG TGC TTA GTA TTT ACA TTG GAT GCC
1765 AGT TTT GTA ATC ACT GAC TTA TGT GCA AAC TGG TGC
1801 AGA AAT TCT ATA AAC TCT TTG CTG TTT TTG ATA CCT
1837 GCT TTT TGT TTC ATT TTG TTT TGT TTT GTA AAA ATG
1873 ATA AAA CTT CAG AAA ATA AAA TGT CAG TGT TGA ATA
1909 ATT AAA AAA AAA AAA AA

Fig. 16

1 GAA GAG CGA GTA CTT GAG AAA GAA GAG GAA GAA GAT
glu glu arg val leu glu lys glu glu glu glu asp

37 GAT GAT GAA GAT GAA GAT GAA GAA GAT GAT GTG TCA
asp asp glu asp glu asp glu glu asp asp val ser 73 GAG GGC TCT GAA GTG CCC GAG AGT GAC CGT CCT GCA
glu gly ser glu val pro glu ser asp arg pro ala 109 GGT GCC CAG CAC CAC CAG CTT AAC GGC GAG CGG GGA
gly ala gln his his gln leu asn gly glu arg gly 145 CCT CAG AGT GCC AAG GAG AGG GTC AAG GAG TGG ACC
pro gln ser ala lys glu arg val lys glu trp thr

181 CCC TGC GGA CCG CAC CAG GGC CAG GAT GAA GGG CGG
pro cys gly pro his gln gly gln asp glu gly arg 217 GGG CCA GCC CCG GGC AGC GGC ACC CGC CAG GTG TTC
gly pro ala pro gly ser gly thr arg gln val phe 253 TCC ATG GCA GCC ATG AAC AAG GAA GGG GGA ACA GCT
ser met ala ala met asn lys glu gly gly thr ala 289 TCT GTT GCC ACC GGG CCA GAC TCC CCG TCC CCC GTG
ser val ala thr gly pro asp ser pro ser pro val 325 CCT TTG CCC CCA GGC AAA CCA GCC CTA CCT GGG GCC
pro leu pro pro gly lys pro ala leu pro gly ala 361 GAC GGG ACC CCC TTT GGC TGT CCT CCC GGG CGC AAA
asp gly thr pro phe gly cys pro pro gly arg lys 397 GAG AAG CCA TCT GAT CCC GTC GAG TGG ACC GTG ATG
glu lys pro ser asp pro val glu trp thr val met 433 GAT GTC GTC GAA TAT TTT ACT GAG GCT GGA TTC CCG
asp val val glu tyr phe thr glu ala gly phe pro 469 GAG CAG GCG ACA GCT TTC CAA GAG CAG GAA ATT GAT
glu gln ala thr ala phe gln glu gln glu ile asp Fig. 16 (continued)

505 GGC AAA TCT TTG CTG CTC ATG CAG CGC ACA GAT GTG
gly lys ser leu leu leu met gln arg thr asp val 541 CTC ACC GGC CTG TCC ATC CGC CTC GGG CCA GCC CTG
leu thr gly leu ser ile arg leu gly pro ala leu 577 AAA ATC TAC GAG CAC CAC ATC AAG GTG CTT CAG CAA
lys ile tyr glu his his ile lys val leu gln gln 613 GGC CAC TTT GAG GAT GAT GAC CCC GAT GGC TTC TTA
gly his phe glu asp asp asp pro asp gly phe leu 649 GGC TGA GCG CCC AGC CTC ACC CCT GCC CCA GCC CAT
gly 685 TCC GGC CCC CAT CTC ACC CAA GAT CCC CCA GAG TCC
721 AGG AGC TGG ACG GGG ACA CCC TCA GCC CTC ATA ACA
757 GAT TCC AAG GAG AGG GCA CCC TCT TGT CCT TAT CTT
793 TGC CCC TTG TNT CTG TCT CAC ACA CAT CTG CTC CTC
829 AGC ACG TCG GTG TGG GGA GGG GAT TGC TCC TTA AAC
865 CCC AGG TGG CTG ACC CTC CCC ACC CAG TCC AGG ACA
901 TTT TAG GAA AAA AAA AAT GAA ATG TGG GGG GCT TCT
937 CAT CTC CCC AAG ATC CTC TTC CGT TCA GCC AGA TGT
973 TTC CTG TAT AAA TGT TTG GAT CTG CCT GTT TAT TTT
1009 GGT GGG TGG TCT TTC CTC CCT CCC CTA CCA CCC ATG
1045 CCC CCC TTC TCA GTC TGC CCC TGG CCT CCA GCC CCT
1081 AGG GGA CTA GCT GGG TTG GGG TTC CTC GGG CCT TTT
1117 CTC TCC TCC CTC TTT TCT TTC TGT TGA TTG TCG CTC
1153 CAG CTG GCT GTA TTG CTT TTT AAT ATT GCA CCG AAG
1189 GTT TTT TAA ATA AAA TTT TA

Fig. 17

1 CA AAA AGC AGC CCA GGA CAA CCG GAA GCA GGA CCC GAG GGA GCC
lys ser ser pro gly gln pro glu ala gly pro glu gly ala 45 CAG GAG CGG CCC AGC CAG GCG GCT CCT GCA GTA GAA GCA GAA GGT
gln glu arg pro ser gln ala ala pro ala val glu ala glu gly 90 CCC GGC AGC AGC CAG GCT CCT CGG AAG CCG GAG GGG GCT CAA GCC
pro gly ser ser gln ala pro arg lys pro glu gly ala gln ala 135 AGA ACG GCT CAG TCT GGG GCC CTT CGT GAT GTC TCT GAG GAG CTG
arg thr ala gln ser gly ala leu arg asp val ser glu glu leu 180 AGC CGC CAA CTG GAA GAC ATA CTG AGC ACA TAC TGT GTG GAC AAT
ser arg gln leu glu asp ile leu ser thr tyr cys val asp asn 225 AAC CAG GGG GGC CCC GGC GAG GAT GGG GCA CAG GGT GAG CCG GCT
asn gln gly gly pro gly glu asp gly ala gln gly glu pro ala 270 GAA CCC GAA GAT GCA GAG AAG TCC CGG ACC TAT GTG GCA AGG AAT
glu pro glu asp ala glu lys ser arg thr tyr val ala arg asn 315 GGG GAG CCT GAA CCA ACT CCA GTA GTC TAT GGA GAG AAG GAA CCC
gly glu pro glu pro thr pro val val tyr gly glu lys glu pro 360 TCC AAG GGG GAT CCA AAC ACA GAA GAG ATC CGG CAG AGT GAC GAG
ser lys gly asp pro asn thr glu glu ile arg gln ser asp glu 405 GTC GGA GAC CGA GAC CAT CGA AGG CCA CAG GAG AAG AAA AAA GCC
val gly asp arg asp his arg arg pro gln glu lys lys lys ala 450 AAG GGT TTG GGG AAG GAG ATC ACG TTG CTG ATG CAG ACA TTG AAT
lys gly leu gly lys glu ile thr leu leu met gln thr leu asn 495 ACT CTG AGT ACC CCA GAG GAG AAG CTG GCT GCT CTG TGC AAG AAG
thr leu ser thr pro glu glu lys leu ala ala leu cys lys lys 540 TAT GCT GAA CTG CTG GAG GAG CAC CGG AAT TCA CAG AAG CAG ATG
tyr ala glu leu leu glu glu his arg asn ser gln lys gln met 585 AAG CTC CTA CAG AAA AAG CAG AGC CAG CTG GTG CAA GAG AAG GAC
lys leu leu gln lys lys gln ser gln leu val gln glu lys asp 630 CAC CTG CGC GGT GAG CAC AGC AAG GCC GTC CTG GCC CGC AGC AAG
his leu arg gly glu his ser lys ala val leu ala arg ser lys 675 CTT GAG AGC CTA TGC CGT GAG CTG CAG CGG CAC AAC CGC TCC CTC
leu glu ser leu cys arg glu leu gln arg his asn arg ser leu Fig. 17 (continued)

720 AAG GAA GAA GGT GTG CAG CGG GCC CGG GAG GAG GAG GAG AAG CGC
lys glu glu gly val gln arg ala arg glu glu glu glu lys arg 765 AAG GAG GTG ACC TCG CAC TTC CAG GTG ACA CTG AAT GAC ATT CAG
lys glu val thr ser his phe gln val thr leu asn asp ile gln 810 CTG CAG ATG GAA CAG CAC AAT GAG CGC AAC TCC AAG CTG CGC CAA
leu gln met glu gln his asn glu arg asn ser lys leu arg gln 855 GAG AAC ATG GAG CTG GCT GAG AGG CTC AAG AAG CTG ATT GAG CAG
glu asn met glu leu ala glu arg leu lys lys leu ile glu gln 900 TAT GAG CTG CGC GAG GAG CAT ATC GAC AAA GTC TTC AAA CAC AAG
tyr glu leu arg glu glu his ile asp lys val phe lys his lys 945 GAC CTA CAA CAG CAG CTG GTG GAT GCC AAG CTC CAG CAG GCC CAG
asp leu gln gln gln leu val asp ala lys leu gln gln ala gln 990 GAG ATG CTA AAG GAG GCA GAA GAG CGG CAC CAG CGG GAG AAG GAT
glu met leu lys glu ala glu glu arg his gln arg glu lys asp 1035 TTT CTC CTG AAA GAG GCA GTA GAG TCC CAG AGG ATG TGT GAG CTG
phe leu leu lys glu ala val glu ser gln arg met cys glu leu 1080 ATG AAG CAG CAA GAG ACC CAC CTG AAG CAA CAG CTT GCC CTA TAC
met lys gln gln glu thr his leu lys gln gln leu ala leu tyr 1125 ACA GAG AAG TTT GAG GAG TTC CAG AAC ACA CTT TCC AAA AGC AGC
thr glu lys phe glu glu phe gln asn thr leu ser lys ser ser 1170 GAG GTA TTC ACC ACA TTC AAG CAG GAG ATG GAA AAG ATG ACT AAG
glu val phe thr thr phe lys gln glu met glu lys met thr lys 1215 AAG ATC AAG AAG CTG GAG AAA GAA ACC ACC ATG TAC CGG TCC CGG
lys ile lys lys leu glu lys glu thr thr met tyr arg ser arg 1260 TGG GAG AGC AGC AAC AAG GCC CTG CTT GAG ATG GCT GAG GAG AAA
trp glu ser ser asn lys ala leu leu glu met ala glu glu lys 1305 ACA GTC CGG GAT AAA GAA CTG GAG GGC CTG CAG GTA AAA ATC CAA
thr val arg asp lys glu leu glu gly leu gln val lys ile gln 1350 CGG CTG GAG AAG CTG TGC CGG GCA CTG CAG ACA GAG CGC AAT GAC
arg leu glu lys leu cys arg ala leu gln thr glu arg asn asp 1395 CTG AAC AAG AGG GTA CAG GAC CTG AGT GCT GGT GGC CAG GGC TCC
leu asn lys arg val gln asp leu ser ala gly gly gln gly ser 1440 CTC ACT GAC AGT GGC CCT GAG AGG AGG CCA GAG GGG CCT GGG GCT
leu thr asp ser gly pro glu arg arg pro glu gly pro gly ala Fig. 17 (continued)

1485 CAA GCA CCC AGC TCC CCC AGG GTC ACA GAA GCG CCT TGC TAC CCA
gln ala pro ser ser pro arg val thr glu ala pro cys tyr pro 1530 GGA GCA CCG AGC ACA GAA GCA TCA GGC CAG ACT GGG CCT CAA GAG
gly ala pro ser thr glu ala ser gly gln thr gly pro gln glu 1575 CCC ACC TCC GCC AGG GCC TAG AGA GCC TGG TGT TGG GTC ATG CTG
pro thr ser ala arg ala ***

1620 GGA AGG GAG CGG CAG CCC AGC CAG GCC TGG CCC ATA AAA GGC TCC
1665 CAT GCT GAG CAG CCC ATT GCT GAA GCC AGG ATG TTC TTG ACC TGG
1710 CTG GCA TCT GGC ACT TGC AAT TTT GGA TTT TGT GGG TCA GTT TTA
1755 CGT ACA TAG GGC ATT TTG CAA GGC CTT GCA AAT GCA TTT ATA CCT
1800 GTA AGT GTA CAG TGG GCT TGC ATT GGG GAT GGG GGT GTG TAC AGA
1845 TGA AGT CAG TGG CTT GTC TGT GAG CTG AAG AGT CTT GAG AGG GGC
1890 TGT CAT CTG TAG CTG CCA TCA CAG TGA GTT GGC AGA AGT GAC TTG
1935 AGC ATT TCT CTG TCT GAT TTG AGG CTC AGA CCC CTC CCT GCC CTT
1980 TCA GAG CTC AAA ACA AGT AAT ACA CCA AGG TCT TGA CTG CAT TTG
2025 TCT TGT GAG CAG GGC TTG CTT GGT CAG CTC AGG CCC TCC TAG CTG
2070 CTT GGA GGC TCC TTT GAT TCT CTA GAC CTG GAA AAG GTG TCC CTA
2115 GGC AGA GCC CTG GCA GGG CGC TCA GAG CTG GGA TTT CCT GCC TGG
2160 AAC AAG GGA CCT GGA GAA TGT TTT TGC GTG GGA TGA TGT GCT GGT
2205 CAG GAG CCC CTT GGG CAT CGC TTC CCC TGC CCT TTG GTA GTG CCA
2250 GGA CCA GGC CAA TGA TGC TTC TCA GTA GCC TTA TCA TTC ACA GGT
2295 GCC TCT CTA GCC TGC ACA AAT GAT TGA CAA GAG ATC ACC CAA AGG
2340 ATT ATT TCT GAA GGT GTT TTT TTC TTT ATT TCT TTT TCT TTT TTT
2385 TTT TTT CTT TTT CTT TTT TTT TTG CAC ATG ACA GTG TTT GTA TTG
2430 AGG ACC TTC CAA GGA AAA GGG ATG CTG TAC CAG TGG TGC CTG GGT
2475 GCC TGG CCT CCA GTG TCC CAC CTC CTT CAC CAC CCC ACT TGG CTC
2520 CTT TGC CAT CTT GAT GCT GAG GTT TCC TGT TTG GTG AGA TCA GGT
2565 TGT TTG TGG TAA AAG AAA GGA AAG GGC TTC TGA TGG CTT TGC CAC
2610 AAG CTT ACC TGT GGG TTT CAG TCC TGA GAG GCC ACC ACC AGT TCC
2655 CAT CAG CAC TGT CTC CAT GCA GCA GTT GCT GGG TCC CAT GTC CAG
2700 CTG CCT CTT TGG CTT CAT GGG TTT TTC TGC TTC CTG CCC CCA CCC
2745 CCA CAT GTG CAA TCC TCA AGA TTT GTC CTG ATT CTA TTT CCT GGC
2790 ACC TCC CTG CCT GTC CTT GGG GAT TCT ACT TCT TCC TGT GTG GGG
2835 CCC ATA GCT GTT GTC TAA CAG GTA AGA AAT GAA ATT GAA CTA TTG
2880 ACT GGG CCC CAG AAA TCC ATA AAA TGG CTG CAG ACA GTT GTT TCT
2925 GTG TCC TGT TCT ACC CCC ACT CCA GTA CAT AAC TAC TAT GTA CTG
2970 TGT AGA GCC ATT CTA TAT GCT GAA TGT TCT GCT GTT GCA AAC TTG
3015 CCA GGG TAT TAG CCA GTG TTT GTG CCA AGC AGT TTT CGG GGA CAA
3060 CAG AAT GAC TCA GAC CAA GAT GGA TAG GAT GGT TAG GGC TTT GCT
3105 TCT TGC TGT TTT TCT TTG AAC TAG TCA TTG TCC TGC AGG TCC CTT
3150 CAT CTT CCA TAC CTA GCC CAC TCT TTT AGC CCT TAC CTT AAA TCT
3195 CTC AGA TAA GTT GGT TCA CAA AGA ATG TTA AGT ACT GAA TCA TGT
3240 GTG ACT GAG ACC AGA GAT GGC AAA TGA ATG GCA CAC CAT TTC TCC
3285 TTC TCC TGC CCC AGG GCA GGT ACC ACT GAT CTG CAT CAG AGT TGC
3330 CTG CTA TTC TCT GGT GTA TCC TTC ACA TCT AGG TGC CCT CAA GCA
3375 GCT GTG TGA GTG TTG AGA TCT CTG CCA TCT CTG GCT GAG ATA CTG
3420 CTG TCC TGT GAA GTG TTT CCC ATG ACC TTT TTC TTC CCC TTT GAA
3465 TCC CTC TTG TCT GGA GTA GTC CTT GCC TTC TTC TTG CTC CAG TAG

Fig. 17 (continued)

3510 GCC TTT TCC TTA CCC CAG CCC TTG TGC CAG GCT AAG CTG GTA CAA
3555 GAG CTG CCA ACT CAC AGA GTT TTG CTA GGC GAG AGA GGT GCA GGG
3600 AAG AGG CAG AGG TAT GCA CCT TCC CCC TTG AAG AGA GGG GAA AGG
3645 CCT ACA GTG GCC CAC ATA ATT GCC TGA CTC ACA CTT CAG CTA CCT
3690 CTT AAT GCC TGT GGA GGG ACT GGA GCT GCT GGA TCC CAG TGT GGT
3735 GGT GTA GGA GGC CAC AGT GAG CAG GTG GCC CCA GCT GGG TTT CCC
3780 AGG TCA GGA ATG TGG GCC CCA GGC AAG GTG CAG CCT TTG CTC ACA
3825 GCT CCA TCC ATG TCT AGA CCT TCA GGC CAG TCT GCA GAT GAG GTT
3870 CCC TAC CTT TTT CTT CTC TTC ATT GAC CAA ATC AAC CAA TCA CTA
3915 CAG CTG CTC TGC TTC TGC TTT CCA AAG TAG CCC AGG TCC TGG GCC
3960 AGA TGC AGG GGA GGT GCC TAT CCA TGA GTG AAG GCC AGT GTC TTC
4005 CTC ACC TGG GTG GTC CCA CAC TTG TGA CCC TCA GTT TTA GGA CCC
4050 AAG ATC TGT GTT GGT TTC TTA GAT TGC TAG CTT TTC CTC CAG GGG
4095 ACC ACA GCA GGT GAA GCT CAA GAG CGC ATG GCT CTG CTA ATA GTA
4140 AAT TGT TTT CAG GGC CTT GTC CAG CTG AGA GCT TCA TGT CCA CCA
4185 GAT TCT GAG AGG TGT CAG CAG CAC TTT TTT TTT TTA TTT GTT GTT
4230 TGT TTT CCA TGA GGT TAT CGG ACC ATG GGC TGA GCT CAG GCA CTT
4275 TCT GTA GGA GAC TGT TAT TTC TGT AAA GAT GGT TAT TTA ACC CTC
4320 CTC CAC CCC ATC ACG GTG GCC CTG AGG GCT GAC CCG GAG GCC AGT
4365 GGA GCT GCC TGG TGT CCA CGG GGG AGG GCC AAG GCC TGC TGA GCT
4410 GAT TCT CCA GCT GCT GCC CCA GCC TTT CCG CCT TGC ACA GCA CAG
4455 AGG TGG TCA CCC CAG GGA CAG CCA GGC ACC TGC TCC TCT TGC CCT
4500 TCC TGG GGG AAA GGA GCT GCC TTC TGT CCC TGT AAC TGC TTT CCT
4545 TAT GGC CCA ACC CGG CCA CTC AGA CTT GTT TGA AGC TGC ACT GGC
4590 AGC TTT TTT GTC TCC TTT GGG TAT TCA CAA CAG CCA GGG ACT TGA
4635 TTT TGA TGT ATT TTA AAC CAC ATT AAA TAA AGA GTC TGT TGC CTT
4680 AAA AAA AAA AAA AAA AAA

Fig. 18

```
GTG GAC GTG GAT GAG TAC GAC GAG AAC AAG TTC GTG
val asp val asp glu tyr asp glu asn lys phe val

GAC GAG GAA GAC GGC GGC GAC GGC
asp glu glu asp gly gly asp gly
```

Fig. 19

```
        1                                                  50
Rabbit  MSKNTVSSAR FRKVDVDEYD ENKFVDEEDG GDGQAGPDEG EVDSCLRQGN
Human   .......... .......... .......... .......... ..........

        51                                                100
Rabbit  MTAALQAALK NPPINTRSQA VKDRAGSIVL KVLISFKAGD IEKAVQSLDR
Human   .......... ......K... .......... ........N. .........K

        101                                               150
Rabbit  NGVDLLMKYI YKGFESPSDN SSAVLLQWHE KALAAGGVGS IVRVLTARKT
Human   .......... .......... ...M...... .......... ..........

        151
Rabbit  V
Human   .
```

Fig. 20

```
        1                                                  50
Rabbit  EERVLEKEEE EEEEEDDEDD DDDVVSEGSE VPESDRPAGA QHHQLNGGER
Human   .......... .DDD..EDEE ..--...... .......... ......-...

        51                                                100
Rabbit  GPQTAKERAK EWSLCGPHPG QEEGRGPAAG SGTRQVFSMA ALSKEGGSAS
Human   ...S....V. ..TP....Q. .D......P. .......... .MN....T..

        101                                               150
Rabbit  STTGPDSPSP VPLPPGKPAL PGADGTPFGC PAGRKEKPAD PVEWTVMDVV
Human   VA........ .......... .......... .P......S. ..........

        151                                               200
Rabbit  EYFTEAGFPE QATAFQEQEI DGKSLLLMQR TDVLTGLSIR LGPALKIYEH
Human   .......... .......... .......... .......... ..........

        201                  220
Rabbit  HIKVLQQGHF EDDDPEGFLG
Human   .......... .....D....
```

Fig. 21

```
        1                                                 50
Rabbit  MKNQDKKNGA AKQPNPKSSP GQPEAGAEGA QGRPGRPAPA REAEG-ASSQ
Human   ---------- ------.... ......P... .E..SQA... V....PG...

        51                                               100
Rabbit  APGRPEGAQA KTAQPGALCD VSEELSRQLE DILSTYCVDN NQGAPGEDGV
Human   ..RK...... R...S...R. .......... .......... ...G.....A

        101                                              150
Rabbit  QGEPPEPEDA EKSRAYVARN GEPEPGTPVV NGEKETSKAE PGTEEIRTSD
Human   ....A..... ....T..... .....-.... Y....P..GD .N.....Q..

        151                                              200
Rabbit  EVGDRDHRRP QEKKKAKGLG KEITLLMQTL NTLSTPEEKL AALCKKYAEL
Human   .......... .......... .......... .......... ..........

        201                                              250
Rabbit  LEEHRNSQKQ MKLLQKKQSQ LVQEKDHLRG EHSKAILARS KLESLCRELQ
Human   .......... .......... .......... .....V.... ..........

        251                                              300
Rabbit  RHNRSLKEEG VQRAREEEEK RKEVTSHFQM TLNDIQLQME QHNERNSKLR
Human   .......... .......... .........V .......... ..........

        301                                              350
Rabbit  QENMELAERL KKLIEQYELR EEHIDKVFKH KDLQQQLVDA KLQQAQEMLK
Human   .......... .......... .......... .......... ..........

        351                                              400
Rabbit  EAEERHQREK DFLLKEAVES QRMCELMKQQ ETHLKQQLAL YTEKFEEFQN
Human   .......... .......... .......... .......... ..........

        401                                              450
Rabbit  TLSKSSEVFT TFKQEMEKMT KKIKKLEKET TMYRSRWESS NKALLEMAEE
Human   .......... .......... .......... .......... ..........

        451                                              500
Rabbit  KTLRDKELEG LQVKIQRLEK LCRALQTERN DLNKRVQDLS AGGQGPVSDS
Human   ..V....... .......... .......... .......... .....SLT..

        501                                              550
Rabbit  GPERRPEPAT TSKEQGVEGP GAQVPNSPRA TDASCCAGAP STEASGQTGP
Human   ......---- -------... ...A.S...V .E.P.YP... ..........

        551
Rabbit  QEPTTATA
Human   ....S.R.
```

Fig. 22 (1/5)

```
   1  AAGCTTTATAAAGATTTAACTACCTAATAAGGTAGAGAAGTAATTTATGTGCCCACTAAA    60
  61  AAATACTCAATTTCTGAATGTTCGTCCAAAATTAACTTGTCAGATCATTAAATCATTGAC   120
 121  TAGAAACACGTTGAGTACCTATTATGTACTAGGCACTTAGATCATTGTGAGACAATAAAA   180
 181  AATACTGCATTAGAAAAGGACATTTTTCACATCTTAAATGCAATAAGCATTATTTGGCTG   240
 241  GCAGTTAATTACATTTAACACATTAAACATATAGAGCAAAATTCTGAGCAATCAAAATAA   300
 301  TTATACCCTTGAGCAATCGATTATTTAAATTTCTTTCACTATTCCCTTAAGCTGATTTCT   360
 361  ACTCTGGGATTCTTTCATAGTTCTCAAATAAGAAAATAAAAAATTTCCTAAATAAGGCAA   420
 421  TACAAAAGAATAGAAATGTAAGAGAAGAGATATATTAGCTCTTGAATCCCTGTTTCCATT   480
 481  TGCTGTCAATAGTGCCTCTAATGTTCGATTTTCTCTTCAAAGAAAAATCTTGATTTAAAA   540
 541  GGAAGAAAAAGTACAATCACCTTTAACAGCTAAAGTATACTGATTAGCATCTACTAAAGT   600
 601  TAGCAAAGACTGAAACTGAAAAAAAATTGTAAAATCTTTATTCTAAGTTATATAACGCCA   660
 661  TTCACCATAGTAATGATTTTATACTTTGGTATATGGCTTTTTAAAATAAATATTGCCAAC   720
 721  AGGTAAAAATTTTTCCTTTGCTGTCTTAAGGCATTCCTAAGAGAATTTTTACCAGTGTGT   780
 781  GTTCATAACTTGAATGTTAATTTAAACAATGTTACTTCTATCACCTAAATGATATACTTA   840
 841  TAGAAGAGTGGTTTAATTGGGAACAGAAAAACACCACATTGCTTCTTCCCAAGAAAAAGG   900
 901  GATGTATTCCATTCTCGAGGTCTCTCTCCCACTCTCTATTTATATATAATATACTGCATA   960
 961  GATAAATATACACACATTATATATGTATTTTTTTGAACTTAAAGAAGACTGGACATATGT  1020
1021  ATTTACATGTATATATCCAACAAATATTTAATTTTGAGATCTCTCTCCCTCTTCTGATTT  1080
1081  ATTATTCTCAGTATGAATTCTCAAACTGTACGGTCTTTCACATTTCATTCATTCATCAAG  1140
1141  CATGTATCGAGTCCCTTCTGCATGCTTAGCTTTTTGTCATATGGAAGGAAGATACAAAAG  1200
1201  AAAAACTGTTTCTGCCCTTCAGAATCTTTCCATCTCTTCTAGGAAGGAGATAAAACACCA  1260
1261  TATATCATTAAGAAATTTATAAGACTAGTCCCAAAACCAATGGTACAAGCAACATGCATT  1320
1321  TTACATTTATGTAGAATTTTAGAGCTTGGAAACACTTTCGTGATATATAATCCTAAGAAC  1380
1381  AATCTTGTAAAGTGCACATTATTAGCTCCATTTCAGTGATGAGGAATCTGAGACAGAATT  1440
1441  TTAAGTGACATGTCTCGTTCAAACATTATGAGTGGAAGAGTCAACACTTAAGCCTGAGTT  1500
1501  TTCTGATTCTAAGCCTAGTGCTCTTTTCAACACAGCACTGGAAACCAAAGATTGTGGTAC  1560
1561  ACAACAAGGCAACAGCCAGTCTTCTTGCTCGAGGTCCAACTAAACTGGACCCATACCGAG  1620
1621  CAGTGTCCAGCCAAATGTCCAAATTAATTTTATCCTGCAAATATTTGTTCTTCAGTGTAA  1680
1681  TACACACAGCACAACTACCATTTCCTTCGTCTTAGTGCCTTTATCTCCTACATTCCAGAA  1740
1741  ATGGGGATGTCAAATATTTTTTTAAATCTGGCCTAGATGGAATCATATAAATCTCAAATC  1800
1801  ATAATATAAATCTTAAAGGTCTGGTTTCCACCAATCCTTCCACATTTTGTTTTCCCCCAG  1860
1861  CACTAGAGAGCCTAACCTACCCTCACCCCTTTCGAGCATTCTTGCTCCAAACGACCACCT  1920
1921  ATTTTAAGATGTCAATGACCCTTTCCCAAATTCTACAAATTCACCCCAGTTTTGCCACCC  1980
1981  GACCCCAGCGCCTGCCCGGACACGTTCCCCTCCCTCCCAATAGATTTGATACCGAGTTCA  2040
2041  GGTTCTGCAGATCCCGTTGCGATGCTGTCACACAGCACTGACAGATAAGATTTGACCTTT  2100
2101  CGACTCCGTCCTTGGGGACTTCCCGCTGGCCAAGAAGGGTAGTTCCAATCCCAGGAAACG  2160
2161  GGCTTCCTGCTCAGGAACGCAGCCTCTAGCAGCGCACAGTCTGAGGCAATGTCTCCGGCA  2220
2221  ATTAGAACGATGCTGGGCGCCCGGGTGTGCATCACTCTGCCTCATACTCCTACCAACTGC  2280
2281  AGGGCACTCGGTCCGGCAGCCAGTCCATCCCACCCACACCCAAGTCCCAGCCAGCCGGAC  2340
2341  CTTACGCAGGACCCCGATGATAGGTCGTTGACGGCTGCAGCAAAAGCCAAGGCCACCTGC  2400
2401  CGCTGCTGCCCATCCCCGCCAATCTGAGACCCCCTAGACTGGACCGCAGAAAAGCGTTTC  2460
2461  TATGGGAACCCCCCCACCGAGAATCACGTGACGCAATCGGACGACCAATCGCTTCTTACC  2520
2521  TCTGCCCGCGGTCCAGCTTTTGGCCCTCCCTCTCGCCCCCGCCTCCTTCGCCCAGCCCCG  2580
2581  CCCCTTGCCTGCGGAGAGCCCGCGCCTGCGCGCTGTGTCCTGCGCGCTCCTTCCCTCGCG  2640
2641  CGCGCTCTCCGTGGAAGAGCAGGGGCAGCGTGGGAGGCGCCAAGGGAGCGCGAACCTGAG  2700
2701  GAGGAAGAAACGGGGCTAGCGCGCAGGCCCAGAACGGTCCGAGCCGCGGCAGTCGGCGAC  2760
2761  GCCTCAGAGCGGAAGAGGGAAGTGAATCAGGCGCCGGGTAGTGGGTTGCTGGGCTGGGCT  2820

2821  TGCTGAGGTAGAGGCAGCGCCAAGAAGAGGCCTTTGCCGCTGGTCGGGATTGGGATGTCG  2880
                                                             M  S

2881  AAGAACACAGTGTCGTCGGCCCGCTTCCGGAAGGTGGACGTGGATGAATATGACGAGAAC  2940
      K  N  T  V  S  S  A  R  F  R  K  V  D  V  D  E  Y  D  E  N
```

Fig. 22 (continued; 2/5)

```
2941   AAGTTCGTGGACGAAGAAGATGGGGGCGACGGCCAGGCCGGGCCCGACGAGGGCGAGGTG   3000
       K  F  V  D  E  E  D  G  G  D  G  Q  A  G  P  D  E  G  E  V

3001   GACTCCTGCCTGCGGCAATATCCTTGCATTCACCGCCCTCCCCACCCCAGCCCAGCCCAG   3060
       D  S  C  L  R  Q

3061   CCCGCCCTTCTCCTGGGACCCGGGAGCCTGCAGGATCCGCGGGGCACCGGCGCGGAGCTG   3120
3121   CCTCTCAACCTGCGGCTTAACCTGTCTCTTTGGGATCGCCCGCTCTGAGAGGGCAAGGGG   3180
3181   GAAGCCCCCGTTTCCTACCCAGTCGGCAGGAGACGCGAGGGTCCCACTCTTGGAAGCCTG   3240
3241   CCCTACCCCGCGCGCCTTCCACGCCCCCAGATTCCTCAGGTTGCACCCGAGTGCCTGCCT   3300
3301   GCCTCGGGAACTGGTCCCGCCGCCCGCGCCCTCGCGGCGCTGGGGAAGGCGGCCCCGGCT   3360
3361   GGTGGGGAAGGCTGGTGCCGACCGCCTTAGTTTTTCTTCCTAGAACTCTGATTTCCTGGG   3420
3421   GTCACATTAGCTCCAGAAATTTCTGATTGTGGGGAACCTGCATCTTTCCTTAGTGGTTTT   3480
3481   GTTTTTGGTTGTGTTTTTGTTATTGGTAGCGTTAAGGTAGTTTATTGCTTACCGGGGGG   3540
3541   CCGGGGGAGATGGGACTGTTCGAAAATTGAGGGTCCCTGTGCTTTCAGCCCATTGGCCTT   3600
3601   TTTAAAAAAAAAAAAAAAAAAAGAAGAAGAAGGGGATTTGGCAAAATATACATTGTACAG   3660
3661   AATTTGTTAACTGGGGGAGGGGAATGAATACAAAAAATACAAAACTCCTAGAAGGAAGCT   3720
3721   TGGAGCCTTTTACCTGCTAAGAAAAGGACAATAGAAAAAACAACGGGGAATGCGTGTGGA   3780
3781   GAATCCTTGGAAATATTTAAAATAAACCCCAATGAATAAGATAGAAGATGAGTCATTCGT   3840
3841   ATAAAGCAGAATCATTTTTGTAATCCTAAAATTGTTTCCATTTTAGTTAAAATATGGCAG   3900
3901   TCAGTTCCCGGTTTCTGTTTTTGCATATTTGAATATTCATAACTTTGGCTTCGCATTTGC   3960
3961   ATTACATCTTTTTTAGAAAAATGTAAATGTTGCAAAAAAACCGAAGCTGTAGTTTTAGAA   4020
4021   AATCTCAGACACTGAATTTGTATGCATTTCTAATTCTTGGGTGTATTCATAAGGAAGACT   4080
4081   CTCAACAATGTCCTGTTATAGTGGGAAATATGAGAGTGAAAATATTTAATGGCAACAAT   4140
4141   ATCCTTTTTTAAAGGCACCTAAATAGAGCATTAGACATTTATCAATATATAGATAGTGCT   4200
4201   TTGCCCAACTTTCACAATTAATTAGCTGTTGCTCTTTTGCATTATTTAAATACTTAAGTG   4260
4261   CTTGGAGTTATAAAAAATGAGCTAATCTACATCAGGCATGCTTCTCTAGAAATCCCTGCA   4320
4321   GCCTTGAAAATAACAGCTTGTCAACCAGAGATTTTGTGTAAGAACTTTTTCTTTAGAAAA   4380
4381   TAAATGGTGAACATGCTTCCTAAAAACATTATTTGTGATGGGATAAGATGGTGTTTTATG   4440
4441   AAACCCCAGTGTATTTTAGGTAATTTGTGGTGACTTTTAAAAGGTACTGCTGTATCCATA   4500
4501   TCAGTGGATCTGCTTTTTGATCAGTTCATCTTAAAATATAAAGATACTGTCTCTTCTTAC   4560
4561   CGTTACATACAGCCAGGAAAGACAGCCCTAGTGGTGGGGTACTAGAGTTGGAGGAACAAG   4620
4621   TGAACTCTGTGGTTTTCCTTTTAGGGGAATGTTTGTACATTCTGACAGTCTGATTGGCCT   4680
4681   TCTGTTTCTCATGCTTGCTAACTCACTAGTGCTTTCAAAGAGAGCCTGAATTTAATAGGT   4740
4741   ATGGTCTAACACAGTTTGAATAACCTTTGTGAAATATGAGAGAAAATATCTAAAGCAAAA   4800
4801   AATTAAGCTGCCACCTAAGGGACATATGAATTATTACATCTTCTGTGATGCCTCTTTTCA   4860
4861   TCAATATTGAGAGATTGCTAATGTGTATCATTCAGATTGCTAATCTGCCAGCATGTTCTA   4920
4921   CCAGCATTTCAGATAATACAGAATATGGTTCTAGCAAAAGTTTGGTCTTTATTTTTTCAA   4980
4981   TTAGAATCACAGGAAAAGACATATTTTGGTTGATAATAGGTTATTTCATTTGGGGGACTA   5040
5041   ATAATTCTGATATATATATTTTAGGATTTCTTTAACACCACTCTAGGTAATGTTTGCATATG   5100
5101   TATCTCACTGGGAAATGAAAGACTATCAAGGTGTTCACTTGATAGTTAGAACCAAGGGTG   5160
5161   AAACAGTCTTTGCTTTATTAAAAAAAAGTCTAATGTTCTATTTTGCTTTTGATATTTTGC   5220
5221   CTTTGATTAACATCCTGGAAACCAACACATTGAATTTCCAGTATTGAACATAGTGACCAA   5280
5281   AGTAATTTTCTTTTTATATGTAAATCAAGTCATAAAGAACCAGTGGTTATAATGCTTTCT   5340

5341   GGGGGCCATCCTTTGCTGTTACACCCTTAACTTCCATCACAGGAAACATGACAGCTGCCC   5400
                                                   G  N  M  T  A  A  L

5401   TACAGGCAGCTCTGAAGAACCCCCCTATCAACACCAAGAGTCAGGCAGTGAAGGTGAGTC   5460
         Q  A  A  L  K  N  P  P  I  N  T  K  S  Q  A  V  K
```

Fig. 22 (continued; 3/5)

```
5461   GCAGACTACAACACAGTGATCTCTGCTGATATCTTATTCTTAGTAAAATCCTTGCAGTGC   5520
5521   AAAAAAAAATCAATATTTTAACTGTTTGCTATCTTTGACAAGAAGAGTTTATAATGTAGT   5580
5581   TTGATAGGTAAAAATTTCACGTGAAAAAATAGCCCTATAATGTAGTTATGATAATGCTGC   5640
5641   ATGGTAAGATACAGTAAGTTCAAACGATAGTGAAATCATTTGTGTGTGTTTTTAGAGGAG   5700
5701   ACCACTCAGGCTGAATTTGAGCAAAGGTTTGAAAAATAAGTTAAACCTTTACAAAAATAA   5760
5761   ACAGATTGTAATTGCTTTTTAAAGATTTTTTAAAACCATACAAATACTAAATACTTATTA   5820
5821   TAGAAAGCTCAGACATATGAGAAGGTTAAAAAGATAGTGGTTTGTGGTCCCAGCACCCAG   5880
5881   AGATAACAGTTACTACTTTGGGGCCTTGCTGTATTGTTACAGAGTTCCCTTTTGTTTTTT   5940
5941   TAAGAATGAATTTTTAAAACGGGCTTTTTCAGCTATATGCAATGGTACATGAGCTTTCCT   6000
6001   TCCCCAATAAGTTAATAGCCTTTTTTAACACTTGTATATGGATAAGCTCCAGTGTATACA   6060
6061   TAACTAATCTTTTGTTTATATTTAGACTGACTTTTTTTTTCCTATTGTAAACCACTGAAA   6120
6121   TCAATATTTTTTGGTAAATTTTTAATTGTTCTCTTTGAGTAAATTGCTAGCAGTGAATTA   6180
6181   CTGGATCAAAGAATGCACTTTTTTTTAAGGCTTTTGGTATGCAGTATTGCCAAATTGCCC   6240
6241   TTCAGAACAGTTGTGCAACTTACATTCTCTGCAGTCTTTTACTAATTCTTAACCTATTTA   6300
6301   CGTATTTATTTAAAATGATGCCCATAGCATCAACCCCGTTGTCCATAGCTATTCATACAT   6360
6361   CCTAGGAGCTTCAAGAATCTCAATTGAATAGTAGTAAGTAATAACTTAGGTAAATGCATA   6420
6421   ATAATTATCTAGGTAACATAATTTTTTATTGGGGAAAATTTCTTTGGTTTTTACAAGTTG   6480
6481   TAAAGATTGTCGTTGAAATTTCATTTTTACCGTGGATGCAAAGATATTTTTCTAAATCTG   6540
6541   GTAATTGCAGTCTTTAAACCAAAGATAACAGTAGGTGGTAGAAACATTCTGTGAAATCCT   6600
6601   GACCAGTAGGAATGCTGGAGGTATCACTTTGTGTTGAATGGAAGGAGAAACGAATTGTTG   6660
6661   AAAAGGTCAGTTAAGTGTTTCCTTTGCTTGGCCGGATGGGTAAGAAAATAACTGCTTTTG   6720
6721   AAGCAGGCTTTTGCCAAAGAAAAAAGATCATTATTAATGAACATCACTATATTTCATATC   6780
6781   TACAGTCAATTCATATAAATTACAGTCAATTTTCTTTTAAGACAGCTTGGTTTATTAAAA   6840
6841   TTTTTAAATAAAAAAGTTTTTAAGAAAAAATTACTTCTGAAGGATAATTCAAGGTGAAAC   6900
6901   TGCAAATCTGCCTCCTTGTTTTGTTGGGAATTTTTTTTTTTTTTTTTTTTTTTTGAGACG   6960
6961   GAGTCTCACTCTATCACCCAGGTTGGAGTGCAGTGGTGCAATCTCAACTCACTGCACCCT   7020
7021   CCGCCTCCCGGGTTTAAGCAATCCTCCTGCTTCAGCCTCCCGAGTAGCTGGGATCACAGG   7080
7081   CACACACCACCATGCCTGGATAATTTCTGTATTTTTAGAAGAAAACAGGGTTTTACCATT   7140
7141   TTGGCCAGGCTGGTCTCGAACTCCTGACCTCAGGTGATCTGCCCATCTCGGCCTCCCAAA   7200
7201   GTGCTGGGATTACAGCTGTGGGCCACCACACCCGGCCGTTTTGTTGGGATTTTTTTTTTT   7260
7261   TAAGATCAAGACATAAATTTAAATGTTGTTTTAATAAATTGTTAAATTATCACATTGATC   7320
7321   TGTTAGCAAATCCTCTCAGCTCTGCCTTCAATTATGTTAATAGTCTGTCAAGTTTCTTAC   7380
7381   CACCTCCACTGCTACTATGCTTACCACATCCAGCCTGTATTATTGCAATTGCCTCCTAAT   7440
7441   TGCTCTCCCTGCTTCTACCTTATCCCCTACTCCCACAGCTTATTTTCTGTAACATAGATG   7500
7501   CCAAAGCAATCCTGTTAAAATGTGAGTCAGATTATGGCACTGCTCTTAAAACCTTCCAAT   7560
7561   GTCTTCTCATTTCTCTCAGTAAAAGCCAAACTCCTTACAATGCCTGTAGGCCTTACACGA   7620
7621   TCTGTCCTCCCATAACCTCTGACTTACTCACGTGCTTTTCTCCCACCAATCCACTCCAAC   7680
7681   CACATTGGGTTTTTTTCTGTTCCTGGAACACACTGAACACACACTAATAGCACTGTTCTT   7740
7741   TCCTCTGTCTGAAACACTTTCCTCAGTTATCCCAAGCCTTCTTTCACGTCCTTCAGGTCC   7800
7801   TTACTCAAATGTCACATTCATAGTGTAGACTTTCTGAAATTCTAAACCCTCCTCATACAG   7860


7861   ATATGTCTAAATGTTCTGTTATTTATTGACCCACCAGGACCGGGCAGGCAGCATTGTCTT   7920
                                                 D  R  A  G  S  I  V  L

7921   GAAGGTGCTCATCTCTTTTAAAGCTAATGATATAGAAAAGGCAGTTCAATCTCTGGACAA   7980
        K  V  L  I  S  F  K  A  N  D  I  E  K  A  V  Q  S  L  D  K

7981   GAATGGTGTGGATCTCCTAATGAAGTATATTTATAAAGGATTTGAGAGCCCGTCTGACAA   8040
        N  G  V  D  L  L  M  K  Y  I  Y  K  G  F  E  S  P  S  D  N

8041   TAGCAGTGCTATGTTACTGCAATGGCATGAAAAGGTAAGTTATGAATTATAAATCTATAT   8100
        S  S  A  M  L  L  Q  W  H  E  K
```

Fig. 22 (continued; 4/5)

```
8101   GACTGGTTCTTTTACAATAGGGAATGACAATGACAACCTCTCTCACCTAAATAACCATTT   8160
8161   TGATTTGTTGTACATTTTTGTTATTACAAATAAAATGCATGAAAAGGATAGTTCATATTT   8220
8221   ATGTTTACTAGCCTTGGTCTTAAGAGATTCTGATTCCAACACTTGTGTTTATTCAACAAT   8280
8281   GATTATTAGTAATTAAACATAATCTTGAACTCTGAATTAAATCAAAACTTTGTAAAAGAA   8340
8341   AATAAGCAATACAAATCAAGAATTCTTTCACAGTGACCAAAAGGTGAAAACAACACAAGG   8400
8401   ATCGAATATGATTCAACCA                                            8419
8420   TTAAAAGGAATGACATTCTGACACATGCTATAACATTAATAAACCTTGAAAACATACCAA   8479
8480   GTGAAATGAGCCAAACACAAAAGAACTAATATTTTATAATTTTACTTATATGAAATAATC   8539
8540   TAGGATAGGCAAACACAAAGGGACAGAAAGTCCTTAGAGGTTACTAGGAAGTAGGGAAAG   8599
8600   CAAGGAATAGGGAGTTAGTGCTTAATAGGTACAGAGTTCCTCCTTGGAGTGGTAAAAAAG   8659
8660   TTTTGGAAACAGATAGTGGTGATGGCTACAGTACATTGTGAATATAATTAATGCCAATGG   8719
8720   ATTTTACACTTAAAGATGGTTAAAATGGCAAATTTTGTGTTAGATATTTTACAACTTTTT   8779
8780   TAAAGAATTAGGAGTTTGGAGGATCAAGAATTCTTAAATCATGTTTTTCTATTTTCATGT   8839
8840   GTATATTTTGCAATGTAAGTAGATGCTGGTACATCATCTGTCAAAAGAGTATAAGTGATT   8899
8900   TTGAGCTTTGGGTAAAAAACTGGATAACATGTAAATAGAACCAGTCATAAAAATATTGAG   8959
8960   TGTTTGAAGTGTATCTGAGTGAAAACACAAACATAAGAAAAAAGCACATAGTAAAACAAT   9019
9020   AGTTCCCCCTTTTACTCTAAAATGCACCAATTTGGGTAGTAATTTATATGGCACCCTATT   9079
9080   CATGGAACACTTTCTGTTGCCAGGTACCATACTATTAATGTTTTATTTAACCTTTACAAC   9139
9140   AACCCTGTGGAAGTATATAAATATCTTTATCATCCTCAATTTACAGATGAAAAGCTAGCT   9199
9200   TTAAAACCCAAGCCAGCGTAGTTCTAGCATAGCCTCAAGATTGCAGTGAACATTGATTAC   9259
9260   TTATTATATTCCACATATTCTTCAAAGGACTTTATAAATATTAACTCATTTAATCCTCAT   9319
9320   AAAAATGGAGGGAAATGCTTGCTATTATTCCTCTTTTGTCACTGAGGAAACTGAGGCATG   9379
9380   TGTGAAGTCTTCATTTCTTCCAAATGTCAGTCACCAGTTTTTACCAATCTTCGAAGTATT   9439
9440   TCTGAAATCTATCTGTTCAAGCGTATCTAATGCAGCTGTTCACAGCATCTCTCCCAGTCT   9499
9500   GTTGCCATAGCTTCCTGACTGGTTTCCCAGTTAACAGTTTTGCCTCCTTCAAATCTGTTC   9559
9560   TCCACCCAGCCATCAAAATGATATCTTTAAAATCAAAATTGCCCTTGTCAGTCACCTGCA   9619
9620   GGGATAAAGTCAAAGTTCCCAAGTCTAGCTTCATCTTCCATGTCATTCTTCCCCTCAGGC   9679
9680   TATAGCAATGCCAGCCTTTTTCCTGAATGCACCATATTGTTTCACACCTCCATACATTTG   9739
9740   CTCATGATTTTCTGGTGTTAGCCTGTCACCTACTCATTCTTTTAATGTGTCATTTCCTCC   9799
9800   ATGAAGCCTTAGCTGAAACATTCCTCTATACTGTTAATCTGGGTATAAGCCTCTCCCTGG   9859
9860   TGCTTTAATAGCACCTGCAGCACAACTCTCATTTCATACATTAGATTAAAATTACCTGTT   9919
9920   TATATGTCTGTCTCCTCATGCTAGACCAGAAAATGCTGTATTTGTTCACTTTTGTATCCC   9979
9980   CAGCATCTAGCACAGTACTCAGTATACAAAGGTATTCCATAAATATTTTTTGAACAGAAA   10039
10040  GAAACCAGAGCTCAGATTCCTAATACTTGATCATTACTCTCTATTTTTCAAATTAGAGTC   10099
10100  AGAGTTAAAGTTTCTAAGTTCTTAGCTATTAAACAATACCTTCTTTCTTTGGGAGAAAAA   10159
10160  AAATCTGACAAAGGCTGACTAATCGAAGTGGAAGTTGGGATGGTTGATCCCAGTTTGAAT   10219
10220  TTTCTTCTGACTATGTGGTGAGAATGAGAAATGCAGAATGTCCACCTGTTTTGAGCAGGA   10279
10280  ACACTATGCTGCAGATTTTTTTTTTTTTTTTTTTTTTTTTTTGAGACGGAGTCTTGC      10339
10340  TCTGTCGCCCAGGCTGGAGTGCAGTGGCGCAATCTCGGCTCACTGCAAGCTCCGCCTCCT   10399
10400  GGGTTCACACCATTGTCCTGCCTCAGCCTCCCGAGTAGCTGGGACTACAGGCACCCGCCA   10459
10460  CCACGCCCGGCTAATTTTTTGTATTTTTAGTAGAGACGGGGTTTCACCATGTTAGCCAGG   10519
10520  ATGGTCTTGATCTCCTGACCTCGTGATCCGCCGGCCTCGGCCTCCCAAAGTGCTGGGATT   10579
10580  ACAGGCGTGAGCCACCGCGCCCGGCCTATGCTGCAGATTTTTTAAAACATTATTTAGAAT   10639
10640  TAATGTACTAAAATGTAAACTAGTATCTCACTAGAATGTAACTTCATGAGGGCAGGGACT   10699
10700  TTCAAGGTTTTGTTTATTACTGTAACCTCAGTGCCAAGAACAGTACCTGGTGCATAATTG   10759
10760  GTGCTCAAGAATTTATTATTTGTTAACTAATAAATTCAGGGTCTATAGCAGTGCCCATTC   10819
10820  CTTCTTTAAGAAAAATGTTTACCAAATATGAGAATTGACCTTTTATTATTCTGTCAACA    10879


10880  TTTACATCCTGGTTTGTTTTTAGGCACTTGCTGCTGGAGGAGTAGGGTCCATTGTTCGTG   10939
                                   A  L  A  A  G  G  V  G  S  I  V  R  V

10940  TCTTGACTGCAAGAAAAACTGTGTAGTCTGGCAGGAAGTGGATTATCTGCCTCGGGAGTG   10999
         L  T  A  R  K  T  V  *
```

Fig. 22 (continued; 5/5)

11000 GGAATTGCTGGTACAAAGACCAAAACAACCAAATGCCACCGCTGCCCTGTGGGTAGCATC 11059
11060 TGTTTCTCTCAGCTTTGCCTTCTTGCTTTTTCATATCTGTAAAGAAAAAAATTACATATC 11119
11120 AGTTGTCCTTTAATGAAAATTGGGATAATATAGAAGAAATTGTGTTAAAATAGAAGTGTT 11179
11180 TCATCCTTTCAAAACCATTTCAGTGATGTTTATACCAATCTGTATATAGTATAATTTACA 11239
11240 TTCAAGTTTAATTGTGCAACTTTTAACCCCTGTTGGCTGGTTTTTTGTTCTGTTTTGTTT 11299
11300 TGTATTATTTTTAACTAATACTGAGAGATTTGGTCAGAATTTGAGGCCAGTTTCCTAGCT 11359
11360 CATTGCTAGTCAGGGAAATGATATTTATAAAAAATATGAGAGACTGGCAGCTATTAACAT 11419
11420 TGCAAAACTGGACCATATTTCCCTTATTTAATAAGCAAAATATGTTTTTGGAATAAGTGG 11479
11480 TGGGTGAATACCACTGCTAAGTTATAGCTTTGTTTTTGCTTGCCTCCTGATTATCTGTAC 11539
11540 TGTGGGTTTAAGTATGCTACTTTCTCTCAGCATCCAATAATCATGGCCCCTCAATTTATT 11599
11600 TGTGGTCACCCAGGGTTCAGAGCAAGAAGTCTTGCTTTATACAAATGTATCCATAAAATA 11659
11660 TCAGAGCTTGTTGGGCATGAACATCAAACTTTTGTTCCACTAATATGGCTCTGTTTGGAA 11719
11720 AAAACTGCAAATCAGAAAGAATGATTTGCAGAAAGAAAGAAAAACTATGGTGTAATTTAA 11779
11780 ACTCTGGGCAGCCTCTGAATGAAATGCTACTTTCTTTAGAAATATAATAGCTGCCTTAGA 11839
11840 CATTATGAGGTATACAACTAGTATTTAAGATACCATTTAATATGCCCCGTAAATGTCTTC 11899
11900 AGTGTTCTTCAGGGTAGTTGGGATCTCAAAAGATTTGGTTCAGATCCAAACAAATACACA 11959
11960 TTCTGTGTTTTAGCTCAGTGTTTTCTAAAAAAAGAAACTGCCACACAGCAAAAAATTGTT 12019
12020 TACTTTGTTGGACAAACCAAATCAGTTCTCAAAAAATGACCGGTGCTTATAAAAAGTTAT 12079
12080 AAATATCGAGTAGCTCTAAAACAAACCACCTGACCAAGAGGGAAGTGAGCTTGTGCTTAG 12139
12140 TATTTACATTGGATGCCAGTTTTGTAATCACTGACTTATGTGCAAACTGGTGCAGAAATT 12199
12200 CTATAAACTCTTTGCTGTTTTTGATACCTGCTTTTTGTTTCATTTTGTTTTGTTTTGTAA 12259
12260 AAATGATAAAACTTCAGAAAATAAAATGTCAGTGTTGAATAATTTATTTTTCTCTGACAC 12319
12320 TTTAACAATTATGAATGTATGGTTAATTAAGAGGAAAGGTTTTCTGCTTCTACCACCAAG 12379
12380 TACTGTACTCTTAACAAGAACAGTTTGGTAGGGTTTTTATAAGACTATATAGATATAAGA 12439
12440 TGATAGAGAAGAGAGTCATGAATGATGTCAGAGCACTACTGAAGCCTTTGGAGTGATTCC 12499
12500 ATAGCCTTCTGGATGGCAGCTGAATACCTATATGTAGTATCACTGCCCAAAGACCTAGAC 12559
12560 TAGAAAGTGCAAAGTAGCTTAGCAGCTGCAGTCATTCACTCCCAGCCTCCAAAATTCTCT 12619

Fig. 23 (1/6)

```
   1 -                                     GATCCCTCTCCAGGTGGAAG - 60    /|\
  61 - CTCCCTTCATACCAAAGTTTAAAGGCCCTGGGATACGAGTAACTTTGACGACTATGAGG - 120
 121 - AAGAAGAAATCCGGGTCTCCATCAATGAGAAGTGTGGCAAGGAGTTTTCTGAGTTTTAGG - 180
 181 - GGCATGCCTGTGCCCCCATGGGTTTTCTTTTTTCTTTTTTCTTTTTTTGGTCGGGGGG - 240
 241 - TGGGAGGGTTGGATTGAACAGCCAGAGGGCCCCAGAGTTCCTTGCATCTAATTTCACCCC - 300
 301 - CACCCCACCCTCCAGGGTTAGGGGGAGCAGGAAGCCCAGATAATCAGAGGGACAGAAACA - 360
 361 - CCAGCTGCTCCCCCTCATCCCCTTCACCCTCCTGCCCCCTCTCCCACTTTTCCCTTCCTC - 420
 421 - TTTCCCCACAGCCCCCCAGCCCCTCAGCCCTCCCAGCCCACTTCTGCCTGTTTTAAACGA - 480
 481 - GTTTCTCAACTCCAGTCAGACCAGGTCTTGCTGGTGTATCCAGGGACAGGGTATGGAAAG - 540
 541 - AGGGGCTCACGCTTAACTCCAGCCCCCACCCACACCCCCATCCCACCCAACCACAGGCCC - 600
                                           Human cAMP-dependent protein kinase
                                           catalytic subunit alpha
                                           Accession number X07767 (until *)
                                        -  follow arrow until line that
                                           begins 1561 -
 601 - CACTTGCTAAGGGCAAATGAACGAAGCGCCAACCTTCCTTTCGGAGTAATCCTGCCTGGG - 660
 661 - AAGGAGAGATTTTTAGTGACATGTTCAGTGGGTTGCTTGCTAGAATTTTTTTAAAAAAAC - 720
 721 - AACAATTTAAAATCTTATTTAAGTTCCACCAGTGCCTCCCTCCCTCCTTCCTCTACTCCC - 780
 781 - ACCCCTCCCATGTCCCCCCATTCCTCAAATCCATTTTAAAGAGAAGCAGACTGACTTTGG - 840
 841 - AAAGGGAGGCGCTGGGGTTTGAACCTCCCCGCTGCTAATCTCCCCTGGGCCCCTCCCCGG - 900
 901 - GGAATCCTCTCTGCCAATCCTGCGAGGGTCTAGGCCCCTTTAGGAAGCCTCCGCTCTCTT - 960
 961 - TTTCCCCAACAGACCTGTCTTCACCCTTGGGCTTTGAAAGCCAGACAAAGCAGCTGCCCC - 1020
1021 - TCTCCCTGCCAAAGAGGAGTCATCCCCCAAAAAGACAGAGGGGGAGCCCCAAGCCCAAGT - 1080
1081 - CTTTCCTCCCAGCAGCGTTTCCCCCCAACTCCTTAATTTTATTCTCCGCTAGATTTTAAC - 1140
1141 - GTCCAGCCTTCCCTCAGCTGAGTGGGGAGGGCATCCCTGCAAAAGGGAACAGAAGAGGCC - 1200
1201 - AAGTCCCCCCAAGCCACGGCCCGGGGTTCAAGGCTAGAGCTGCTGGGGAGGGGCTGCCTG - 1260
1261 - TTTTACTCACCCACCAGCTTCCGCCTCCCCCATCCTGGGCGCCCCTCCTCCAGCTTAGCT - 1320
1321 - GTCAGCTGTCCATCACCTCTCCCCCACTTTCTCATTTGTGCTTTTTTCTCTCGTAATAGA - 1380
1381 - AAAGTGGGGAGCCGCTGGGGAGCCACCCCATTCATCCCCGTATTTCCCCCTCTCATAACT - 1440
1441 - TCTCCCCATCCCAGGAGGAGTTCTCAGGCCTGGGGTGGGGCCCCGGGTGGGTGCGGGGGC - 1500
1501 - GATTCAACCTGTGTGCTGCGAAGGACGAGACTTCCTCTTGAACAGTGTGCTGTTGTAAAC - 1560
1561 - ATATTTGAAAACTATTACCAATAAAGTTTTGTT*TAAAAAAAAAGTGTCGCTGGTGTTCTC - 1620
1621 - GACTTCGATCACCCACCCACACACCCCCAGGGGGTTGGAAAGGGAATTTCGGACCCCAGC - 1680
1681 - GTGCAGGCCGATCAGGTCCTGGCTTGAAGTCCTTGTAACCAGGGTTTAGCTGAAATTCCG - 1740
1741 - GCACTCCTTCGGCCCCGCAGGAGAAACGAGCGTCAAACTGCCCTTTGACCCCAGATTCGG - 1800
1801 - GGTCCCCAAATCTGCGGCGCGCCCCCTCGGCGTCCAGCCCGGGACCGAGAGGGCGCTCTA - 1860
1861 - GGGAGGCGCTGGGGCTGGCGCGCCAGGAGGCCGAGCGGCGGCGGGGGCGGCCCTGGCAGG - 1920
1921 - GGGAGTAGAAGGGGGAGAGGGTGCGCGCCCCCCTTCCCGCATCCTCAGCGCCGGGCCAGG - 1980
1981 - CGCGCCTGAGGGACGCGGGGGCGGCGGCAGCAGGAGGGTCCCCGCAGCACCCTGCGAGCG - 2040
2041 - CGGCAGCCCCGGCCCGCGGGCGGCGAGTTCCCGGTAAGTGCGGTCCCGAGAGCGGAGCGC - 2100
2101 - GCTGGAGAGGCGTGGAGAGGGGGGCTGGGCGCCGGGGACGTCTGGGTCCCGCGCCCAATG - 2160
2161 - GCTGGAGGGCGGCCGAGCGCCGCCCGCCCGCCCTGCCCGCCCCCTCTCCCCTCCCCCCGG - 2220
2221 - CACTCCCCTCCCCCTCCCCCGCCCGCCGCTTTCCCCCGCCCCCGCCCCGGCGCCAACTCC - 2280
2281 - GCGGCGCCTCCTTAAAAAGCGCGCGGGAGTTGTAAGGGGGGGCCGGAGCGAGCCGGAGTG - 2340
2341 - AGCGAGAGCGCAGGGTAAAGGGGGCGGGCGGGGGGCCCGGGCTCCACCTTAAAAGCGGGC - 2400
2401 - GCGTGGGGGTGGGAGGGAGGAAGGCGGGCGGCGGGGAGGAGGGAGGGAGGGAAGGAAGGG - 2460
2461 - GGGCCGGAGTGTCCCGGGCGCAGGGCGCGCGTGCGGCGGCGGCGGCGGCGGGGAGGGGCC - 2520
2521 - GGCCGCGCCGCGCTCCCCTCCTCCCCCTCGCATCCCCGGCCCCGCGCGCGCCCAGCAGAA - 2580
2581 - GCGGGTCTGTGTGTGCGTGCGTGCGAGTGAGTGAGTGTGTGCATATTTTTTTCTCTCTTT - 2640
2641 - TCTTTCTCTCTCACTGTTTTTTCCTCTCTCTCTCTCTCCCTCTCTCTCTCTTTTTTTTTT - 2700
2701 - TTTTTTTTTTGCAAAGAAACAGCAGCGCCGCCGCCGCTCCGCCGAGGCGCTGCGCCCCCC - 2760
2761 - GGGGGGGGAGGCGGAGGAGGCGGGCAGCGGCGGAGGGAGGGGAGCCGGGGAGGGGGGCGC - 2820
```

Fig. 23 (continued; 2/6)

2821 - CGCGCTGGAGGGAGGCAGCGCGCACGGTGCAGCCGGGCCGGGCGGGAGGCATGGCGGGG - 2880
- M A G

2881 - CCCCCGGCCCTACCCCCGCCGGAGACGGCGGCGGCCGCCACCACGGCGGCCGCCGCCTCG - 2940
- P P A L P P P E T A A A A T T A A A A S

2941 - TCGTCCGCCGCTTCCCCGCACTACCAAGAGTGGATCCTGGACACCATCGACTCGCTGCGC - 3000
- S S A A S P H Y Q E W I L D T I D S L R

3001 - TCGCGCAAGGCGCGGCCGGACCTGGAGCGCATCTGCCGGATGGTGCGGCGGCGGCACGGC - 3060
- S R K A R P D L E R I C R M V R R R H G

3061 - CCGGAGCCGGAGCGCACGCGCGCCGAGCTCGAGAAACTGATCCAGCAGCGCGCCGTGCTC - 3120
- P E P E R T R A E L E K L I Q Q R A V L

3121 - CGGGTCAGCTACAAGGGGAGCATCTCGTACCGCAACGCGGCGCGCGTCCAGCCGCCCCGG - 3180
- R V S Y K G S I S Y R N A A R V Q P P R

3181 - CGCGGAGCCACCCCGCCGGCCCCGCCGCGCGCCCCCCGCGGGGCCCCGCCGCCGCCGCC - 3240
- R G A T P P A P P R A P R G A P A A A A

3241 - GCCGCCGCGCCGCCGCCCACGCCCGCCCCGCCGCCACCGCCCGCGCCCGTCGCCGCCGCC - 3300
- A A A P P P T P A P P P P P A P V A A A

3301 - GCCCCGGCCCGGGCGCCCCGCGCGGCCGCCGCCGCCGCCACAGCGCCCCCCTCGCCTGGC - 3360
- A P A R A P R A A A A A A T A P P S P G

3361 - CCCGCGCAGCCGGGCCCCCGCGCGCAGCGGGCCGCGCCCCTGGCCGCGCCGCCGCCCGCG - 3420
- P A Q P G P R A Q R A A P L A A P P P A

3421 - CCAGCCGCTCCCCCGGCGGTGGCGCCCCCGGCCGGCCCGCGCCGCGCCCCCCCGCCCCGCC - 3480
- P A A P P A V A P P A G P R R A P P P A

3481 - GTCGCCGCCCGGGAGCCGCCGCTGCCGCCGCCGCCACAGCCGCCGGCGCCGCCACAGCAG - 3540
- V A A R E P P L P P P P Q P P A P P Q Q

3541 - CAGCAGCCGCCGCCGCCGCAGCCACAGCCGCCGCCGGAGGGGGGCGCGGTGCGGGCCGGC - 3600
- Q Q P P P P Q P Q P P P E G G A V R A G

3601 - GGCGCGGCGCGGCCCGTGAGCCTGCGGGAAGTCGTGCGCTACCTCGGGGGCAGCGGCGGC - 3660
- G A A R P V S L R E V V R Y L G G S G G

3661 - GCCGGCGGTCGCCTAACCCGCGGCCGCGTGCAGGGGCTGCTGGAGGAGGAGGCGGCGGCT - 3720
- A G G R L T R G R V Q G L L E E E A A A

3721 - CGAGGCCGTCTGGAGCGCACCCGTCTCGGAGCGCTTGCGCTGCCCCGCGGGGACAGGCCC - 3780
- R G R L E R T R L G A L A L P R G D R P

3781 - GGACGGGCGCCGCCGGCCGCCAGCGCCCGCCCGTCTCGCAGCAAGGTGAGCGCGCCGGGG - 3840
- G R A P P A A S A R P S R S K

3841 - AGCGGGGGCGCCGCGCGGTGGGCAGGTGCGGGCGAAGTTGGTGGCGGGGGCGCGAGTCCC - 3900
3901 - GGGAGGAACTGGGTGGCGGGTGGCTGGGGCTTTGCGCGCGTTTCCTGCGGGCTCGGTGCG - 3960

Fig. 23 (continued; 3/6)

```
3961 - TGGTGACCTTGGCAAGTGATTGAATCTCCCGGAGCCTCAGTTTCCTCCGCTGTAAACGCG - 4020
4021 - GTTTAATAACAGTAGCGACCCCTTGGGGTTGTTGAGCGAGTTTAGTAAGATTTGGTTGTC - 4080
4081 - GAGGGCTTTAGTTAACACAGAGCCTGGCACGGAGTGAATGCGTAAAAGTTAGTCCGTATT - 4140
4141 - GTTCTTAAAGGTGGAATCGGTTCCTCCTCCCCACCGCCCGGACGCCACAGTCAGGGTCTG - 4200

4201 - GGATTAGAACAGCTACTAATTTTGCATGCTTCTCTCCTCGGCTCCAGAGAGGTGGAGAAG - 4260
       -                                                    R  G  G  E  E

4261 - AGCGAGTACTTGAGAAAGAAGAGGAAGAAGATGATGATGAAGATGAAGATGAAGAAGATG - 4320
       -  R  V  L  E  K  E  E  E  D  D  D  E  D  E  D  E  E  D  D

4321 - ATGTGTCAGAGGGCTCTGAAGTGCCCGAGAGTGACCGTCCTGCAGGTGCCCAGCACCACC - 4380
       -  V  S  E  G  S  E  V  P  E  S  D  R  P  A  G  A  Q  H  H  Q

4381 - AGCTTAACGGCGAGCGGGGACCTCAGAGTGCCAAGGAGAGGGTCAAGGAGTGGACCCCCT - 4440
       -  L  N  G  E  R  G  P  Q  S  A  K  E  R  V  K  E  W  T  P  C

4441 - GCGGACCGCACCAGGGCCAGGATGAAGGGCGGGGCCAGCCCCGGGCAGCGGCACCCGCC - 4500
       -  G  P  H  Q  G  Q  D  E  G  R  G  P  A  P  G  S  G  T  R  Q

   1 - AGGTGTTCTCCATGGCAGCCATGAACAAGGAAGGGGAACAGGTAAGGATCCCTCTGGGT -   60
       -  V  F  S  M  A  A  M  N  K  E  G  G  T

  61 - GGGGAAGAGTGCTAGGTGGAGAGGAACTCAGCCCGAAGACAAAGCCAAAGACAGGTGTTT -  120

 121 - TTTTCCTTCCCAGCTTCTGTTGCCACCGGGCCAGACTCCCCGTCCCCGTGCCTTTGCCC -  180
       -                A  S  V  A  T  G  P  D  S  P  S  P  V  P  L  P

 181 - CCAGGCAAACCAGCCCTACCTGGGGCCGACGGGACCCCCTTTGGCTGTCCGTAAGTTGGG -  240
       -  P  G  K  P  A  L  P  G  A  D  G  T  P  F  G  C  P

 241 - GTATTGGAGACATGGGGGTGCTGCTCAGGTGTGTGGTACAGCCAGAGAGACATCCGTGTT -  300

 301 - CACTGGTGTCTGTTTGTTTTGATGCAGTCCCGGGCGCAAAGAGAAGCCATCTGATCCCGT -  360
       -                                P  G  R  K  E  K  P  S  D  P  V

 361 - CGAGTGGACCGTGATGGATGTCGTCGAATATTTTACTGAGGCTGGATTCCCGGAGCAGGC -  420
       -  E  W  T  V  M  D  V  V  E  Y  F  T  E  A  G  F  P  E  Q  A

 421 - GACAGCTTTCCAAGAGCAGGTGAGTTTCCAGCCCAGGACTACACACTGACAGACACAGAG -  480
       -  T  A  F  Q  E  Q

 481 - GGCCTCCCTGGGATGTGCCCTGATCCCGGCTTTCTCTGTTCCTGTCCCACCCAGGAAATT -  540
       -                                                          E  I

 541 - GATGGCAAATCTTTGCTGCTCATGCAGCGCACAGATGTGCTCACCGGCCTGTCCATCCGC -  600
       -  D  G  K  S  L  L  L  M  Q  R  T  D  V  L  T  G  L  S  I  R

 601 - CTCGGGCCAGCCCTGAAAATCTACGAGCACCACATCAAGGTGCTTCAGCAAGGCCACTTT -  660
       -  L  G  P  A  L  K  I  Y  E  H  H  I  K  V  L  Q  Q  G  H  F
```

Fig. 23 (continued; 4/6)

```
 661 - GAGGATGATGACCCCGATGGCTTCTTAGGCTGAGCGCCCAGCCTCACCCCTGCCCCAGCC - 720
     - E  D  D  D  P  D  G  F  L  G  -

 721 - CATTCCGGCCCCCATCTCACCCAAGATCCCCCAGAGTCCAGGAGCTGGACGGGGACACCC - 780
 781 - TCAGCCCTCATAACAGATTCCAAGGAGAGGGCACCCTCTTGTCCTTATCTTTGCCCCTTG - 840
 841 - TGTCTGTCTCACACACATCTGCTCCTCAGCACGTCGGTGTGGGGAGGGGATTGCTCCTTA - 900
 901 - AACCCCAGGTGGCTGACCCTCCCCACCCAGTCCAGGACATTTTAGGAAAAAAAAAATGAA - 960
 961 - ATGTGGGGGGCTTCTCATCTCCCCAAGATCCTCTTCCGTTCAGCCAGATGTTTCCTGTAT - 1020
1021 - AAATGTTTGGATCTGCCTGTTTATTTTGGTGGGTGGTCTTTCCTCCCTCCCCTACCACCC - 1080
1081 - ATGCCCCCCTTCTCAGTCTGCCCCTGGCCTCCAGCCCCTAGGGGACTAGCTGGGTTGGGG - 1140
1141 - TTCCTCGGGCCTTTTCTCTCCTCCCTTTTTCTTTCTGTTGATTGTCGCTCCAGCTGGCTG - 1200
1201 - TATTGCTTTTTAATATTGCACCGAAGGTTTTTTAAATAAAATTTTAAAAAAAGAAAAAGG - 1260
1261 - GAAAAAAAAGCCACGGAGTCCATTTTATGAATGGGGTGGGGAGAGGGCACTAAAGAGCCT - 1320
1321 - CCTAAGAGAGCCTCAGGTTAGGACAGAATTGTTTGGGGAGGGAGAAAAACAGAAACAATG - 1380
1381 - AATTATAGCTGCCTCACAGCCATGTATAACAATAATTGCTCCAGGAAGGTGGGAATATTT - 1440
1441 - GCTTTTTTTTCTTCTGTAATCTCACCGTGTCCGTGTCCAGAACAGAGCTAGGCACACAGC - 1500
1501 - AGGTGCTCAATTTTTGTTTTTCGTTTAGACAGGTTTCATTCTTTCACCCAGGCTGGAGTG - 1560
1561 - CAGTGGTGCTATCATAGCTCATTGTAGCCTCAAACTCCTGGGCTGAAGTGATCCTCCCAC - 1620
1621 - CTCAGCCTCCTGAGTAGCTGGGACTACAGGTGCACTCTGCCATGCCGGGCTAACTTTTAA - 1680
1681 - AAATTTTTGTCCGGGCACAGTGGCTCATGCCTGTAATCCCAGCACTTTGGGAGGCCGAGG - 1740
1741 - TGGGTGGATCATGAGGTCAGGAGTTCAAGATCAGCCTGGCCAAGATGATGAAACCCTGTC - 1800
1801 - TCTACTAAAAATATAAAAAAAAATTAGCTGGGCGTGGTGGTGGGTGCCTGTAATCCTAGC - 1860
1861 - TATTCAGGAGGCTGAGGCAGAGGATTGCTTACACCTGGGAGGCGGAGGGTGCAGTGAGCC - 1920
1921 - AAGATCGTGCCACTGCACTCCAGCCTGGGTGACAAAGTGAGACTCTGTCTCAAAAAAAAA - 1980
1981 - TCTTTGTGTGTGTGTGGAGATGAGGGTATGCACTTTGTTGGCCAGGTTGGCCTCGAACTC - 2040
2041 - CCAGCCAAGCAATTCTGCCTGGGATTACAAGCGTGAGCCACCATGCCTGGCCTCAAATAT - 2100
2101 - TGTTGAATGGCTAGCAGTTAAGTCCTTGGGTTTATAAGCATTTCCTCAACTGTCCTCCCA - 2160
2161 - AGTCCCCATAAGACAAAAAACTCATAAAATCCCACCTTACAGAAGAGGCAGCTGGCCCGG - 2220
2221 - CACAGAGATGCTGTCTGCCCCGGGTCACACAGGGTGGCATCTGACACCCTGTCTGAGTTC - 2280
2281 - TTCACTCAGAGTCTTTAAATATAATTAGCGTATTTGACATAATGTACATTAAAAACTATA - 2340
2341 - AACCTGTCAGCCTTTGTCTACTGCAAAGAATCCACTACAAATATTGGGGCAGGGATCTGT - 2400
2401 - TCTTGGACCATAGTAGTGTCTCCAGACCTCATGGTCCTCTTCATTAAAACAACAGAAAAT - 2460
2461 - TCCTTCTGGGCCATCAGATGAGACCATGAGATAGAAGATTTCCAAGTGAAGATTTTGTTT - 2520
2521 - CAAGACAGAGTCTTGCTCTGTCACTCAGGCTAGAGTGTACTGGTGCAATCATAACTGTGG - 2580
2581 - TGACAGCCTCGAACTTTTGGGTACAAGTGATTCTCATGCCTCAGACAACACCCAACTAAT - 2640
2641 - ATTTTGGTTTTTGTATAGACAGGGTCTTGCTATGTGGCTTAGGCTGGTCTTGAACTCCTG - 2700
2701 - GCCTCAAGCAGTCCTCCCGCTTCAGCCTCCTAAAGTGTCAGGATTACAGACATGAGCCAC - 2760
2761 - CAAGTCCAGCCTGAAGATTTTTAAAAATTATTGTTAGTAGTAGTCGCCAGAGTTACTACA - 2820
2821 - TCCAAAGTCCCTACTAAGTTCTAAGTAGTCCCTACTAAGTTCTAAGGCAGTTTCTCAACT - 2880
2881 - CATTAGAGTTGTTTTTTGTTTTTAAAGAAAAAAAGAGGCTGGGCACTTTAGGAGACCGAC - 2940
2941 - ACGGGAGGATCGCTTGAGTCCAGGAGTTTGAGACCAACCTGGGCAACATGGCCCCCCATC - 3000
3001 - TCTAAAAATTTTAAATTAAAAAAATGTTTTAACAACAAAAAGCGTTCTGGGAGTGAGGGG - 3060
3061 - CTGGGGCCTGGGCGGCCTCATTCCATATACCTGTGCCGGGTTGAGGGGTTGGAGACACGT - 3120
3121 - TTAGAGACCCCTCCACTCTAGGAATCCACCTCGAGAGATAAAGGTCCCGGCCCTAGCCAC - 3180
3181 - ACCCCCAGGACACGGCCAGAGGCCACCTCCCTAGGCGGGTCCCTCCCCACCGCCAGGTTC - 3240
3241 - CTGGAGCGCGTGCGGCGCGTGTGCAGGGGTAGGGGGCCGCAGGCGCGCGGACTGGAGAGG - 3300
3301 - CGCGCCCCTCCCGCGTGTTGAAATTCAAAAGAGGCGAACGGCCCCCGGCGCGGCGGCGCG - 3360
3361 - GCTCCGGTGGAGAGGTCAAGGCAGGGGCCAGTCGGAGGCTCCCGGGGCGGGGTCGAACCC - 3420
3421 - GCGGCCAACCTGAGCAGCAGCGGAAGCTTAAAGAGCTCAGGTTCCCGCCCCCCGGCCCTA - 3480
3481 - CCATGGCTACAGAGCAGTGGTTCGAGGGGTCGCTCCCCCTGGACCCTGGAGAAACACCGC - 3540
3541 - CTCCAGACGCCTTGGAACCTGGGACGCCGCCCTGCGGAGACCCCTCCAGGTCGACGCCCC - 3600
3601 - CTGGCAGGCCTGGGAACCCATCTGAGCCGGATCCTGAAGATGCCGAGGGGCGGCTGGCTG - 3660
3661 - AGGCCCGGGCCTCCACGTCTTCCCCCAAACCTCTGGTCCCCCGGCCTGGGCCAGCACCTC - 3720
```

Fig. 23 (continued; 5/6)

```
3721 - CCCGCCTATCCCTGGACACTTTGTTCAGCCCCATCACCCAACAGCTGCGCTACCTACTGA - 3780
3781 - AGAAGGCAGATGATTTCCAGAGCTACTTGCTCTACAGGTGATGCTGGACAGGGTCCCAGG - 3840
3841 - TCCCCATGGGTAAGGAGACTTGGAGGGGAGGCGACAGGATGGGTGACACACACCAGGGTC - 3900
3901 - GCAAAATTACAAGCGCTAGGAGCCAGAGGGAGACAGTGGAAGAAGCTAGCATATTAGAAT - 3960
3961 - CCAGTTTAAGAGAATGAGGAAGACTGTAGAATTGCGGGTAGGGGATGGCTGCTATTACTG - 4020
4021 - TCGTGGCAGGGTGGGCCTGGGGTTGTCAAGTCTCTAGGACTTTTTCTCCCAGTTTTTAAG - 4080
4081 - TGCTGTCTTACATTTTGAGCCCTGTGCTGGCTAAACAAGACCCACCTGAGCCAAACTTGG - 4140
4141 - CCTGCAGGACATCAGTTTGAGACTCCAAAGGATAATGTGATTCCCAGACCAGGTTTCCCT - 4200
4201 - GTGACTCTCAATTTCAGTGTCCATTGGAATTTCCTAGGAGGCTGGGTTGGGTTTGTTTGC - 4260
4261 - GTGTTTGTTTTTGAGATGGAGTCTCACTCTGTCGCCCAGGCTGGAGTGCAGTGGTGCAAT - 4320
4321 - CTCAGCTCACTGCAACCTCCGCCTCCCGGATTGAAGCAATTCTCTGCCTCAGCCTCCCGA - 4380
4381 - GTAGCTGGGATTACAGGCGCCCACCAACATGTGTTGCCCGGCTAATTTTTTTCTTTTCTT - 4440
4441 - AGTAGAGACAGAGTTTCACCATCTTGGCCAGACTGGTCTTGAGCTCCTGACCTCATGATC - 4500
4501 - CACCCGCCTTGGCCTCCCAAAGTGCTGGAATTACAGACGTGAGCCACCGCGCCTACCCGA - 4560
4561 - GGCTGGGTTTTTTTGTTTTGTTTTGTTGTTATGTGTTTTTTTGAAATGGAGTCTTGCTCT - 4620
4621 - GTCACCTAGGCTGGAGTGCAGTGGGGCGAACTCAGCTCACTGCAACCTCCGCCTCCCAGG - 4680
4681 - TTCGAGGGATTCTCATGAGGCTGTTTTTTTTTTTTTAATGAGACAGGGTCTCGCTCTGTC - 4740
4741 - ACCCAAGCTGGAGTGCAAGTGGGGCAGTCATAGCTCACTGCACCCTCGAACTCCTGGTCT - 4800
4801 - CAAGCAATCTTCCACCTCCCCTCCTGGGTAACTGGGACTACAGGTGCCACCATGCCCAGC - 4860
4861 - TAATTATTTTTGTGTAGAGATGGGTTCTTGCTATGTTGCCTAGGCTTGTCTGGAACTCCT - 4920
4921 - GGCCTCAAGCAATCCTCCAGCCTCAGCCTCCCAAAACTCTAGGATTGCAGGCGTGAGCCA - 4980
4981 - CTGTGCCCAGACCCTGCAGGAAGCTCTGGGTCCTAAGTGTTGTGACACTCAGGTGTCAGC - 5040
5041 - ACTTTAACAAGTGTTCCAAATGGGTTTGATGCAGGTAAACCAGAAAGATGTTCAGAAAAG - 5100
5101 - ACCTGAAACTGGGGGCTTTTCTAATGGGTCAAAGCCAGGGATACAGGTTGGGATTGAGTA - 5160
5161 - GAATGGGGAAAACTGCGGGGTGGGGAGGGGTTGTGAGGGATTCCAGGCAAAGGCCCCCTT - 5220
5221 - CTTCCTTCAGCAGAGACCAAGTACAGAAGGAGCAGCTGGCCAAGGCCATGCCCACCTTCT - 5280
5281 - TACAGATGTGTGAGCCCTACTTCCTGTACCTGGAGGCAGCCGCGAGAAGCATACCCCCCA - 5340
5341 - TCTATGGACCCCTGCAGGAGCTGGTCCGAAAGGGGGTGTGTGGAGGTTTCTTAGACCCCA - 5400
5401 - CGCCCCTTTCTTCTCGCAGCTCTGAGCCTGTGGGGATGGTGGAGGGGGAGGCCCACTCCT - 5460
5461 - CGCAGGCCAGCTGATCTCACTGTACCCCCCTCTTGTATGCAGCTGTTAGAGATCTCCCAA - 5520
5521 - CAGCTGACCCTGCGCCTGGAACAGCTGGTCCTCATGTACGCTTCCTTTGGGTTCGTGGAC - 5580
5581 - CTGGAGGAGATGAACCCCCTTAGGTAAAATGGTAGGAGACTCAGATGGGGGGATGAAGGA - 5640
5641 - GTCCAAGGCCCAGCCTCACCCCTCCATTCTCTCATGTCTCGCCAGCATCTCCTGTTTCTT - 5700
5701 - TTGCGGGAGGTTCTCCATCAGCCTGTCCCATGAGGTCTCCATCTTCAGATACTGTGCCCC - 5760
5761 - AACCGCCTACACTGCCAGCCGCTTCCCCCGCTACCTCTATAAGAAGATGCGCTGGCACCT - 5820
5821 - GGAAGCCACCCCAGAGGCCCCTGGTCGGGGACAAGATTCCCTTGTGGATTAGTAAGTCCT - 5880
5881 - CTTACCCAAATCAAAGTCCTCCCCTTTCTATGATGAATGCCAATATGACCCTCCAAACCG - 5940
5941 - TCACCAGCAAAGTGAAAAGTGAGCCAGGGCCCGAGGCAGTGGCTCACGCCTGTAATCCCA - 6000
6001 - ACACTTTGGGAGGCCGAGGCAGGAGGATCACTTGAGCTCAAGAGTTTGAGATCAGCCTGG - 6060
6061 - GCAAGATGGCAAGACCCTGTCTCAACAACAAAGAAATTCGCCAGGCGTGATGGCTGGCAC - 6120
6121 - CTGTAGTCCCAGCTACTTGGGAGGCTTAGGCAGGAGGAGCACTTGAGCCCAGGAATCAAG - 6180
6181 - GCTACGGTGAGCTGTGATTGTGCCACTGCACTCCACCCTGAGTGGAAGCAATAATCTGTC - 6240
6241 - TCTTAAAAAAAAAAAAAAAGTGAACCAGGAAACTAAAGGCTTTTGAAAGGCTACCTCTATT - 6300
6301 - TTCTTAAAACCCACCCTCCCACCAAAATAAAAGTTCTCATCTTAAAAGTAGGCTGGCAGG - 6360
6361 - GAGAAAAGGCCTTGGAGTCACATTCCTACCTGAGAACTTCAGGGCAACTTCTGATGAGTT - 6420
6421 - CCCACCTCAACTCCAAAATTAAAGCCCTCAACAGAAGTAGCTAGGAAGCTGATCACTTCT - 6480
6481 - AATTACAGCTCCCTCCCCTCCTAGCTACTTTCTGTGCTATCGAGATACTTGGGAAGACAC - 6540
6541 - AGGCCAGAGTCCAGCCAATTCGTGCCCACAGATCCAGAAGCTGTGGTCCATCGGCCGATG - 6600
6601 - GGTGCCCCTAGGACCAGCCGAGGATGACCTTTATTCATGGTAGGAGCTAGGGCAATAGCA - 6660
6661 - ACGTGGGCCTGGGAGCTGGAGGGGGAGGCAGAACCCCACCAAAGACAATCCACCTTCCCA - 6720
6721 - AACACTTTGCTTCCCTTAGTAGTGATAGCATTTTATTGTGCCCTGAAAAGCACTTCATGC - 6780
6781 - AGACCCCAGTAACAACCCATGGAGATCTATGCTATTGGCCCCATTTAACAAAGAAAACAG - 6840
6841 - GGTGCTCAGAGAAGTTGTTACCTGCCCAAGGACACACAGCTAGCAGAGCGAATGGACAGG - 6900
6901 - TCAGGACCAGTTATTCAGCCTCTAGGAGCCATTACTAAGTCTCTGATCAACAAGGAAACA - 6960
6961 - AGTTTCCCCCGGGGGTTTTTCCCACCCGCAGCTGAAACAAAGCCTCTTTCACCTGAGCCT - 7020
```

Fig. 23 (continued; 6/6)

7021 - CTCACTCAAAGGGAGGGACTCCCGAGGGGCAGGGGGCACTCAAGTCCAGGCCTGTCTATC - 7080
7081 - CCTGGCCCCCCCACCCCAGGATTTTGTGCCCGCACCGCTTGGGGACTACCAGCAGCTGCT - 7140
7141 - GACCATCGGCTTCGAGGAGCCCACGCCCACGCTGGCCACCGACCTGCTGGTGCAGATCCT - 7200
7201 - CACGGGCCAGGCAGGCCAGGCCCGGCCTCCGAGCGCAGCCGGGCCTGCGGGGTGGGCAGC - 7260
7261 - GCAGGGGTCTTGAACCTGGGGAAGAGGGTAGGAGCTGGAACTTGACAGTTCCAAACTCCA - 7320
7321 - GAATAGGGGGCAGGGGAGGGGCTCACTCGTTCTCGCAGTGCAGCCGGGCCTCGCCTTCCA - 7380
7381 - AAGGGCCAGGCCGAGCTGACCTGTCTGCACCGAGTCCGGCTTGGCCGTGGGGCCCTGAAT - 7440
7441 - GCGGACACGTCAGTTTTGTGTTAAATAAAAGAAAGAAAGAGGTCACAGGCTCAGCGTCCG - 7500
7501 - CTGCGAATGCCGCGCCCCTCCCCCGGGGGATTGCCCCACCCACTCGCGTGGCCTTCTGGG - 7560
7561 - AAATGTAGTCTTTTGAAAGAAGCCTGGAATTCGCCAATAGGCGGACGAGAGTTTGGCGCA - 7620
7621 - TGCGCATAGGCGCACATGAAGCAAAAAGGGAAGTGGTGCCCGTCAACACCGGAACCCAGA - 7680
7681 - AAACTGCAAGTTTAGGGTACCGGGGAAATTCAACGTCCACTGGAGGAAGAGACTTAAGGC - 7740
7741 - TACGCCCACTCCCATATTTTGACCCGGAAGTTATTTATTTTAGCGTAGAAGACTACTTTT - 7800
7801 - CCCGACGCGCCCCAGGAAAGTGCCCTCGATCAGTTTCCTAAGGGCCCGAGTTAGACTTTT - 7860
7861 - TTTTTCTCTTCCAGCTTTTGGGACTTGGGGGCCGGACAGGTCGTCGTCTTTCTTGGGGTA - 7920
7921 - TCCGGGGTGCGGACAAGGTGGGAGAGCCCTACGGTATCCAAGCTT - 7965

Fig. 24 (1/9)

```
   1 - CAACATGCTTGGGACCAGAAGTGTTTCCAATTTGGGATTTTCTCAAATTTTACCGGTTGA - 60
  61 - GCTTCCCCAATCTGAAAATCTGAAATCCAACATGCACGGCTCTGAAGTCTTTCACTGAGC - 120
 121 - CTTTGGGGGAAATATTTAACATCCTAACAGCCCTAAACCAACGCTCAATTAGCACAACAG - 180
 181 - TTTACAATCTTCTCTACCCACAGCCTGATGCGAGGCTCTGGGACTAGACTATTTAGCCAA - 240
 241 - CAGTTCTTGCAAAATTAACTGACTTATAAGTAAATAGTAATTTCAACACCTCACTGCTAA - 300
 301 - TGCTGTAACAACTCTGCAGACCTAGGGAGCAAGTACGGTTTGCAGAGCACTGGGAAGGCT - 360
 361 - CTGAAGTGACCTTTGAACTGGGCCTCAAAAAATTTTGGGTTTGGCAAAAGTCAAATCTCT - 420
 421 - TAGGCTTCAAATTCCAGGCACAAGGATTGTTGGGTTTGATTTCATTATCCAGAAGCAATG - 480
 481 - GGGATACAGAATTGTGATCTCATGTGTAGGGAACTGTGGGGGTTTTTTCTACTTTAACCC - 540
 541 - CAGTGAGACTTTGTAGAGTGTGGGGTAGAGAAAAGGCTCATGAATATGCCTGAAGCCTAA - 600
 601 - CTCAGCACCTTTCTGAGGAACTGACTGCCAAAATGGTAATGGAGAGGGGAAAATATGACC - 660
 661 - TACTTTCACAAGTTACCTTGACTGCCTCAGGGAAACCTGCTGTGGTAGTGTTTCTTCTGG - 720
 721 - GTGAAAGACCAGGTAATTACCTGGGTGCTGGTCTCAGACTTACCAGTTTTGAATCCCTGT - 780
 781 - TTTAACCACTCACTATCGATATGACCTTGGATAAGTTACCTAACCTTTCTCTTACTGTCC - 840
 841 - TTTTCCGTAAAATGGGGATAACAGATAGTAGTTATTTCTATGAGTGGTTATGAGAACCAA - 900
 901 - GCTATTAGATAGCGGGAAAGCACACAGTAAGCGTTCAAGGAACTGCTATTGTTATTAAAA - 960
 961 - GCCTCCTTTGGAAGAAGGACATTGAGGCCCAGAGAGAGAACAGAACGTCCAGCCACACAG - 1020
1021 - CAAATCCGTGATGAAGTTGGGACTGGAGTATGGGTCTCCTGAGTCTCAGCCCAGGACTCT - 1080
1081 - ATCCCTCTTCCCGAGTCCTCGGAGTTCCCGGATGGAGTCACATTTGTTCACGGCCAGGGA - 1140
1141 - GGAAGGTTTGATGGAGGCCTGCAGGAAACAACAGCCAGGCGCAAGGCTTTGGGAGTTGAA - 1200
1201 - GCATAGCTTCTGCGAGATAGAAACAAGGTTGACATGGGCACTCGTGCAGAATGACGGGCT - 1260
1261 - CCTTTTGGACTCCCAGGACTACAGTCCCTTATGCACCTTGGGATCTGCGGCTAGCCCCTG - 1320
1321 - CGTAAAGAGGGACGCGTAGTCTTTTCCCTGCCCCGCCCTGCCGGGGCGCCCGCCTCCGAG - 1380
1381 - GCCGCCCTCGCTTCGTCCTTCCCAGCAAGCTCCGCGCCGGCGCCGGCTATTGATTGGCTG - 1440
1441 - AGGCGGGAGCAGGCGGCTGGCCGGCAGCAGTTACTCGGGGTTTCCGGTGCGAGGCCAGAG - 1500
1501 - GTGGGGAAGCCATCGGACGTCGGCGGTGAGGTACGTGCAGCGGCGGCCGGTGGGCGAGAC - 1560
1561 - TATTTGAGAGTGTGCGGGCCGGGATGTTCTCGGCCTGTGGGGAAATCACGCCAACTCCCC - 1620
1621 - GCGTGGGCCGGGGGCTGTCTGGGGATATGCGCATGCGCGGGCGTGCCTCGCGGCTTGAGG - 1680
1681 - GCGCGCGGGGCGTGGGTGGCTGCGCGCGCGGGGGGCGCACGTGGGGCCTGAGGGGCGGGG - 1740
1741 - GCGGTGCCGGGAGTCCCGCCACGTCAGTCTCCGGCCCTGAGCCAATCCCGCGCCCGGCCT - 1800
1801 - GCCGCGAGGGGGCCGGTTGTGCCGGGAAGTGGCTCCAGGGAGAAGAGGCCTCTTCCCTCA - 1860
1861 - CCCGCTGTGGGAGCTGCGCCCCGAAAGCCTGCCCCGGCACGTCGGGCTCTCCTGACCCGC - 1920
1921 - CAAGACCAGAGAGCCGTTGGCGCCCTCCGCCCGGGCCTGCCGGTCCGTTTATTTTAAGAA - 1980
1981 - GCTTTGTGCGCCTGCTGTGGGGATTTCTGATCCAGGCTGCGAAGAATTTCGAAGTCTGGA - 2040


2041 - AAATAGCAACTGTGTTTGTTTCTAAAGGATCTTCTCCTGACCCAGCATCGCTCATCACAA - 2100
     -                                                            M

2101 - TGAAGAACCAAGACAAAAAGAACGGGGCTGCCAAACAATCCAATCCAAAAAGCAGCCCAG - 2160
     -   K  N  Q  D  K  K  N  G  A  A  K  Q  S  N  P  K  S  S  P  G

2161 - GACAACCGGAAGCAGGACCCGAGGGAGCCCAGGAGCGGCCCAGCCAGGCGGCTCCTGCAG - 2220
     -   Q  P  E  A  G  P  E  G  A  Q  E  R  P  S  Q  A  A  P  A  V

2221 - TAGAAGCAGAAGGTCCCGGCAGCAGCCAGGCTCCTCGGAAGCCGGAGGGTGTGTGCCAGC - 2280
     -   E  A  E  G  P  G  S  S  Q  A  P  R  K  P  E  G


2281 - TCTGCGTTGCCAGCGGGCAGGGGGAGGAGCTGTGGGGTCGGCCTCGCTTCTGGACTTACA - 2340
2341 - GGCCGAGGCCAGGTTGTCCGGGAGGAGGAGATGTAGAATGAGAGGACAGTGCTGGGGGCC - 2400
2401 - GCGGTCCCCCCTGCGCTCTGGCGAGTTGGCGGAGCTGCCCCCTCTAAGCACAGGAACAGA - 2460
2461 - GTTCTGGAGAGAAGCTCCGACGGGATTAAGTCAGGTGGCAGCCAAACGAGGCACCCAGTC - 2520
```

Fig. 24 (continued; 2/9)

2521 - AGGAAATCCAGGTCCCGTTAGAAACACCTCAGCCACCAGCAGCTAACTGCCCTTCCTGTT - 2580
2581 - TGAGGCATTTCTAGAATGATCTGAATGGCAAGAAATGGGTTTTGTGGGGGGGAAGGAGAT - 2640
2641 - GGACTAGAAGTTGCTCCGTGCCATCCCTGTGTGCTGATGCTTTACATACTTTTATGATCT - 2700
2701 - AACAAATATGTTCGGGTGGTAGTGAGAAATAGTTGTGTCATTTTACAAGTAAACAGACTT - 2760
2761 - AAAGAAGTTAGGCAACGATTACTATAATTTCTTGATTTAAAAGATGTTTCGAATCTAAAT - 2820
2821 - TCTGACAGGAACTAGATTTGCTGAATGATACTCCATTCTTGCTTCTCAGTTTCCATAAAA - 2880
2881 - AAAAAAGTTAGGCAACATTTAACTCAAACTGATGAGTTTGGCTGGGCCTGAAAAATCCCA - 2940

2941 - ACCAGTGGTATAATCGTCTTCTTTCTCACTCTACCCCTCATCCTCTCCTGCTGTAGGGGC - 3000
- A

3001 - TCAAGCCAGAACGGCTCAGTCTGGGGCCCTTCGTGATGTCTCTGAGGAGCTGAGCCGCCA - 3060
- Q A R T A Q S G A L R D V S E E L S R Q

3061 - ACTGGAAGACATACTGAGCACATACTGTGTGGACAATAACCAGGGGGGCCCCGGCGAGGA - 3120
- L E D I L S T Y C V D N N Q G G P G E D

3121 - TGGGGCACAGGGTGAGCCGGCTGAACCCGAAGATGCAGAGAAGTCCCGGACCTATGTGGC - 3180
- G A Q G E P A E P E D A E K S R T Y V A

3181 - AAGGAATGGGGAGCCTGAACCAACTCCAGTAGTCAATGGAGAGAAGGAACCCTCCAAGGG - 3240
- R N G E P E P T P V V N G E K E P S K G

3241 - GGATCCAAACACAGAAGAGATCCGGCAGAGTGACGAGGTCGGAGACCGAGACCATCGAAG - 3300
- D P N T E E I R Q S D E V G D R D H R R

3301 - GCCACAGGAGAAGAAAAAAGCCAAGGGTTTGGGTGAGCAGAGGGCGGCTCTTTGTGAAGC - 3360
- P Q E K K K A K G L G

3361 - TGGTGAGGAGAGGGAGTTTGGACTTGACGTTCTCTGGGCCAGTCTGTTCTGCCAGGATTC - 3420
3421 - AAAGGAAAACGGTACTTCTCAGAGCAGCAAGTCACTCTAGTCTAATCAAAGCCAGGGATG - 3480
3481 - TGGGGGCCACGGCATAGAGAGATGCAGGAGTTACCAGCACAAAGCCTTCTGGGTTTTGGA - 3540
3541 - GCAACTGGAGCTTGGCATGGGACCTGTTCTCTCTTTGAGAAAATGGAGACGGGAGGCTAG - 3600
3601 - GGTAGGCTCCTGTGCCAGCCAGTACTACCTGCTGTGTGACCTTGGGTGTGTCCCTTCTCC - 3660
3661 - TCTCTGGGTCTTAGTTTATATTTCTCTTTACAGTAAGAAAATTAGACTAGGCCAGAGTTG - 3720
3721 - AAAACCCAAATATCTGCATAAGCTGGGCTTGGCCATGGGGCCACCTGAAGATGGAGGCTT - 3780
3781 - TACTGCTTCCCTGATTAGTTGCTCTCACTAGCCAACTGAGAGCAGGCAAAACTACAGGCT - 3840
3841 - GGGTGCAGTCAGGCTTTTTTTTTTTTTTTTTTTTTAAATAAAGAAAAGCCAGAAATCT - 3900
3901 - AGAGTTATGTGAGAACTCTAGATTTTTTCATAGTTAGCAGCTAAAATGGTAAGAGCCAAA - 3960
3961 - CAAAACCCATCCGTGGGTTGGATTTGGCACACATGCCTGCGAATTGCAGTCTCCATGCTG - 4020
4021 - ATCTCTTGGGCCCTTCTGGGGAGGCAGAGGGAAGGCTCCCTGACTCAGTCACAGGCAATG - 4080
4081 - GGGAATAGGCAGTGACAGTCATTTTACAGCAGGGTATGTATGTTTAAGAGTCTAGGCCGG - 4140
4141 - GGTGTGGTGGCTCACGCCTGTAATTGCAGCACTTTGGGAGGCCGAGGCGGGTGGATCACC - 4200
4201 - TGAGGGTCAGGAGTTCGAGAACAGCCTGGCCAACATGATGAAATCCCGTCTCTACTAAAA - 4260
4261 - ATACAAAAATTAGCTGGACATGCTGGCACACGCCTGTAATCCCAGCTACTTGGGAGGCTG - 4320
4321 - AGGCAGGAGAATGGCTTGAACCCGGGAGGCAGAGGTTGCAGTGAACTGAGATTGTGCCAC - 4380
4381 - TACATCCAGCCTGGGTGACAAGAGTGAAACTCTGTCTCAAAAAAAAAAAAAAAAGAATCTA - 4440
4441 - GAATCTAAGTCGAGTGTCATTATATCCATGTTTTATTCCTATTCCCTTTTCCCCTTATGT - 4500
4501 - ATCCTCTTACTTTAAAGAGGAACTTTAAAAAATCTTAGGGACGACTAGGCAGAGTGGCTC - 4560
4561 - ACACCTGTAACTCCAGCACTTTGGGAGGCCAAGGCAGGCAGATTATGAGGTCAGGAGTTC - 4620
4621 - GAGACCAGCCTGGCCAACATGGTGAAACCCCAGTTCTACTAAAGATACAAAAAATCAGCC - 4680
4681 - GGGCGTGGTGGCACGTGCCTATAATCCCAGATACTCGGGAGGCTGAGGCAGGAGAATCAC - 4740
4741 - TTGAACCCGTGAGGCAAAGTTTTCAGTGAGCTGAGATCATGCCATTGCACTCCACCTGGG - 4800

Fig. 24 (continued; 3/9)

4801 - TGACAGGGTGAGACTCCATCTCAAAAAAAGAAAAAGGAAAAAATCTTAACGTCACATACA - 4860
4861 - TGGAAAGATCATCTTTTTCACCCCCCACCCCCAACTGAGATGGAGTTTTGCTCTTGTCAC - 4920
4921 - CCAAGCTGGAGTGCACTGGCGCGATCTAGCTCCCTGCAAGCTCCGCCTCCCGGGTTCACA - 4980
4981 - CCATTCTCCCTGCCTCAGCCTCCCGAGTAGCTGGGACTACAGGCTCCTGCTACCATGCCC - 5040
5041 - GGCTAATTTTTTTGTATTTTTTTAGTAGAGACGGGGTTTCATCTGTGTTAGCCAGGATG - 5100
5101 - GTTTTGATCTCCTGACCTCGTGATCCGCCCGCCTCAGCCTCCCAAAGTGCTGGGATTACA - 5160
5161 - GGCGTAAGCCACTGCACCCCGCCTTTTTTTTTAATTAATTAATTTTTTTAGACAGAGTC - 5220
5221 - TCGCTCTGTCCCAAGCTGGAGTGCAGTGGCGCGATCTGGGCTCACTGCAACCTCCGCCTC - 5280
5281 - CTGGGTTCACGGCGATTCTCCTGCCTCAGCCTCCCGAGTAGCTGGGACTACAGGCTCCTG - 5340
5341 - CTACCATGCCCGGCTAATTTTTTGTATTTTTTTAGTAGAGACGGGGTTTCACTGTGTT - 5400
5401 - AGCCAGGATGGTTTTGATCTCCTGACCTCGTGATCCGCCCGCCTCAGCCTCCCAAAGTCC - 5460
5461 - GCCTCAGCCTCCCAAAGTGCTGGGATTACAGGCGTAAGCCACTGTACCCTGCCTTTTTTT - 5520
5521 - TTTAATTAATTAATTTTTTTAGACAGAGTCTCGCTCTGTCACCAAGCTGGAGTGCAGTGG - 5580
5581 - CGCGATTTGGGCTCACTGCAACCTCCGCTTCTTGGGTTCAAGCGATTTTCCTACCTCAGC - 5640
5641 - CTCCGGAGTAACTGGGACTACAGGCGCGTGCCACCACACCAAGCTAATTTTTTTGTGTAT - 5700
5701 - GTCTTTAGTAGAGATGGGGTTTCACCATGTTAGGATGGTCTCGATCTCTTGACCTCGTGA - 5760
5761 - TCCGCCTGCCTCGGCCTCCCAAAGTGCTGGGATTACAGGCATGAGCCACCTTGCCTGGCC - 5820
5821 - GAAAGTATCTTCATTTTAAAGTTCACTGTTTGGCTACTCTGTTGACAAGAGTTTAGTATT - 5880
5881 - TCTCAAGGAGGCTAAGATACCTATTCCTTTTTGGATCCTACCTCTATCAGGAGGGTGGGC - 5940
5941 - CTTCCTTGCATTGAAACAGTATGAAAACAGTAGCCCTGAATTCATAAGTGGGACACCTTT - 6000
6001 - CTTCTATTGGTAGAGCAGGCAGTTTTTTTCTCCTGCCAATGGTGCCCTACTAAGGAGATTT - 6060
6061 - CACTAGGGTACAGTCGTTCATTTGATAAGCATTTGTTGAGCATATCCTCTGTGATGGTAC - 6120
6121 - TATGGACAGTACTGGGGCTATAGTGAGGGCAGGATTGAGTTGGTCCTTATGGCAAGGAAG - 6180
6181 - GCAGCTAATCAACAAGCAAAATATAAAGTATGATGGGGAGGGCTGTCTTCAGCACTCATG - 6240
6241 - AGTGTGAGCCCAGGCCTGGAGGGGACACCTGGAGAAGAGGGTGCATGTCTTTGCTCCTGT - 6300

6301 - GCTTTTCAGGGAAGGAGATCACGTTGCTGATGCAGACATTGAATACTCTGAGTACCCCAG - 6360
- K E I T L L M Q T L N T L S T P E

6361 - AGGAGAAGCTGGCTGCTCTGTGCAAGAAGTATGCTGAACTGGTCAGTTCCCCCCTCCGCG - 6420
- E K L A A L C K K Y A E L

6421 - GGCACCTTCCCTGCGTTGGGAAAATCAGCATGCCACCTGGTGTAAGGTTGGGGGTGCAGA - 6480
6481 - GTCAAGTAGGTGGCTTAATTCCTGTTCAGCTTTTCTCTGAACTATCTGTTAAATGGGGAA - 6540
6541 - TCACTTCCAGCCAGCCTCTTCAGGGCTGTGCAGCAAGAGGAGAAACTGCATATTCCTTGA - 6600
6601 - AAGAAATTTCTCAAAGAATGATTCCAAGGTGGTAGAGCCCTTGTTCCTGGCCTGAGTCCA - 6660
6661 - AGACACCTTGTGATCTTGATGCTTCTTCCTCAAATACAGATGCATAGAGCCATTATCACA - 6720
6721 - GTTAATAAAACTAACACTAGTCACTTGATACTTTTTCCTTTTACTCCAGAGCAGTCTTCT - 6780
6781 - TGTCACTGCCTCCTCATATTCCCCATGACATTGACTTTTAACAGAAACTAGACTAGCTGT - 6840
6841 - CTTGTAGGATGCCCCCTTCTAGCTTTGTCATCTCTGTGGTATCATTTTACTTCTTTACCT - 6900
6901 - CCTGGTACATGTAAGTGAAGTAGAAGTTAGCTCTAAAGCTTGATCCAATTCAGCTTCAAC - 6960
6961 - TTTTTGACAAGAATTCTTCATAAGTACTTCATGTTCCATCACAATAAATGCAAAGCATGC - 7020
7021 - TCTTCCCACTTTGTTGTAACATTGTTCAGTGGGTTGGGGGTGGGGCAGCCAGATTCTTCC - 7080
7081 - ATCATCAGGTCCCTTGTCAGAATTTGAACTAACAGATTTATCCATTGATGGTCACAGCCT - 7140
7141 - GTGTATGTATGTATGTATGTATGTATGTATGTATTTATTTATTTATTTATTTATTTTTGAGAC - 7200
7201 - GGGGTCTTGCTCTGTCGCCCAGGCTGGGGTGCAGTGGCACGATCTCGGCTCGCTGCAAGC - 7260
7261 - TCCGCCTTCTGGGTTCATGCCATTCTCCTGCCTCAGCCTCCCGAGTAGCTGGGTCTACAG - 7320
7321 - GCGCCCGCCACCATGCTAGGCTATTTTTTTTTTTTTTTTTTTTTAGTAGAGACGGGGT - 7380
7381 - TTCACCGTGTTAGCCAGGATGGTCTCGATCTCTTGACCTCGTGATCCGCCCGCCTCGGCC - 7440
7441 - TCCCAAAGTGCTGGGATTACAGGCTTGAGCCACCACGCCTGGCCTATTTATTTATTTATT - 7500
7501 - CAGAGTCAGAGTCTCGCTCTGTCACCAGGCTGGAGTGCAGTGGCGCGATCTCGGCTCATT - 7560
7561 - GCAACCTCCACCTCCCAGGTTCAAGCGAGTCTCCTGCCTCAGCCTCCCGAGTAGCTGGGA - 7620
7621 - TTACAGGTGCATGTCACCATGCCTGGCTAAATTTTGTATGTTTTAGTAGAGACAGAGTTT - 7680

Fig. 24 (continued; 4/9)

7681 - CAGTATGTTGGCCAGGATGGTCTTGATCTCTTGGCCTCGTGATCCGCCCGTCTCAGCCTC - 7740
7741 - CCAAAGTGCTGGGATTACAGGTGTGAGCCACTGTGCCTGGCCTCTAAGTATTTATTTTAA - 7800
7801 - AATTAATTCATTCCACACACATTTATTAATATTTTCCTGTAAGGAACTTTACTCATCTTT - 7860
7861 - AAAATGGGGAATGTCATACCTGCCTAATGACATTCTTGTAAGGATTAAATAAAAGGTATA - 7920
7921 - AGGAAGATAAGCACCCTTTTGGAGTGATCCAGCCAGGGGAAAATTGCTGATGCAAGAGAG - 7980
7981 - GAAATGAGTTGCTAGAGTGGTGTTGTGAGTAGAGGAGGGGAGCTGAGGCCTGCCCAAGAA - 8040
8041 - GGGGGCTTGGCTGTGGTAACCACATGGCTAGGTCTGTGTGACTGGAGGAGAGGACGGGGC - 8100
8101 - AGGTGGACTGGTAGATGTGCAGCTTGTGCCCCTGATTCTCTAGTTTCTTCTGTGTTTTGA - 8160
8161 - GATTTGATGAGAACGATGAAATAGTTGTCTGGAAGGAGAGGAGTGTGAATAGCATATGCA - 8220
8221 - TTGTATTGGGATTGCTGGTCTTCCTGAAATTGGTGGCCATGAATTTAAAGTGAGACTCTT - 8280
8281 - CAAGTAGGGTTGTTATAGTACTGGTGTAAAGCAGGAAGGTGCTTTACTAGGGTTGCAGTA - 8340
8341 - CTACTGGGGAAGGGCCAAGAGAGTTGAGGGTGTAAGAAATCCAAGCCAGGTAATGTAGTT - 8400
8401 - ATTTTAAAGGAGAGTGGAAGGATGGTTGAGTCAATGGATTGGAGGTCCTATAGGGTAAGA - 8460
8461 - GACTTTCTGAGGATCACAGATACTGATTGGAATGAGCTAAAAAGATAGGTGATGGTAGTC - 8520
8521 - CTGGACTGGGATGCTGGAAATTGAGATAGTGGGTGTGCTCTCTGGTAGTGACAAATCTAG - 8580
8581 - ATCTGCGCTGTCCAAGATAAATTCGTCTCTAGCTAATTGACATGTGGCCAGTTTGAATTT - 8640
8641 - GAACATGCTATAAATGTAAGATACACATCAGCTTTTGAAGACTTAAGCAAAAACAAAGAA - 8700
8701 - TATAAAACATCTTTTTGTGAGAGAGTGTCTCAGTCACCCAGGCTGGAGTGCAGTGGCGTG - 8760
8761 - ATGTCCTGCTTCCAGGTTCAAACGATTCTCCTGCCTCACAGCCTCCTGGAGTAACTGAGA - 8820
8821 - TTACAGGCGCATGCCACCAAACTGGCTACTTTTTTGTATTTTTTTTTTAGTAGAAACGGT - 8880
8881 - TTCACCATGTTGGCCAGGCTGGTCTTGAACTCCTGACCTCAAGTGATCTGCCTGCCTCAG - 8940
8941 - CCTCCCAAAGTGCTGGGATTACAGGCATGAGCCACCACTCCCGGCCTCACTTTTTTACAT - 9000
9001 - TGATTCCGTGTTGAAATTGTAATGTTTTGGATATTAGGTTAAATACATATATTACTAAAA - 9060
9061 - TTAATTTCACCTGTTTTTTACTTTTTTAGTGCGGCCAGTAGAATATTTTTAATTACTTAT - 9120
9121 - GTGGTTTGCATTATATTTCTGTTGTACAGGCCTGGATAGGGTCATGGGAGGGGAACTGAG - 9180
9181 - CTGGGGAAAGGAGTGGGTTTGTGGAAGAGGTGATGGACTGTGAGGCCAGGGAGTTAGAAG - 9240
9241 - GATTATCTGTTGATACTGAAGTGGCCACAAATGAGAAAAGTAATTGTGTTGGGGAGAGCG - 9300
9301 - CTGATGAACGCAGCGCTAACGTTTTGAAGGAATGCGAGGGAGCGATGGGGGTCTGTCTGT - 9360
9361 - TAATAGGCACAAGGTACGGTAGCAGGTGGTCTCATCCTCGGGCATGAGTGTCCAGCAAGT - 9420
9421 - TGGGGAAATGCAACAGCTTGAAGTGGCTCTAGTGGCCCAGAGTCAGAGCTGGAATAGGAA - 9480
9481 - TTGGCATCTGCTGGCTGTGTGGCCCCTGCTTGCCCTAGTGAGTTACCATTTCTCTGTCCC - 9540
9541 - TACGGTGGAGCCTTTGGGGTTATTGTGAGTTCATGGGAGGAGCGTGTAAGCACCGGCACA - 9600
9601 - GCATCAGCCCATGAGAGTGCTCCTGGCCTGAGAGGGTAAGGGTCAGGGCAGCTCAGGAGA - 9660
9661 - CCCTAGACCTGCATAGTGATCCCCCCACCAGGAAGGCCCCACAAGATGCTCACCTGCCCT - 9720

9721 - CCCTATCCCTGTCCCCAGCTGGAGGAGCACCGGAATTCACAGAAGCAGATGAAGCTCCTA - 9780
- L E E H R N S Q K Q M K L L

9781 - CAGAAAAAGCAGAGCCAGCTGGTGCAAGAGAAGGACCACCTGCGCGGTGAGCACAGCAAG - 9840
- Q K K Q S Q L V Q E K D H L R G E H S K

9841 - GCCGTCCTGGCCCGCAGCAAGCTTGAGAGCCTATGCCGTGAGCTGCAGCGGCACAACCGC - 9900
- A V L A R S K L E S L C R E L Q R H N R

9901 - TCCCTCAAGGTAGGCCTGGGCCCCCTGGAACAGGTGACTCTGGTTTCCTTGACTTCCACT - 9960
- S L K

9961 - TAATGTTTCTTTCATGGGCTTTCCTCTTAAAAAGTAGTGCAGGCTAGGGCCAGGCGCAGT - 10020
10021 - GGCACACATAAGTGATTAAAAATCTTCTGGCCACTAAAAAACAGAAATTAATTTTAGTAA - 10080
10081 - TATACTTAACCCAATATCCAAAACATTACAATTTCAACATGAAATCAGTGTAAAAAAGCA - 10140
10141 - AGGCTGGGTGTGGTGGCTCACACCTGTAATCCCAACACTTTGGGAGGCTGAGGTGGATGG - 10200
10201 - ATCACTTGAGGCCAGGAGTTTGAGACCAACCTGGTCAACGCAGTGAAACCCCATTCTACT - 10260
10261 - AAAAATACAAAAATTAGCCGAGTGTGCTGGCAAATGCCTATAATCCCAGCTACTCAGGTG - 10320

Fig. 24 (continued; 5/9)

```
10321 - GCTCAGGCATGAGAATTGCTTGCACCTGGGAGGCTGAGGTTGCAGTGAGCCGAGATTGCA - 10380
10381 - TCACTGCATTACAGCCTGGGCAACAGAGTGAGACTCAGTGTCCAAAAAAAAAAAAAAGTA - 10440
10441 - GTGCAGGCTTGTGGCATAGAAATACACTTTCTCAATAATGCCTTACGTTAAGAGAGTACT - 10500
10501 - GCTTGTAATCATTTGACATGTATTAGATAAGGTGAAGGATAAAGTACTAAGAGAATCCAT - 10560
10561 - AATGCACTGGCGTTAGTATTTCTCAATGAAATGACAGTCCCCTGGTAAGCGGAGGCCTGG - 10620
10621 - CTCTGACAAGCAGCTCTTGTCCCAGACGTTGGTCAGTCAGGAACCTGGGTCCTTCCCATG - 10680
10681 - TTCTGCTGCTTCTATGGTGAGGTCAGTCTGTGGTTACACCAAGTTTAAATACAGCCTTTT - 10740
10741 - AACTTTCTTTTTTATATGTAAAATCTTACATGTAGTTTTTAGAATGAAATTATTATACAT - 10800
10801 - GTACCATTTCATATCCTGTGCCTTTTTTTCACTTTACATAACATTTTTCCCTATCAGTAT - 10860
10861 - GTGTAGGGCTATCTTCTCATTATATGGATATATTATATCAGTGCCCTAGTTAAAGCATTT - 10920
10921 - TGGGGGTTGTTTACAATTTTTCATTATTACATATAGAACTATAGTGAAAATTCTTGTTAT - 10980
10981 - ATTTATCACTGGTCAGTTATATAGAACTTATCTGTAGGATAAGTCATGGAATTGAAATGG - 11040
11041 - CTAGGTCACAGTATATGCAGATTTTTCATTTTAATAGATTTTGCTGGATTGCCTTCCAGT - 11100
11101 - GAGGGGGCAGTGTGCCTTCCCCATCAAAAGTGTTGAGTGCCTAATTCTGCACAACTTTGC - 11160
11161 - AAACCCTGGGTGTTACTAAATTTTAACAGCTTGGTCTCTGGGGGTACAGAGGGGACAAAT - 11220
11221 - GCACATTAATCTGAAATCTGGAAGAATAGGCCTTAGGAGATCCGACTTGCTTCAGAATGG - 11280
11281 - CACTTAGCACTTACATGTGTGCATGTGTGCCTGCATTTTTTCTTCCTTTTTTTTTTTTTG - 11340
11341 - GGGACGGAGTCTTGCTCTGTGGCCCATCGCCCAGGCTGGAGTGCAGTGGCGCGATCATAG - 11400
11401 - CTCACCACAACCTCCGCCTCCCAGGTTCAAATGACTCCTCTGCCTCAGCCTCCCAAGCAG - 11460
11461 - CTGGGACCACAGGTGCACACCATCACGCCGGCTAATTTTTGTATTTTAGTAGAAACGGGG - 11520
11521 - TTTCACCATATTGGCCAGGCTGGTCTCAAACTCCTGACCTCGTGATCCGCCCACCTCAGC - 11580
11581 - CTCCCAAAGTGCTGGGATTACAGGCGTGAGCCACCGCGCCTGCCATGTGCCTGCATTTTT - 11640
11641 - CTAGGGGGAGAATCTCACTTGATGTCACCTGATATACAGAGGGGCCCATTGGAACCCGCA - 11700
11701 - TTGCACAACATCCTGGAGTCTGGCTACTCCACGCTTTGGGAGCAGGGAGGGCTGTTGGCA - 11760
11761 - GAGACCATCTGTGGACTAGCTGGGGGACCCTTGTGAGGTAGCAGTGGATGATGGCTCTCG - 11820


11821 - GGCTGACTTCTTTGCCCAGGAAGAAGGTGTGCAGCGGGCCCGGGAGGAGGAGGAGAAGCG - 11880
      -                         E  E  G  V  Q  R  A  R  E  E  E  E  K  R

11881 - CAAGGAGGTGACCTCGCACTTCCAGGTGACACTGAATGACATTCAGCTGCAGATGGAACA - 11940
      -  K  E  V  T  S  H  F  Q  V  T  L  N  D  I  Q  L  Q  M  E  Q

11941 - GCACAATGAGCGCAACTCCAAGCTGCGCCAAGAGAACATGGAGCTGGCTGAGAGGCTCAA - 12000
      -  H  N  E  R  N  S  K  L  R  Q  E  N  M  E  L  A  E  R  L  K

12001 - GAAGCTGATTGAGCAGTATGAGCTGCGCGAGGAGGTAAGGGTATCACGGACAGCAGTCAT - 12060
      -  K  L  I  E  Q  Y  E  L  R  E  E


12061 - GGCCCAGAAATTGTGAGGTTTTGAGTGTGTGCTAGGCACTGGGACAGTACCTTTTCAGGC - 12120
12121 - TTCATCCCATTCTCCCTTTCTTCCTCCTCCTCCTCCTTGGGAGGAGAGTAATGTTATTCC - 12180
12181 - TCATAGATAAAAAACAGGTGTGGAGAAGAGACTCACTTACAGCCACACAGCCCCAGGTCC - 12240
12241 - ACAGTGCCTTGTCCCAAATGACTGGGCCAGGCATCTTTTGGAATTAGAACTATCCACATT - 12300
12301 - TTAGAATGGAGGTACATGTATGGACTGTGTGTTATATAGCACCCTCAGCAGGGCCTTGGG - 12360
12361 - GAAGCCAGACACATTAATGTATTTATGCAGTAGAACTTCCAAATACTCACCTACATTATG - 12420
12421 - GGCTTACAATGATGCAGGTCAAGTCTGGCTGCCAGCTTATGACAATTTCCATTTTCAGAA - 12480
12481 - CTTTGTAGAATTTGGAATTGCAGGGGAGGGGTGTACCTGTGATCAGTGATGGACTCCAGA - 12540
12541 - GACTGTGTCCACTGATTCCTTGCTGCTCCTGCCACTCAAAAGGCAGAATTTATCAGGCTG - 12600
12601 - GGCGTGGTGGCTCATGCCTGTAATCCCAACACTTTGGGAGGCCAAAGCGGGCGGATCACC - 12660
12661 - TGAGGTCAGGAGTTCAAGACCAGCCTGGCCAACATGGTGAAACCCTGTCTCTACTAAAAA - 12720
12721 - TACAAAAAATTAGCCAGGTGTGGTGGTGCACGGCTGTAGTCCCAGCTACTCAGGAGGCTG - 12780
12781 - AGGCAGGAGAATTGCTTGAACCCAGGAGGCAGAGGTTGCAATGAGCCAAGATTGTGCTAC - 12840
12841 - TGCACTCTAGCCTGGGTGATATACCGAGACTCCATCTCAAAAAAAAAAAAAAAAAAAAGC - 12900
12901 - AGGATGTCACTCCCTTTGTCACTGCGTTGGCTGCCACCCCAGGCACTTGAATCTTTGGAT - 12960
```

Fig. 24 (continued; 6/9)

```
12961 - CTTCCCTGCCAGTCACCTGGCTGTTCTGGGCGCGTTCTCATCATGAGAAGGGAGACCTGC - 13020
13021 - AGCCCCCTTACAGGGCTGGCAGAGGACCTGCTCTGGATTAGGCCCTTTCCTAGCCCCTGG - 13080
13081 - GGTGTGGCAGTGGGTGAGACCGGGAAGATCTGCCCTCTTAGGTTCATAGGCCAAAGTGAT - 13140
13141 - GATCGTGTGTGCAGGACCTAGAGGGCGCTCCCCTGACCCACCCCTTTCCTTGCCATACTT - 13200
13201 - CATCCTCTGGGAACAAAGCTGCTTGTTTGGTTTGAGGGGAGTTGGTTTGGTTCTTATCCC - 13260
13261 - TCAGCGCTGAGACATAGAGGCTTCCTGGGCCACTACAGTGAGACACGAACTTCAAGAATC - 13320
13321 - TGAATACCCCCGTTTTCTCTCCCCGCCAAGGCAAAAAAGGACTTAGTACTACCTGTGGAG - 13380
13381 - AAGGAGGTGCAGGACTACCAGGCCCTGCTGCTTTGCATTTACAGCCCTCCCCAGACAGAC - 13440
13441 - ACAGGCACCCTCATCATACCCAAACTGGACTTACCTGCTAGGCACCTTCCCTTCCCCATC - 13500
13501 - CAAAAAAATGGAGTTATTTTCCCTTATTTCAGCAAGTCCAGTTGATTTTACCTTTGAAGT - 13560
13561 - AGCACCTGAGTCCTTCACCTTCTCTCCATCCCTTCTCTCTCACCTGACACAGGTCTGCAG - 13620
13621 - CGCTCCTCTAGTAGGCAGGACAGCCATTCCTTGGGGATGCACATGTCTAGTCTTTGCCTA - 13680
13681 - GATATGGCAAGTCTTTGCCAACTGAGCTAGGCTGTTATGTTCTTAGAGGCATTGTTTTTG - 13740
13741 - CCCATTCTTCCCATTTACAAGAGAATCAGGGACACAGAAGTGAGGGCTTCCAGCCCCATA - 13800
13801 - GGTGATCAATCCTGGGGTCAGAGATTTGAGTGTGTTTATTGCTTGCCTTCTTGGGAGCAG - 13860
13861 - ATTCCATCCATAAACCATGTGCTTACCAAGGTCTGACTCACTGGGAGAGAAACGACGTGA - 13920
13921 - GGTTGGAAAGCTGACCTTCCAGAGACTTGGGGCCCATGTTGTGTGGTACACATGGGAGTC - 13980
13981 - CATCATATCAGATTGAGATGGGGGGCTGGGCAAAGTGCCCTGGTCTGTGGCTGTGGGGCT - 14040

14041 - ACCCTGAGAAAGGGAGCGCCTGACAAGCCGACTGCTCCCACCATCTTTGTTGCAGCATAT - 14100
      -                                                      H  I

14101 - CGACAAAGTCTTCAAACACAAGGACCTACAACAGCAGCTGGTGGATGCCAAGCTCCAGCA - 14160
      -  D  K  V  F  K  H  K  D  L  Q  Q  Q  L  V  D  A  K  L  Q  Q

14161 - GGCCCAGGAGATGCTAAAGGAGGCAGAAGAGCGGCACCAGCGGGAGAAGGATTTTGTGAG - 14220
      -  A  Q  E  M  L  K  E  A  E  E  R  H  Q  R  E  K  D  F

14221 - GCTCAGGCCCCAGGGTTGGGGTGGGGGTGTGGGAGGAGACAGGCTGGGCTCTGGCTCAGC - 14280
14281 - TCATAGCCGGGTTATATGGGAGAAGTCTGGCCAGACCAGGCACAGATTCCTTGAGTACCA - 14340
14341 - GTCTGAGAGCAGGAAGCCTCAGTGGGTCTGGTGCTTGTGGCTAAAAACCAAACATAGCCC - 14400

14401 - CTGGGGGCTTCTGACAGGATCTGGGGTTCTGTCTTGGAAATAGCTCCTGAAAGAGGCAGT - 14460
      -                                              L  L  K  E  A  V

14461 - AGAGTCCCAGAGGATGTGTGAGCTGATGAAGCAGCAAGAGACCCACCTGAAGCAACAGGT - 14520
      -  E  S  Q  R  M  C  E  L  M  K  Q  Q  E  T  H  L  K  Q  Q

14521 - GAGAGCATATAACCTGACCCTGTGCCTTCAAGTTTCCCTCACTGGGCCCCATCCTGGGGG - 14580
14581 - TAGTGAAATGGGACCCTCATTCTAGGACTGGCTGTGTCCTGGCTGCTATGACGCCTTGGT - 14640
14641 - TGAGCTTAGGTGGGCTCAGAGGACTTCATTTGTAGCTCAGAAATGTATTGCTTTTGAGGA - 14700
14701 - GGTAGGAACAGAAGAGTTTGAAAATCAACATAAAGGCAAAATAAAAGTCACCCTAAGTCT - 14760
14761 - CCTACTTTCCAGGCTTAGCATTTTGGATTATATCCTTCCAAATATATAGCTTTGCTTTGT - 14820
14821 - TTTAAGGAAAAATAGTATCTCAATAGAATTACTGGTCAGAGAGTCAAGGACGGGTCTGAG - 14880
14881 - TGTGTTGACCAGAGTGCCTCCCAGAGAAACCCAGTCTTATCTGTGGGCTGCTTTCTCCCC - 14940

14941 - ACAGCTTGCCCTATACACAGAGAAGTTTGAGGAGTTCCAGAACACACTTTCCAAAAGCAG - 15000
      -    L  A  L  Y  T  E  K  F  E  E  F  Q  N  T  L  S  K  S  S
```

Fig. 24 (continued; 7/9)

```
15001 - CGAGGTATTCACCACATTCAAGCAGGAGATGGAAAAGGTAACTGTGGTCCAGGCCAGGCA - 15060
      -  E   V   F   T   T   F   K   Q   E   M   E   K

15061 - TGGCTGCTGGGGCATAAGCTGCTTCATTCAAAATTGTTGGGCCTGCCTTCAGGAAGCTCC - 15120
15121 - CATCTGGGGTGTCTCAAGGGCAGGGCTGTTAGGAAGGTTCACAGCCTTTCCCCTCTTGAG - 15180
15181 - GCAGTATCAGTGGTATGTATACACTCCAGGTTGTCCCAGGGAATGGGGCAGTCTTTTCTG - 15240
15241 - TTTGTTTGGTTTTTTTGGGGGGTTTGTTGTTGTTGTTGTTGTTGTTGTTGTTGTTTGAGA - 15300
15301 - TGGAGACTCACCTATTGCCCAGGCTGGAGTGCAGTGGCATGATCTCAGCTCATTGCAGCC - 15360
15361 - TTTGCCCCCCGGGTTCAAGTGATTCTCCTGCCTCAGCCTCCTGACTAGCTGGAATTACAG - 15420
15421 - GCGCGTGCCACCATGCCTGGCTAATTTTTCTTTCTTTTTTTTTTGTATTTTTAGTAGAG - 15480
15481 - ACGGGGTTTCACCATGTTGGCCAGGCTGGTCTCGAACTCTTGGCCTCAAGTGATCTGCCC - 15540
15541 - GCCTTGGCCTCCCAAAGTGCTGGGATTATAGGCGTGAGCCACCATGCCTGGCCCCTTACC - 15600
15601 - ATTCCTTGTTATTGGTGGTGGACACCTCTGACTTCCTGGTGGTGAGGTGGCACAGAGGGC - 15660
15661 - ATTGACTGCATCCTGTAATGCCTTGCGCCTTGGGATCAATCATTCCCCACCTTGGAGACA - 15720
15721 - CAGGTGCAGTCCCCACCTTGGAGACACAGACCTTGGAGAGGCCAGCTCTGACCATTTCCT - 15780

15781 - TCTGTCTGTCACATAACCTAGATGACTAAGAAGATCAAGAAGCTGGAGAAAGAAACCACC - 15840
      -                         M   T   K   K   I   K   K   L   E   K   E   T   T

15841 - ATGTACCGGTCCCGGTGGGAGAGCAGCAACAAGGCCCTGCTTGAGATGGCTGAGGAGGTGG - 15901
      - M   Y   R   S   R   W   E   S   S   N   K   A   L   L   E   M   A   E   E

15902 - GCTGTCTGTGATCTGCAGCCAGGGTGGGGGTGTGCACTTAGCGCATATCAGGCCCTTTCC - 15961
15962 - TGTATGTTCTACCCATCAGTGACACAGCTAGCATGAGGTAGAGGTGAGATTTGCACACAA - 16021
16022 - TGTCCAAGTCCAAAGTTAATGCTGTTCTCTCCCCATGGGAGGTGGTGAGCCCAGTGGTAG - 16081
16082 - GTCTCCAGTGGGAGTGAAGGGAGCAAATGGAAGAAAGGAATAAAAGAGCAGAAAAAAACG - 16141
16142 - GGTGCCAGTGATGTGCCTGGTTTACATGTAAAGCAGCCCAGGTAGTTTGTGATTTCACAG - 16201
16202 - CTTGTAATGTAGAAGAAAGGAACTAACGATGGAGCAGCAACTGCAAGCCAGACCTTGCTG - 16261
16262 - AAAGTTTTTGGGTTTTTTTTGTCTTTTTTGCTGCTGAATGTTTTTAGGTACGTTGTTCAT - 16321
16322 - TGAACCTTCTCTTGAGCTCTGAGGATGGTATTAGTAGTCCTGTTTTATAGATGAGACAGG - 16381
16382 - CTCAAAAGTCAAGTCCTTTGCCAAGGTCACGTGGTAGATAAATGGAGGAATACGTTATCT - 16441
16442 - CCAAGCCGTGCCCCTTTTCTGCACCATGCTGCCCCACCTGACAGCCTAGTCATGGCTTCA - 16501
16502 - ACTAGGACTGTTTCCTAAAGGGGGCCAGCTTTGGACTCGGTCTGCTCTCAGCCTTGTTAA - 16561
16562 - AGTGTTTGCCGCCAAGTGGTGATGGTAAGTGGGAGGTTGATGGGGCACGGCACTGAAGGT - 16621

16622 - CTCATTTCTTTCCCTAGAAAACAGTCCGGGATAAAGAACTGGAGGGCCTGCAGGTAAAAA - 16681
      -                  K   T   V   R   D   K   E   L   E   G   L   Q   V   K   I

16682 - TCCAACGGCTGGAGAAGCTGTGCCGGGCACTGCAGACAGAGCGCAATGACCTGAACAAGA - 16741
      -   Q   R   L   E   K   L   C   R   A   L   Q   T   E   R   N   D   L   N   K   R

16742 - GGGTACAGGACCTGAGTGCTGGTGGCCAGGGCTCCCTCACTGACAGTGGCCCTGAGAGGA - 16801
      -   V   Q   D   L   S   A   G   G   Q   G   S   L   T   D   S   G   P   E   R   R

16802 - GGCCAGAGGGGCCTGGGGCTCAAGCACCCAGCTCCCCCAGGGTCACAGAAGCGCCTTGCT - 16861
      -   P   E   G   P   G   A   Q   A   P   S   S   P   R   V   T   E   A   P   C   Y

16862 - ACCCAGGAGCACCGAGCACAGAAGCATCAGGCCAGACTGGGCCTCAAGAGCCCACCTCCG - 16921
      -   P   G   A   P   S   T   E   A   S   G   Q   T   G   P   Q   E   P   T   S   A

16922 - CCAGGGCCTAGAGAGCCTGGTGTTGGGTCATGCTGGGAAGGGAGCGGCAGCCCAGCCAGG - 16981
      -   R   A   *
```

Fig. 24 (continued; 8/9)

```
16982 - CCTGGCCCATAAAAGGCTCCCATGCTGAGCAGCCCATTGCTGAAGCCAGGATGTTCTGAC - 17041
17042 - CTGGCTGGCATCTGGCACTTGCAATTTTGGATTTTGTGGGTCAGTTTTACGTACATAGGG - 17101
17102 - CATTTTGCAAGGCCTTGCAAATGCATTTATACCTGTAAGTGTACAGTGGGCTTGCATTGG - 17161
17162 - GGATGGGGGTGTGTACAGATGAAGTCAGTGGCTTGTCTGTGAGCTGAAGAGTCTTGAGAG - 17221
17222 - GGGCTCTCATCTGTAGCTGCCATCACAGTGAGTTGGCAGAAGTGACTTGAGCATTTCTCT - 17281
17282 - GTCTGATTTGAGGCTCAGACCCCTCCCTGCCCTTCAGAGCTCAAGACAAGTAATACACCC - 17341
17342 - AGGTCTTGACTGCATTTGTCTTGTGAGCAGGGCTTGCTTGGTCAGCTCAGGCCCTCCTAG - 17401
17402 - CTGCTCTGGAGGCTCCTTTGATTCTCTAGACCTGGAAAAGGTGTCCCTAGGCAGAGCCCT - 17461
17462 - GGCAGGGCGCTCAGAGCTGGGGATTTGCTGCCTGGAACAAGGGACCTGGAGAATGTTTTT - 17521
17522 - GCGTGGGATGATGTGCTGGTCAGGAGCCCCTTGGGCATCGCTTCCCCTGCCCTTTGGTAG - 17581
17582 - TGCCAGGACCAGGCCAATGATGCTTCTCAGTAGCCTTATCATTCACAGGTGCCTCTCTAG - 17641
17642 - CCTGCACAAATGATTGACAAGAGATCACCCAAAGGATTATTTCTGAAGGTGTTTTTTTCT - 17701
17702 - TTATTTCTTTTTCTTTTTTTTTTTTTTCTTTTTCTTTTTTTTTTGCACATGACAGTGTT - 17761
17762 - TGTATTGAGGACCTTCCAAGGAAGAGGGATGCTGTAGCAGTGGTGCCTGGGTGCCTGGCC - 17821
17822 - TCCAGTGTCCCACCTCCTTCACCACCCCACTTGGCTCCTTTGCCATCTTGATGCTGAGGT - 17881
17882 - TTCCTGTTTGGTGAGATCAGGTTGTTTGTGGTAAAAGAAAGGAAAGGGCTTCTGATGGCT - 17941
17942 - TTGCCACAAGCTTACCTGTGGGTTTCAGTCCTGAGAGGCCACCACCAGTTCCCATCAGCA - 18001
18002 - CTGTCTCCATGCAGCAGTTGCTGGGTCCCATGTCCAGCTGCCTCTTTGGCTTCATGGGTT - 18061
18062 - TTTCTGCTTCCTGCCCCCACCCCCACATGTGCAATCCTCAAGATTTGTCCTGATTCTATT - 18121
18122 - TCCTGGCACCTCCCTGCCTGTCCTTGGGGATTCTACTTCTTCCTGTGTGGGAGCCCATAG - 18181
18182 - CTGTTGTCTAACAGGTAAGAAATGAAATTGAACTATTGACTGGGCCCCAGAAATCCATAA - 18241
18242 - AATGGCTGCAGACAGTTGTTTCTGTGTCCTGTTCTACCCCCACTCCAGTACATAACTACT - 18301
18302 - ATGTACTGTGTAGAGCCATTCTATATGCTGAATGTTCTGCTGTTGCAAACTTGCCAGGGT - 18361
18362 - ATTAGCCAGTGTTTGTGCCAAGCAGTTTTCTGGGACAACAGAATGACTCAGACCAAGATG - 18421
18422 - GATAGGATGGTTAGGGCTTTGCTTCTTGCTGTTTTTCTTTGAAGCTAGTTCATTGTCCTG - 18481
18482 - CAGGTCCCTTCATCTTCCATACCTAGCCCACTCTTTTAGCCCTTACCTTAAATCTCTCAG - 18541
18542 - ATAAGTTGGTTCACAAAGAATGTTAAGTACTGAATCATGTGTGACTGAGACCAGAGATGG - 18601
18602 - CAAATGAATGGCACACCATTTCTCCTTCTCCTGCCCCAGGGCAGGTACCACTGATCTGCA - 18661
18662 - TCAGAGTTGCCTGCTATTCTCTGGTGTATCCTTCACATCTAGGTGCCCTCAAGCAGCTGT - 18721
18722 - GTGAGTGTTGAGATCTCTGCCATCTCTGGCTGAGATACTGCTGTCCTGTGAAGTGTTTCC - 18781
18782 - CATGACCTTTTTCTTCCCCTTTGAATCCCTCTGTCTGGAGTAGTCCTTGCCTCTTCCTGC - 18841
18842 - TCCAGTAGGGCCTTTTCCCTACCCCAGCCCCTGTGCCAGGCTAAGCTGGTACAAGAGCTG - 18901
18902 - CCAACCTCACAGAGTGTTTGCTAGGCGAGAGAGGTGCAGGGAAGAGGCAGAGGTATGCAC - 18961
18962 - CTTCCCCCTTGAAGAGAGGGGAAAGGCCTACAGTGGCCCACATAATTGCCTGACTCACAC - 19021
19022 - TTCAGCTACCTCTTAATGCCTGTGGAGGGACTGGAGCTGCTGGATCCCAGTGTGGTGGTG - 19081
19082 - TAGGAGGCCACAGTGAGCAGGTGGCCCCAGCTGGGTTTCCCAGGTCAGGAATGTGGGCCC - 19141
19142 - CAGGCAAGGTGCAGCCTTTGCTCACAGCTCCATCCATGTCTAGACCTTCAGGCCAGTCTG - 19201
19202 - CAGATGAGGTTCCCTACCTTTTTCTTCTCTTCATTGACCAAATCAACCAATCACTACAGC - 19261
19262 - TGCTCTGCTTCTGCTTTCCAAAGTAGCCCAGGTCCTGGGCCAGATGCAGGGGAGGTGCCT - 19321
19322 - ATCCATGAGTGAAGGCCAGTGTCTTCCTCACCTGGGTGGGTCCCACACTTGTGACCTCAG - 19381
19382 - TTTTAGGACCAAGATCTGTGTTGGTTTCTTAGATTGCTAGCTTTTCCTCCAGGGGACCAC - 19441
19442 - AGCAGGTGAAGCTCAAGAGCGCATGGCTCTGCTAATAGTAAATTGTTTTCAGGGCCTTGT - 19501
19502 - CCAGCTGAGAGCTTCATGTCCACCAGATTCTGAGAGGTGTCAGCAGCACTTTTTTTTTTT - 19561
19562 - ATTTGTTGTTTGTTTTCCATGAGGTTATCGGACCATGGGCTGAGCTCAGGCACTTTCTGT - 19621
19622 - AGGAGACTGTTATTTCTGTAAAGATGGTTATTTAACCCTTCTCACCCCATCACGGTGGCC - 19681
19682 - CTGAGGGCTGACCCGGAGGCCAGTGGAGCTGCCTGGTGTCCACGGGGGAGGGCCAAGGCC - 19741
19742 - TGCTGAGCTGATTCTCCAGCTGCTGCCCCAGCCTTTCCGCCTTGCACAGCACAGAGGTGG - 19801
19802 - TCACCCCAGGGACAGCCAGGCACCTGCTCCTCTTGCCCTTCCTGGGGGAAGGGAGCTGCC - 19861
19862 - TTCTGTCCCTGTAACTGCTTTCCTTATGGCCCAGCCCGGCCACTCAGACTTGTTTGAAGC - 19921
19922 - TGCACTGGCAGCTTTTTGTCTCCTTTGGGTATTCACAACAGCCAGGGACTTGATTTTGA - 19981
19982 - TGTATTTTAAACCACATTAAATAAAGAGTCTGTTGCCTTACTTGTTTCTCTCCTGACCTG - 20041
20042 - TGTATTCCTTTGTTTCTGGATCTGATCCATTCAGCCCCTTCCATCATCACTGACTTGTTC - 20101
20102 - AGGTCTGCTGCAGAGCGCCCATGGTGGTTCCCTGGTATCTTACATATTCCACAGTGTCTT - 20161
20162 - TGAGCAGTCGCCACAGCCTCAGGATGCTGGCATATTCACTTGAGCTGCCTGAGTGGAGCC - 20221
20222 - CTTGGCAAAGTTGGCAAGACCCTTGCCTCAGAGAGGATCACACACACACAAAAAAGTTTT - 20281
```

Fig. 24 (continued; 9/9)

20282 - CCCTGACCTGGGGGCTCACAGGCTAGTGAAGGAAAAGGTACTTTTAGCTATAGACAGGT - 20341
20342 - CAATGGTGCTGAGAGCAGAGAGGAGGCCCCTGCCCCCTTCAGCAAGGTGAGGGGGTGATA - 20401
20402 - CCTGGAATGGCCTTCTGAACCACAGGGCAGGTAGAAGATGAACGTCATTTAGTGATTAAA - 20461
20462 - TGGTACAGCTGGGAAGCAGGTCCATGGGACTGGGAGAGGGGGTGAGGCTGGGCCCAGAGT - 20521
20522 - CTGGGTACCAGGTTAAGGAATGTGGGCTAGATCCAGAGGGCAGGGGGGGCAACTGAAGGT - 20581
20582 - GTTTCAATAGGAAATTGATAGGCTCCAGCAGTAAGGCAAAAGGCATGGAGCCAGGCATAG - 20641
20642 - GCCATTTGAGGCCCAGGTTAAGAGGGGTGGACACTCATCACTGCTATTTGGGTCTGAGCT - 20701
20702 - GTGGGTAGGCTCCTATAGCCCTGGCCTGCCCAAGGGAATTCACAGGGGCCTCTAATTGTA - 20761
20762 - TGCATTCCTTAAGGAGAGCACATTCTCTGTTCAGTTTTACACCCCCCATTTACCCACCT - 20821
20822 - CAAGCATGGGACTCCTATATGGGAGACATGCTGCTGGTGGCCTCACCCAGCACCCTGTTC - 20881
20882 - TCTCTGGGTCCTGGGTTGGTCAGGCACAAAGGATGATATGTGCTGAATGCCCAGGAAATG - 20941
20942 - GCAGAGACAACCCACCTGCCCTTCCCTCCAGGCCTCCACAAATAGATGTGCCCACAATGA - 21001
21002 - CTGTGACAGTCCCAGCAGAGCCTCTGACCCTTCTAGCTGGGTCCTGATACATGTTTTCCA - 21061
21062 - TGCTGGCCATGTTATTTCTAGTCGCAGATCCTCTGGAGGGTGTGGGGGGGGTGCCGCCCC - 21121
21122 - AACTCTTGGAGATTCCAAGCAAAGCAGCTCTGAGAATAATGAGGTTTCTGACCCCCCAGT - 21181
21182 - GAAGCAGCTGAGGATGGGAACCACAGGGGTGCTCCCTCTGTCAGCAGCATTACCACTGTC - 21241
21242 - TACTCTAGCAGCTCCGGTGGGGAAGGAGAGGGATTTCTGTTGTCCCCAGTCTGGGCCCCT - 21301
21302 - GGTTATTGAAAAAGTTCGGAATTACTCTTTACCCTTGTGGAGTGTTCTGAGTGTTGGAAG - 21361
21362 - TACCCAGGAAGAAGCCCTGAGCAGGTGCCCTCAGGAGCAGTGCCCATGGCTCCCCACATC - 21421
21422 - AGCCAAGAGGCCCAACCCCAGGAAGCCACTCCTGCCCGGGGATGGGGAAGGTGGGCTGGG - 21481
21482 - TGGCTGTGTGCACTGCCCTGGGCCAGCTCACTTGAGCCTGCTGAGCCGCCTGGCCAAACA - 21541
21542 - TGAGCCTCTCTCCTGTTGTATCAGATGCTGTTCTGGGGACCTGCGCCAGGAGCCTCTGCC - 21601
21602 - AGGGCTTTAAATAGCTGCCCCCATTGATCTGGCTGCAGGCAGCAGCAGTCACACTGGGTC - 21661
21662 - AGCCTCCATCAGGTGCTCAGGTTTCCCTGAGGACTGGAGTCAGGTGCCAGGGAATCGCGT - 21721
21722 - GGTCTACCTTATGACCTGGTGCTCCCCACACCTGTCTCCTAGGCCTGGGGGGTGGGGAGG - 21781
21782 - ACTCCTGTCACTTCATCTGCGGCAAAATACAGCCCCCACCACTTACCAGAGAAAACTGTC - 21841
21842 - TGGCATTGTAGAGAGAGGGGTTTTGCCCTCAAAAGACTGTTGCTTACTTTCAGTAGAATG - 21901
21902 - GGGAATGACACTGGTATCTTCCTTAAGGGTTGTTATGGGGATGAAATGTATGTAAAGTGC - 21961
21962 - TCAATAGGGCACTGGACTCACTCCATTGATGGCTGTCTTTGCTCGAAGTGTCTTCCTGAT - 22021
22022 - GCTGCTGCTGTTGCTGCTTGTGCTTCTTCTGTGCTTACATTCTCTCTCTCTCACTCACTC - 22081
22082 - ACTCTGTCTCTCCTCTCCCCCGCCCCACCCCCTTTCTGACAAAGCCACCACCATTTTGTA - 22141
22142 - AGGAACTGTAGCTTCTCTCTGAAACTGCCGGGAAAGGGAAAATCTTTTTAAAATAGACAT - 22201
22202 - CACACAACCAACAGGGTCCCCTAGGTTCAGGCGGGGAGGTGAGGTCGAGTGAGA - 22255

SEQUENCE LISTING

```
<160> NUMBER OF SEQ ID NOS: 53

<210> SEQ ID NO 1
<211> LENGTH: 151
<212> TYPE: PRT
<213> ORGANISM: Oryctolagus cuniculus

<400> SEQUENCE: 1

Met Ser Lys Asn Thr Val Ser Ser Ala Arg Phe Arg Lys Val Asp Val
 1               5                  10                  15

Asp Glu Tyr Asp Glu Asn Lys Phe Val Asp Glu Glu Asp Gly Gly Asp
            20                  25                  30

Gly Gln Ala Gly Pro Asp Glu Gly Glu Val Asp Ser Cys Leu Arg Gln
        35                  40                  45

Gly Asn Met Thr Ala Ala Leu Gln Ala Ala Leu Lys Asn Pro Pro Ile
    50                  55                  60

Asn Thr Arg Ser Gln Ala Val Lys Asp Arg Ala Gly Ser Ile Val Leu
65                  70                  75                  80

Lys Val Leu Ile Ser Phe Lys Ala Gly Asp Ile Glu Lys Ala Val Gln
                85                  90                  95

Ser Leu Asp Arg Asn Gly Val Asp Leu Leu Met Lys Tyr Ile Tyr Lys
            100                 105                 110

Gly Phe Glu Ser Pro Ser Asp Asn Ser Ser Ala Val Leu Leu Gln Trp
        115                 120                 125

His Glu Lys Ala Leu Ala Ala Gly Gly Val Gly Ser Ile Val Arg Val
    130                 135                 140

Leu Thr Ala Arg Lys Thr Val
145                 150


<210> SEQ ID NO 2
<211> LENGTH: 317
<212> TYPE: PRT
```

-continued

```
<213> ORGANISM: Oryctolagus cuniculus
<220> FEATURE:
<221> NAME/KEY: VARIANT
<222> LOCATION: (1)...(317)
<223> OTHER INFORMATION: Xaa = Any Amino Acid

<400> SEQUENCE: 2

Asp Cys Arg Ser Ser Ser Asn Asn Arg Xaa Pro Lys Gly Gly Ala Ala
 1               5                  10                  15

Arg Ala Gly Gly Pro Ala Arg Pro Val Ser Leu Arg Glu Val Val Arg
            20                  25                  30

Tyr Leu Gly Gly Ser Ser Gly Ala Gly Gly Arg Leu Thr Arg Gly Arg
        35                  40                  45

Val Gln Gly Leu Leu Glu Glu Glu Ala Ala Ala Arg Gly Arg Leu Glu
    50                  55                  60

Arg Thr Arg Leu Gly Ala Leu Ala Leu Pro Arg Gly Asp Arg Pro Gly
65                  70                  75                  80

Arg Ala Pro Pro Ala Ala Ser Ala Arg Ala Ala Arg Asn Lys Arg Ala
                85                  90                  95

Gly Glu Glu Arg Val Leu Glu Lys Glu Glu Glu Glu Glu Glu Glu Glu
            100                 105                 110

Asp Asp Glu Asp Asp Asp Asp Asp Val Val Ser Glu Gly Ser Glu Val
        115                 120                 125

Pro Glu Ser Asp Arg Pro Ala Gly Ala Gln His His Gln Leu Asn Gly
    130                 135                 140

Gly Glu Arg Gly Pro Gln Thr Ala Lys Glu Arg Ala Lys Glu Trp Ser
145                 150                 155                 160

Leu Cys Gly Pro His Pro Gly Gln Glu Glu Gly Arg Gly Pro Ala Ala
                165                 170                 175

Gly Ser Gly Thr Arg Gln Val Phe Ser Met Ala Ala Leu Ser Lys Glu
            180                 185                 190

Gly Gly Ser Ala Ser Ser Thr Thr Gly Pro Asp Ser Pro Ser Pro Val
        195                 200                 205

Pro Leu Pro Pro Gly Lys Pro Ala Leu Pro Gly Ala Asp Gly Thr Pro
    210                 215                 220

Phe Gly Cys Pro Ala Gly Arg Lys Glu Lys Pro Ala Asp Pro Val Glu
225                 230                 235                 240

Trp Thr Val Met Asp Val Val Glu Tyr Phe Thr Glu Ala Gly Phe Pro
                245                 250                 255

Glu Gln Ala Thr Ala Phe Gln Glu Gln Glu Ile Asp Gly Lys Ser Leu
            260                 265                 270

Leu Leu Met Gln Arg Thr Asp Val Leu Thr Gly Leu Ser Ile Arg Leu
        275                 280                 285

Gly Pro Ala Leu Lys Ile Tyr Glu His His Ile Lys Val Leu Gln Gln
    290                 295                 300

Gly His Phe Glu Asp Asp Asp Pro Glu Gly Phe Leu Gly
305                 310                 315


<210> SEQ ID NO 3
<211> LENGTH: 232
<212> TYPE: PRT
<213> ORGANISM: Oryctolagus cuniculus

<400> SEQUENCE: 3

Ala Ser Ala Arg Ala Ala Arg Asn Lys Arg Ala Gly Glu Glu Arg Val
 1               5                  10                  15
```

-continued

```
Leu Glu Lys Glu Glu Glu Glu Glu Glu Glu Glu Asp Asp Glu Asp Asp
            20                  25                  30

Asp Asp Asp Val Val Ser Glu Gly Ser Glu Val Pro Glu Ser Asp Arg
        35                  40                  45

Pro Ala Gly Ala Gln His His Gln Leu Asn Gly Gly Glu Arg Gly Pro
    50                  55                  60

Gln Thr Ala Lys Glu Arg Ala Lys Glu Trp Ser Leu Cys Gly Pro His
65                  70                  75                  80

Pro Gly Gln Glu Glu Gly Arg Gly Pro Ala Ala Gly Ser Gly Thr Arg
                85                  90                  95

Gln Val Phe Ser Met Ala Ala Leu Ser Lys Glu Gly Gly Ser Ala Ser
            100                 105                 110

Ser Thr Thr Gly Pro Asp Ser Pro Ser Pro Val Pro Leu Pro Pro Gly
        115                 120                 125

Lys Pro Ala Leu Pro Gly Ala Asp Gly Thr Pro Phe Gly Cys Pro Ala
    130                 135                 140

Gly Arg Lys Glu Lys Pro Ala Asp Pro Val Glu Trp Thr Val Met Asp
145                 150                 155                 160

Val Val Glu Tyr Phe Thr Glu Ala Gly Phe Pro Glu Gln Ala Thr Ala
                165                 170                 175

Phe Gln Glu Gln Glu Ile Asp Gly Lys Ser Leu Leu Leu Met Gln Arg
            180                 185                 190

Thr Asp Val Leu Thr Gly Leu Ser Ile Arg Leu Gly Pro Ala Leu Lys
        195                 200                 205

Ile Tyr Glu His His Ile Lys Val Leu Gln Gln Gly His Phe Glu Asp
    210                 215                 220

Asp Asp Pro Glu Gly Phe Leu Gly
225                 230


<210> SEQ ID NO 4
<211> LENGTH: 252
<212> TYPE: PRT
<213> ORGANISM: Oryctolagus cuniculus

<400> SEQUENCE: 4

Thr Arg Leu Gly Ala Leu Ala Leu Pro Arg Gly Asp Arg Pro Gly Arg
 1               5                  10                  15

Ala Pro Pro Ala Ala Ser Ala Arg Ala Ala Arg Asn Lys Arg Ala Gly
            20                  25                  30

Glu Glu Arg Val Leu Glu Lys Glu Glu Glu Glu Glu Glu Glu Glu Asp
        35                  40                  45

Asp Glu Asp Asp Asp Asp Asp Val Val Ser Glu Gly Ser Glu Val Pro
    50                  55                  60

Glu Ser Asp Arg Pro Ala Gly Ala Gln His His Gln Leu Asn Gly Gly
65                  70                  75                  80

Glu Arg Gly Pro Gln Thr Ala Lys Glu Arg Ala Lys Glu Trp Ser Leu
                85                  90                  95

Cys Gly Pro His Pro Gly Gln Glu Glu Gly Arg Gly Pro Ala Ala Gly
            100                 105                 110

Ser Gly Thr Arg Gln Val Phe Ser Met Ala Ala Leu Ser Lys Glu Gly
        115                 120                 125

Gly Ser Ala Ser Ser Thr Thr Gly Pro Asp Ser Pro Ser Pro Val Pro
    130                 135                 140

Leu Pro Pro Gly Lys Pro Ala Leu Pro Gly Ala Asp Gly Thr Pro Phe
145                 150                 155                 160
```

-continued

```
Gly Cys Pro Ala Gly Arg Lys Glu Lys Pro Ala Asp Pro Val Glu Trp
                165                 170                 175

Thr Val Met Asp Val Val Glu Tyr Phe Thr Glu Ala Gly Phe Pro Glu
            180                 185                 190

Gln Ala Thr Ala Phe Gln Glu Gln Glu Ile Asp Gly Lys Ser Leu Leu
        195                 200                 205

Leu Met Gln Arg Thr Asp Val Leu Thr Gly Leu Ser Ile Arg Leu Gly
    210                 215                 220

Pro Ala Leu Lys Ile Tyr Glu His His Ile Lys Val Leu Gln Gln Gly
225                 230                 235                 240

His Phe Glu Asp Asp Asp Pro Glu Gly Phe Leu Gly
                245                 250


<210> SEQ ID NO 5
<211> LENGTH: 557
<212> TYPE: PRT
<213> ORGANISM: Oryctolagus cuniculus

<400> SEQUENCE: 5

Met Lys Asn Gln Asp Lys Lys Asn Gly Ala Ala Lys Gln Pro Asn Pro
 1               5                  10                  15

Lys Ser Ser Pro Gly Gln Pro Glu Ala Gly Ala Glu Gly Ala Gln Gly
            20                  25                  30

Arg Pro Gly Arg Pro Ala Pro Ala Arg Glu Ala Glu Gly Ala Ser Ser
        35                  40                  45

Gln Ala Pro Gly Arg Pro Glu Gly Ala Gln Ala Lys Thr Ala Gln Pro
    50                  55                  60

Gly Ala Leu Cys Asp Val Ser Glu Glu Leu Ser Arg Gln Leu Glu Asp
65                  70                  75                  80

Ile Leu Ser Thr Tyr Cys Val Asp Asn Asn Gln Gly Ala Pro Gly Glu
                85                  90                  95

Asp Gly Val Gln Gly Glu Pro Pro Glu Pro Glu Asp Ala Glu Lys Ser
            100                 105                 110

Arg Ala Tyr Val Ala Arg Asn Gly Glu Pro Glu Pro Gly Thr Pro Val
        115                 120                 125

Val Asn Gly Glu Lys Glu Thr Ser Lys Ala Glu Pro Gly Thr Glu Glu
    130                 135                 140

Ile Arg Thr Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205

Gln Met Lys Leu Leu Gln Lys Lys Gln Ser Gln Leu Val Gln Glu Lys
    210                 215                 220

Asp His Leu Arg Gly Glu His Ser Lys Ala Ile Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Lys Arg Lys Glu
            260                 265                 270

Val Thr Ser His Phe Gln Met Thr Leu Asn Asp Ile Gln Leu Gln Met
```

-continued

```
        275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
            340                 345                 350

Glu Arg His Gln Arg Glu Lys Asp Phe Leu Leu Lys Glu Ala Val Glu
        355                 360                 365

Ser Gln Arg Met Cys Glu Leu Met Lys Gln Gln Glu Thr His Leu Lys
    370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
            420                 425                 430

Arg Ser Arg Trp Glu Ser Ser Asn Lys Ala Leu Leu Glu Met Ala Glu
        435                 440                 445

Glu Lys Thr Leu Arg Asp Lys Glu Leu Glu Gly Leu Gln Val Lys Ile
    450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gly Gln Gly Pro Val
                485                 490                 495

Ser Asp Ser Gly Pro Glu Arg Arg Pro Glu Pro Ala Thr Thr Ser Lys
            500                 505                 510

Glu Gln Gly Val Glu Gly Pro Gly Ala Gln Val Pro Asn Ser Pro Arg
        515                 520                 525

Ala Thr Asp Ala Ser Cys Cys Ala Gly Ala Pro Ser Thr Glu Ala Ser
    530                 535                 540

Gly Gln Thr Gly Pro Gln Glu Pro Thr Thr Ala Thr Ala
545                 550                 555


<210> SEQ ID NO 6
<211> LENGTH: 151
<212> TYPE: PRT
<213> ORGANISM: Homo sapiens

<400> SEQUENCE: 6

Met Ser Lys Asn Thr Val Ser Ser Ala Arg Phe Arg Lys Val Asp Val
 1               5                  10                  15

Asp Glu Tyr Asp Glu Asn Lys Phe Val Asp Glu Glu Asp Gly Gly Asp
            20                  25                  30

Gly Gln Ala Gly Pro Asp Glu Gly Glu Val Asp Ser Cys Leu Arg Gln
        35                  40                  45

Gly Asn Met Thr Ala Ala Leu Gln Ala Ala Leu Lys Asn Pro Pro Ile
    50                  55                  60

Asn Thr Lys Ser Gln Ala Val Lys Asp Arg Ala Gly Ser Ile Val Leu
65                  70                  75                  80

Lys Val Leu Ile Ser Phe Lys Ala Asn Asp Ile Glu Lys Ala Val Gln
                85                  90                  95
```

-continued

Ser Leu Asp Lys Asn Gly Val Asp Leu Leu Met Lys Tyr Ile Tyr Lys
100 105 110

Gly Phe Glu Ser Pro Ser Asp Asn Ser Ser Ala Met Leu Leu Gln Trp
115 120 125

His Glu Lys Ala Leu Ala Ala Gly Gly Val Gly Ser Ile Val Arg Val
130 135 140

Leu Thr Ala Arg Lys Thr Val
145 150

<210> SEQ ID NO 7
<211> LENGTH: 217
<212> TYPE: PRT
<213> ORGANISM: Homo sapiens

<400> SEQUENCE: 7

Glu Glu Arg Val Leu Glu Lys Glu Glu Glu Glu Asp Asp Asp Glu Asp
1 5 10 15

Glu Asp Glu Glu Asp Asp Val Ser Glu Gly Ser Glu Val Pro Glu Ser
20 25 30

Asp Arg Pro Ala Gly Ala Gln His His Gln Leu Asn Gly Glu Arg Gly
35 40 45

Pro Gln Ser Ala Lys Glu Arg Val Lys Glu Trp Thr Pro Cys Gly Pro
50 55 60

His Gln Gly Gln Asp Glu Gly Arg Gly Pro Ala Pro Gly Ser Gly Thr
65 70 75 80

Arg Gln Val Phe Ser Met Ala Ala Met Asn Lys Glu Gly Gly Thr Ala
85 90 95

Ser Val Ala Thr Gly Pro Asp Ser Pro Ser Pro Val Pro Leu Pro Pro
100 105 110

Gly Lys Pro Ala Leu Pro Gly Ala Asp Gly Thr Pro Phe Gly Cys Pro
115 120 125

Pro Gly Arg Lys Glu Lys Pro Ser Asp Pro Val Glu Trp Thr Val Met
130 135 140

Asp Val Val Glu Tyr Phe Thr Glu Ala Gly Phe Pro Glu Gln Ala Thr
145 150 155 160

Ala Phe Gln Glu Gln Glu Ile Asp Gly Lys Ser Leu Leu Leu Met Gln
165 170 175

Arg Thr Asp Val Leu Thr Gly Leu Ser Ile Arg Leu Gly Pro Ala Leu
180 185 190

Lys Ile Tyr Glu His His Ile Lys Val Leu Gln Gln Gly His Phe Glu
195 200 205

Asp Asp Asp Pro Asp Gly Phe Leu Gly
210 215

<210> SEQ ID NO 8
<211> LENGTH: 530
<212> TYPE: PRT
<213> ORGANISM: Homo sapiens

<400> SEQUENCE: 8

Lys Ser Ser Pro Gly Gln Pro Glu Ala Gly Pro Glu Gly Ala Gln Glu
1 5 10 15

Arg Pro Ser Gln Ala Ala Pro Ala Val Glu Ala Glu Gly Pro Gly Ser
20 25 30

Ser Gln Ala Pro Arg Lys Pro Glu Gly Ala Gln Ala Arg Thr Ala Gln
35 40 45

-continued

```
Ser Gly Ala Leu Arg Asp Val Ser Glu Glu Leu Ser Arg Gln Leu Glu
    50                  55                  60

Asp Ile Leu Ser Thr Tyr Cys Val Asp Asn Asn Gln Gly Gly Pro Gly
65                  70                  75                  80

Glu Asp Gly Ala Gln Gly Glu Pro Ala Glu Pro Glu Asp Ala Glu Lys
                85                  90                  95

Ser Arg Thr Tyr Val Ala Arg Asn Gly Glu Pro Glu Pro Thr Pro Val
            100                 105                 110

Val Tyr Gly Glu Lys Glu Pro Ser Lys Gly Asp Pro Asn Thr Glu Glu
        115                 120                 125

Ile Arg Gln Ser Asp Glu Val Gly Asp Arg Asp His Arg Arg Pro Gln
    130                 135                 140

Glu Lys Lys Lys Ala Lys Gly Leu Gly Lys Glu Ile Thr Leu Leu Met
145                 150                 155                 160

Gln Thr Leu Asn Thr Leu Ser Thr Pro Glu Glu Lys Leu Ala Ala Leu
                165                 170                 175

Cys Lys Lys Tyr Ala Glu Leu Leu Glu Glu His Arg Asn Ser Gln Lys
            180                 185                 190

Gln Met Lys Leu Leu Gln Lys Lys Gln Ser Gln Leu Val Gln Glu Lys
        195                 200                 205

Asp His Leu Arg Gly Glu His Ser Lys Ala Val Leu Ala Arg Ser Lys
    210                 215                 220

Leu Glu Ser Leu Cys Arg Glu Leu Gln Arg His Asn Arg Ser Leu Lys
225                 230                 235                 240

Glu Glu Gly Val Gln Arg Ala Arg Glu Glu Glu Glu Lys Arg Lys Glu
                245                 250                 255

Val Thr Ser His Phe Gln Val Thr Leu Asn Asp Ile Gln Leu Gln Met
            260                 265                 270

Glu Gln His Asn Glu Arg Asn Ser Lys Leu Arg Gln Glu Asn Met Glu
        275                 280                 285

Leu Ala Glu Arg Leu Lys Lys Leu Ile Glu Gln Tyr Glu Leu Arg Glu
    290                 295                 300

Glu His Ile Asp Lys Val Phe Lys His Lys Asp Leu Gln Gln Gln Leu
305                 310                 315                 320

Val Asp Ala Lys Leu Gln Gln Ala Gln Glu Met Leu Lys Glu Ala Glu
                325                 330                 335

Glu Arg His Gln Arg Glu Lys Asp Phe Leu Leu Lys Glu Ala Val Glu
            340                 345                 350

Ser Gln Arg Met Cys Glu Leu Met Lys Gln Gln Glu Thr His Leu Lys
        355                 360                 365

Gln Gln Leu Ala Leu Tyr Thr Glu Lys Phe Glu Glu Phe Gln Asn Thr
    370                 375                 380

Leu Ser Lys Ser Ser Glu Val Phe Thr Thr Phe Lys Gln Glu Met Glu
385                 390                 395                 400

Lys Met Thr Lys Lys Ile Lys Lys Leu Glu Lys Glu Thr Thr Met Tyr
                405                 410                 415

Arg Ser Arg Trp Glu Ser Ser Asn Lys Ala Leu Leu Glu Met Ala Glu
            420                 425                 430

Glu Lys Thr Val Arg Asp Lys Glu Leu Glu Gly Leu Gln Val Lys Ile
        435                 440                 445

Gln Arg Leu Glu Lys Leu Cys Arg Ala Leu Gln Thr Glu Arg Asn Asp
    450                 455                 460

Leu Asn Lys Arg Val Gln Asp Leu Ser Ala Gly Gly Gln Gly Ser Leu
```

-continued

```
465                 470                 475                 480

Thr Asp Ser Gly Pro Glu Arg Arg Pro Glu Gly Pro Gly Ala Gln Ala
                485                 490                 495

Pro Ser Ser Pro Arg Val Thr Glu Ala Pro Cys Tyr Pro Gly Ala Pro
            500                 505                 510

Ser Thr Glu Ala Ser Gly Gln Thr Gly Pro Gln Glu Pro Thr Ser Ala
        515                 520                 525

Arg Ala
    530


<210> SEQ ID NO 9
<211> LENGTH: 20
<212> TYPE: PRT
<213> ORGANISM: Homo sapiens

<400> SEQUENCE: 9

Val Asp Val Asp Glu Tyr Asp Glu Asn Lys Phe Val Asp Glu Glu Asp
 1               5                  10                  15

Gly Gly Asp Gly
            20


<210> SEQ ID NO 10
<211> LENGTH: 1404
<212> TYPE: DNA
<213> ORGANISM: Oryctolagus cuniculus
<220> FEATURE:
<221> NAME/KEY: CDS
<222> LOCATION: (58)...(510)

<400> SEQUENCE: 10

aagcctcgca gcggtcgggg cggcgccgcg gaggctcgag ggcggcgggc ggcggcg atg      60
                                                               Met
                                                                1

tcg aag aac acg gtg tcg tcg gcg cgg ttc cgg aag gtg gac gtg gat        108
Ser Lys Asn Thr Val Ser Ser Ala Arg Phe Arg Lys Val Asp Val Asp
            5                  10                  15

gag tac gac gag aac aag ttc gtg gac gag gaa gac ggc ggc gac ggc        156
Glu Tyr Asp Glu Asn Lys Phe Val Asp Glu Glu Asp Gly Gly Asp Gly
        20                  25                  30

cag gcg ggg ccg gac gag ggc gag gtg gac tcg tgc ctg cgg caa ggg        204
Gln Ala Gly Pro Asp Glu Gly Glu Val Asp Ser Cys Leu Arg Gln Gly
    35                  40                  45

aac atg aca gcc gcc ctg cag gcg gcg ctg aag aac cct ccc atc aac        252
Asn Met Thr Ala Ala Leu Gln Ala Ala Leu Lys Asn Pro Pro Ile Asn
 50                  55                  60                  65

acc agg agc cag gcg gtg aag gac cgg gca ggc agc atc gtg ctg aag        300
Thr Arg Ser Gln Ala Val Lys Asp Arg Ala Gly Ser Ile Val Leu Lys
                70                  75                  80

gtg ctc atc tcc ttc aag gcc ggc gac ata gaa aag gcc gtg cag tcc        348
Val Leu Ile Ser Phe Lys Ala Gly Asp Ile Glu Lys Ala Val Gln Ser
            85                  90                  95

ctg gac agg aac ggc gtg gac ctg ctc atg aag tac atc tac aag ggc        396
Leu Asp Arg Asn Gly Val Asp Leu Leu Met Lys Tyr Ile Tyr Lys Gly
        100                 105                 110

ttc gag agc ccc tcc gac aac agc agc gcc gtg ctc ctg cag tgg cac        444
Phe Glu Ser Pro Ser Asp Asn Ser Ser Ala Val Leu Leu Gln Trp His
    115                 120                 125

gag aag gcg ctg gct gca gga gga gtg ggc tcc atc gtc cgt gtc ctg        492
Glu Lys Ala Leu Ala Ala Gly Gly Val Gly Ser Ile Val Arg Val Leu
130                 135                 140                 145
```

-continued

```
act gca agg aaa acc gtg tagcctggca ggaacgggtg cctgccgggg           540
Thr Ala Arg Lys Thr Val
                150

agcgggagct gccggtacaa agaccaaaac gcccagatgc cgccgctgcc ctgtgggcgg    600

cgtctgttcc cagcttcgct tttcccttt cccgtgtctg tcaggattac ataaggtttc     660

ccttcgtgag aatcggagtg gcgcagaggg tcctgttcat acgcgccgtg cgtccggctg    720

tgtaagaccc ctgccttcag tgtccttgag caacggtagc gtgtcgccgg ctgggtttgg    780

ttttgtcgtg gagggatctg gtcagaattt gaggccagtt tcctaactca ttgctggtca    840

ggaaatgatc ttcatttaaa aaaaaaaaaa agactggcag ctattatgca aaactggacc    900

ctcttccctt atttaagcag agtgagtttc tggaaccagt ggtgcccccc cccccgcccc    960

ggccgccgtc ctgctcaagg gaagcctccc tgcagagcag cagagcccct gggcaggagc   1020

gccgcgtccc gctcccagga gacagcatgc gcggtcacgc ggcacttcct gtgcctccca   1080

gccccagtgc cccggagttc ttcagggcga cagggacctc agaagactgg atccgatcca   1140

gacagacgcc cattcttggt tcagctcagt gttttcaaaa ggaacgtgct accgtgggta   1200

gagcacactg gttctcagaa cacggccggc gcttgacggt tgtcacagct ccagaacaaa   1260

tcctgggaga caggcgagcg cgagtcgccg ggcaggaatt ccacacactc gtgctgtttt   1320

tgatacctgc tttttgtttt gttttgtaaa aatgatgcac ttgagaaaat aaaacgtcag   1380

tgttgacaaa aaaaaaaaaa aaaa                                          1404


<210> SEQ ID NO 11
<211> LENGTH: 1617
<212> TYPE: DNA
<213> ORGANISM: Oryctolagus cuniculus
<220> FEATURE:
<221> NAME/KEY: CDS
<222> LOCATION: (1)...(951)

<400> SEQUENCE: 11

gac tgc cgc agc agc agc aac aac cgc tag ccg aag ggt ggc gcg gcg       48
Asp Cys Arg Ser Ser Ser Asn Asn Arg  *  Pro Lys Gly Gly Ala Ala
 1               5                       10                  15

cgg gcc ggc ggc ccg gcg cgg ccc gtg agc ctg cgg gaa gtc gtg cgc       96
Arg Ala Gly Gly Pro Ala Arg Pro Val Ser Leu Arg Glu Val Val Arg
                20                  25                  30

tac ctc ggg ggt agc agc ggc gct ggc ggc cgc ctg acc cgc ggc cgc      144
Tyr Leu Gly Gly Ser Ser Gly Ala Gly Gly Arg Leu Thr Arg Gly Arg
            35                  40                  45

gtg cag ggt ctg ctg gaa gag gag gcg gcg gcg cgg ggc cgc ctg gag      192
Val Gln Gly Leu Leu Glu Glu Glu Ala Ala Ala Arg Gly Arg Leu Glu
        50                  55                  60

cgc acc cgt ctc gga gcg ctt gcg ctg ccc cgc ggg gac agg ccc gga      240
Arg Thr Arg Leu Gly Ala Leu Ala Leu Pro Arg Gly Asp Arg Pro Gly
    65                  70                  75

cgg gcg cca ccg gcc gcc agc gcc cgc gcg gcg cgg aac aag aga gct      288
Arg Ala Pro Pro Ala Ala Ser Ala Arg Ala Ala Arg Asn Lys Arg Ala
80                  85                  90                  95

ggc gag gag cga gtg ctt gaa aag gag gag gag gag gag gag gag gaa      336
Gly Glu Glu Arg Val Leu Glu Lys Glu Glu Glu Glu Glu Glu Glu Glu
                100                 105                 110

gac gac gag gac gac gac gac gac gtc gtg tcc gag ggc tcg gag gtg      384
Asp Asp Glu Asp Asp Asp Asp Asp Val Val Ser Glu Gly Ser Glu Val
            115                 120                 125

ccc gag agc gat cgt ccc gcg ggt gcg cag cat cac cag ctg aat ggc      432
Pro Glu Ser Asp Arg Pro Ala Gly Ala Gln His His Gln Leu Asn Gly
```

-continued

```
        130                 135                 140

ggc gag cgc ggc ccg cag acc gcc aag gag cgg gcc aag gag tgg tcg      480
Gly Glu Arg Gly Pro Gln Thr Ala Lys Glu Arg Ala Lys Glu Trp Ser
    145                 150                 155

ctg tgt ggc ccc cac cct ggc cag gag gaa ggg cgg ggg ccg gcc gcg      528
Leu Cys Gly Pro His Pro Gly Gln Glu Glu Gly Arg Gly Pro Ala Ala
160                 165                 170                 175

ggc agt ggc acc cgc cag gtg ttc tcc atg gcg gcc ttg agt aag gag      576
Gly Ser Gly Thr Arg Gln Val Phe Ser Met Ala Ala Leu Ser Lys Glu
                180                 185                 190

ggg gga tca gcc tct tcg acc acc ggg cct gac tcc ccg tcc ccg gtg      624
Gly Gly Ser Ala Ser Ser Thr Thr Gly Pro Asp Ser Pro Ser Pro Val
            195                 200                 205

cct ttg ccc ccc ggg aag cca gcc ctc cca gga gcc gat ggg acc ccc      672
Pro Leu Pro Pro Gly Lys Pro Ala Leu Pro Gly Ala Asp Gly Thr Pro
        210                 215                 220

ttt ggc tgc cct gcc ggg cgc aaa gag aag ccg gca gac ccc gtg gag      720
Phe Gly Cys Pro Ala Gly Arg Lys Glu Lys Pro Ala Asp Pro Val Glu
    225                 230                 235

tgg aca gtc atg gac gtc gtg gag tac ttc acc gag gcg ggc ttc cct      768
Trp Thr Val Met Asp Val Val Glu Tyr Phe Thr Glu Ala Gly Phe Pro
240                 245                 250                 255

gag caa gcc acg gct ttc cag gag cag gag atc gac ggc aag tcc ctg      816
Glu Gln Ala Thr Ala Phe Gln Glu Gln Glu Ile Asp Gly Lys Ser Leu
                260                 265                 270

ctg ctc atg cag cgc acc gat gtc ctc acc ggc ctg tcc atc cgc ctg      864
Leu Leu Met Gln Arg Thr Asp Val Leu Thr Gly Leu Ser Ile Arg Leu
            275                 280                 285

ggg cca gcg ttg aaa atc tat gag cac cat atc aag gtg ctg cag cag      912
Gly Pro Ala Leu Lys Ile Tyr Glu His His Ile Lys Val Leu Gln Gln
        290                 295                 300

ggt cac ttc gag gac gat gac ccg gaa ggc ttc ctg gga tgagcacaga       961
Gly His Phe Glu Asp Asp Asp Pro Glu Gly Phe Leu Gly
    305                 310                 315

gccgccgcgc cccttgtccc cacccccacc ccgcctggac ccattcctgc ctccatgtca   1021

cccaaggtgt cccagaggcc aggagctgga ctgggcaggc gaggggtgcg gacctaccct   1081

gattctggta gggggcgggg ccttgctgtg ctcattgcta cccccccacc ccgtgtgtgt   1141

ctctgcacct gcccccagca cacccctccc ggagcctgga tgtcgcctgg gactctggcc   1201

tgctcatttt gcccccagat cagccccctc cctccctcct gtcccaggac attttttaaa   1261

agaaaaaaag gaaaaaaaaa aattggggag ggggctggga aggtgcccca agatcctcct   1321

cggcccaacc aggtgtttat tcctatatat atatatatat gttttgttct gcctgttttt   1381

cgtttttggg tgcgtggcct ttcttccctc ccaccaccac tcatggcccc agccctgctc   1441

gccctgtcgg cgggagcagc tgggaatggg aggagggtgg gaccttgggt ctgtctccca   1501

ccctctctcc cgttggttct gttgtcgctc cagctggctg tattgctttt taatattgca   1561

ccgaagggtt gttttttttt ttttaaataa aattttaaaa aaaggaaaaa aaaaaa       1617
```

```
<210> SEQ ID NO 12
<211> LENGTH: 1362
<212> TYPE: DNA
<213> ORGANISM: Oryctolagus cuniculus
<220> FEATURE:
<221> NAME/KEY: CDS
<222> LOCATION: (1)...(696)

<400> SEQUENCE: 12
```

-continued

```
gcc agc gcc cgc gcg gcg cgg aac aag aga gct ggc gag gag cga gtg        48
Ala Ser Ala Arg Ala Ala Arg Asn Lys Arg Ala Gly Glu Glu Arg Val
 1               5                  10                  15

ctt gaa aag gag gag gag gag gag gag gag gaa gac gac gag gac gac        96
Leu Glu Lys Glu Glu Glu Glu Glu Glu Glu Glu Asp Asp Glu Asp Asp
            20                  25                  30

gac gac gac gtc gtg tcc gag ggc tcg gag gtg ccc gag agc gat cgt       144
Asp Asp Asp Val Val Ser Glu Gly Ser Glu Val Pro Glu Ser Asp Arg
        35                  40                  45

ccc gcg ggt gcg cag cat cac cag ctg aat ggc ggc gag cgc ggc ccg       192
Pro Ala Gly Ala Gln His His Gln Leu Asn Gly Gly Glu Arg Gly Pro
    50                  55                  60

cag acc gcc aag gag cgg gcc aag gag tgg tcg ctg tgt ggc ccc cac       240
Gln Thr Ala Lys Glu Arg Ala Lys Glu Trp Ser Leu Cys Gly Pro His
 65                 70                  75                  80

cct ggc cag gag gaa ggg cgg ggg ccg gcc gcg ggc agt ggc acc cgc       288
Pro Gly Gln Glu Glu Gly Arg Gly Pro Ala Ala Gly Ser Gly Thr Arg
                85                  90                  95

cag gtg ttc tcc atg gcg gcc ttg agt aag gag ggg gga tca gcc tct       336
Gln Val Phe Ser Met Ala Ala Leu Ser Lys Glu Gly Gly Ser Ala Ser
            100                 105                 110

tcg acc acc ggg cct gac tcc ccg tcc ccg gtg cct ttg ccc ccc ggg       384
Ser Thr Thr Gly Pro Asp Ser Pro Ser Pro Val Pro Leu Pro Pro Gly
        115                 120                 125

aag cca gcc ctc cca gga gcc gat ggg acc ccc ttt ggc tgc cct gcc       432
Lys Pro Ala Leu Pro Gly Ala Asp Gly Thr Pro Phe Gly Cys Pro Ala
    130                 135                 140

ggg cgc aaa gag aag ccg gca gac ccc gtg gag tgg aca gtc atg gac       480
Gly Arg Lys Glu Lys Pro Ala Asp Pro Val Glu Trp Thr Val Met Asp
145                 150                 155                 160

gtc gtg gag tac ttc acc gag gcg ggc ttc cct gag caa gcc acg gct       528
Val Val Glu Tyr Phe Thr Glu Ala Gly Phe Pro Glu Gln Ala Thr Ala
                165                 170                 175

ttc cag gag cag gag atc gac ggc aag tcc ctg ctg ctc atg cag cgc       576
Phe Gln Glu Gln Glu Ile Asp Gly Lys Ser Leu Leu Leu Met Gln Arg
            180                 185                 190

acc gat gtc ctc acc ggc ctg tcc atc cgc ctg ggg cca gcg ttg aaa       624
Thr Asp Val Leu Thr Gly Leu Ser Ile Arg Leu Gly Pro Ala Leu Lys
        195                 200                 205

atc tat gag cac cat atc aag gtg ctg cag cag ggt cac ttc gag gac       672
Ile Tyr Glu His His Ile Lys Val Leu Gln Gln Gly His Phe Glu Asp
    210                 215                 220

gat gac ccg gaa ggc ttc ctg gga tgagcacaga gccgccgcgc cccttgtccc      726
Asp Asp Pro Glu Gly Phe Leu Gly
225                 230

cacccccacc ccgcctggac ccattcctgc ctccatgtca cccaaggtgt cccagaggcc     786

aggagctgga ctgggcaggc gaggggtgcg gacctaccct gattctggta gggggcgggg     846

ccttgctgtg ctcattgcta ccccccccacc ccgtgtgtgt ctctgcacct gcccccagca    906

cacccctccc ggagcctgga tgtcgcctgg gactctggcc tgctcatttt gcccccagat     966

cagccccctc cctccctcct gtcccaggac attttttaaa agaaaaaaag gaaaaaaaaa    1026

aattggggag gggctggga aggtgcccca agatcctcct cggcccaacc aggtgtttat     1086

tcctatatat atatatatat gttttgttct gcctgttttt cgttttttgg tgcgtggcct    1146

ttcttccctc ccaccaccac tcatggcccc agccctgctc gccctgtcgg cgggagcagc    1206

tgggaatggg aggagggtgg gaccttgggt ctgtctccca ccctctctcc cgttggttct    1266

gttgtcgctc cagctggctg tattgctttt taatattgca ccgaagggtt gttttttttt    1326
```

-continued

```
ttttaaataa aattttaaaa aaaggaaaaa aaaaaa                          1362


<210> SEQ ID NO 13
<211> LENGTH: 1422
<212> TYPE: DNA
<213> ORGANISM: Oryctolagus cuniculus
<220> FEATURE:
<221> NAME/KEY: CDS
<222> LOCATION: (1)...(756)

<400> SEQUENCE: 13

acc cgt ctc gga gcg ctt gcg ctg ccc cgc ggg gac agg ccc gga cgg       48
Thr Arg Leu Gly Ala Leu Ala Leu Pro Arg Gly Asp Arg Pro Gly Arg
 1               5                  10                  15

gcg cca ccg gcc gcc agc gcc cgc gcg gcg cgg aac aag aga gct ggc       96
Ala Pro Pro Ala Ala Ser Ala Arg Ala Ala Arg Asn Lys Arg Ala Gly
            20                  25                  30

gag gag cga gtg ctt gaa aag gag gag gag gag gag gag gag gaa gac      144
Glu Glu Arg Val Leu Glu Lys Glu Glu Glu Glu Glu Glu Glu Glu Asp
        35                  40                  45

gac gag gac gac gac gac gac gtc gtg tcc gag ggc tcg gag gtg ccc      192
Asp Glu Asp Asp Asp Asp Asp Val Val Ser Glu Gly Ser Glu Val Pro
    50                  55                  60

gag agc gat cgt ccc gcg ggt gcg cag cat cac cag ctg aat ggc ggc      240
Glu Ser Asp Arg Pro Ala Gly Ala Gln His His Gln Leu Asn Gly Gly
 65                  70                  75                  80

gag cgc ggc ccg cag acc gcc aag gag cgg gcc aag gag tgg tcg ctg      288
Glu Arg Gly Pro Gln Thr Ala Lys Glu Arg Ala Lys Glu Trp Ser Leu
                85                  90                  95

tgt ggc ccc cac cct ggc cag gag gaa ggg cgg ggg ccg gcc gcg ggc      336
Cys Gly Pro His Pro Gly Gln Glu Glu Gly Arg Gly Pro Ala Ala Gly
           100                 105                 110

agt ggc acc cgc cag gtg ttc tcc atg gcg gcc ttg agt aag gag ggg      384
Ser Gly Thr Arg Gln Val Phe Ser Met Ala Ala Leu Ser Lys Glu Gly
       115                 120                 125

gga tca gcc tct tcg acc acc ggg cct gac tcc ccg tcc ccg gtg cct      432
Gly Ser Ala Ser Ser Thr Thr Gly Pro Asp Ser Pro Ser Pro Val Pro
   130                 135                 140

ttg ccc ccc ggg aag cca gcc ctc cca gga gcc gat ggg acc ccc ttt      480
Leu Pro Pro Gly Lys Pro Ala Leu Pro Gly Ala Asp Gly Thr Pro Phe
145                 150                 155                 160

ggc tgc cct gcc ggg cgc aaa gag aag ccg gca gac ccc gtg gag tgg      528
Gly Cys Pro Ala Gly Arg Lys Glu Lys Pro Ala Asp Pro Val Glu Trp
                165                 170                 175

aca gtc atg gac gtc gtg gag tac ttc acc gag gcg ggc ttc cct gag      576
Thr Val Met Asp Val Val Glu Tyr Phe Thr Glu Ala Gly Phe Pro Glu
           180                 185                 190

caa gcc acg gct ttc cag gag cag gag atc gac ggc aag tcc ctg ctg      624
Gln Ala Thr Ala Phe Gln Glu Gln Glu Ile Asp Gly Lys Ser Leu Leu
       195                 200                 205

ctc atg cag cgc acc gat gtc ctc acc ggc ctg tcc atc cgc ctg ggg      672
Leu Met Gln Arg Thr Asp Val Leu Thr Gly Leu Ser Ile Arg Leu Gly
   210                 215                 220

cca gcg ttg aaa atc tat gag cac cat atc aag gtg ctg cag cag ggt      720
Pro Ala Leu Lys Ile Tyr Glu His His Ile Lys Val Leu Gln Gln Gly
225                 230                 235                 240

cac ttc gag gac gat gac ccg gaa ggc ttc ctg gga tgagcacaga           766
His Phe Glu Asp Asp Asp Pro Glu Gly Phe Leu Gly
                245                 250

gccgccgcgc cccttgtccc cacccccacc ccgcctggac ccattcctgc ctccatgtca    826
```

-continued

```
cccaaggtgt cccagaggcc aggagctgga ctgggcaggc gaggggtgcg gacctaccct    886

gattctggta gggggcgggg ccttgctgtg ctcattgcta cccccccacc ccgtgtgtgt    946

ctctgcacct gcccccagca cacccctccc ggagcctgga tgtcgcctgg gactctggcc   1006

tgctcatttt gcccccagat cagccccctc cctccctcct gtcccaggac attttttaaa   1066

agaaaaaaag gaaaaaaaaa aattggggag ggggctggga aggtgcccca agatcctcct   1126

cggcccaacc aggtgtttat tcctatatat atatatatat gttttgttct gcctgttttt   1186

cgtttttggg tgcgtggcct ttcttccctc ccaccaccac tcatggcccc agccctgctc   1246

gccctgtcgg cgggagcagc tgggaatggg aggagggtgg gaccttgggt ctgtctccca   1306

ccctctctcc cgttggttct gttgtcgctc cagctggctg tattgctttt taatattgca   1366

ccgaagggtt gttttttttt ttttaaataa aattttaaaa aaaggaaaaa aaaaaa       1422
```

<210> SEQ ID NO 14
<211> LENGTH: 4722
<212> TYPE: DNA
<213> ORGANISM: Oryctolagus cuniculus
<220> FEATURE:
<221> NAME/KEY: CDS
<222> LOCATION: (61)...(1731)

<400> SEQUENCE: 14

```
gtggaaaata gcaactgtgt ttctcaagga tccaatccca acctaaggtg gcagcgcaca     60

atg aag aat caa gac aaa aag aac ggg gct gcc aaa cag ccc aac ccc      108
Met Lys Asn Gln Asp Lys Lys Asn Gly Ala Ala Lys Gln Pro Asn Pro
 1               5                  10                  15

aaa agc agc ccg gga cag ccg gaa gca gga gcg gag gga gcc cag ggg      156
Lys Ser Ser Pro Gly Gln Pro Glu Ala Gly Ala Glu Gly Ala Gln Gly
            20                  25                  30

cgg ccc ggc cgg ccg gcc ccc gcc cga gaa gcc gaa ggt gcc agc agc      204
Arg Pro Gly Arg Pro Ala Pro Ala Arg Glu Ala Glu Gly Ala Ser Ser
        35                  40                  45

cag gct ccc ggg agg ccg gag ggg gct caa gcc aaa act gct cag cct      252
Gln Ala Pro Gly Arg Pro Glu Gly Ala Gln Ala Lys Thr Ala Gln Pro
    50                  55                  60

ggg gcg ctc tgt gat gtc tct gag gag ctg agc cgc cag ttg gaa gac      300
Gly Ala Leu Cys Asp Val Ser Glu Glu Leu Ser Arg Gln Leu Glu Asp
 65                  70                  75                  80

ata ctc agt aca tac tgt gtg gac aac aac cag ggg gcc ccg ggt gag      348
Ile Leu Ser Thr Tyr Cys Val Asp Asn Asn Gln Gly Ala Pro Gly Glu
                85                  90                  95

gat ggg gtc cag ggt gag ccc cct gaa cct gaa gat gca gag aag tct      396
Asp Gly Val Gln Gly Glu Pro Pro Glu Pro Glu Asp Ala Glu Lys Ser
            100                 105                 110

cgc gcc tat gtg gca agg aat ggg gag ccg gag ccg ggc acc cca gta      444
Arg Ala Tyr Val Ala Arg Asn Gly Glu Pro Glu Pro Gly Thr Pro Val
        115                 120                 125

gtc aat ggc gag aag gag acc tcc aag gca gag ccg ggc acg gaa gag      492
Val Asn Gly Glu Lys Glu Thr Ser Lys Ala Glu Pro Gly Thr Glu Glu
    130                 135                 140

atc cgg acg agc gat gag gtc gga gac cga gac cac cgg agg cca cag      540
Ile Arg Thr Ser Asp Glu Val Gly Asp Arg Asp His Arg Arg Pro Gln
145                 150                 155                 160

gaa aag aag aag gcc aag ggt ctg gga aag gag atc acg ctg ctg atg      588
Glu Lys Lys Lys Ala Lys Gly Leu Gly Lys Glu Ile Thr Leu Leu Met
                165                 170                 175

cag aca ctg aac acg ctg agc acc cca gag gag aag ctg gcg gct ctg      636
```

-continued

```
Gln Thr Leu Asn Thr Leu Ser Thr Pro Glu Glu Lys Leu Ala Ala Leu
            180                 185                 190

tgc aag aag tat gcg gaa ctg ctc gag gag cac cgg aac tcg cag aag      684
Cys Lys Lys Tyr Ala Glu Leu Leu Glu Glu His Arg Asn Ser Gln Lys
        195                 200                 205

cag atg aag ctg ctg cag aag aag cag agc cag ctg gtg cag gag aag      732
Gln Met Lys Leu Leu Gln Lys Lys Gln Ser Gln Leu Val Gln Glu Lys
    210                 215                 220

gac cac ctg cgt ggc gag cac agc aag gcc atc ctg gcc cgc agc aag      780
Asp His Leu Arg Gly Glu His Ser Lys Ala Ile Leu Ala Arg Ser Lys
225                 230                 235                 240

ctc gag agc ctg tgc cgg gag ctg cag cgg cac aac cgc tcg ctc aag      828
Leu Glu Ser Leu Cys Arg Glu Leu Gln Arg His Asn Arg Ser Leu Lys
                245                 250                 255

gaa gaa ggt gtg cag cga gcc cga gag gag gag gag aag cgc aag gag      876
Glu Glu Gly Val Gln Arg Ala Arg Glu Glu Glu Glu Lys Arg Lys Glu
            260                 265                 270

gtg acg tca cac ttc cag atg acg ctc aac gac att cag ctg cag atg      924
Val Thr Ser His Phe Gln Met Thr Leu Asn Asp Ile Gln Leu Gln Met
        275                 280                 285

gag cag cac aac gag cgc aac tcc aag ctg cgc cag gag aac atg gag      972
Glu Gln His Asn Glu Arg Asn Ser Lys Leu Arg Gln Glu Asn Met Glu
    290                 295                 300

ctg gcc gag cgg ctc aag aag ctg att gag cag tac gag ctg cga gaa     1020
Leu Ala Glu Arg Leu Lys Lys Leu Ile Glu Gln Tyr Glu Leu Arg Glu
305                 310                 315                 320

gag cac atc gac aaa gtc ttc aaa cac aag gat ctg cag cag cag ctg     1068
Glu His Ile Asp Lys Val Phe Lys His Lys Asp Leu Gln Gln Gln Leu
                325                 330                 335

gtg gac gcc aag ctc cag cag gcc cag gag atg ctg aag gag gca gag     1116
Val Asp Ala Lys Leu Gln Gln Ala Gln Glu Met Leu Lys Glu Ala Glu
            340                 345                 350

gag cgg cac cag cgg gag aag gac ttt ctc ctg aag gag gcc gtg gag     1164
Glu Arg His Gln Arg Glu Lys Asp Phe Leu Leu Lys Glu Ala Val Glu
        355                 360                 365

tcc cag agg atg tgc gag ctg atg aag caa cag gag acc cac ctg aag     1212
Ser Gln Arg Met Cys Glu Leu Met Lys Gln Gln Glu Thr His Leu Lys
    370                 375                 380

cag cag ctt gcc cta tac aca gag aag ttt gag gag ttc cag aac act     1260
Gln Gln Leu Ala Leu Tyr Thr Glu Lys Phe Glu Glu Phe Gln Asn Thr
385                 390                 395                 400

ctt tcc aaa agc agc gag gtg ttc acc aca ttc aaa cag gaa atg gaa     1308
Leu Ser Lys Ser Ser Glu Val Phe Thr Thr Phe Lys Gln Glu Met Glu
                405                 410                 415

aag atg aca aag aag atc aag aag ctg gag aaa gag acc acc atg tac     1356
Lys Met Thr Lys Lys Ile Lys Lys Leu Glu Lys Glu Thr Thr Met Tyr
            420                 425                 430

cgt tcc cgg tgg gag agc agc aac aag gcc ctg ctt gag atg gct gag     1404
Arg Ser Arg Trp Glu Ser Ser Asn Lys Ala Leu Leu Glu Met Ala Glu
        435                 440                 445

gag aaa aca ctc cgg gac aaa gag ctg gaa ggc ctg cag gtg aaa atc     1452
Glu Lys Thr Leu Arg Asp Lys Glu Leu Glu Gly Leu Gln Val Lys Ile
    450                 455                 460

cag cgg ctg gag aag ctg tgc cgg gca ctg cag aca gag cgc aat gac     1500
Gln Arg Leu Glu Lys Leu Cys Arg Ala Leu Gln Thr Glu Arg Asn Asp
465                 470                 475                 480

ctg aac aag agg gtg cag gac ctg agt gcc ggt ggc cag ggc ccc gtc     1548
Leu Asn Lys Arg Val Gln Asp Leu Ser Ala Gly Gly Gln Gly Pro Val
                485                 490                 495
```

-continued

```
tcc gac agc ggt cct gag cgg agg cca gag ccc gcc acc acc tcc aag      1596
Ser Asp Ser Gly Pro Glu Arg Arg Pro Glu Pro Ala Thr Thr Ser Lys
            500                 505                 510

gag cag ggt gtc gag ggc ccc ggg gct caa gta ccc aac tct cca agg      1644
Glu Gln Gly Val Glu Gly Pro Gly Ala Gln Val Pro Asn Ser Pro Arg
        515                 520                 525

gcc aca gac gct tcc tgc tgc gca ggt gca ccc agc aca gag gca tca      1692
Ala Thr Asp Ala Ser Cys Cys Ala Gly Ala Pro Ser Thr Glu Ala Ser
    530                 535                 540

ggc cag aca ggg ccc cag gag ccc acc act gcc act gcc tagagagctt      1741
Gly Gln Thr Gly Pro Gln Glu Pro Thr Thr Ala Thr Ala
545                 550                 555

ggtgctgggg tgtgccagga agggagcagg cagcccagcc aggcctggcc cagcccaggc    1801

tcccatgcta agcagtccgg tgctgaggcc aggatgttct gacctggctg gcacctgacc    1861

ctctgcagtc ttggattttg tgggtcagtt ttacatgcat atggcacaca tgcaaggcct    1921

cacacatttg tgtctctaag tgtactgtgg gcttgcatcg gggtgacga tggacagatg     1981

aagccagcgg ctcccttgtg agctgaagtc ttacggagga gacggcgtct gcactgccat    2041

cgcagtgacc tgcaggacga gttccttgag ctttccctgc ctgctttgag gctgagaccc    2101

ctcccggccc ttcagagctc ctgacaggtg atacacaccc agccttgacc gcacttctct    2161

tgggtagctg ggctctccta gcctccccca gaggcgccat tgcttctctt gacttggaga    2221

ggggatgccc aggcgtggcc ttggcaggca ctgggagcta gtgattgggc tgctctcctg    2281

cctcgagcag gggcaggagt gtttctggtg ggatgatgcg ctcgctggtc aggagccccg    2341

tgggcgctgc ttcccccgcc ctctggtgat gccaggacca ggccagtgat gcttctcagt    2401

agccttacca ttcacaggtg cctctccagc ccgcacagtg agtgacaaga tcatccaaag    2461

gattccttct gaaggtgttc gtttcgtttt gttttgttgc acgtgacggt ttgtattgag    2521

gaccctctga ggaagagggg tgctgtagca gtggtccctg cgtgcctggc tccagtgtcc    2581

tgccctcccc cccctcgcca tggctcctcg gccgccttgg tgctgaggtt tctgtttggt    2641

gagatcaggt tgtctgttca gagagaagag gcgtctgatg gctttgccgc cagcttgcct    2701

gcgggcctca atcccgggag gccgcccggt tcccgtcact gttgtccccg tgcagtgcgt    2761

tgctggtccc caggaccagc tgctcgtttg ctgtatgggt cagtttctgc ttcctgcccc    2821

ccactccacc taactgcaat ccttggggtt tccctggttc tcgtccctgg tacctctgtg    2881

cccaagaagt agccttcttt gggattcttg ttctgcccat gcgggagctg ctgctgtctg    2941

acaggtgagg cctgagactc agcggctgac agagctgcag agctctgcac ggtggctccc    3001

ggggcggcct ctgtgtgctg cacaccgctg ctctgctggc actggccagt ctgtgcagag    3061

catttgagta ctggctcagg agggagggct ctgctggcct cgagggacag cgccacgtct    3121

ccagctgggc tcagggagag ccccagactg gctgcgtagg gtgcttgggg tttgcttctt    3181

gcagtatttc ttggaagctg ttttgttgtc ctgctattcc ttcatcttcc acagtccacg    3241

ctcagccttt aacttggatc cctcacataa cagggttcat gagacccgca agtacgccca    3301

agctacgtat ggctgaggcc agctggcagg tgaatggcac gccattgctg ctgctaatcc    3361

ctggcatatc tttagttcac ctcgaaatgc ccccgccaca gtgcaagcag tgagtccacg    3421

tgccaccctg ggctgaatcc cacccccctgt gagtgttgcc cgagattgtg tctcttctga   3481

atgccttcac tgggaatggc ctctgccgcc tcctgctcag ggaggctttc cccttccctc    3541

agcccctgtg ccagactgag gtacaagaac cgccaagccc atgcaaggtg tggctaggcg    3601

ccagggtgca ggaaggaggc aggtagctgc ctgcaccctt gaaagccaag aggcctacgg    3661
```

-continued

```
tggcctccat cctggcttgc ctcacttcag ctacctcgca tagcccaggg gtggggctat   3721

tggattccag ggtgggggga tgggaagctg caggggggcag gtggctctca ctaggcttcc   3781

cagctcagga atgtgggcct caggtagggg agagcctttg ctccactcca cccatttgca   3841

ggcatctagg ccagtctaga tggcgacccc ttctcttcct ctccattgac caaatcgtac   3901

ctgtctctcc agctgctcgc ttgctctgct ttccaaagtc agcccaggta cccaggtgcc   3961

gcccacattg gcctggaacc tggaccagag gcaagggagg tggcctatcc ttgagtgata   4021

gccagtgcct tcctcacccg gtggcttcca tgcctgtgac ctcagattta ggaccaagag   4081

ctgtgttggt ttcttacgtt gtgagctttc cctccagggg accacagcag gtgaggctcg   4141

gagcccagag cccttggcgc cgccagcagt aacttgtgtc cggaccttgt ccagctgagc   4201

gcttcgtgta tgactcagct tcgtgtgtga gtccagcgga gtgcgtcacg tgacctagac   4261

tcagcggtgt cagccgcact ttgatttgtt tgttttccat gaggtttttg gaccatgggc   4321

ttagctcagg caacttttct gtaaggagaa tgttaacttt ctgtaaagat gcttatttaa   4381

ctaacgcctg cttcccccac tcccaaccag gtggccaccg agagctcacc aggaggccaa   4441

tagagctgct ccagctctcc catcttgcac cgcacaaagg tggccgcccc agggacagcc   4501

aggcacctgc ctgggggagg ggcttctctt ccttatggcc tggccatcta gattgtttaa   4561

agttgtgctg acagcttttt ttggtttttt ggtttttgtt tttgtttttg tttttgtttt   4621

tgtctacttt tggtattcac aacagccagg gacttgattt tgatgtattt taagccacat   4681

taaataaaga gtctgttgcc ttaaaaaaaa aaaaaaaaaa a                        4722


<210> SEQ ID NO 15
<211> LENGTH: 1925
<212> TYPE: DNA
<213> ORGANISM: Homo sapiens
<220> FEATURE:
<221> NAME/KEY: CDS
<222> LOCATION: (118)...(570)

<400> SEQUENCE: 15

gacgcctcag agcggaacag ggaagtgaat caggcgccgg gtagtgggtt gctgggctgg     60

gcttgctgag gtagaggcag cgccaagaag aggcctttgc cgctggtcgg gattggg atg   120
                                                               Met
                                                                1

tcg aag aac aca gtg tcg tcg gcc cgc ttc cgg aag gtg gac gtg gat      168
Ser Lys Asn Thr Val Ser Ser Ala Arg Phe Arg Lys Val Asp Val Asp
            5                  10                  15

gaa tat gac gag aac aag ttc gtg gac gaa gaa gat ggg ggc gac ggc      216
Glu Tyr Asp Glu Asn Lys Phe Val Asp Glu Glu Asp Gly Gly Asp Gly
        20                  25                  30

cag gcc ggg ccc gac gag ggc gag gtg gac tcc tgc ctg cgg caa gga      264
Gln Ala Gly Pro Asp Glu Gly Glu Val Asp Ser Cys Leu Arg Gln Gly
    35                  40                  45

aac atg aca gct gcc cta cag gca gct ctg aag aac ccc cct atc aac      312
Asn Met Thr Ala Ala Leu Gln Ala Ala Leu Lys Asn Pro Pro Ile Asn
 50                  55                  60                  65

acc aag agt cag gca gtg aag gac cgg gca ggc agc att gtc ttg aag      360
Thr Lys Ser Gln Ala Val Lys Asp Arg Ala Gly Ser Ile Val Leu Lys
                 70                  75                  80

gtg ctc atc tct ttt aaa gct aat gat ata gaa aag gca gtt caa tct      408
Val Leu Ile Ser Phe Lys Ala Asn Asp Ile Glu Lys Ala Val Gln Ser
            85                  90                  95

ctg gac aag aat ggt gtg gat ctc cta atg aag tat att tat aaa gga      456
```

-continued

```
Leu Asp Lys Asn Gly Val Asp Leu Leu Met Lys Tyr Ile Tyr Lys Gly
        100                 105                 110

ttt gag agc ccg tct gac aat agc agt gct atg tta ctg caa tgg cat      504
Phe Glu Ser Pro Ser Asp Asn Ser Ser Ala Met Leu Leu Gln Trp His
    115                 120                 125

gaa aag gca ctt gct gct gga gga gta ggg tcc att gtt cgt gtc ttg      552
Glu Lys Ala Leu Ala Ala Gly Gly Val Gly Ser Ile Val Arg Val Leu
130                 135                 140                 145

act gca aga aaa act gtg tagtctggca ggaagtggat tatctgcctc             600
Thr Ala Arg Lys Thr Val
                150

gggagtggga attgctggta caaagaccaa aacaaccaaa tgccaccgct gccctgtggg    660

tagcatctgt ttctctcagc tttgccttct tgctttttca tatctgtaaa gaaaaaaatt    720

acatatcagt tgtcccttta atgaaaattg ggataatata gaagaaattg tgttaaaata    780

gaagtgtttc atcctttcaa aaccatttca gtgatgttta taccaatctg tatatagtat    840

aatttacatt caagttttaa ttgtgcaact tttaaccctg ttggctggtt tttggttctg    900

tttggttttg tattattttt aactaatact gaaaaatttg gtcagaattt gaggccagtt    960

tcctagctca ttgctagtca ggaaatgata tttataaaaa atatgagaga ctggcagcta   1020

ttaacattgc aaaactggac catatttccc ttatttaata agcaaaatat gtttttggaa   1080

taagtggtgg gtgaatacca ctgctaagtt atagctttgt ttttgcttgc ctcctcatta   1140

tctgtactgt gggtttaagt atgctacttt ctctcagcat ccaataatca tggcccctca   1200

atttatttgt ggtcacgcag ggttcagagc aagaagtctt gctttataca aatgtatcca   1260

taaaatatca gagcttgttg ggcatgaaca tcaaactttt gttccactaa tatggctctg   1320

tttggaaaaa actgcaaatc agaaagaatg atttgcagaa agaaagaaaa actatggtgt   1380

aatttaaact ctgggcagcc tctgaatgaa atgctacttt ctttagaaat ataatagctg   1440

ccttagacat tatgaggtat acaactagta tttaagatac catttaatat gccccgtaaa   1500

tgtcttcagt gttcttcagg gtagttggga tctcaaaaga tttggttcag atccaaacaa   1560

atacacattc tgtgttttag ctcagtgttt tctaaaaaaa gaaactgcca cacagcaaaa   1620

aattgtttac tttgttggac aaaccaaatc agttctcaaa aaatgaccgg tgcttataaa   1680

aagttataaa tatcgagtag ctctaaaaca aaccacctga ccaagaggga agtgagcttg   1740

tgcttagtat ttacattgga tgccagtttt gtaatcactg acttatgtgc aaactggtgc   1800

agaaattcta taaactcttt gctgtttttg atacctgctt tttgtttcat tttgttttgt   1860

tttgtaaaaa tgataaaact tcagaaaata aaatgtcagt gttgaataat taaaaaaaaa   1920

aaaaa                                                                1925


<210> SEQ ID NO 16
<211> LENGTH: 1208
<212> TYPE: DNA
<213> ORGANISM: Homo sapiens
<220> FEATURE:
<221> NAME/KEY: CDS
<222> LOCATION: (1)...(651)

<400> SEQUENCE: 16

gaa gag cga gta ctt gag aaa gaa gag gaa gaa gat gat gat gaa gat       48
Glu Glu Arg Val Leu Glu Lys Glu Glu Glu Glu Asp Asp Asp Glu Asp
 1               5                  10                  15

gaa gat gaa gaa gat gat gtg tca gag ggc tct gaa gtg ccc gag agt       96
Glu Asp Glu Glu Asp Asp Val Ser Glu Gly Ser Glu Val Pro Glu Ser
             20                  25                  30
```

-continued

```
gac cgt cct gca ggt gcc cag cac cac cag ctt aac ggc gag cgg gga      144
Asp Arg Pro Ala Gly Ala Gln His His Gln Leu Asn Gly Glu Arg Gly
         35                  40                  45

cct cag agt gcc aag gag agg gtc aag gag tgg acc ccc tgc gga ccg      192
Pro Gln Ser Ala Lys Glu Arg Val Lys Glu Trp Thr Pro Cys Gly Pro
     50                  55                  60

cac cag ggc cag gat gaa ggg cgg ggg cca gcc ccg ggc agc ggc acc      240
His Gln Gly Gln Asp Glu Gly Arg Gly Pro Ala Pro Gly Ser Gly Thr
 65                  70                  75                  80

cgc cag gtg ttc tcc atg gca gcc atg aac aag gaa ggg gga aca gct      288
Arg Gln Val Phe Ser Met Ala Ala Met Asn Lys Glu Gly Gly Thr Ala
                 85                  90                  95

tct gtt gcc acc ggg cca gac tcc ccg tcc ccc gtg cct ttg ccc cca      336
Ser Val Ala Thr Gly Pro Asp Ser Pro Ser Pro Val Pro Leu Pro Pro
            100                 105                 110

ggc aaa cca gcc cta cct ggg gcc gac ggg acc ccc ttt ggc tgt cct      384
Gly Lys Pro Ala Leu Pro Gly Ala Asp Gly Thr Pro Phe Gly Cys Pro
        115                 120                 125

ccc ggg cgc aaa gag aag cca tct gat ccc gtc gag tgg acc gtg atg      432
Pro Gly Arg Lys Glu Lys Pro Ser Asp Pro Val Glu Trp Thr Val Met
    130                 135                 140

gat gtc gtc gaa tat ttt act gag gct gga ttc ccg gag cag gcg aca      480
Asp Val Val Glu Tyr Phe Thr Glu Ala Gly Phe Pro Glu Gln Ala Thr
145                 150                 155                 160

gct ttc caa gag cag gaa att gat ggc aaa tct ttg ctg ctc atg cag      528
Ala Phe Gln Glu Gln Glu Ile Asp Gly Lys Ser Leu Leu Leu Met Gln
                165                 170                 175

cgc aca gat gtg ctc acc ggc ctg tcc atc cgc ctc ggg cca gcc ctg      576
Arg Thr Asp Val Leu Thr Gly Leu Ser Ile Arg Leu Gly Pro Ala Leu
            180                 185                 190

aaa atc tac gag cac cac atc aag gtg ctt cag caa ggc cac ttt gag      624
Lys Ile Tyr Glu His His Ile Lys Val Leu Gln Gln Gly His Phe Glu
        195                 200                 205

gat gat gac ccc gat ggc ttc tta ggc tgagcgccca gcctcacccc            671
Asp Asp Asp Pro Asp Gly Phe Leu Gly
    210                 215

tgccccagcc cattccggcc cccatctcac ccaagatccc ccagagtcca ggagctggac    731

ggggacaccc tcagccctca taacagattc caaggagagg gcaccctctt gtccttatct    791

ttgccccttg tgtctgtctc acacacatct gctcctcagc acgtcggtgt ggggaggga    851

ttgctcctta aaccccaggt ggctgaccct ccccacccag tccaggacat tttaggaaaa    911

aaaaaatgaa atgtgggggg cttctcatct ccccaagatc ctcttccgtt cagccagatg    971

tttcctgtat aaatgtttgg atctgcctgt ttattttggt gggtggtctt tcctccctcc   1031

cctaccaccc atgcccccct tctcagtctg cccctggcct ccagccccta ggggactagc   1091

tgggttgggg ttcctcgggc cttttctctc ctccctcttt tctttctgtt gattgtcgct   1151

ccagctggct gtattgcttt ttaatattgc accgaaggtt ttttaaataa aattta       1208
```

```
<210> SEQ ID NO 17
<211> LENGTH: 4697
<212> TYPE: DNA
<213> ORGANISM: Homo sapiens
<220> FEATURE:
<221> NAME/KEY: CDS
<222> LOCATION: (3)...(1592)

<400> SEQUENCE: 17

ca aaa agc agc cca gga caa ccg gaa gca gga ccc gag gga gcc cag        47
```

-continued

```
   Lys Ser Ser Pro Gly Gln Pro Glu Ala Gly Pro Glu Gly Ala Gln
    1               5                  10                  15

gag cgg ccc agc cag gcg gct cct gca gta gaa gca gaa ggt ccc ggc       95
Glu Arg Pro Ser Gln Ala Ala Pro Ala Val Glu Ala Glu Gly Pro Gly
                20                  25                  30

agc agc cag gct cct cgg aag ccg gag ggg gct caa gcc aga acg gct      143
Ser Ser Gln Ala Pro Arg Lys Pro Glu Gly Ala Gln Ala Arg Thr Ala
            35                  40                  45

cag tct ggg gcc ctt cgt gat gtc tct gag gag ctg agc cgc caa ctg      191
Gln Ser Gly Ala Leu Arg Asp Val Ser Glu Glu Leu Ser Arg Gln Leu
        50                  55                  60

gaa gac ata ctg agc aca tac tgt gtg gac aat aac cag ggg ggc ccc      239
Glu Asp Ile Leu Ser Thr Tyr Cys Val Asp Asn Asn Gln Gly Gly Pro
    65                  70                  75

ggc gag gat ggg gca cag ggt gag ccg gct gaa ccc gaa gat gca gag      287
Gly Glu Asp Gly Ala Gln Gly Glu Pro Ala Glu Pro Glu Asp Ala Glu
 80                  85                  90                  95

aag tcc cgg acc tat gtg gca agg aat ggg gag cct gaa cca act cca      335
Lys Ser Arg Thr Tyr Val Ala Arg Asn Gly Glu Pro Glu Pro Thr Pro
                100                 105                 110

gta gtc tat gga gag aag gaa ccc tcc aag ggg gat cca aac aca gaa      383
Val Val Tyr Gly Glu Lys Glu Pro Ser Lys Gly Asp Pro Asn Thr Glu
            115                 120                 125

gag atc cgg cag agt gac gag gtc gga gac cga gac cat cga agg cca      431
Glu Ile Arg Gln Ser Asp Glu Val Gly Asp Arg Asp His Arg Arg Pro
        130                 135                 140

cag gag aag aaa aaa gcc aag ggt ttg ggg aag gag atc acg ttg ctg      479
Gln Glu Lys Lys Lys Ala Lys Gly Leu Gly Lys Glu Ile Thr Leu Leu
    145                 150                 155

atg cag aca ttg aat act ctg agt acc cca gag gag aag ctg gct gct      527
Met Gln Thr Leu Asn Thr Leu Ser Thr Pro Glu Glu Lys Leu Ala Ala
160                 165                 170                 175

ctg tgc aag aag tat gct gaa ctg ctg gag gag cac cgg aat tca cag      575
Leu Cys Lys Lys Tyr Ala Glu Leu Leu Glu Glu His Arg Asn Ser Gln
                180                 185                 190

aag cag atg aag ctc cta cag aaa aag cag agc cag ctg gtg caa gag      623
Lys Gln Met Lys Leu Leu Gln Lys Lys Gln Ser Gln Leu Val Gln Glu
            195                 200                 205

aag gac cac ctg cgc ggt gag cac agc aag gcc gtc ctg gcc cgc agc      671
Lys Asp His Leu Arg Gly Glu His Ser Lys Ala Val Leu Ala Arg Ser
        210                 215                 220

aag ctt gag agc cta tgc cgt gag ctg cag cgg cac aac cgc tcc ctc      719
Lys Leu Glu Ser Leu Cys Arg Glu Leu Gln Arg His Asn Arg Ser Leu
    225                 230                 235

aag gaa gaa ggt gtg cag cgg gcc cgg gag gag gag gag aag cgc aag      767
Lys Glu Glu Gly Val Gln Arg Ala Arg Glu Glu Glu Glu Lys Arg Lys
240                 245                 250                 255

gag gtg acc tcg cac ttc cag gtg aca ctg aat gac att cag ctg cag      815
Glu Val Thr Ser His Phe Gln Val Thr Leu Asn Asp Ile Gln Leu Gln
                260                 265                 270

atg gaa cag cac aat gag cgc aac tcc aag ctg cgc caa gag aac atg      863
Met Glu Gln His Asn Glu Arg Asn Ser Lys Leu Arg Gln Glu Asn Met
            275                 280                 285

gag ctg gct gag agg ctc aag aag ctg att gag cag tat gag ctg cgc      911
Glu Leu Ala Glu Arg Leu Lys Lys Leu Ile Glu Gln Tyr Glu Leu Arg
        290                 295                 300

gag gag cat atc gac aaa gtc ttc aaa cac aag gac cta caa cag cag      959
Glu Glu His Ile Asp Lys Val Phe Lys His Lys Asp Leu Gln Gln Gln
    305                 310                 315
```

-continued

```
ctg gtg gat gcc aag ctc cag cag gcc cag gag atg cta aag gag gca      1007
Leu Val Asp Ala Lys Leu Gln Gln Ala Gln Glu Met Leu Lys Glu Ala
320                 325                 330                 335

gaa gag cgg cac cag cgg gag aag gat ttt ctc ctg aaa gag gca gta      1055
Glu Glu Arg His Gln Arg Glu Lys Asp Phe Leu Leu Lys Glu Ala Val
                340                 345                 350

gag tcc cag agg atg tgt gag ctg atg aag cag caa gag acc cac ctg      1103
Glu Ser Gln Arg Met Cys Glu Leu Met Lys Gln Gln Glu Thr His Leu
            355                 360                 365

aag caa cag ctt gcc cta tac aca gag aag ttt gag gag ttc cag aac      1151
Lys Gln Gln Leu Ala Leu Tyr Thr Glu Lys Phe Glu Glu Phe Gln Asn
        370                 375                 380

aca ctt tcc aaa agc agc gag gta ttc acc aca ttc aag cag gag atg      1199
Thr Leu Ser Lys Ser Ser Glu Val Phe Thr Thr Phe Lys Gln Glu Met
    385                 390                 395

gaa aag atg act aag aag atc aag aag ctg gag aaa gaa acc acc atg      1247
Glu Lys Met Thr Lys Lys Ile Lys Lys Leu Glu Lys Glu Thr Thr Met
400                 405                 410                 415

tac cgg tcc cgg tgg gag agc agc aac aag gcc ctg ctt gag atg gct      1295
Tyr Arg Ser Arg Trp Glu Ser Ser Asn Lys Ala Leu Leu Glu Met Ala
                420                 425                 430

gag gag aaa aca gtc cgg gat aaa gaa ctg gag ggc ctg cag gta aaa      1343
Glu Glu Lys Thr Val Arg Asp Lys Glu Leu Glu Gly Leu Gln Val Lys
            435                 440                 445

atc caa cgg ctg gag aag ctg tgc cgg gca ctg cag aca gag cgc aat      1391
Ile Gln Arg Leu Glu Lys Leu Cys Arg Ala Leu Gln Thr Glu Arg Asn
        450                 455                 460

gac ctg aac aag agg gta cag gac ctg agt gct ggt ggc cag ggc tcc      1439
Asp Leu Asn Lys Arg Val Gln Asp Leu Ser Ala Gly Gly Gln Gly Ser
    465                 470                 475

ctc act gac agt ggc cct gag agg agg cca gag ggg cct ggg gct caa      1487
Leu Thr Asp Ser Gly Pro Glu Arg Arg Pro Glu Gly Pro Gly Ala Gln
480                 485                 490                 495

gca ccc agc tcc ccc agg gtc aca gaa gcg cct tgc tac cca gga gca      1535
Ala Pro Ser Ser Pro Arg Val Thr Glu Ala Pro Cys Tyr Pro Gly Ala
                500                 505                 510

ccg agc aca gaa gca tca ggc cag act ggg cct caa gag ccc acc tcc      1583
Pro Ser Thr Glu Ala Ser Gly Gln Thr Gly Pro Gln Glu Pro Thr Ser
            515                 520                 525

gcc agg gcc tagagagcct ggtgttgggt catgctggga agggagcggc             1632
Ala Arg Ala
        530

agcccagcca ggcctggccc ataaaaggct cccatgctga gcagcccatt gctgaagcca   1692

ggatgttctt gacctggctg gcatctggca cttgcaattt tggattttgt gggtcagttt   1752

tacgtacata gggcattttg caaggccttg caaatgcatt tatacctgta agtgtacagt   1812

gggcttgcat tggggatggg ggtgtgtaca gatgaagtca gtggcttgtc tgtgagctga   1872

agagtcttga gaggggctgt catctgtagc tgccatcaca gtgagttggc agaagtgact   1932

tgagcatttc tctgtctgat ttgaggctca gacccctccc tgccctttca gagctcaaaa   1992

caagtaatac accaaggtct tgactgcatt tgtcttgtga gcagggcttg cttggtcagc   2052

tcaggccctc ctagctgctt ggaggctcct ttgattctct agacctggaa aaggtgtccc   2112

taggcagagc cctggcaggg cgctcagagc tgggatttcc tgcctggaac aagggacctg   2172

gagaatgttt ttgcgtggga tgatgtgctg gtcaggagcc ccttgggcat cgcttcccct   2232

gccctttggt agtgccagga ccaggccaat gatgcttctc agtagcctta tcattcacag   2292

gtgcctctct agcctgcaca aatgattgac aagagatcac ccaaaggatt atttctgaag   2352
```

-continued

```
gtgttttttt ctttatttct ttttcttttt tttttttttct ttttcttttt tttttgcaca   2412
tgacagtgtt tgtattgagg accttccaag gaaaagggat gctgtaccag tggtgcctgg   2472
gtgcctggcc tccagtgtcc cacctccttc accaccccac ttggctcctt tgccatcttg   2532
atgctgaggt ttcctgtttg gtgagatcag gttgtttgtg gtaaaagaaa ggaaagggct   2592
tctgatggct ttgccacaag cttacctgtg ggtttcagtc ctgagaggcc accaccagtt   2652
cccatcagca ctgtctccat gcagcagttg ctgggtccca tgtccagctg cctctttggc   2712
ttcatgggtt tttctgcttc ctgcccccac ccccacatgt gcaatcctca agatttgtcc   2772
tgattctatt tcctggcacc tccctgcctg tccttgggga ttctacttct tcctgtgtgg   2832
ggcccatagc tgttgtctaa caggtaagaa atgaaattga actattgact gggccccaga   2892
aatccataaa atggctgcag acagttgttt ctgtgtcctg ttctaccccc actccagtac   2952
ataactacta tgtactgtgt agagccattc tatatgctga atgttctgct gttgcaaact   3012
tgccagggta ttagccagtg tttgtgccaa gcagttttcg gggacaacag aatgactcag   3072
accaagatgg ataggatggt tagggctttg cttcttgctg tttttctttg aactagtcat   3132
tgtcctgcag gtcccttcat cttccatacc tagcccactc ttttagccct taccttaaat   3192
ctctcagata agttggttca caaagaatgt taagtactga atcatgtgtg actgagacca   3252
gagatggcaa atgaatggca caccatttct ccttctcctg ccccagggca ggtaccactg   3312
atctgcatca gagttgcctg ctattctctg gtgtatcctt cacatctagg tgccctcaag   3372
cagctgtgtg agtgttgaga tctctgccat ctctggctga gatactgctg tcctgtgaag   3432
tgtttcccat gaccttttc ttccccttttg aatccctctt gtctggagta gtccttgcct   3492
tcttcttgct ccagtaggcc ttttccttac cccagccctt gtgccaggct aagctggtac   3552
aagagctgcc aactcacaga gttttgctag gcgagagagg tgcagggaag aggcagaggt   3612
atgcaccttc ccccttgaag agaggggaaa ggcctacagt ggcccacata attgcctgac   3672
tcacacttca gctacctctt aatgcctgtg gagggactgg agctgctgga tcccagtgtg   3732
gtggtgtagg aggccacagt gagcaggtgg ccccagctgg gtttcccagg tcaggaatgt   3792
gggccccagg caaggtgcag cctttgctca cagctccatc catgtctaga ccttcaggcc   3852
agtctgcaga tgaggttccc taccttttc ttctcttcat tgaccaaatc aaccaatcac   3912
tacagctgct ctgcttctgc tttccaaagt agcccaggtc ctgggccaga tgcaggggag   3972
gtgcctatcc atgagtgaag gccagtgtct tcctcacctg ggtggtccca cacttgtgac   4032
cctcagtttt aggacccaag atctgtgttg gtttcttaga ttgctagctt ttcctccagg   4092
ggaccacagc aggtgaagct caagagcgca tggctctgct aatagtaaat tgttttcagg   4152
gccttgtcca gctgagagct tcatgtccac cagattctga gaggtgtcag cagcactttt   4212
tttttttatt tgttgtttgt tttccatgag gttatcggac catgggctga gctcaggcac   4272
tttctgtagg agactgttat ttctgtaaag atggttattt aaccctcctc caccccatca   4332
cggtggccct gagggctgac ccggaggcca gtggagctgc ctggtgtcca cgggggaggg   4392
ccaaggcctg ctgagctgat tctccagctg ctgccccagc ctttccgcct tgcacagcac   4452
agaggtggtc accccaggga cagccaggca cctgctcctc ttgcccttcc tgggggaaag   4512
gagctgcctt ctgtccctgt aactgctttc cttatggccc aacccggcca ctcagacttg   4572
tttgaagctg cactggcagc ttttttgtct cctttgggta ttcacaacag ccagggactt   4632
gattttgatg tattttaaac cacattaaat aaagagtctg ttgccttaaa aaaaaaaaaa   4692
```

-continued

```
aaaaa                                                                  4697


<210> SEQ ID NO 18
<211> LENGTH: 60
<212> TYPE: DNA
<213> ORGANISM: Homo sapiens
<220> FEATURE:
<221> NAME/KEY: CDS
<222> LOCATION: (1)...(60)

<400> SEQUENCE: 18

gtg gac gtg gat gag tac gac gag aac aag ttc gtg gac gag gaa gac        48
Val Asp Val Asp Glu Tyr Asp Glu Asn Lys Phe Val Asp Glu Glu Asp
 1               5                  10                  15

ggc ggc gac ggc                                                        60
Gly Gly Asp Gly
            20


<210> SEQ ID NO 19
<211> LENGTH: 15
<212> TYPE: PRT
<213> ORGANISM: Homo sapiens

<400> SEQUENCE: 19

Glu Glu Glu Glu Asp Asp Asp Glu Asp Glu Asp Glu Glu Asp Asp
 1               5                  10                  15


<210> SEQ ID NO 20
<211> LENGTH: 26
<212> TYPE: PRT
<213> ORGANISM: Homo sapiens

<400> SEQUENCE: 20

Glu Glu Glu Glu Asp Asp Asp Glu Asp Glu Asp Glu Glu Asp Asp Val
 1               5                  10                  15

Ser Glu Gly Ser Glu Val Pro Glu Ser Asp
            20                  25


<210> SEQ ID NO 21
<211> LENGTH: 11
<212> TYPE: PRT
<213> ORGANISM: Homo sapiens

<400> SEQUENCE: 21

Val Ser Glu Gly Ser Glu Val Pro Glu Ser Asp
 1               5                  10


<210> SEQ ID NO 22
<211> LENGTH: 10
<212> TYPE: PRT
<213> ORGANISM: Homo sapiens

<400> SEQUENCE: 22

Glu Asp Asp Asp Pro Asp Gly Phe Leu Gly
 1               5                  10


<210> SEQ ID NO 23
<211> LENGTH: 30
<212> TYPE: PRT
<213> ORGANISM: Oryctolagus cuniculus

<400> SEQUENCE: 23

Val Asp Val Asp Glu Tyr Asp Glu Asn Lys Phe Val Asp Glu Glu Asp
 1               5                  10                  15
```

-continued

```
Gly Gly Asp Gly Gln Ala Gly Pro Asp Glu Gly Glu Val Asp
            20                  25                  30


<210> SEQ ID NO 24
<211> LENGTH: 6
<212> TYPE: PRT
<213> ORGANISM: Oryctolagus cuniculus

<400> SEQUENCE: 24

Asp Glu Gly Glu Val Asp
 1               5


<210> SEQ ID NO 25
<211> LENGTH: 16
<212> TYPE: PRT
<213> ORGANISM: Oryctolagus cuniculus

<400> SEQUENCE: 25

Glu Glu Glu Glu Glu Glu Glu Glu Asp Asp Glu Asp Asp Asp Asp Asp
 1               5                  10                  15


<210> SEQ ID NO 26
<211> LENGTH: 28
<212> TYPE: PRT
<213> ORGANISM: Oryctolagus cuniculus

<400> SEQUENCE: 26

Glu Glu Glu Glu Glu Glu Glu Glu Asp Asp Glu Asp Asp Asp Asp Asp
 1               5                  10                  15

Val Val Ser Glu Gly Ser Glu Val Pro Glu Ser Asp
            20                  25


<210> SEQ ID NO 27
<211> LENGTH: 12
<212> TYPE: PRT
<213> ORGANISM: Oryctolagus cuniculus

<400> SEQUENCE: 27

Val Val Ser Glu Gly Ser Glu Val Pro Glu Ser Asp
 1               5                  10


<210> SEQ ID NO 28
<211> LENGTH: 10
<212> TYPE: PRT
<213> ORGANISM: Oryctolagus cuniculus

<400> SEQUENCE: 28

Pro Pro Gly Lys Pro Ala Leu Pro Gly Ala
 1               5                  10


<210> SEQ ID NO 29
<211> LENGTH: 15
<212> TYPE: PRT
<213> ORGANISM: Oryctolagus cuniculus

<400> SEQUENCE: 29

Glu Asp Gly Val Gln Gly Glu Pro Pro Glu Pro Glu Asp Ala Glu
 1               5                  10                  15


<210> SEQ ID NO 30
<211> LENGTH: 45
<212> TYPE: DNA
<213> ORGANISM: Homo sapiens

<400> SEQUENCE: 30
```

-continued gaagaggaag aagatgatga tgaagatgaa gatgaagaag atgat 45

<210> SEQ ID NO 31
<211> LENGTH: 78
<212> TYPE: DNA
<213> ORGANISM: Homo sapiens

<400> SEQUENCE: 31
gaagaggaag aagatgatga tgaagatgaa gatgaagaag atgatgtgtc agagggctct 60
gaagtgcccg agagtgac 78

<210> SEQ ID NO 32
<211> LENGTH: 33
<212> TYPE: DNA
<213> ORGANISM: Homo sapiens

<400> SEQUENCE: 32
gtgtcagagg gctctgaagt gcccgagagt gac 33

<210> SEQ ID NO 33
<211> LENGTH: 30
<212> TYPE: DNA
<213> ORGANISM: Homo sapiens

<400> SEQUENCE: 33
gaggatgatg accccgatgg cttcttaggc 30

<210> SEQ ID NO 34
<211> LENGTH: 90
<212> TYPE: DNA
<213> ORGANISM: Homo sapiens

<400> SEQUENCE: 34
gtggacgtgg atgaatatga cgagaacaag ttcgtggacg aagaagatgg gggcgacggc 60
caggccgggc ccgacgaggg cgaggtggac 90

<210> SEQ ID NO 35
<211> LENGTH: 18
<212> TYPE: DNA
<213> ORGANISM: Homo sapiens

<400> SEQUENCE: 35
gacgagggcg aggtggac 18

<210> SEQ ID NO 36
<211> LENGTH: 48
<212> TYPE: DNA
<213> ORGANISM: Homo sapiens

<400> SEQUENCE: 36
gaggaggagg aggaggagga ggaagacgac gaggacgacg acgacgac 48

<210> SEQ ID NO 37
<211> LENGTH: 84
<212> TYPE: DNA
<213> ORGANISM: Homo sapiens

<400> SEQUENCE: 37
gaggaggagg aggaggagga ggaagacgac gaggacgacg acgacgacgt cgtgtccgag 60
ggctcggagg tgcccgagag cgat 84

-continued

<210> SEQ ID NO 38
<211> LENGTH: 36
<212> TYPE: DNA
<213> ORGANISM: Homo sapiens

<400> SEQUENCE: 38
gtcgtgtccg agggctcgga ggtgcccgag agcgat 36

<210> SEQ ID NO 39
<211> LENGTH: 30
<212> TYPE: DNA
<213> ORGANISM: Homo sapiens

<400> SEQUENCE: 39
ccccccggga agccagccct cccaggagcc 30

<210> SEQ ID NO 40
<211> LENGTH: 45
<212> TYPE: DNA
<213> ORGANISM: Homo sapiens

<400> SEQUENCE: 40
gaggatgggg tccagggtga gccccctgaa cctgaagatg cagag 45

<210> SEQ ID NO 41
<211> LENGTH: 7
<212> TYPE: PRT
<213> ORGANISM: Homo sapiens

<400> SEQUENCE: 41

Arg Asp Val Ser Glu Glu Leu
1 5

<210> SEQ ID NO 42
<211> LENGTH: 21
<212> TYPE: DNA
<213> ORGANISM: Homo sapiens

<400> SEQUENCE: 42
cgtgatgtct ctgaggagct g 21

<210> SEQ ID NO 43
<211> LENGTH: 538
<212> TYPE: PRT
<213> ORGANISM: Homo sapiens

<400> SEQUENCE: 43

Met Ala Gly Pro Pro Ala Leu Pro Pro Pro Glu Thr Ala Ala Ala Ala
1 5 10 15

Thr Thr Ala Ala Ala Ala Ser Ser Ser Ala Ala Ser Pro His Tyr Gln
20 25 30

Glu Trp Ile Leu Asp Thr Ile Asp Ser Leu Arg Ser Arg Lys Ala Arg
35 40 45

Pro Asp Leu Glu Arg Ile Cys Arg Met Val Arg Arg Arg His Gly Pro
50 55 60

Glu Pro Glu Arg Thr Arg Ala Glu Leu Glu Lys Leu Ile Gln Gln Arg
65 70 75 80

Ala Val Leu Arg Val Ser Tyr Lys Gly Ser Ile Ser Tyr Arg Asn Ala
85 90 95

Ala Arg Val Gln Pro Pro Arg Arg Gly Ala Thr Pro Pro Ala Pro Pro
100 105 110

-continued

```
Arg Ala Pro Arg Gly Ala Pro Ala Ala Ala Ala Ala Ala Ala Pro Pro
        115                 120                 125

Pro Thr Pro Ala Pro Pro Pro Pro Pro Ala Pro Val Ala Ala Ala Ala
    130                 135                 140

Pro Ala Arg Ala Pro Arg Ala Ala Ala Ala Ala Ala Thr Ala Pro Pro
145                 150                 155                 160

Ser Pro Gly Pro Ala Gln Pro Gly Pro Arg Ala Gln Arg Ala Ala Pro
                165                 170                 175

Leu Ala Ala Pro Pro Pro Ala Pro Ala Ala Pro Pro Ala Val Ala Pro
            180                 185                 190

Pro Ala Gly Pro Arg Arg Ala Pro Pro Pro Ala Val Ala Ala Arg Glu
        195                 200                 205

Pro Pro Leu Pro Pro Pro Pro Gln Pro Pro Ala Pro Pro Gln Gln Gln
    210                 215                 220

Gln Pro Pro Pro Pro Gln Pro Gln Pro Pro Pro Glu Gly Gly Ala Val
225                 230                 235                 240

Arg Ala Gly Gly Ala Ala Arg Pro Val Ser Leu Arg Glu Val Val Arg
                245                 250                 255

Tyr Leu Gly Gly Ser Gly Gly Ala Gly Gly Arg Leu Thr Arg Gly Arg
            260                 265                 270

Val Gln Gly Leu Leu Glu Glu Glu Ala Ala Ala Arg Gly Arg Leu Glu
        275                 280                 285

Arg Thr Arg Leu Gly Ala Leu Ala Leu Pro Arg Gly Asp Arg Pro Gly
    290                 295                 300

Arg Ala Pro Pro Ala Ala Ser Ala Arg Pro Ser Arg Ser Lys Arg Gly
305                 310                 315                 320

Gly Glu Glu Arg Val Leu Glu Lys Glu Glu Glu Glu Asp Asp Asp Glu
                325                 330                 335

Asp Glu Asp Glu Glu Asp Asp Val Ser Glu Gly Ser Glu Val Pro Glu
            340                 345                 350

Ser Asp Arg Pro Ala Gly Ala Gln His His Gln Leu Asn Gly Glu Arg
        355                 360                 365

Gly Pro Gln Ser Ala Lys Glu Arg Val Lys Glu Trp Thr Pro Cys Gly
    370                 375                 380

Pro His Gln Gly Gln Asp Glu Gly Arg Gly Pro Ala Pro Gly Ser Gly
385                 390                 395                 400

Thr Arg Gln Val Phe Ser Met Ala Ala Met Asn Lys Glu Gly Gly Thr
                405                 410                 415

Ala Ser Val Ala Thr Gly Pro Asp Ser Pro Ser Pro Val Pro Leu Pro
            420                 425                 430

Pro Gly Lys Pro Ala Leu Pro Gly Ala Asp Gly Thr Pro Phe Gly Cys
        435                 440                 445

Pro Pro Gly Arg Lys Glu Lys Pro Ser Asp Pro Val Glu Trp Thr Val
    450                 455                 460

Met Asp Val Val Glu Tyr Phe Thr Glu Ala Gly Phe Pro Glu Gln Ala
465                 470                 475                 480

Thr Ala Phe Gln Glu Gln Glu Ile Asp Gly Lys Ser Leu Leu Leu Met
                485                 490                 495

Gln Arg Thr Asp Val Leu Thr Gly Leu Ser Ile Arg Leu Gly Pro Ala
            500                 505                 510

Leu Lys Ile Tyr Glu His His Ile Lys Val Leu Gln Gln Gly His Phe
        515                 520                 525
```

-continued

```
Glu Asp Asp Asp Pro Asp Gly Phe Leu Gly
    530                 535


<210> SEQ ID NO 44
<211> LENGTH: 546
<212> TYPE: PRT
<213> ORGANISM: Homo sapiens

<400> SEQUENCE: 44

Met Lys Asn Gln Asp Lys Lys Asn Gly Ala Ala Lys Gln Ser Asn Pro
 1               5                  10                  15

Lys Ser Ser Pro Gly Gln Pro Glu Ala Gly Pro Glu Gly Ala Gln Glu
            20                  25                  30

Arg Pro Ser Gln Ala Ala Pro Ala Val Glu Ala Glu Gly Pro Gly Ser
        35                  40                  45

Ser Gln Ala Pro Arg Lys Pro Glu Gly Ala Gln Ala Arg Thr Ala Gln
    50                  55                  60

Ser Gly Ala Leu Arg Asp Val Ser Glu Glu Leu Ser Arg Gln Leu Glu
65                  70                  75                  80

Asp Ile Leu Ser Thr Tyr Cys Val Asp Asn Asn Gln Gly Gly Pro Gly
                85                  90                  95

Glu Asp Gly Ala Gln Gly Glu Pro Ala Glu Pro Glu Asp Ala Glu Lys
            100                 105                 110

Ser Arg Thr Tyr Val Ala Arg Asn Gly Glu Pro Glu Pro Thr Pro Val
        115                 120                 125

Val Asn Gly Glu Lys Glu Pro Ser Lys Gly Asp Pro Asn Thr Glu Glu
    130                 135                 140

Ile Arg Gln Ser Asp Glu Val Gly Asp Arg Asp His Arg Arg Pro Gln
145                 150                 155                 160

Glu Lys Lys Lys Ala Lys Gly Leu Gly Lys Glu Ile Thr Leu Leu Met
                165                 170                 175

Gln Thr Leu Asn Thr Leu Ser Thr Pro Glu Glu Lys Leu Ala Ala Leu
            180                 185                 190

Cys Lys Lys Tyr Ala Glu Leu Leu Glu Glu His Arg Asn Ser Gln Lys
        195                 200                 205

Gln Met Lys Leu Leu Gln Lys Lys Gln Ser Gln Leu Val Gln Glu Lys
    210                 215                 220

Asp His Leu Arg Gly Glu His Ser Lys Ala Val Leu Ala Arg Ser Lys
225                 230                 235                 240

Leu Glu Ser Leu Cys Arg Glu Leu Gln Arg His Asn Arg Ser Leu Lys
                245                 250                 255

Glu Glu Gly Val Gln Arg Ala Arg Glu Glu Glu Glu Lys Arg Lys Glu
            260                 265                 270

Val Thr Ser His Phe Gln Val Thr Leu Asn Asp Ile Gln Leu Gln Met
        275                 280                 285

Glu Gln His Asn Glu Arg Asn Ser Lys Leu Arg Gln Glu Asn Met Glu
    290                 295                 300

Leu Ala Glu Arg Leu Lys Lys Leu Ile Glu Gln Tyr Glu Leu Arg Glu
305                 310                 315                 320

Glu His Ile Asp Lys Val Phe Lys His Lys Asp Leu Gln Gln Gln Leu
                325                 330                 335

Val Asp Ala Lys Leu Gln Gln Ala Gln Glu Met Leu Lys Glu Ala Glu
            340                 345                 350

Glu Arg His Gln Arg Glu Lys Asp Phe Leu Leu Lys Glu Ala Val Glu
        355                 360                 365
```

-continued

```
Ser Gln Arg Met Cys Glu Leu Met Lys Gln Gln Glu Thr His Leu Lys
    370                 375                 380

Gln Gln Leu Ala Leu Tyr Thr Glu Lys Phe Glu Glu Phe Gln Asn Thr
385                 390                 395                 400

Leu Ser Lys Ser Ser Glu Val Phe Thr Thr Phe Lys Gln Glu Met Glu
                405                 410                 415

Lys Met Thr Lys Lys Ile Lys Lys Leu Glu Lys Glu Thr Thr Met Tyr
            420                 425                 430

Arg Ser Arg Trp Glu Ser Ser Asn Lys Ala Leu Leu Glu Met Ala Glu
        435                 440                 445

Glu Lys Thr Val Arg Asp Lys Glu Leu Glu Gly Leu Gln Val Lys Ile
    450                 455                 460

Gln Arg Leu Glu Lys Leu Cys Arg Ala Leu Gln Thr Glu Arg Asn Asp
465                 470                 475                 480

Leu Asn Lys Arg Val Gln Asp Leu Ser Ala Gly Gly Gln Gly Ser Leu
                485                 490                 495

Thr Asp Ser Gly Pro Glu Arg Arg Pro Glu Gly Pro Gly Ala Gln Ala
            500                 505                 510

Pro Ser Ser Pro Arg Val Thr Glu Ala Pro Cys Tyr Pro Gly Ala Pro
        515                 520                 525

Ser Thr Glu Ala Ser Gly Gln Thr Gly Pro Gln Glu Pro Thr Ser Ala
    530                 535                 540

Arg Ala
545


<210> SEQ ID NO 45
<211> LENGTH: 1614
<212> TYPE: DNA
<213> ORGANISM: Homo sapiens
<220> FEATURE:
<221> NAME/KEY: CDS
<222> LOCATION: (1)...(1614)

<400> SEQUENCE: 45

atg gcg ggg ccc ccg gcc cta ccc ccg ccg gag acg gcg gcg gcc gcc       48
Met Ala Gly Pro Pro Ala Leu Pro Pro Pro Glu Thr Ala Ala Ala Ala
 1               5                  10                  15

acc acg gcg gcc gcc gcc tcg tcg tcc gcc gct tcc ccg cac tac caa       96
Thr Thr Ala Ala Ala Ala Ser Ser Ser Ala Ala Ser Pro His Tyr Gln
            20                  25                  30

gag tgg atc ctg gac acc atc gac tcg ctg cgc tcg cgc aag gcg cgg      144
Glu Trp Ile Leu Asp Thr Ile Asp Ser Leu Arg Ser Arg Lys Ala Arg
        35                  40                  45

ccg gac ctg gag cgc atc tgc cgg atg gtg cgg cgg cgg cac ggc ccg      192
Pro Asp Leu Glu Arg Ile Cys Arg Met Val Arg Arg Arg His Gly Pro
     50                  55                  60

gag ccg gag cgc acg cgc gcc gag ctc gag aaa ctg atc cag cag cgc      240
Glu Pro Glu Arg Thr Arg Ala Glu Leu Glu Lys Leu Ile Gln Gln Arg
 65                  70                  75                  80

gcc gtg ctc cgg gtc agc tac aag ggg agc atc tcg tac cgc aac gcg      288
Ala Val Leu Arg Val Ser Tyr Lys Gly Ser Ile Ser Tyr Arg Asn Ala
                85                  90                  95

gcg cgc gtc cag ccg ccc cgg cgc gga gcc acc ccg ccg gcc ccg ccg      336
Ala Arg Val Gln Pro Pro Arg Arg Gly Ala Thr Pro Pro Ala Pro Pro
            100                 105                 110

cgc gcc ccc cgc ggg gcc ccc gcc gcc gcc gcc gcc gcc gcg ccg ccg      384
Arg Ala Pro Arg Gly Ala Pro Ala Ala Ala Ala Ala Ala Ala Pro Pro
        115                 120                 125
```

-continued

```
ccc acg ccc gcc ccg ccg cca ccg ccc gcg ccc gtc gcc gcc gcc gcc      432
Pro Thr Pro Ala Pro Pro Pro Pro Pro Ala Pro Val Ala Ala Ala Ala
    130                 135                 140

ccg gcc cgg gcg ccc cgc gcg gcc gcc gcc gcc gcc aca gcg ccc ccc      480
Pro Ala Arg Ala Pro Arg Ala Ala Ala Ala Ala Ala Thr Ala Pro Pro
145                 150                 155                 160

tcg cct ggc ccc gcg cag ccg ggc ccc cgc gcg cag cgg gcc gcg ccc      528
Ser Pro Gly Pro Ala Gln Pro Gly Pro Arg Ala Gln Arg Ala Ala Pro
                165                 170                 175

ctg gcc gcg ccg ccg ccc gcg cca gcc gct ccc ccg gcg gtg gcg ccc      576
Leu Ala Ala Pro Pro Pro Ala Pro Ala Ala Pro Pro Ala Val Ala Pro
            180                 185                 190

ccg gcc ggc ccg cgc cgc gcc ccc ccg ccc gcc gtc gcc gcc cgg gag      624
Pro Ala Gly Pro Arg Arg Ala Pro Pro Pro Ala Val Ala Ala Arg Glu
        195                 200                 205

ccg ccg ctg ccg ccg ccg cca cag ccg ccg gcg ccg cca cag cag cag      672
Pro Pro Leu Pro Pro Pro Pro Gln Pro Pro Ala Pro Pro Gln Gln Gln
    210                 215                 220

cag ccg ccg ccg ccg cag cca cag ccg ccg ccg gag ggg ggc gcg gtg      720
Gln Pro Pro Pro Pro Gln Pro Gln Pro Pro Pro Glu Gly Gly Ala Val
225                 230                 235                 240

cgg gcc ggc ggc gcg gcg cgg ccc gtg agc ctg cgg gaa gtc gtg cgc      768
Arg Ala Gly Gly Ala Ala Arg Pro Val Ser Leu Arg Glu Val Val Arg
                245                 250                 255

tac ctc ggg ggc agc ggc ggc gcc ggc ggt cgc cta acc cgc ggc cgc      816
Tyr Leu Gly Gly Ser Gly Gly Ala Gly Gly Arg Leu Thr Arg Gly Arg
            260                 265                 270

gtg cag ggg ctg ctg gag gag gag gcg gcg gct cga ggc cgt ctg gag      864
Val Gln Gly Leu Leu Glu Glu Glu Ala Ala Ala Arg Gly Arg Leu Glu
        275                 280                 285

cgc acc cgt ctc gga gcg ctt gcg ctg ccc cgc ggg gac agg ccc gga      912
Arg Thr Arg Leu Gly Ala Leu Ala Leu Pro Arg Gly Asp Arg Pro Gly
    290                 295                 300

cgg gcg ccg ccg gcc gcc agc gcc cgc ccg tct cgc agc aag aga ggt      960
Arg Ala Pro Pro Ala Ala Ser Ala Arg Pro Ser Arg Ser Lys Arg Gly
305                 310                 315                 320

gga gaa gag cga gta ctt gag aaa gaa gag gaa gaa gat gat gat gaa     1008
Gly Glu Glu Arg Val Leu Glu Lys Glu Glu Glu Glu Asp Asp Asp Glu
                325                 330                 335

gat gaa gat gaa gaa gat gat gtg tca gag ggc tct gaa gtg ccc gag     1056
Asp Glu Asp Glu Glu Asp Asp Val Ser Glu Gly Ser Glu Val Pro Glu
            340                 345                 350

agt gac cgt cct gca ggt gcc cag cac cac cag ctt aac ggc gag cgg     1104
Ser Asp Arg Pro Ala Gly Ala Gln His His Gln Leu Asn Gly Glu Arg
        355                 360                 365

gga cct cag agt gcc aag gag agg gtc aag gag tgg acc ccc tgc gga     1152
Gly Pro Gln Ser Ala Lys Glu Arg Val Lys Glu Trp Thr Pro Cys Gly
    370                 375                 380

ccg cac cag ggc cag gat gaa ggg cgg ggg cca gcc ccg ggc agc ggc     1200
Pro His Gln Gly Gln Asp Glu Gly Arg Gly Pro Ala Pro Gly Ser Gly
385                 390                 395                 400

acc cgc cag gtg ttc tcc atg gca gcc atg aac aag gaa ggg gga aca     1248
Thr Arg Gln Val Phe Ser Met Ala Ala Met Asn Lys Glu Gly Gly Thr
                405                 410                 415

gct tct gtt gcc acc ggg cca gac tcc ccg tcc ccc gtg cct ttg ccc     1296
Ala Ser Val Ala Thr Gly Pro Asp Ser Pro Ser Pro Val Pro Leu Pro
            420                 425                 430

cca ggc aaa cca gcc cta cct ggg gcc gac ggg acc ccc ttt ggc tgt     1344
Pro Gly Lys Pro Ala Leu Pro Gly Ala Asp Gly Thr Pro Phe Gly Cys
```

-continued

```
        435                 440                 445

ccg ccc ggg cgc aaa gag aag cca tct gat ccc gtc gag tgg acc gtg     1392
Pro Pro Gly Arg Lys Glu Lys Pro Ser Asp Pro Val Glu Trp Thr Val
    450                 455                 460

atg gat gtc gtc gaa tat ttt act gag gct gga ttc ccg gag cag gcg     1440
Met Asp Val Val Glu Tyr Phe Thr Glu Ala Gly Phe Pro Glu Gln Ala
465                 470                 475                 480

aca gct ttc caa gag cag gaa att gat ggc aaa tct ttg ctg ctc atg     1488
Thr Ala Phe Gln Glu Gln Glu Ile Asp Gly Lys Ser Leu Leu Leu Met
                485                 490                 495

cag cgc aca gat gtg ctc acc ggc ctg tcc atc cgc ctc ggg cca gcc     1536
Gln Arg Thr Asp Val Leu Thr Gly Leu Ser Ile Arg Leu Gly Pro Ala
            500                 505                 510

ctg aaa atc tac gag cac cac atc aag gtg ctt cag caa ggc cac ttt     1584
Leu Lys Ile Tyr Glu His His Ile Lys Val Leu Gln Gln Gly His Phe
        515                 520                 525

gag gat gat gac ccc gat ggc ttc tta ggc                             1614
Glu Asp Asp Asp Pro Asp Gly Phe Leu Gly
    530                 535


<210> SEQ ID NO 46
<211> LENGTH: 1638
<212> TYPE: DNA
<213> ORGANISM: Homo sapiens
<220> FEATURE:
<221> NAME/KEY: CDS
<222> LOCATION: (1)...(1638)

<400> SEQUENCE: 46

atg aag aac caa gac aaa aag aac ggg gct gcc aaa caa tcc aat cca       48
Met Lys Asn Gln Asp Lys Lys Asn Gly Ala Ala Lys Gln Ser Asn Pro
 1               5                  10                  15

aaa agc agc cca gga caa ccg gaa gca gga ccc gag gga gcc cag gag       96
Lys Ser Ser Pro Gly Gln Pro Glu Ala Gly Pro Glu Gly Ala Gln Glu
            20                  25                  30

cgg ccc agc cag gcg gct cct gca gta gaa gca gaa ggt ccc ggc agc      144
Arg Pro Ser Gln Ala Ala Pro Ala Val Glu Ala Glu Gly Pro Gly Ser
        35                  40                  45

agc cag gct cct cgg aag ccg gag ggt gct caa gcc aga acg gct cag      192
Ser Gln Ala Pro Arg Lys Pro Glu Gly Ala Gln Ala Arg Thr Ala Gln
    50                  55                  60

tct ggg gcc ctt cgt gat gtc tct gag gag ctg agc cgc caa ctg gaa      240
Ser Gly Ala Leu Arg Asp Val Ser Glu Glu Leu Ser Arg Gln Leu Glu
 65                  70                  75                  80

gac ata ctg agc aca tac tgt gtg gac aat aac cag ggg ggc ccc ggc      288
Asp Ile Leu Ser Thr Tyr Cys Val Asp Asn Asn Gln Gly Gly Pro Gly
                85                  90                  95

gag gat ggg gca cag ggt gag ccg gct gaa ccc gaa gat gca gag aag      336
Glu Asp Gly Ala Gln Gly Glu Pro Ala Glu Pro Glu Asp Ala Glu Lys
            100                 105                 110

tcc cgg acc tat gtg gca agg aat ggg gag cct gaa cca act cca gta      384
Ser Arg Thr Tyr Val Ala Arg Asn Gly Glu Pro Glu Pro Thr Pro Val
        115                 120                 125

gtc aat gga gag aag gaa ccc tcc aag ggg gat cca aac aca gaa gag      432
Val Asn Gly Glu Lys Glu Pro Ser Lys Gly Asp Pro Asn Thr Glu Glu
    130                 135                 140

atc cgg cag agt gac gag gtc gga gac cga gac cat cga agg cca cag      480
Ile Arg Gln Ser Asp Glu Val Gly Asp Arg Asp His Arg Arg Pro Gln
145                 150                 155                 160

gag aag aaa aaa gcc aag ggt ttg ggt aag gag atc acg ttg ctg atg      528
Glu Lys Lys Lys Ala Lys Gly Leu Gly Lys Glu Ile Thr Leu Leu Met
```

-continued

```
                165                 170                 175

cag aca ttg aat act ctg agt acc cca gag gag aag ctg gct gct ctg      576
Gln Thr Leu Asn Thr Leu Ser Thr Pro Glu Glu Lys Leu Ala Ala Leu
            180                 185                 190

tgc aag aag tat gct gaa ctg ctg gag gag cac cgg aat tca cag aag      624
Cys Lys Lys Tyr Ala Glu Leu Leu Glu Glu His Arg Asn Ser Gln Lys
        195                 200                 205

cag atg aag ctc cta cag aaa aag cag agc cag ctg gtg caa gag aag      672
Gln Met Lys Leu Leu Gln Lys Lys Gln Ser Gln Leu Val Gln Glu Lys
    210                 215                 220

gac cac ctg cgc ggt gag cac agc aag gcc gtc ctg gcc cgc agc aag      720
Asp His Leu Arg Gly Glu His Ser Lys Ala Val Leu Ala Arg Ser Lys
225                 230                 235                 240

ctt gag agc cta tgc cgt gag ctg cag cgg cac aac cgc tcc ctc aag      768
Leu Glu Ser Leu Cys Arg Glu Leu Gln Arg His Asn Arg Ser Leu Lys
                245                 250                 255

gaa gaa ggt gtg cag cgg gcc cgg gag gag gag gag aag cgc aag gag      816
Glu Glu Gly Val Gln Arg Ala Arg Glu Glu Glu Glu Lys Arg Lys Glu
            260                 265                 270

gtg acc tcg cac ttc cag gtg aca ctg aat gac att cag ctg cag atg      864
Val Thr Ser His Phe Gln Val Thr Leu Asn Asp Ile Gln Leu Gln Met
        275                 280                 285

gaa cag cac aat gag cgc aac tcc aag ctg cgc caa gag aac atg gag      912
Glu Gln His Asn Glu Arg Asn Ser Lys Leu Arg Gln Glu Asn Met Glu
    290                 295                 300

ctg gct gag agg ctc aag aag ctg att gag cag tat gag ctg cgc gag      960
Leu Ala Glu Arg Leu Lys Lys Leu Ile Glu Gln Tyr Glu Leu Arg Glu
305                 310                 315                 320

gag cat atc gac aaa gtc ttc aaa cac aag gac cta caa cag cag ctg     1008
Glu His Ile Asp Lys Val Phe Lys His Lys Asp Leu Gln Gln Gln Leu
                325                 330                 335

gtg gat gcc aag ctc cag cag gcc cag gag atg cta aag gag gca gaa     1056
Val Asp Ala Lys Leu Gln Gln Ala Gln Glu Met Leu Lys Glu Ala Glu
            340                 345                 350

gag cgg cac cag cgg gag aag gat ttt ctc ctg aaa gag gca gta gag     1104
Glu Arg His Gln Arg Glu Lys Asp Phe Leu Leu Lys Glu Ala Val Glu
        355                 360                 365

tcc cag agg atg tgt gag ctg atg aag cag caa gag acc cac ctg aag     1152
Ser Gln Arg Met Cys Glu Leu Met Lys Gln Gln Glu Thr His Leu Lys
    370                 375                 380

caa cag ctt gcc cta tac aca gag aag ttt gag gag ttc cag aac aca     1200
Gln Gln Leu Ala Leu Tyr Thr Glu Lys Phe Glu Glu Phe Gln Asn Thr
385                 390                 395                 400

ctt tcc aaa agc agc gag gta ttc acc aca ttc aag cag gag atg gaa     1248
Leu Ser Lys Ser Ser Glu Val Phe Thr Thr Phe Lys Gln Glu Met Glu
                405                 410                 415

aag atg act aag aag atc aag aag ctg gag aaa gaa acc acc atg tac     1296
Lys Met Thr Lys Lys Ile Lys Lys Leu Glu Lys Glu Thr Thr Met Tyr
            420                 425                 430

cgg tcc cgg tgg gag agc agc aac aag gcc ctg ctt gag atg gct gag     1344
Arg Ser Arg Trp Glu Ser Ser Asn Lys Ala Leu Leu Glu Met Ala Glu
        435                 440                 445

gag aaa aca gtc cgg gat aaa gaa ctg gag ggc ctg cag gta aaa atc     1392
Glu Lys Thr Val Arg Asp Lys Glu Leu Glu Gly Leu Gln Val Lys Ile
    450                 455                 460

caa cgg ctg gag aag ctg tgc cgg gca ctg cag aca gag cgc aat gac     1440
Gln Arg Leu Glu Lys Leu Cys Arg Ala Leu Gln Thr Glu Arg Asn Asp
465                 470                 475                 480

ctg aac aag agg gta cag gac ctg agt gct ggt ggc cag ggc tcc ctc     1488
```

-continued

```
Leu Asn Lys Arg Val Gln Asp Leu Ser Ala Gly Gly Gln Gly Ser Leu
                485                 490                 495

act gac agt ggc cct gag agg agg cca gag ggg cct ggg gct caa gca      1536
Thr Asp Ser Gly Pro Glu Arg Arg Pro Glu Gly Pro Gly Ala Gln Ala
            500                 505                 510

ccc agc tcc ccc agg gtc aca gaa gcg cct tgc tac cca gga gca ccg      1584
Pro Ser Ser Pro Arg Val Thr Glu Ala Pro Cys Tyr Pro Gly Ala Pro
        515                 520                 525

agc aca gaa gca tca ggc cag act ggg cct caa gag ccc acc tcc gcc      1632
Ser Thr Glu Ala Ser Gly Gln Thr Gly Pro Gln Glu Pro Thr Ser Ala
    530                 535                 540

agg gcc                                                              1638
Arg Ala
545


<210> SEQ ID NO 47
<211> LENGTH: 550
<212> TYPE: PRT
<213> ORGANISM: Oryctolagus cuniculus

<400> SEQUENCE: 47

Met Ala Gly Pro Pro Ala Leu Pro Pro Pro Glu Thr Ala Ala Ala Ala
 1               5                  10                  15

Thr Thr Ala Ala Ala Ala Ala Ser Ser Ser Ala Ala Ser Pro His Tyr
            20                  25                  30

Gln Glu Trp Ile Leu Asp Thr Ile Asp Ser Leu Arg Ser Arg Lys Ala
        35                  40                  45

Arg Pro Asp Leu Glu Arg Ile Cys Arg Met Val Arg Arg Arg His Gly
    50                  55                  60

Pro Glu Pro Glu Arg Thr Arg Ala Glu Leu Glu Lys Leu Ile Gln Gln
65                  70                  75                  80

Arg Ala Val Leu Arg Val Ser Tyr Lys Gly Ser Ile Ser Tyr Arg Asn
                85                  90                  95

Ala Ala Arg Val Gln Pro Pro Arg Arg Gly Ala Thr Pro Pro Ala Pro
            100                 105                 110

Pro Arg Ala Pro Arg Gly Gly Pro Ala Ala Ala Ala Ala Pro Pro Pro
        115                 120                 125

Thr Pro Ala Pro Pro Pro Pro Pro Ala Pro Val Ala Ala Ala Ala Ala
    130                 135                 140

Pro Ala Arg Ala Pro Arg Ala Ala Ala Ala Ala Ala Ala Ala Thr Ala
145                 150                 155                 160

Pro Pro Ser Pro Gly Pro Ala Gln Pro Gly Pro Arg Ala Gln Arg Ala
                165                 170                 175

Ala Pro Leu Ala Ala Pro Pro Pro Ala Pro Ala Ala Pro Pro Ala Ala
            180                 185                 190

Ala Pro Pro Ala Gly Pro Arg Arg Ala Pro Pro Pro Ala Ala Ala Val
        195                 200                 205

Ala Ala Arg Glu Ser Pro Leu Pro Pro Pro Pro Gln Pro Pro Ala Pro
    210                 215                 220

Pro Gln Gln Gln Gln Gln Pro Pro Pro Pro Pro Pro Pro Gln Gln Pro
225                 230                 235                 240

Gln Pro Pro Pro Glu Gly Gly Ala Ala Arg Ala Gly Gly Pro Ala Arg
                245                 250                 255

Pro Val Ser Leu Arg Glu Val Val Arg Tyr Leu Gly Gly Ser Ser Gly
            260                 265                 270

Ala Gly Gly Arg Leu Thr Arg Gly Arg Val Gln Gly Leu Leu Glu Glu
```

-continued

```
        275                 280                 285

Glu Ala Ala Ala Arg Gly Arg Leu Glu Arg Thr Arg Leu Gly Ala Leu
    290                 295                 300

Ala Leu Pro Arg Gly Asp Arg Pro Gly Arg Ala Pro Pro Ala Ala Ser
305                 310                 315                 320

Ala Arg Ala Ala Arg Asn Lys Arg Ala Gly Glu Glu Arg Val Leu Glu
                325                 330                 335

Lys Glu Glu Glu Glu Glu Glu Glu Glu Asp Asp Glu Asp Asp Asp Asp
            340                 345                 350

Asp Val Val Ser Glu Gly Ser Glu Val Pro Glu Ser Asp Arg Pro Ala
        355                 360                 365

Gly Ala Gln His His Gln Leu Asn Gly Gly Glu Arg Gly Pro Gln Thr
    370                 375                 380

Ala Lys Glu Arg Ala Lys Glu Trp Ser Leu Cys Gly Pro His Pro Gly
385                 390                 395                 400

Gln Glu Glu Gly Arg Gly Pro Ala Ala Gly Ser Gly Thr Arg Gln Val
                405                 410                 415

Phe Ser Met Ala Ala Leu Ser Lys Glu Gly Gly Ser Ala Ser Ser Thr
            420                 425                 430

Thr Gly Pro Asp Ser Pro Ser Pro Val Pro Leu Pro Pro Gly Lys Pro
        435                 440                 445

Ala Leu Pro Gly Ala Asp Gly Thr Pro Phe Gly Cys Pro Ala Gly Arg
    450                 455                 460

Lys Glu Lys Pro Ala Asp Pro Val Glu Trp Thr Val Met Asp Val Val
465                 470                 475                 480

Glu Tyr Phe Thr Glu Ala Gly Phe Pro Glu Gln Ala Thr Ala Phe Gln
                485                 490                 495

Glu Gln Glu Ile Asp Gly Lys Ser Leu Leu Leu Met Gln Arg Thr Asp
            500                 505                 510

Val Leu Thr Gly Leu Ser Ile Arg Leu Gly Pro Ala Leu Lys Ile Tyr
        515                 520                 525

Glu His His Ile Lys Val Leu Gln Gln Gly His Phe Glu Asp Asp Asp
    530                 535                 540

Pro Glu Gly Phe Leu Gly
545                 550


<210> SEQ ID NO 48
<211> LENGTH: 2561
<212> TYPE: DNA
<213> ORGANISM: Oryctolagus cuniculus
<220> FEATURE:
<221> NAME/KEY: CDS
<222> LOCATION: (246)...(1895)

<400> SEQUENCE: 48

ggtctgtgtg tgcgtgcgtg cgagtgagtg agtgtgtgca tattttttt tctcttttct      60

ttctctctct ttttttttt tttgcaaaga aacagcagcg ccgccgccgc tccgccgagg    120

cgctgcgccc cccgggggg ggaggcggag gaggcgggca gcggcggagg gaggggagcc    180

ggggaggggg gcgccgcgct gggagggagg cagcgcgcac ggtgcagccg ggccgggcgg    240

gaggc atg gcg ggg ccc ccg gcc cta ccc ccg ccg gag acg gcg gcg gcc    290
      Met Ala Gly Pro Pro Ala Leu Pro Pro Pro Glu Thr Ala Ala Ala
        1               5                  10                  15

gcc acc acg gcc gcg gcc gcc gcc tcg tcg tcc gcc gct tcc ccg cac      338
Ala Thr Thr Ala Ala Ala Ala Ala Ser Ser Ser Ala Ala Ser Pro His
                20                  25                  30
```

-continued

```
tac caa gag tgg att ctg gac acc atc gac tcg ctg cgc tcg cgc aag      386
Tyr Gln Glu Trp Ile Leu Asp Thr Ile Asp Ser Leu Arg Ser Arg Lys
            35                  40                  45

gcg cgg ccg gac ctg gag cgc atc tgc cgg atg gtg cgg cgg cgg cac      434
Ala Arg Pro Asp Leu Glu Arg Ile Cys Arg Met Val Arg Arg Arg His
        50                  55                  60

ggc ccg gag ccg gag cgc acg cgc gcc gag ctc gag aaa ctg atc cag      482
Gly Pro Glu Pro Glu Arg Thr Arg Ala Glu Leu Glu Lys Leu Ile Gln
    65                  70                  75

cag cgc gcc gtg ctc cgg gtc agc tac aag ggg agc atc tcg tac cgc      530
Gln Arg Ala Val Leu Arg Val Ser Tyr Lys Gly Ser Ile Ser Tyr Arg
 80                  85                  90                  95

aac gcg gcg cgc gtc cag ccg ccc cgg cgc gga gcc acc ccg ccg gcc      578
Asn Ala Ala Arg Val Gln Pro Pro Arg Arg Gly Ala Thr Pro Pro Ala
                100                 105                 110

ccg ccg cgc gcc ccc cgc ggg ggc ccc gcc gcc gcc gcc gcg ccg ccg      626
Pro Pro Arg Ala Pro Arg Gly Gly Pro Ala Ala Ala Ala Ala Pro Pro
            115                 120                 125

ccc acg ccc gcc ccg ccg ccg ccg ccc gcg ccc gtc gcc gcc gcc gcc      674
Pro Thr Pro Ala Pro Pro Pro Pro Pro Ala Pro Val Ala Ala Ala Ala
        130                 135                 140

gcc ccg gcc cgg gcg ccc cgc gcg gcc gcc gcc gcc gct gcc gcc aca      722
Ala Pro Ala Arg Ala Pro Arg Ala Ala Ala Ala Ala Ala Ala Ala Thr
    145                 150                 155

gcg ccc ccc tcg ccc ggc ccc gcg cag ccg ggc ccc cgc gcg cag cgg      770
Ala Pro Pro Ser Pro Gly Pro Ala Gln Pro Gly Pro Arg Ala Gln Arg
160                 165                 170                 175

gcc gcg ccc ctg gcc gcg ccg ccg ccc gcg ccc gcc gct ccc ccg gcg      818
Ala Ala Pro Leu Ala Ala Pro Pro Pro Ala Pro Ala Ala Pro Pro Ala
                180                 185                 190

gcg gcg ccc ccg gcc ggc ccg cgc cgc gcc ccc ccg ccc gcc gcc gcc      866
Ala Ala Pro Pro Ala Gly Pro Arg Arg Ala Pro Pro Pro Ala Ala Ala
            195                 200                 205

gtc gcc gcc cgg gag tcg ccg ctg ccg ccg ccg cca cag ccg ccg gcg      914
Val Ala Ala Arg Glu Ser Pro Leu Pro Pro Pro Pro Gln Pro Pro Ala
        210                 215                 220

ccg cca cag cag cag cag cag ccg ccg ccg cca ccg ccg ccg cag cag      962
Pro Pro Gln Gln Gln Gln Gln Pro Pro Pro Pro Pro Pro Pro Gln Gln
    225                 230                 235

cca cag ccg ccg ccg gag ggg ggc gcg gcg cgg gcc ggc ggc ccg gcg     1010
Pro Gln Pro Pro Pro Glu Gly Gly Ala Ala Arg Ala Gly Gly Pro Ala
240                 245                 250                 255

cgg ccc gtg agc ctg cgg gaa gtc gtg cgc tac ctc ggg ggt agc agc     1058
Arg Pro Val Ser Leu Arg Glu Val Val Arg Tyr Leu Gly Gly Ser Ser
                260                 265                 270

ggc gct ggc ggc cgc ctg acc cgc ggc cgc gtg cag ggt ctg ctg gaa     1106
Gly Ala Gly Gly Arg Leu Thr Arg Gly Arg Val Gln Gly Leu Leu Glu
            275                 280                 285

gag gag gcg gcg gcg cgg ggc cgc ctg gag cgc acc cgt ctc gga gcg     1154
Glu Glu Ala Ala Ala Arg Gly Arg Leu Glu Arg Thr Arg Leu Gly Ala
        290                 295                 300

ctt gcg ctg ccc cgc ggg gac agg ccc gga cgg gcg cca ccg gcc gcc     1202
Leu Ala Leu Pro Arg Gly Asp Arg Pro Gly Arg Ala Pro Pro Ala Ala
    305                 310                 315

agc gcc cgc gcg gcg cgg aac aag aga gct ggc gag gag cga gtg ctt     1250
Ser Ala Arg Ala Ala Arg Asn Lys Arg Ala Gly Glu Glu Arg Val Leu
320                 325                 330                 335

gaa aag gag gag gag gag gag gag gag gaa gac gac gag gac gac gac     1298
Glu Lys Glu Glu Glu Glu Glu Glu Glu Glu Asp Asp Glu Asp Asp Asp
```

-continued

```
            340                 345                 350

gac gac gtc gtg tcc gag ggc tcg gag gtg ccc gag agc gat cgt ccc      1346
Asp Asp Val Val Ser Glu Gly Ser Glu Val Pro Glu Ser Asp Arg Pro
            355                 360                 365

gcg ggt gcg cag cat cac cag ctg aat ggc ggc gag cgc ggc ccg cag      1394
Ala Gly Ala Gln His His Gln Leu Asn Gly Gly Glu Arg Gly Pro Gln
        370                 375                 380

acc gcc aag gag cgg gcc aag gag tgg tcg ctg tgt ggc ccc cac cct      1442
Thr Ala Lys Glu Arg Ala Lys Glu Trp Ser Leu Cys Gly Pro His Pro
    385                 390                 395

ggc cag gag gaa ggg cgg ggg ccg gcc gcg ggc agt ggc acc cgc cag      1490
Gly Gln Glu Glu Gly Arg Gly Pro Ala Ala Gly Ser Gly Thr Arg Gln
400                 405                 410                 415

gtg ttc tcc atg gcg gcc ttg agt aag gag ggg gga tca gcc tct tcg      1538
Val Phe Ser Met Ala Ala Leu Ser Lys Glu Gly Gly Ser Ala Ser Ser
            420                 425                 430

acc acc ggg cct gac tcc ccg tcc ccg gtg cct ttg ccc ccc ggg aag      1586
Thr Thr Gly Pro Asp Ser Pro Ser Pro Val Pro Leu Pro Pro Gly Lys
        435                 440                 445

cca gcc ctc cca gga gcc gat ggg acc ccc ttt ggc tgc cct gcc ggg      1634
Pro Ala Leu Pro Gly Ala Asp Gly Thr Pro Phe Gly Cys Pro Ala Gly
        450                 455                 460

cgc aaa gag aag ccg gca gac ccc gtg gag tgg aca gtc atg gac gtc      1682
Arg Lys Glu Lys Pro Ala Asp Pro Val Glu Trp Thr Val Met Asp Val
    465                 470                 475

gtg gag tac ttc acc gag gcg ggc ttc cct gag caa gcc acg gct ttc      1730
Val Glu Tyr Phe Thr Glu Ala Gly Phe Pro Glu Gln Ala Thr Ala Phe
480                 485                 490                 495

cag gag cag gag atc gac ggc aag tcc ctg ctg ctc atg cag cgc acc      1778
Gln Glu Gln Glu Ile Asp Gly Lys Ser Leu Leu Leu Met Gln Arg Thr
            500                 505                 510

gat gtc ctc acc ggc ctg tcc atc cgc ctg ggg cca gcg ttg aaa atc      1826
Asp Val Leu Thr Gly Leu Ser Ile Arg Leu Gly Pro Ala Leu Lys Ile
        515                 520                 525

tat gag cac cat atc aag gtg ctg cag cag ggt cac ttc gag gac gat      1874
Tyr Glu His His Ile Lys Val Leu Gln Gln Gly His Phe Glu Asp Asp
        530                 535                 540

gac ccg gaa ggc ttc ctg gga tgagcacaga gccgccgcgc cccttgtccc         1925
Asp Pro Glu Gly Phe Leu Gly
    545                 550

cacccccacc ccgcctggac ccattcctgc ctccatgtca cccaaggtgt cccagaggcc   1985

aggagctgga ctgggcaggc gaggggtgcg gacctaccct gattctggta gggggcgggg   2045

ccttgctgtg ctcattgcta ccccccccacc ccgtgtgtgt ctctgcacct gcccccagca   2105

cacccctccc ggagcctgga tgtcgcctgg gactctggcc tgctcatttt gcccccagat   2165

cagccccctc cctccctcct gtcccaggac attttttaaa agaaaaaaag gaaaaaaaaa   2225

aattggggag ggggctggga aggtgcccca agatcctcct cggcccaacc aggtgtttat   2285

tcctatatat atatatatat gttttgttct gcctgttttt cgtttttttgg tgcgtggcct   2345

ttcttccctc ccaccaccac tcatggcccc agccctgctc gccctgtcgg cgggagcagc   2405

tgggaatggg aggagggtgg gaccttgggt ctgtctccca ccctctctcc cgttggttct   2465

gttgtcgctc cagctggctg tattgctttt taatattgca ccgaagggtt gttttttttt   2525

ttttaaataa aattttaaaa aaaggaaaaa aaaaaa                             2561

<210> SEQ ID NO 49
<211> LENGTH: 12619
```

-continued

<212> TYPE: DNA
<213> ORGANISM: Homo sapiens

<400> SEQUENCE: 49

```
aagctttata aagatttaac tacctaataa ggtagagaag taatttatgt gcccactaaa     60
aaatactcaa tttctgaatg ttcgtccaaa attaacttgt cagatcatta aatcattgac    120
tagaaacacg ttgagtacct attatgtact aggcacttag atcattgtga gacaataaaa    180
aatactgcat tagaaaagga catttttcac atcttaaatg caataagcat tatttggctg    240
gcagttaatt acatttaaca cattaaacat atagagcaaa attctgagca atcaaaataa    300
ttatacctt gagcaatcga ttatttaaat ttctttcact attcccttaa gctgatttct    360
actctgggat tctttcatag ttctcaaata agaaaataaa aaatttccta aataaggcaa    420
tacaaaagaa tagaaatgta agagaagaga tatattagct cttgaatccc tgtttccatt    480
tgctgtcaat agtgcctcta atgttcgatt ttctcttcaa agaaaaatct tgatttaaaa    540
ggaagaaaaa gtacaatcac ctttaacagc taaagtatac tgattagcat ctactaaagt    600
tagcaaagac tgaaactgaa aaaaaattgt aaaatcttta ttctaagtta tataacgcca    660
ttcaccatag taatgatttt atactttggt atatggcttt ttaaaataaa tattgccaac    720
aggtaaaaat ttttcctttg ctgtcttaag gcattcctaa gagaattttt accagtgtgt    780
gttcataact tgaatgttaa tttaaacaat gttacttcta tcacctaaat gatatactta    840
tagaagagtg gtttaattgg gaacagaaaa acaccacatt gcttcttccc aagaaaaagg    900
gatgtattcc attctcgagg tctctctccc actctctatt tatatataat atactgcata    960
gataaatata cacacattat atatgtattt ttttgaactt aaagaagact ggacatatgt   1020
atttacatgt atatatccaa caaatattta attttgagat ctctctccct cttctgattt   1080
attattctca gtatgaattc tcaaactgta cggtctttca catttcattc attcatcaag   1140
catgtatcga gtcccttctg catgcttagc tttttgtcat atggaaggaa gatacaaaag   1200
aaaaactgtt tctgcccttc agaatctttc catctcttct aggaaggaga taaaacacca   1260
tatatcatta agaaatttat aagactagtc ccaaaaccaa tggtacaagc aacatgcatt   1320
ttacatttat gtagaatttt agagcttgga aacactttcg tgatatataa tcctaagaac   1380
aatcttgtaa agtgcacatt attagctcca tttcagtgat gaggaatctg agacagaatt   1440
ttaagtgaca tgtctcgttc aaacattatg agtggaagag tcaacactta agcctgagtt   1500
ttctgattct aagcctagtg ctcttttcaa cacagcactg gaaaccaaag attgtggtac   1560
acaacaaggc aacagccagt cttcttgctc gaggtccaac taaactggac ccataccgag   1620
cagtgtccag ccaaatgtcc aaattaattt tatcctgcaa atatttgttc ttcagtgtaa   1680
tacacacagc acaactacca tttccttcgt cttagtgcct ttatctccta cattccagaa   1740
atggggatgt caaatatttt tttaaatctg gcctagatgg aatcatataa atctcaaatc   1800
ataatataaa tcttaaaggt ctggtttcca ccaatccttc cacattttgt tttcccccag   1860
cactagagag cctaacctac cctcacccct ttcgagcatt cttgctccaa acgaccacct   1920
attttaagat gtcaatgacc ctttcccaaa ttctacaaat tcaccccagt tttgccaccc   1980
gaccccagcg cctgcccgga cacgttcccc tccctcccaa tagatttgat accgagttca   2040
ggttctgcag atcccgttgc gatgctgtca cacagcactg acagataaga tttgaccttt   2100
cgactccgtc cttggggact tcccgctggc caagaagggt agttccaatc ccaggaaacg   2160
ggcttcctgc tcaggaacgc agcctctagc agcgcacagt ctgaggcaat gtctccggca   2220
```

-continued

```
attagaacga tgctgggcgc ccgggtgtgc atcactctgc ctcatactcc taccaactgc   2280
agggcactcg gtccggcagc cagtccatcc cacccacacc caagtcccag ccagccggac   2340
cttacgcagg accccgatga taggtcgttg acggctgcag caaaagccaa ggccacctgc   2400
cgctgctgcc catccccgcc aatctgagac cccctagact ggaccgcaga aaagcgtttc   2460
tatgggaacc cccccaccga gaatcacgtg acgcaatcgg acgaccaatc gcttcttacc   2520
tctgcccgcg gtccagcttt tggccctccc tctcgccccc gcctccttcg cccagccccg   2580
ccccttgcct gcggagagcc cgcgcctgcg cgctgtgtcc tgcgcgctcc ttccctcgcg   2640
cgcgctctcc gtggaagagc aggggcagcg tgggaggcgc caagggagcg cgaacctgag   2700
gaggaagaaa cggggctagc gcgcaggccc agaacggtcc gagccgcggc agtcggcgac   2760
gcctcagagc ggaagaggga agtgaatcag gcgccgggta gtgggttgct gggctgggct   2820
tgctgaggta gaggcagcgc caagaagagg cctttgccgc tggtcgggat tgggatgtcg   2880
aagaacacag tgtcgtcggc ccgcttccgg aaggtggacg tggatgaata tgacgagaac   2940
aagttcgtgg acgaagaaga tggggggcgac ggccaggccg ggcccgacga gggcgaggtg   3000
gactcctgcc tgcggcaata tccttgcatt caccgccctc cccaccccag cccagcccag   3060
cccgcccttc tcctgggacc cgggagcctg caggatccgc ggggcaccgg cgcggagctg   3120
cctctcaacc tgcggcttaa cctgtctctt tgggatcgcc cgctctgaga gggcaagggg   3180
gaagcccccg tttcctaccc agtcggcagg agacgcgagg gtcccactct tggaagcctg   3240
ccctaccccg cgcgccttcc acgcccccag attcctcagg ttgcacccga gtgcctgcct   3300
gcctcgggaa ctggtcccgc cgcccgcgcc ctcgcggcgc tggggaaggc ggccccggct   3360
ggtggggaag gctggtgccg accgccttag tttttcttcc tagaactctg atttcctggg   3420
gtcacattag ctcccagaaat ttctgattgt ggggaacctg catctttcct tagtggtttt   3480
gttttttggt tgtgtttttg ttattggtag cgttaaggta gtttattgct taccgggggg   3540
ccgggggaga tgggactgtt cgaaaattga gggtccctgt gctttcagcc cattggcctt   3600
tttaaaaaaa aaaaaaaaag aagaagaaga aggggatttg gcaaaatata cattgtacag   3660
aatttgttaa ctgggggagg ggaatgaata caaaaaatac aaaactccta gaaggaagct   3720
tggagccttt tacctgctaa gaaaaggaca atagaaaaaa caacggggaa tgcgtgtgga   3780
gaatccttgg aaatatttaa aataaacccc aatgaataag atagaagatg agtcattcgt   3840
ataaagcaga atcattttttg taatcctaaa attgtttcca ttttagttaa aatatggcag   3900
tcagttcccg gtttctgttt ttgcatattt gaatattcat aactttggct tcgcatttgc   3960
attacatctt ttttagaaaa atgtaaatgt tgcaaaaaaa ccgaagctgt agttttagaa   4020
aatctcagac actgaatttg tatgcatttc taattcttgg gtgtattcat aaggaagact   4080
ctcaacaatg tcctgttata gtggggaaat atgagagtga aaatatttaa tggcaacaat   4140
atcctttttt aaaggcacct aaatagagca ttagacattt atcaatatat agatagtgct   4200
ttgcccaact ttcacaatta attagctgtt gctcttttgc attatttaaa tacttaagtg   4260
cttggagtta taaaaaatga gctaatctac atcaggcatg cttctctaga aatccctgca   4320
gccttgaaaa taacagcttg tcaaccagag attttgtgta agaacttttt ctttagaaaa   4380
taaatggtga acatgcttcc taaaaacatt atttgtgatg ggataagatg gtgttttatg   4440
aaaccccagt gtattttagg taatttgtgg tgacttttaa aaggtactgc tgtatccata   4500
tcagtggatc tgctttttga tcagttcatc ttaaaatata aagatactgt ctcttcttac   4560
cgttacatac agccaggaaa gacagcccta gtggtggggt actagagttg gaggaacaag   4620
```

-continued

```
tgaactctgt ggttttcctt ttaggggaat gtttgtacat tctgacagtc tgattggcct   4680
tctgtttctc atgcttgcta actcactagt gctttcaaag agagcctgaa tttaataggt   4740
atggtctaac acagtttgaa taacctttgt gaaatatgag agaaaatatc taaagcaaaa   4800
aattaagctg ccacctaagg gacatatgaa ttattacatc ttctgtgatg cctcttttca   4860
tcaatattga gagattgcta atgtgtatca ttcagattgc taatctgcca gcatgttcta   4920
ccagcatttc agataataca gaatatggtt ctagcaaaag tttggtcttt attttttcaa   4980
ttagaatcac aggaaaagac atattttggt tgataatagg ttatttcatt tgggggacta   5040
ataattctga tatatatttt aggatttctt taacaccact ctaggtaatg tttgcatatg   5100
tatctcactg ggaaatgaaa gactatcaag gtgttcactt gatagttaga accaagggtg   5160
aaacagtctt tgctttatta aaaaaaagtc taatgttcta ttttgctttt gatattttgc   5220
ctttgattaa catcctggaa accaacacat tgaatttcca gtattgaaca tagtgaccaa   5280
agtaattttc tttttatatg taaatcaagt cataaagaac cagtggttat aatgctttct   5340
gggggccatc ctttgctgtt acacccttaa cttccatcac aggaaacatg acagctgccc   5400
tacaggcagc tctgaagaac ccccctatca acaccaagag tcaggcagtg aaggtgagtc   5460
gcagactaca acacagtgat ctctgctgat atcttattct tagtaaaatc cttgcagtgc   5520
aaaaaaaaat caatatttta actgtttgct atctttgaca agaagagttt ataatgtagt   5580
ttgataggta aaaatttcac gtgaaaaaat agccctataa tgtagttatg ataatgctgc   5640
atggtaagat acagtaagtt caaacgatag tgaaatcatt tgtgtgtgtt tttagaggag   5700
accactcagg ctgaatttga gcaaaggttt gaaaaataag ttaaaccttt acaaaaataa   5760
acagattgta attgcttttt aaagattttt taaaaccata caaatactaa atacttatta   5820
tagaaagctc agacatatga gaaggttaaa aagatagtgg tttgtggtcc cagcacccag   5880
agataacagt tactactttg gggccttgct gtattgttac agagttccct tttgtttttt   5940
taagaatgaa tttttaaaac gggctttttc agctatatgc aatggtacat gagctttcct   6000
tccccaataa gttaatagcc ttttttaaca cttgtatatg gataagctcc agtgtataca   6060
taactaatct tttgtttata tttagactga cttttttttt cctattgtaa accactgaaa   6120
tcaatatttt ttggtaaatt tttaattgtt ctctttgagt aaattgctag cagtgaatta   6180
ctggatcaaa gaatgcactt ttttttaagg cttttggtat gcagtattgc caaattgccc   6240
ttcagaacag ttgtgcaact tacattctct gcagtctttt actaattctt aacctattta   6300
cgtatttatt taaaatgatg cccatagcat caacccccgtt gtccatagct attcatacat   6360
cctaggagct tcaagaatct caattgaata gtagtaagta ataacttagg taaatgcata   6420
ataattatct aggtaacata atttttttatt ggggaaaatt tctttggttt ttacaagttg   6480
taaagattgt cgttgaaatt tcatttttac cgtggatgca aagatatttt tctaaatctg   6540
gtaattgcag tctttaaacc aaagataaca gtaggtggta gaaacattct gtgaaatcct   6600
gaccagtagg aatgctggag gtatcacttt gtgttgaatg gaaggagaaa cgaattgttg   6660
aaaaggtcag ttaagtgttt cctttgcttg gccggatggg taagaaaata actgcttttg   6720
aagcaggctt ttgccaaaga aaaaagatca ttattaatga acatcactat atttcatatc   6780
tacagtcaat tcatataaat tacagtcaat tttcttttaa gacagcttgg tttattaaaa   6840
tttttaaata aaaaagtttt taagaaaaaa ttacttctga aggataattc aaggtgaaac   6900
tgcaaatctg cctccttgtt ttgttgggaa tttttttttt tttttttttt ttttgagacg   6960
```

-continued

```
gagtctcact ctatcaccca ggttggagtg cagtggtgca atctcaactc actgcaccct   7020
ccgcctcccg ggtttaagca atcctcctgc ttcagcctcc cgagtagctg ggatcacagg   7080
cacacaccac catgcctgga taatttctgt atttttagaa gaaaacaggg ttttaccatt   7140
ttggccaggc tggtctcgaa ctcctgacct caggtgatct gcccatctcg gcctcccaaa   7200
gtgctgggat tacagctgtg ggccaccaca cccggccgtt ttgttgggat tttttttttt   7260
taagatcaag acataaattt aaatgttgtt ttaataaatt gttaaattat cacattgatc   7320
tgttagcaaa tcctctcagc tctgccttca attatgttaa tagtctgtca agtttcttac   7380
cacctccact gctactatgc ttaccacatc cagcctgtat tattgcaatt gcctcctaat   7440
tgctctccct gcttctacct tatcccctac tcccacagct tattttctgt aacatagatg   7500
ccaaagcaat cctgttaaaa tgtgagtcag attatggcac tgctcttaaa accttccaat   7560
gtcttctcat ttctctcagt aaaagccaaa ctccttacaa tgcctgtagg ccttacacga   7620
tctgtcctcc cataacctct gacttactca cgtgcttttc tcccaccaat ccactccaac   7680
cacattgggt ttttttctgt tcctggaaca cactgaacac acactaatag cactgttctt   7740
tcctctgtct gaaacacttt cctcagttat cccaagcctt ctttcacgtc cttcaggtcc   7800
ttactcaaat gtcacattca tagtgtagac tttctgaaat tctaaaccct cctcatacag   7860
atatgtctaa atgttctgtt atttattgac ccaccaggac cgggcaggca gcattgtctt   7920
gaaggtgctc atctctttta aagctaatga tatagaaaag gcagttcaat ctctggacaa   7980
gaatggtgtg gatctcctaa tgaagtatat ttataaagga tttgagagcc cgtctgacaa   8040
tagcagtgct atgttactgc aatggcatga aaaggtaagt tatgaattat aaatctatat   8100
gactggttct tttacaatag ggaatgacaa tgacaacctc tctcacctaa ataaccattt   8160
tgatttgttg tacatttttg ttattacaaa taaaatgcat gaaaaggata gttcatattt   8220
atgtttacta gccttggtct taagagattc tgattccaac acttgtgttt attcaacaat   8280
gattattagt aattaaacat aatcttgaac tctgaattaa atcaaaactt tgtaaaagaa   8340
aataagcaat acaaatcaag aattctttca cagtgaccaa aaggtgaaaa caacacaagg   8400
atcgaatatg attcaaccat taaaaggaat gacattctga cacatgctat aacattaata   8460
aaccttgaaa acataccaag tgaaatgagc caaacacaaa agaactaata ttttataatt   8520
ttacttatat gaaataatct aggataggca aacacaaagg gacagaaagt ccttagaggt   8580
tactaggaag tagggaaagc aaggaatagg gagttagtgc ttaataggta cagagttcct   8640
ccttggagtg gtaaaaaagt tttggaaaca gatagtggtg atggctacag tacattgtga   8700
atataattaa tgccaatgga ttttacactt aaagatggtt aaaatggcaa attttgtgtt   8760
agatatttta caactttttt aaagaattag gagtttggag gatcaagaat tcttaaatca   8820
tgtttttcta ttttcatgtg tatattttgc aatgtaagta gatgctggta catcatctgt   8880
caaaagagta taagtgattt tgagctttgg gtaaaaaact ggataacatg taaatagaac   8940
cagtcataaa aatattgagt gtttgaagtg tatctgagtg aaaacacaaa cataagaaaa   9000
aagcacatag taaaacaata gttcccccttttactctaaa atgcaccaat ttgggtagta   9060
atttatatgg caccctattc atggaacact ttctgttgcc aggtaccata ctattaatgt   9120
tttatttaac ctttacaaca accctgtgga agtatataaa tatctttatc atcctcaatt   9180
tacagatgaa aagctagctt taaaacccaa gccagcgtag ttctagcata gcctcaagat   9240
tgcagtgaac attgattact tattatattc cacatattct tcaaaggact ttataaatat   9300
taactcattt aatcctcata aaaatggagg gaaatgcttg ctattattcc tcttttgtca   9360
```

-continued

```
ctgaggaaac tgaggcatgt gtgaagtctt catttcttcc aaatgtcagt caccagtttt   9420
taccaatctt cgaagtattt ctgaaatcta tctgttcaag cgtatctaat gcagctgttc   9480
acagcatctc tcccagtctg ttgccatagc ttcctgactg gtttcccagt taacagtttt   9540
gcctccttca aatctgttct ccacccagcc atcaaaatga tatctttaaa atcaaaattg   9600
cccttgtcag tcacctgcag ggataaagtc aaagttccca agtctagctt catcttccat   9660
gtcattcttc ccctcaggct atagcaatgc cagccttttt cctgaatgca ccatattgtt   9720
tcacacctcc atacatttgc tcatgatttt ctggtgttag cctgtcacct actcattctt   9780
ttaatgtgtc atttcctcca tgaagcctta gctgaaacat tcctctatac tgttaatctg   9840
ggtataagcc tctccctggt gctttaatag cacctgcagc acaactctca tttcatacat   9900
tagattaaaa ttacctgttt atatgtctgt ctcctcatgc tagaccagaa aatgctgtat   9960
ttgttcactt ttgtatcccc agcatctagc acagtactca gtatacaaag gtattccata  10020
aatatttttt gaacagaaag aaaccagagc tcagattcct aatacttgat cattactctc  10080
tatttttcaa attagagtca gagttaaagt ttctaagttc ttagctatta aacaatacct  10140
tctttctttg ggagaaaaaa aatctgacaa aggctgacta atcgaagtgg aagttgggat  10200
ggttgatccc agtttgaatt ttcttctgac tatgtggtga gaatgagaaa tgcagaatgt  10260
ccacctgttt tgagcaggaa cactatgctg cagatttttt tttttttttt tttttttttt  10320
ttttgagacg gagtcttgct ctgtcgccca ggctggagtg cagtggcgca atctcggctc  10380
actgcaagct ccgcctcctg ggttcacacc attgtcctgc ctcagcctcc cgagtagctg  10440
ggactacagg cacccgccac cacgcccggc taattttttg tatttttagt agagacgggg  10500
tttcaccatg ttagccagga tggtcttgat ctcctgacct cgtgatccgc cggcctcggc  10560
ctcccaaagt gctgggatta caggcgtgag ccaccgcgcc cggcctatgc tgcagatttt  10620
ttaaaacatt atttagaatt aatgtactaa aatgtaaact agtatctcac tagaatgtaa  10680
cttcatgagg gcagggactt tcaaggtttt gtttattact gtaacctcag tgccaagaac  10740
agtacctggt gcataattgg tgctcaagaa tttattattt gttaactaat aaattcaggg  10800
tctatagcag tgcccattcc ttctttaaga aaaatgtttt accaaatatg agaattgacc  10860
ttttattatt ctgtcaacat ttacatcctg gtttgttttt aggcacttgc tgctggagga  10920
gtagggtcca ttgttcgtgt cttgactgca agaaaaactg tgtagtctgg caggaagtgg  10980
attatctgcc tcgggagtgg gaattgctgg tacaaagacc aaaacaacca aatgccaccg  11040
ctgccctgtg ggtagcatct gtttctctca gctttgcctt cttgcttttt catatctgta  11100
aagaaaaaaa ttacatatca gttgtccttt aatgaaaatt gggataatat agaagaaatt  11160
gtgttaaaat agaagtgttt catcctttca aaaccatttc agtgatgttt ataccaatct  11220
gtatatagta taatttacat tcaagtttaa ttgtgcaact tttaacccct gttggctggt  11280
tttttgttct gttttgtttt gtattatttt taactaatac tgagagattt ggtcagaatt  11340
tgaggccagt ttcctagctc attgctagtc agggaaatga tatttataaa aaatatgaga  11400
gactggcagc tattaacatt gcaaaactgg accatatttc ccttatttaa taagcaaaat  11460
atgtttttgg aataagtggt gggtgaatac cactgctaag ttatagcttt gtttttgctt  11520
gcctcctgat tatctgtact gtgggtttaa gtatgctact ttctctcagc atccaataat  11580
catggcccct caatttattt gtggtcaccc agggttcaga gcaagaagtc ttgctttata  11640
caaatgtatc cataaaatat cagagcttgt tgggcatgaa catcaaactt ttgttccact  11700
```

-continued

```
aatatggctc tgtttggaaa aaactgcaaa tcagaaagaa tgatttgcag aaagaaagaa  11760
aaactatggt gtaatttaaa ctctgggcag cctctgaatg aaatgctact ttctttagaa  11820
atataatagc tgccttagac attatgaggt atacaactag tatttaagat accatttaat  11880
atgccccgta aatgtcttca gtgttcttca gggtagttgg gatctcaaaa gatttggttc  11940
agatccaaac aaatacacat tctgtgtttt agctcagtgt tttctaaaaa aagaaactgc  12000
cacacagcaa aaaattgttt actttgttgg acaaaccaaa tcagttctca aaaaatgacc  12060
ggtgcttata aaaagttata aatatcgagt agctctaaaa caaaccacct gaccaagagg  12120
gaagtgagct tgtgcttagt atttacattg gatgccagtt ttgtaatcac tgacttatgt  12180
gcaaactggt gcagaaattc tataaactct ttgctgtttt tgatacctgc tttttgtttc  12240
attttgtttt gttttgtaaa aatgataaaa cttcagaaaa taaaatgtca gtgttgaata  12300
atttattttt ctctgacact ttaacaatta tgaatgtatg gttaattaag aggaaaggtt  12360
ttctgcttct accaccaagt actgtactct taacaagaac agtttggtag ggtttttata  12420
agactatata gatataagat gatagagaag agagtcatga atgatgtcag agcactactg  12480
aagcctttgg agtgattcca tagccttctg gatggcagct gaatacctat atgtagtatc  12540
actgcccaaa gacctagact agaaagtgca aagtagctta gcagctgcag tcattcactc  12600
ccagcctcca aaattctct                                               12619
```

<210> SEQ ID NO 50
<211> LENGTH: 12425
<212> TYPE: DNA
<213> ORGANISM: Homo sapiens

<400> SEQUENCE: 50

```
gatccctctc caggtggaag ctcccttcat accaaagttt aaaggccctg gggatacgag     60
taactttgac gactatgagg aagaagaaat ccgggtctcc atcaatgaga agtgtggcaa    120
ggagttttct gagttttagg ggcatgcctg tgccccccatg ggttttcttt tttctttttt    180
cttttttttg gtcggggggg tgggagggtt ggattgaaca gccagagggc cccagagttc    240
cttgcatcta atttcacccc caccccaccc tccagggtta gggggagcag gaagcccaga    300
taatcagagg gacagaaaca ccagctgctc cccctcatcc ccttcaccct cctgcccccct    360
ctcccacttt tcccttcctc tttccccaca gccccccagc ccctcagccc tcccagccca    420
cttctgcctg ttttaaacga gtttctcaac tccagtcaga ccaggtcttg ctggtgtatc    480
cagggacagg gtatggaaag aggggctcac gcttaactcc agccccccacc cacacccccca    540
tcccacccaa ccacaggccc cacttgctaa gggcaaatga acgaagcgcc aaccttcctt    600
tcggagtaat cctgcctggg aaggagagat ttttagtgac atgttcagtg ggttgcttgc    660
tagaattttt ttaaaaaaac aacaatttaa aatcttattt aagttccacc agtgcctccc    720
tccctccttc ctctactccc acccctccca tgtcccccca ttcctcaaat ccattttaaa    780
gagaagcaga ctgactttgg aaagggaggc gctggggttt gaacctcccc gctgctaatc    840
tcccctgggc ccctccccgg ggaatcctct ctgccaatcc tgcgagggtc taggcccctt    900
taggaagcct ccgctctctt tttccccaac agacctgtct tcacccttgg gctttgaaag    960
ccagacaaag cagctgcccc tctccctgcc aaagaggagt catcccccaa aaagacagag   1020
ggggagcccc aagcccaagt ctttcctccc agcagcgttt ccccccaact ccttaatttt   1080
attctccgct agattttaac gtccagcctt ccctcagctg agtggggagg gcatccctgc   1140
aaaagggaac agaagaggcc aagtcccccc aagccacggc ccggggttca aggctagagc   1200
```

-continued

```
tgctggggag gggctgcctg ttttactcac ccaccagctt ccgcctcccc catcctgggc   1260
gcccctcctc cagcttagct gtcagctgtc catcacctct cccccacttt ctcatttgtg   1320
ctttttctc tcgtaataga aaagtgggga gccgctgggg agccacccca ttcatccccg    1380
tatttccccc tctcataact tctccccatc ccaggaggag ttctcaggcc tggggtgggg   1440
ccccgggtgg gtgcgggggc gattcaacct gtgtgctgcg aaggacgaga cttcctcttg   1500
aacagtgtgc tgttgtaaac atatttgaaa actattacca ataaagtttt gtttaaaaaa   1560
aaagtgtcgc tggtgttctc gacttcgatc acccacccac acacccccag ggggttggaa   1620
agggaatttc ggaccccagc gtgcaggccg atcaggtcct ggcttgaagt ccttgtaacc   1680
agggtttagc tgaaattccg gcactccttc ggccccgcag gagaaacgag cgtcaaactg   1740
ccctttgacc ccagattcgg ggtccccaaa tctgcggcgc gccccctcgg cgtccagccc   1800
gggaccgaga gggcgctcta gggaggcgct ggggctggcg cgccaggagg ccgagcggcg   1860
gcgggggcgg ccctggcagg gggagtagaa gggggagagg gtgcgcgccc cccttcccgc   1920
atcctcagcg ccgggccagg cgcgcctgag ggacgcgggg gcggcggcag caggagggtc   1980
cccgcagcac cctgcgagcg cggcagcccc ggcccgcggg cggcgagttc ccggtaagtg   2040
cggtcccgag agcggagcgc gctggagagg cgtggagagg ggggctgggc gccggggacg   2100
tctgggtccc gcgcccaatg gctggagggc ggccgagcgc cgcccgcccg ccctgcccgc   2160
cccctctccc ctccccccgg cactcccctc cccctccccc gcccgccgct ttcccccgcc   2220
cccgccccgg cgccaactcc gcggcgcctc cttaaaaagc gcgcgggagt tgtaaggggg   2280
ggccggagcg agccggagtg agcgagagcg cagggtaaag ggggcgggcg gggggcccgg   2340
gctccacctt aaaagcgggc gcgtgggggt gggagggagg aaggcgggcg gcggggagga   2400
gggagggagg gaaggaaggg gggccggagt gtcccgggcg cagggcgcgc gtgcggcggc   2460
ggcggcggcg gggaggggcc ggccgcgccg cgctcccctc ctccccctcg catccccggc   2520
cccgcgcgcg cccagcagaa gcgggtctgt gtgtgcgtgc gtgcgagtga gtgagtgtgt   2580
gcatattttt ttctctcttt tctttctctc tcactgtttt ttcctctctc tctctctccc   2640
tctctctctc tttttttttt tttttttttt gcaaagaaac agcagcgccg ccgccgctcc   2700
gccgaggcgc tgcgcccccc ggggggggag gcggaggagg cgggcagcgg cggagggagg   2760
ggagccgggg agggggcgc cgcgctggga gggaggcagc gcgcacggtg cagccgggcc    2820
gggcgggagg catggcgggg cccccggccc tacccccgcc ggagacggcg gcggccgcca   2880
ccacggcggc cgccgcctcg tcgtccgccg cttccccgca ctaccaagag tggatcctgg   2940
acaccatcga ctcgctgcgc tcgcgcaagg cgcggccgga cctggagcgc atctgccgga   3000
tggtgcggcg gcggcacggc ccggagccgg agcgcacgcg cgccgagctc gagaaactga   3060
tccagcagcg cgccgtgctc cgggtcagct acaaggggag catctcgtac cgcaacgcgg   3120
cgcgcgtcca gccgccccgg cgcggagcca ccccgccggc cccgccgcgc gccccccgcg   3180
gggcccccgc cgccgccgcc gccgccgcgc cgccgcccac gcccgccccg ccgccaccgc   3240
ccgcgcccgt cgccgccgcc gccccggccc gggcgccccg cgcggccgcc gccgccgcca   3300
cagcgccccc ctcgcctggc cccgcgcagc cgggccccg cgcgcagcgg gccgcgcccc    3360
tggccgcgcc gccgcccgcg ccagccgctc ccccggcggt ggcgccccg gccggcccgc    3420
gccgcgcccc cccgcccgcc gtcgccgccc gggagccgcc gctgccgccg ccgccacagc   3480
cgccggcgcc gccacagcag cagcagccgc cgccgccgca gccacagccg ccgccggagg   3540
```

-continued

```
ggggcgcggt gcgggccggc ggcgcggcgc ggcccgtgag cctgcgggaa gtcgtgcgct   3600
acctcggggg cagcggcggc gccggcggtc gcctaacccg cggccgcgtg caggggctgc   3660
tggaggagga ggcggcggct cgaggccgtc tggagcgcac ccgtctcgga gcgcttgcgc   3720
tgccccgcgg ggacaggccc ggacgggcgc cgccggccgc cagcgcccgc ccgtctcgca   3780
gcaaggtgag cgcgccgggg agcgggggcg ccgcgcggtg ggcaggtgcg ggcgaagttg   3840
gtggcggggg cgcgagtccc gggaggaact gggtggcggg tggctggggc tttgcgcgcg   3900
tttcctgcgg gctcggtgcg tggtgacctt ggcaagtgat tgaatctccc ggagcctcag   3960
tttcctccgc tgtaaacgcg gtttaataac agtagcgacc ccttggggtt gttgagcgag   4020
tttagtaaga tttggttgtc gagggcttta gttaacacag agcctggcac ggagtgaatg   4080
cgtaaaagtt agtccgtatt gttcttaaag gtggaatcgg ttcctcctcc ccaccgcccg   4140
gacgccacag tcagggtctg ggattagaac agctactaat tttgcatgct tctctcctcg   4200
gctccagaga ggtggagaag agcgagtact tgagaaagaa gaggaagaag atgatgatga   4260
agatgaagat gaagaagatg atgtgtcaga gggctctgaa gtgcccgaga gtgaccgtcc   4320
tgcaggtgcc cagcaccacc agcttaacgg cgagcgggga cctcagagtg ccaaggagag   4380
ggtcaaggag tggaccccct gcggaccgca ccagggccag gatgaagggc gggggccagc   4440
cccgggcagc ggcacccgcc aggtgttctc catggcagcc atgaacaagg aagggggaac   4500
aggtaaggat ccctctgggt ggggaagagt gctaggtgga gaggaactca gcccgaagac   4560
aaagccaaag acaggtgttt ttttccttcc cagcttctgt tgccaccggg ccagactccc   4620
cgtcccccgt gcctttgccc ccaggcaaac cagccctacc tggggccgac gggacccccct   4680
ttggctgtcc gtaagttggg gtattggaga catgggggtg ctgctcaggt gtgtggtaca   4740
gccagagaga catccgtgtt cactggtgtc tgtttgtttt gatgcagtcc cgggcgcaaa   4800
gagaagccat ctgatcccgt cgagtggacc gtgatggatg tcgtcgaata ttttactgag   4860
gctggattcc cggagcaggc gacagctttc caagagcagg tgagtttcca gcccaggact   4920
acacactgac agacacagag ggcctccctg ggatgtgccc tgatcccggc tttctctgtt   4980
cctgtcccac ccaggaaatt gatggcaaat ctttgctgct catgcagcgc acagatgtgc   5040
tcaccggcct gtccatccgc ctcgggccag ccctgaaaat ctacgagcac cacatcaagg   5100
tgcttcagca aggccacttt gaggatgatg accccgatgg cttcttaggc tgagcgccca   5160
gcctcacccc tgccccagcc cattccggcc cccatctcac ccaagatccc ccagagtcca   5220
ggagctggac ggggacaccc tcagccctca taacagattc caaggagagg gcaccctctt   5280
gtccttatct ttgccccttg tgtctgtctc acacacatct gctcctcagc acgtcggtgt   5340
ggggagggga ttgctcctta aaccccaggt ggctgaccct ccccacccag tccaggacat   5400
tttaggaaaa aaaaaatgaa atgtgggggg cttctcatct ccccaagatc ctcttccgtt   5460
cagccagatg tttcctgtat aaatgtttgg atctgcctgt ttattttggt gggtggtctt   5520
tcctccctcc cctaccaccc atgcccccct tctcagtctg cccctggcct ccagccccta   5580
ggggactagc tgggttgggg ttcctcgggc cttttctctc ctccctttttt ctttctgttg   5640
attgtcgctc cagctggctg tattgctttt taatattgca ccgaaggttt tttaaataaa   5700
attttaaaaa aagaaaaagg gaaaaaaaag ccacggagtc cattttatga atggggtggg   5760
gagagggcac taaagagcct cctaagagag cctcaggtta ggacagaatt gtttggggag   5820
ggagaaaaac agaaacaatg aattatagct gcctcacagc catgtataac aataattgct   5880
ccaggaaggt gggaatattt gctttttttt cttctgtaat ctcaccgtgt ccgtgtccag   5940
```

-continued aacagagcta ggcacacagc aggtgctcaa tttttgtttt tcgtttagac aggtttcatt 6000
ctttcaccca ggctggagtg cagtggtgct atcatagctc attgtagcct caaactcctg 6060
ggctgaagtg atcctcccac ctcagcctcc tgagtagctg ggactacagg tgcactctgc 6120
catgccgggc taacttttaa aaatttttgt ccgggcacag tggctcatgc ctgtaatccc 6180
agcactttgg gaggccgagg tgggtggatc atgaggtcag gagttcaaga tcagcctggc 6240
caagatgatg aaaccctgtc tctactaaaa atataaaaaa aaattagctg ggcgtggtgg 6300
tgggtgcctg taatcctagc tattcaggag gctgaggcag aggattgctt acacctggga 6360
ggcggagggt gcagtgagcc aagatcgtgc cactgcactc cagcctgggt gacaaagtga 6420
gactctgtct caaaaaaaaa tctttgtgtg tgtgtggaga tgagggtatg cactttgttg 6480
gccaggttgg cctcgaactc ccagccaagc aattctgcct gggattacaa gcgtgagcca 6540
ccatgcctgg cctcaaatat tgttgaatgg ctagcagtta agtccttggg tttataagca 6600
tttcctcaac tgtcctccca agtccccata agacaaaaaa ctcataaaat cccaccttac 6660
agaagaggca gctggcccgg cacagagatg ctgtctgccc cgggtcacac agggtggcat 6720
ctgacaccct gtctgagttc ttcactcaga gtctttaaat ataattagcg tatttgacat 6780
aatgtacatt aaaaactata aacctgtcag cctttgtcta ctgcaaagaa tccactacaa 6840
atattggggc agggatctgt tcttggacca tagtagtgtc tccagacctc atggtcctct 6900
tcattaaaac aacagaaaat tccttctggg ccatcagatg agaccatgag atagaagatt 6960
tccaagtgaa gattttgttt caagacagag tcttgctctg tcactcaggc tagagtgtac 7020
tggtgcaatc ataactgtgg tgacagcctc gaacttttgg gtacaagtga ttctcatgcc 7080
tcagacaaca cccaactaat attttggttt ttgtatagac agggtcttgc tatgtggctt 7140
aggctggtct tgaactcctg gcctcaagca gtcctcccgc ttcagcctcc taaagtgtca 7200
ggattacaga catgagccac caagtccagc ctgaagattt ttaaaaatta ttgttagtag 7260
tagtcgccag agttactaca tccaaagtcc ctactaagtt ctaagtagtc cctactaagt 7320
tctaaggcag tttctcaact cattagagtt gttttttgtt tttaaagaaa aaaagaggct 7380
gggcacttta ggagaccgac acgggaggat cgcttgagtc caggagtttg agaccaacct 7440
gggcaacatg ggcccccatc tctaaaaatt ttaaattaaa aaaatgtttt aacaacaaaa 7500
agcgttctgg gagtgagggg ctggggcctg ggcggcctca ttccatatac ctgtgccggg 7560
ttgaggggtt ggagacacgt ttagagaccc ctccactcta ggaatccacc tcgagagata 7620
aaggtcccgg ccctagccac acccccagga cacggccaga ggccacctcc ctaggcgggt 7680
ccctccccac cgccaggttc ctggagcgcg tgcggcgcgt gtgcaggggt agggggccgc 7740
aggcgcgcgg actggagagg cgcgcccctc ccgcgtgttg aaattcaaaa gaggcgaacg 7800
gcccccggcg cggcggcgcg gctccggtgg agaggtcaag gcaggggcca gtcggaggct 7860
cccggggcgg ggtcgaaccc gcggccaacc tgagcagcag cggaagctta aagagctcag 7920
gttcccgccc cccggcccta ccatggctac agagcagtgg ttcgaggggt cgctcccccct 7980
ggaccctgga gaaacaccgc ctccagacgc cttggaacct gggacgccgc cctgcggaga 8040
cccctccagg tcgacgcccc ctggcaggcc tgggaaccca tctgagccgg atcctgaaga 8100
tgccgagggg cggctggctg aggcccgggc ctccacgtct tcccccaaac ctctggtccc 8160
ccggcctggg ccagcacctc cccgcctatc cctggacact ttgttcagcc ccatcaccca 8220
acagctgcgc tacctactga agaaggcaga tgatttccag agctacttgc tctacaggtg 8280

-continued

```
atgctggaca gggtcccagg tccccatggg taaggagact tggaggggag gcgacaggat   8340
gggtgacaca caccagggtc gcaaaattac aagcgctagg agccagaggg agacagtgga   8400
agaagctagc atattagaat ccagtttaag agaatgagga agactgtaga attgcgggta   8460
ggggatggct gctattactg tcgtggcagg gtgggcctgg ggttgtcaag tctctaggac   8520
tttttctccc agtttttaag tgctgtctta cattttgagc cctgtgctgg ctaaacaaga   8580
cccacctgag ccaaacttgg cctgcaggac atcagtttga gactccaaag gataatgtga   8640
ttcccagacc aggtttccct gtgactctca atttcagtgt ccattggaat ttcctaggag   8700
gctgggttgg gtttgtttgc gtgtttgttt ttgagatgga gtctcactct gtcgcccagg   8760
ctggagtgca gtggtgcaat ctcagctcac tgcaacctcc gcctcccgga ttgaagcaat   8820
tctctgcctc agcctcccga gtagctggga ttacaggcgc ccaccaacat gtgttgcccg   8880
gctaattttt ttcttttctt agtagagaca gagtttcacc atcttggcca gactggtctt   8940
gagctcctga cctcatgatc cacccgcctt ggcctcccaa agtgctggaa ttacagacgt   9000
gagccaccgc gcctacccga ggctgggttt ttttgttttg ttttgttgtt atgtgttttt   9060
ttgaaatgga gtcttgctct gtcacctagg ctggagtgca gtggggcgaa ctcagctcac   9120
tgcaacctcc gcctcccagg ttcgagggat tctcatgagg ctgttttttt ttttttaatg   9180
agacagggtc tcgctctgtc acccaagctg gagtgcaagt ggggcagtca tagctcactg   9240
caccctcgaa ctcctggtct caagcaatct tccacctccc ctcctgggta actgggacta   9300
caggtgccac catgcccagc taattatttt tgtgtagaga tgggttcttg ctatgttgcc   9360
taggcttgtc tggaactcct ggcctcaagc aatcctccag cctcagcctc ccaaaactct   9420
aggattgcag gcgtgagcca ctgtgcccag accctgcagg aagctctggg tcctaagtgt   9480
tgtgacactc aggtgtcagc actttaacaa gtgttccaaa tgggtttgat gcaggtaaac   9540
cagaaagatg ttcagaaaag acctgaaact gggggctttt ctaatgggtc aaagccaggg   9600
atacaggttg ggattgagta gaatggggaa aactgcgggg tggggagggg ttgtgaggga   9660
ttccaggcaa aggccccctt cttccttcag cagagaccaa gtacagaagg agcagctggc   9720
caaggccatg cccaccttct tacagatgtg tgagccctac ttcctgtacc tggaggcagc   9780
cgcgagaagc ataccccca tctatggacc cctgcaggag ctggtccgaa agggggtgtg   9840
tggaggtttc ttagacccca cgccccttc ttctcgcagc tctgagcctg tggggatggt   9900
ggagggggag gcccactcct cgcaggccag ctgatctcac tgtaccccc tcttgtatgc   9960
agctgttaga gatctcccaa cagctgaccc tgcgcctgga acagctggtc ctcatgtacg  10020
cttcctttgg gttcgtggac ctggaggaga tgaacccct taggtaaaat ggtaggagac  10080
tcagatgggg ggatgaagga gtccaaggcc cagcctcacc cctccattct ctcatgtctc  10140
gccagcatct cctgtttctt ttgcgggagg ttctccatca gcctgtccca tgaggtctcc  10200
atcttcagat actgtgcccc aaccgcctac actgccagcc gcttcccccg ctacctctat  10260
aagaagatgc gctggcacct ggaagccacc ccagaggccc ctggtcgggg acaagattcc  10320
cttgtggatt agtaagtcct cttacccaaa tcaaagtcct cccctttcta tgatgaatgc  10380
caatatgacc ctccaaaccg tcaccagcaa agtgaaaagt gagccagggc ccgaggcagt  10440
ggctcacgcc tgtaatccca acactttggg aggccgaggc aggaggatca cttgagctca  10500
agagtttgag atcagcctgg gcaagatggc aagaccctgt ctcaacaaca aagaaattcg  10560
ccaggcgtga tggctggcac ctgtagtccc agctacttgg gaggcttagg caggaggagc  10620
acttgagccc aggaatcaag gctacggtga gctgtgattg tgccactgca ctccaccctg  10680
```

-continued

```
agtggaagca ataatctgtc tcttaaaaaa aaaaaaaagt gaaccaggaa actaaaggct  10740

tttgaaaggc tacctctatt ttcttaaaac ccaccctccc accaaaataa aagttctcat  10800

cttaaaagta ggctggcagg gagaaaaggc cttggagtca cattcctacc tgagaacttc  10860

agggcaactt ctgatgagtt cccacctcaa ctccaaaatt aaagccctca acagaagtag  10920

ctaggaagct gatcacttct aattacagct ccctcccctc ctagctactt tctgtgctat  10980

cgagatactt gggaagacac aggccagagt ccagccaatt cgtgccccaca gatccagaag  11040

ctgtggtcca tcggccgatg ggtgccccta ggaccagccg aggatgacct ttattcatgg  11100

taggagctag ggcaatagca acgtgggcct gggagctgga gggggaggca gaacccccacc  11160

aaagacaatc caccttccca aacactttgc ttcccttagt agtgatagca ttttattgtg  11220

ccctgaaaag cacttcatgc agaccccagt aacaacccat ggagatctat gctattggcc  11280

ccatttaaca aagaaaacag ggtgctcaga gaagttgtta cctgcccaag gacacacagc  11340

tagcagagcg aatggacagg tcaggaccag ttattcagcc tctaggagcc attactaagt  11400

ctctgatcaa caaggaaaca agtttccccc gggggttttt cccacccgca gctgaaacaa  11460

agcctctttc acctgagcct ctcactcaaa gggagggact cccgaggggc agggggcact  11520

caagtccagg cctgtctatc cctggccccc ccaccccagg attttgtgcc cgcaccgctt  11580

ggggactacc agcagctgct gaccatcggc ttcgaggagc ccacgcccac gctggccacc  11640

gacctgctgg tgcagatcct cacgggccag gcaggccagg cccggcctcc gagcgcagcc  11700

gggcctgcgg ggtgggcagc gcaggggtct tgaacctggg gaagagggta ggagctggaa  11760

cttgacagtt ccaaactcca gaataggggg caggggaggg gctcactcgt tctcgcagtg  11820

cagccgggcc tcgccttcca aagggccagg ccgagctgac ctgtctgcac cgagtccggc  11880

ttggccgtgg ggccctgaat gcggacacgt cagttttgtg ttaaataaaa gaaagaaaga  11940

ggtcacaggc tcagcgtccg ctgcgaatgc cgcgcccctc ccccgggggga ttgccccacc  12000

cactcgcgtg gccttctggg aaatgtagtc ttttgaaaga agcctggaat tcgccaatag  12060

gcggacgaga gtttggcgca tgcgcatagg cgcacatgaa gcaaaaaggg aagtggtgcc  12120

cgtcaacacc ggaacccaga aaactgcaag tttagggtac cggggaaatt caacgtccac  12180

tggaggaaga gacttaaggc tacgcccact cccatatttt gacccggaag ttatttattt  12240

tagcgtagaa gactactttt cccgacgcgc cccaggaaag tgccctcgat cagtttccta  12300

agggcccgag ttagactttt tttttctctt ccagcttttg ggacttgggg gccggacagg  12360

tcgtcgtctt tcttggggta tccggggtgc ggacaaggtg ggagagccct acggtatcca  12420

agctt                                                               12425
```

<210> SEQ ID NO 51
<211> LENGTH: 22255
<212> TYPE: DNA
<213> ORGANISM: Homo sapiens

<400> SEQUENCE: 51

```
caacatgctt gggaccagaa gtgtttccaa tttgggattt tctcaaattt taccggttga     60

gcttccccaa tctgaaaatc tgaaatccaa catgcacggc tctgaagtct ttcactgagc    120

ctttgggggga aatatttaac atcctaacag ccctaaacca acgctcaatt agcacaacag    180

tttacaatct tctctaccca cagcctgatg cgaggctctg ggactagact atttagccaa    240

cagttcttgc aaaattaact gacttataag taaatagtaa tttcaacacc tcactgctaa    300
```

-continued

```
tgctgtaaca actctgcaga cctagggagc aagtacggtt tgcagagcac tgggaaggct    360
ctgaagtgac ctttgaactg ggcctcaaaa aattttgggt ttggcaaaag tcaaatctct    420
taggcttcaa attccaggca caaggattgt tgggtttgat ttcattatcc agaagcaatg    480
gggatacaga attgtgatct catgtgtagg gaactgtggg ggtttttttct actttaaccc    540
cagtgagact ttgtagagtg tggggtagag aaaaggctca tgaatatgcc tgaagcctaa    600
ctcagcacct ttctgaggaa ctgactgcca aaatggtaat ggagagggga aaatatgacc    660
tactttcaca agttaccttg actgcctcag ggaaacctgc tgtggtagtg tttcttctgg    720
gtgaaagacc aggtaattac ctgggtgctg gtctcagact taccagtttt gaatccctgt    780
tttaaccact cactatcgat atgaccttgg ataagttacc taacctttct cttactgtcc    840
ttttccgtaa aatggggata acagatagta gttatttcta tgagtggtta tgagaaccaa    900
gctattagat agcgggaaag cacacagtaa gcgttcaagg aactgctatt gttattaaaa    960
gcctcctttg gaagaaggac attgaggccc agagagagaa cagaacgtcc agccacacag   1020
caaatccgtg atgaagttgg gactggagta tgggtctcct gagtctcagc ccaggactct   1080
atccctcttc ccgagtcctc ggagttcccg gatggagtca catttgttca cggccaggga   1140
ggaaggtttg atggaggcct gcaggaaaca acagccaggc gcaaggcttt gggagttgaa   1200
gcatagcttc tgcgagatag aaacaaggtt gacatgggca ctcgtgcaga atgacgggct   1260
ccttttggac tcccaggact acagtccctt atgcaccttg ggatctgcgg ctagcccctg   1320
cgtaaagagg gacgcgtagt cttttccctg ccccgccctg ccggggcgcc cgcctccgag   1380
gccgccctcg cttcgtcctt cccagcaagc tccgcgccgg cgccggctat tgattggctg   1440
aggcgggagc aggcggctgg ccggcagcag ttactcgggg tttccggtgc gaggccagag   1500
gtggggaagc catcggacgt cggcggtgag gtacgtgcag cggcggccgg tgggcgagac   1560
tatttgagag tgtgcgggcc gggatgttct cggcctgtgg ggaaatcacg ccaactcccc   1620
gcgtgggccg ggggctgtct ggggatatgc gcatgcgcgg gcgtgcctcg cggcttgagg   1680
gcgcgcgggg cgtgggtggc tgcgcgcgcg gggggcgcac gtggggcctg aggggcgggg   1740
gcggtgccgg gagtcccgcc acgtcagtct ccggccctga gccaatcccg cgcccggcct   1800
gccgcgaggg ggccggttgt gccgggaagt ggctccaggg agaagaggcc tcttccctca   1860
cccgctgtgg gagctgcgcc ccgaaagcct gccccggcac gtcgggctct cctgacccgc   1920
caagaccaga gagccgttgg cgccctccgc ccgggcctgc cggtccgttt attttaagaa   1980
gctttgtgcg cctgctgtgg ggatttctga tccaggctgc gaagaatttc gaagtctgga   2040
aaatagcaac tgtgtttgtt tctaaaggat cttctcctga cccagcatcg ctcatcacaa   2100
tgaagaacca agacaaaaag aacggggctg ccaaacaatc caatccaaaa agcagcccag   2160
gacaaccgga agcaggaccc gagggagccc aggagcggcc cagccaggcg gctcctgcag   2220
tagaagcaga aggtcccggc agcagccagg ctcctcggaa gccggagggt gtgtgccagc   2280
tctgcgttgc cagcgggcag ggggaggagc tgtggggtcg gcctcgcttc tggacttaca   2340
ggccgaggcc aggttgtccg ggaggaggag atgtagaatg agaggacagt gctgggggcc   2400
gcggtccccc ctgcgctctg gcgagttggc ggagctgccc cctctaagca caggaacaga   2460
gttctggaga gaagctccga cgggattaag tcaggtggca gccaaacgag gcacccagtc   2520
aggaaatcca ggtcccgtta gaaacacctc agccaccagc agctaactgc ccttcctgtt   2580
tgaggcattt ctagaatgat ctgaatggca agaaatgggt tttgtggggg ggaaggagat   2640
ggactagaag ttgctccgtg ccatccctgt gtgctgatgc tttacatact tttatgatct   2700
```

-continued

```
aacaaatatg ttcgggtggt agtgagaaat agttgtgtca ttttacaagt aaacagactt   2760
aaagaagtta ggcaacgatt actataattt cttgatttaa aagatgtttc gaatctaaat   2820
tctgacagga actagatttg ctgaatgata ctccattctt gcttctcagt ttccataaaa   2880
aaaaaagtta ggcaacattt aactcaaact gatgagtttg gctgggcctg aaaaatccca   2940
accagtggta taatcgtctt ctttctcact ctacccctca tcctctcctg ctgtaggggc   3000
tcaagccaga acggctcagt ctggggccct tcgtgatgtc tctgaggagc tgagccgcca   3060
actggaagac atactgagca catactgtgt ggacaataac caggggggcc ccggcgagga   3120
tggggcacag ggtgagccgg ctgaacccga agatgcagag aagtcccgga cctatgtggc   3180
aaggaatggg gagcctgaac caactccagt agtcaatgga gagaaggaac cctccaaggg   3240
ggatccaaac acagaagaga tccggcagag tgacgaggtc ggagaccgag accatcgaag   3300
gccacaggag aagaaaaaag ccaagggttt gggtgagcag agggcggctc tttgtgaagc   3360
tggtgaggag agggagtttg gacttgacgt tctctgggcc agtctgttct gccaggattc   3420
aaaggaaaac ggtacttctc agagcagcaa gtcactctag tctaatcaaa gccagggatg   3480
tgggggccac ggcatagaga gatgcaggag ttaccagcac aaagccttct gggttttgga   3540
gcaactggag cttggcatgg gacctgttct ctctttgaga aaatggagac gggaggctag   3600
ggtaggctcc tgtgccagcc agtactacct gctgtgtgac cttgggtgtg tcccttctcc   3660
tctctgggtc ttagtttata tttctcttta cagtaagaaa attagactag gccagagttg   3720
aaaacccaaa tatctgcata agctgggctt ggccatgggg ccacctgaag atggaggctt   3780
tactgcttcc ctgattagtt gctctcacta gccaactgag agcaggcaaa actacaggct   3840
gggtgcagtc aggctttttt tttttttttt ttttttaaa taaagaaaag ccagaaatct   3900
agagttatgt gagaactcta gatttttca tagttagcag ctaaaatggt aagagccaaa   3960
caaaacccat ccgtgggttg gatttggcac acatgcctgc gaattgcagt ctccatgctg   4020
atctcttggg cccttctggg gaggcagagg gaaggctccc tgactcagtc acaggcaatg   4080
gggaataggc agtgacagtc attttacagc agggtatgta tgtttaagag tctaggccgg   4140
ggtgtggtgg ctcacgcctg taattgcagc actttgggag gccgaggcgg gtggatcacc   4200
tgagggtcag gagttcgaga acagcctggc caacatgatg aaatcccgtc tctactaaaa   4260
atacaaaaat tagctggaca tgctggcaca cgcctgtaat cccagctact tgggaggctg   4320
aggcaggaga atggcttgaa cccgggaggc agaggttgca gtgaactgag attgtgccac   4380
tacatccagc ctgggtgaca agagtgaaac tctgtctcaa aaaaaaaaaa aaagaatcta   4440
gaatctaagt cgagtgtcat tatatccatg ttttattcct attccctttt ccccttatgt   4500
atcctcttac tttaaagagg aactttaaaa aatcttaggg acgactaggc agagtggctc   4560
acacctgtaa ctccagcact ttgggaggcc aaggcaggca gattatgagg tcaggagttc   4620
gagaccagcc tggccaacat ggtgaaaccc cagttctact aaagatacaa aaaatcagcc   4680
gggcgtggtg gcacgtgcct ataatcccag atactcggga ggctgaggca ggagaatcac   4740
ttgaacccgt gaggcaaagt tttcagtgag ctgagatcat gccattgcac tccacctggg   4800
tgacagggtg agactccatc tcaaaaaaag aaaaaggaaa aaatcttaac gtcacataca   4860
tggaaagatc atctttttca ccccccaccc ccaactgaga tggagttttg ctcttgtcac   4920
ccaagctgga gtgcactggc gcgatctagc tccctgcaag ctccgcctcc cgggttcaca   4980
ccattctccc tgcctcagcc tcccgagtag ctgggactac aggctcctgc taccatgccc   5040
```

-continued

```
ggctaatttt tttgtatttt ttttagtaga gacggggttt catctgtgtt agccaggatg   5100
gttttgatct cctgacctcg tgatccgccc gcctcagcct cccaaagtgc tgggattaca   5160
ggcgtaagcc actgcacccc gccttttttt tttaattaat taattttttt agacagagtc   5220
tcgctctgtc ccaagctgga gtgcagtggc gcgatctggg ctcactgcaa cctccgcctc   5280
ctgggttcac ggcgattctc ctgcctcagc ctcccgagta gctgggacta caggctcctg   5340
ctaccatgcc cggctaattt ttttgtattt tttttagtag agacggggtt tcactgtgtt   5400
agccaggatg gttttgatct cctgacctcg tgatccgccc gcctcagcct cccaaagtcc   5460
gcctcagcct cccaaagtgc tgggattaca ggcgtaagcc actgtaccct gccttttttt   5520
tttaattaat taattttttt agacagagtc tcgctctgtc accaagctgg agtgcagtgg   5580
cgcgatttgg gctcactgca acctccgctt cttgggttca agcgattttc ctacctcagc   5640
ctccggagta actgggacta caggcgcgtg ccaccacacc aagctaattt ttttgtgtat   5700
gtctttagta gagatggggt ttcaccatgt taggatggtc tcgatctctt gacctcgtga   5760
tccgcctgcc tcggcctccc aaagtgctgg gattacaggc atgagccacc ttgcctggcc   5820
gaaagtatct tcattttaaa gttcactgtt tggctactct gttgacaaga gtttagtatt   5880
tctcaaggag gctaagatac ctattccttt ttggatccta cctctatcag gagggtgggc   5940
cttccttgca ttgaaacagt atgaaaacag tagccctgaa ttcataagtg ggacaccttt   6000
cttctattgg tagagcaggc agttttttttc tcctgccaat ggtgcctact aaggagattt   6060
cactagggta cagtcgttca tttgataagc atttgttgag catatcctct gtgatggtac   6120
tatggacagt actggggcta tagtgagggc aggattgagt tggtccttat ggcaaggaag   6180
gcagctaatc aacaagcaaa atataaagta tgatggggag ggctgtcttc agcactcatg   6240
agtgtgagcc caggcctgga ggggacacct ggagaagagg gtgcatgtct ttgctcctgt   6300
gcttttcagg gaaggagatc acgttgctga tgcagacatt gaatactctg agtaccccag   6360
aggagaagct ggctgctctg tgcaagaagt atgctgaact ggtcagttcc cccctccgcg   6420
ggcaccttcc ctgcgttggg aaaatcagca tgccacctgg tgtaaggttg ggggtgcaga   6480
gtcaagtagg tggcttaatt cctgttcagc ttttctctga actatctgtt aaatggggaa   6540
tcacttccag ccagcctctt cagggctgtg cagcaagagg agaaactgca tattccttga   6600
aagaaatttc tcaaagaatg attccaaggt ggtagagccc ttgttcctgg cctgagtcca   6660
agacaccttg tgatcttgat gcttcttcct caaatacaga tgcatagagc cattatcaca   6720
gttaataaaa ctaacactag tcacttgata ctttttcctt ttactccaga gcagtcttct   6780
tgtcactgcc tcctcatatt ccccatgaca ttgactttta acagaaacta gactagctgt   6840
cttgtaggat gccccccttct agctttgtca tctctgtggt atcattttac ttctttacct   6900
cctggtacat gtaagtgaag tagaagttag ctctaaagct tgatccaatt cagcttcaac   6960
tttttgacaa gaattcttca taagtacttc atgttccatc acaataaatg caaagcatgc   7020
tcttcccact ttgttgtaac attgttcagt gggttggggg tggggcagcc agattcttcc   7080
atcatcaggt cccttgtcag aatttgaact aacagattta tccattgatg gtcacagcct   7140
gtgtatgtat gtatgtatgt atgtatgtat gtatttattt atttatttat tttttgagac   7200
ggggtcttgc tctgtcgccc aggctggggt gcagtggcac gatctcggct cgctgcaagc   7260
tccgccttct gggttcatgc cattctcctg cctcagcctc ccgagtagct gggtctacag   7320
gcgcccgcca ccatgctagg ctattttttt tttttttttt tttttagta gagacggggt   7380
ttcaccgtgt tagccaggat ggtctcgatc tcttgacctc gtgatccgcc cgcctcggcc   7440
```

-continued

```
tcccaaagtg ctgggattac aggcttgagc caccacgcct ggcctattta tttatttatt   7500
cagagtcaga gtctcgctct gtcaccaggc tggagtgcag tggcgcgatc tcggctcatt   7560
gcaacctcca cctcccaggt tcaagcgagt ctcctgcctc agcctcccga gtagctggga   7620
ttacaggtgc atgtcaccat gcctggctaa attttgtatg ttttagtaga gacagagttt   7680
cagtatgttg gccaggatgg tcttgatctc ttggcctcgt gatccgcccg tctcagcctc   7740
ccaaagtgct gggattacag gtgtgagcca ctgtgcctgg cctctaagta tttattttaa   7800
aattaattca ttccacacac atttattaat attttcctgt aaggaacttt actcatcttt   7860
aaaatgggga atgtcatacc tgcctaatga cattcttgta aggattaaat aaaaggtata   7920
aggaagataa gcaccctttt ggagtgatcc agccagggga aaattgctga tgcaagagag   7980
gaaatgagtt gctagagtgg tgttgtgagt agaggagggg agctgaggcc tgcccaagaa   8040
gggggcttgg ctgtggtaac cacatggcta ggtctgtgtg actggaggag aggacggggc   8100
aggtggactg gtagatgtgc agcttgtgcc cctgattctc tagtttcttc tgtgttttga   8160
gatttgatga gaacgatgaa atagttgtct ggaaggagag gagtgtgaat agcatatgca   8220
ttgtattggg attgctggtc ttcctgaaat tggtggccat gaatttaaag tgagactctt   8280
caagtagggt tgttatagta ctggtgtaaa gcaggaaggt gctttactag ggttgcagta   8340
ctactgggga agggccaaga gagttgaggg tgtaagaaat ccaagccagg taatgtagtt   8400
attttaaagg agagtggaag gatggttgag tcaatggatt ggaggtccta tagggtaaga   8460
gactttctga ggatcacaga tactgattgg aatgagctaa aaagataggt gatggtagtc   8520
ctggactggg atgctggaaa ttgagatagt gggtgtgctc tctggtagtg acaaatctag   8580
atctgcgctg tccaagataa attcgtctct agctaattga catgtggcca gtttgaattt   8640
gaacatgcta taaatgtaag atacacatca gcttttgaag acttaagcaa aaacaaagaa   8700
tataaaacat ctttttgtga gagagtgtct cagtcaccca ggctggagtg cagtggcgtg   8760
atgtcctgct tccaggttca aacgattctc ctgcctcaca gcctcctgga gtaactgaga   8820
ttacaggcgc atgccaccaa actggctact tttttgtatt tttttttag tagaaacggt   8880
ttcaccatgt tggccaggct ggtcttgaac tcctgacctc aagtgatctg cctgcctcag   8940
cctcccaaag tgctgggatt acaggcatga gccaccactc ccggcctcac ttttttacat   9000
tgattccgtg ttgaaattgt aatgttttgg atattaggtt aaatacatat attactaaaa   9060
ttaatttcac ctgtttttta cttttttagt gcggccagta gaatattttt aattacttat   9120
gtggtttgca ttatatttct gttgtacagg cctggatagg gtcatgggag gggaactgag   9180
ctggggaaag gagtgggttt gtggaagagg tgatggactg tgaggccagg gagttagaag   9240
gattatctgt tgatactgaa gtggccacaa atgagaaaag taattgtgtt ggggagagcg   9300
ctgatgaacg cagcgctaac gttttgaagg aatgcgaggg agcgatgggg gtctgtctgt   9360
taataggcac aaggtacggt agcaggtggt ctcatcctcg ggcatgagtg tccagcaagt   9420
tggggaaatg caacagcttg aagtggctct agtggcccag agtcagagct ggaataggaa   9480
ttggcatctg ctggctgtgt ggcccctgct tgccctagtg agttaccatt tctctgtccc   9540
tacggtggag cctttggggt tattgtgagt tcatgggagg agcgtgtaag caccggcaca   9600
gcatcagccc atgagagtgc tcctggcctg agagggtaag ggtcagggca gctcaggaga   9660
ccctagacct gcatagtgat ccccccacca ggaaggcccc acaagatgct cacctgccct   9720
ccctatccct gtccccagct ggaggagcac cggaattcac agaagcagat gaagctccta   9780
```

-continued

```
cagaaaaagc agagccagct ggtgcaagag aaggaccacc tgcgcggtga gcacagcaag   9840
gccgtcctgg cccgcagcaa gcttgagagc ctatgccgtg agctgcagcg gcacaaccgc   9900
tccctcaagg taggcctggg ccccctggaa caggtgactc tggtttcctt gacttccact   9960
taatgtttct ttcatgggct ttcctcttaa aaagtagtgc aggctagggc caggcgcagt  10020
ggcacacata agtgattaaa aatcttctgg ccactaaaaa acagaaatta attttagtaa  10080
tatacttaac ccaatatcca aaacattaca atttcaacat gaaatcagtg taaaaaagca  10140
aggctgggtg tggtggctca cacctgtaat cccaacactt tgggaggctg aggtggatgg  10200
atcacttgag gccaggagtt tgagaccaac ctggtcaacg cagtgaaacc ccattctact  10260
aaaaatacaa aaattagccg agtgtgctgg caaatgccta taatcccagc tactcaggtg  10320
gctcaggcat gagaattgct tgcacctggg aggctgaggt tgcagtgagc cgagattgca  10380
tcactgcatt acagcctggg caacagagtg agactcagtg tccaaaaaaa aaaaaaagta  10440
gtgcaggctt gtggcataga aatacacttt ctcaataatg ccttacgtta agagagtact  10500
gcttgtaatc atttgacatg tattagataa ggtgaaggat aaagtactaa gagaatccat  10560
aatgcactgg cgttagtatt tctcaatgaa atgacagtcc cctggtaagc ggaggcctgg  10620
ctctgacaag cagctcttgt cccagacgtt ggtcagtcag gaacctgggt ccttcccatg  10680
ttctgctgct tctatggtga ggtcagtctg tggttacacc aagtttaaat acagcctttt  10740
aactttcttt tttatatgta aaatcttaca tgtagttttt agaatgaaat tattatacat  10800
gtaccatttc atatcctgtg ccttttttc actttacata acatttttcc ctatcagtat  10860
gtgtagggct atcttctcat tatatggata tattatatca gtgccctagt taaagcattt  10920
tgggggttgt ttacaatttt tcattattac atatagaact atagtgaaaa ttcttgttat  10980
atttatcact ggtcagttat atagaactta tctgtaggat aagtcatgga attgaaatgg  11040
ctaggtcaca gtatatgcag atttttcatt ttaatagatt ttgctggatt gccttccagt  11100
gagggggcag tgtgccttcc ccatcaaaag tgttgagtgc ctaattctgc acaactttgc  11160
aaaccctggg tgttactaaa ttttaacagc ttggtctctg gggtacaga ggggacaaat  11220
gcacattaat ctgaaatctg gaagaatagg ccttaggaga tccgacttgc ttcagaatgg  11280
cacttagcac ttacatgtgt gcatgtgtgc ctgcattttt tcttcctttt tttttttttg  11340
gggacggagt cttgctctgt ggcccatcgc ccaggctgga gtgcagtggc gcgatcatag  11400
ctcaccacaa cctccgcctc ccaggttcaa atgactcctc tgcctcagcc tcccaagcag  11460
ctgggaccac aggtgcacac catcacgccg gctaattttt gtattttagt agaaacgggg  11520
tttcaccata ttggccaggc tggtctcaaa ctcctgacct cgtgatccgc ccacctcagc  11580
ctcccaaagt gctgggatta caggcgtgag ccaccgcgcc tgccatgtgc ctgcattttt  11640
ctagggggag aatctcactt gatgtcacct gatatacaga ggggcccatt ggaacccgca  11700
ttgcacaaca tcctggagtc tggctactcc acgctttggg agcagggagg gctgttggca  11760
gagaccatct gtggactagc tgggggaccc ttgtgaggta gcagtggatg atggctctcg  11820
ggctgacttc tttgcccagg aagaaggtgt gcagcgggcc cgggaggagg aggagaagcg  11880
caaggaggtg acctcgcact tccaggtgac actgaatgac attcagctgc agatggaaca  11940
gcacaatgag cgcaactcca agctgcgcca agagaacatg gagctggctg agaggctcaa  12000
gaagctgatt gagcagtatg agctgcgcga ggaggtaagg gtatcacgga cagcagtcat  12060
ggcccagaaa ttgtgaggtt ttgagtgtgt gctaggcact gggacagtac cttttcaggc  12120
ttcatcccat tctccctttc ttcctcctcc tcctccttgg gaggagagta atgttattcc  12180
```

-continued tcatagataa aaaacaggtg tggagaagag actcacttac agccacacag ccccaggtcc 12240
acagtgcctt gtcccaaatg actgggccag gcatcttttg gaattagaac tatccacatt 12300
ttagaatgga ggtacatgta tggactgtgt gttatatagc accctcagca gggccttggg 12360
gaagccagac acattaatgt atttatgcag tagaacttcc aaatactcac ctacattatg 12420
ggcttacaat gatgcaggtc aagtctggct gccagcttat gacaatttcc attttcagaa 12480
ctttgtagaa tttggaattg caggggaggg gtgtacctgt gatcagtgat ggactccaga 12540
gactgtgtcc actgattcct tgctgctcct gccactcaaa aggcagaatt tatcaggctg 12600
ggcgtggtgg ctcatgcctg taatcccaac actttgggag gccaaagcgg gcggatcacc 12660
tgaggtcagg agttcaagac cagcctggcc aacatggtga aaccctgtct ctactaaaaa 12720
tacaaaaaat tagccaggtg tggtggtgca cggctgtagt cccagctact caggaggctg 12780
aggcaggaga attgcttgaa cccaggaggc agaggttgca atgagccaag attgtgctac 12840
tgcactctag cctgggtgat ataccgagac tccatctcaa aaaaaaaaaa aaaaaaaagc 12900
aggatgtcac tccctttgtc actgcgttgg ctgccacccc aggcacttga atctttggat 12960
cttccctgcc agtcacctgg ctgttctggg cgcgttctca tcatgagaag ggagacctgc 13020
agccccctta cagggctggc agaggacctg ctctggatta ggccctttcc tagcccctgg 13080
ggtgtggcag tgggtgagac cgggaagatc tgccctctta ggttcatagg ccaaagtgat 13140
gatcgtgtgt gcaggaccta gagggcgctc ccctgaccca cccctttcct tgccatactt 13200
catcctctgg gaacaaagct gcttgtttgg tttgagggga gttggtttgg ttcttatccc 13260
tcagcgctga gacatagagg cttcctgggc cactacagtg agacacgaac ttcaagaatc 13320
tgaatacccc cgttttctct ccccgccaag gcaaaaaagg acttagtact acctgtggag 13380
aaggaggtgc aggactacca ggccctgctg ctttgcattt acagccctcc ccagacagac 13440
acaggcaccc tcatcatacc caaactggac ttacctgcta ggcaccttcc cttccccatc 13500
caaaaaaatg gagttatttt cccttatttc agcaagtcca gttgatttta cctttgaagt 13560
agcacctgag tccttcacct tctctccatc ccttctctct cacctgacac aggtctgcag 13620
cgctcctcta gtaggcagga cagccattcc ttggggatgc acatgtctag tctttgccta 13680
gatatggcaa gtctttgcca actgagctag gctgttatgt tcttagaggc attgtttttg 13740
cccattcttc ccatttacaa gagaatcagg gacacagaag tgagggcttc cagccccata 13800
ggtgatcaat cctggggtca gagatttgag tgtgtttatt gcttgccttc ttgggagcag 13860
attccatcca taaaccatgt gcttaccaag gtctgactca ctgggagaga aacgacgtga 13920
ggttggaaag ctgaccttcc agagacttgg ggcccatgtt gtgtggtaca catgggagtc 13980
catcatatca gattgagatg gggggctggg caaagtgccc tggtctgtgg ctgtggggct 14040
accctgagaa agggagcgcc tgacaagccg actgctccca ccatctttgt tgcagcatat 14100
cgacaaagtc ttcaaacaca aggacctaca acagcagctg gtggatgcca agctccagca 14160
ggcccaggag atgctaaagg aggcagaaga gcggcaccag cgggagaagg attttgtgag 14220
gctcaggccc cagggttggg gtgggggtgt gggaggagac aggctgggct ctggctcagc 14280
tcatagccgg gttatatggg agaagtctgg ccagaccagg cacagattcc ttgagtacca 14340
gtctgagagc aggaagcctc agtgggtctg gtgcttgtgg ctaaaaacca aacatagccc 14400
ctgggggctt ctgacaggat ctggggttct gtcttggaaa tagctcctga aagaggcagt 14460
agagtcccag aggatgtgtg agctgatgaa gcagcaagag acccacctga agcaacaggt 14520

-continued

```
gagagcatat aacctgaccc tgtgccttca agtttccctc actgggcccc atcctggggg  14580
tagtgaaatg ggaccctcat tctaggactg gctgtgtcct ggctgctatg acgccttggt  14640
tgagcttagg tgggctcaga ggacttcatt tgtagctcag aaatgtattg cttttgagga  14700
ggtaggaaca gaagagtttg aaaatcaaca taaaggcaaa ataaaagtca ccctaagtct  14760
cctactttcc aggcttagca ttttggatta tatccttcca aatatatagc tttgctttgt  14820
tttaaggaaa aatagtatct caatagaatt actggtcaga gagtcaagga cgggtctgag  14880
tgtgttgacc agagtgcctc ccagagaaac ccagtcttat ctgtgggctg ctttctcccc  14940
acagcttgcc ctatacacag agaagtttga ggagttccag aacacacttt ccaaaagcag  15000
cgaggtattc accacattca agcaggagat ggaaaaggta actgtggtcc aggccaggca  15060
tggctgctgg ggcataagct gcttcattca aaattgttgg gcctgccttc aggaagctcc  15120
catctggggt gtctcaaggg cagggctgtt aggaaggttc acagcctttc ccctcttgag  15180
gcagtatcag tggtatgtat acactccagg ttgtcccagg gaatggggca gtcttttctg  15240
tttgtttggt ttttttgggg ggtttgttgt tgttgttgtt gttgttgttg ttgtttgaga  15300
tggagactca cctattgccc aggctggagt gcagtggcat gatctcagct cattgcagcc  15360
tttgcccccc gggttcaagt gattctcctg cctcagcctc ctgactagct ggaattacag  15420
gcgcgtgcca ccatgcctgg ctaatttttt ctttcttttt tttttgtatt tttagtagag  15480
acggggtttc accatgttgg ccaggctggt ctcgaactct tggcctcaag tgatctgccc  15540
gccttggcct cccaaagtgc tgggattata ggcgtgagcc accatgcctg gccccttacc  15600
attccttgtt attggtggtg gacacctctg acttcctggt ggtgaggtgg cacagagggc  15660
attgactgca tcctgtaatg ccttgcgcct tgggatcaat cattccccac cttggagaca  15720
caggtgcagt ccccaccttg gagacacaga ccttggagag gccagctctg accatttcct  15780
tctgtctgtc acataaccta gatgactaag aagatcaaga agctggagaa agaaaccacc  15840
atgtaccggt cccggtggga gagcagcaac aaggccctgc ttgagatggc tgaggaggtg  15900
ggctgtctgt gatctgcagc cagggtgggg gtgtgcactt agcgcatatc aggccctttc  15960
ctgtatgttc tacccatcag tgacacagct agcatgaggt agaggtgaga tttgcacaca  16020
atgtccaagt ccaaagttaa tgctgttctc tccccatggg aggtggtgag cccagtggta  16080
ggtctccagt gggagtgaag ggagcaaatg gaagaaagga ataaaagagc agaaaaaaac  16140
gggtgccagt gatgtgcctg gtttacatgt aaagcagccc aggtagtttg tgatttcaca  16200
gcttgtaatg tagaagaaag gaactaacga tggagcagca actgcaagcc agaccttgct  16260
gaaagttttt gggttttttt tgtctttttt gctgctgaat gtttttaggt acgttgttca  16320
ttgaaccttc tcttgagctc tgaggatggt attagtagtc ctgttttata gatgagacag  16380
gctcaaaagt caagtccttt gccaaggtca cgtggtagat aaatggagga atacgttatc  16440
tccaagccgt gccccttttc tgcaccatgc tgccccacct gacagcctag tcatggcttc  16500
aactaggact gtttcctaaa gggggccagc tttggactcg gtctgctctc agccttgtta  16560
aagtgtttgc cgccaagtgg tgatggtaag tgggaggttg atggggcacg gcactgaagg  16620
tctcatttct ttccctagaa aacagtccgg gataaagaac tggagggcct gcaggtaaaa  16680
atccaacggc tggagaagct gtgccgggca ctgcagacag agcgcaatga cctgaacaag  16740
agggtacagg acctgagtgc tggtggccag ggctccctca ctgacagtgg ccctgagagg  16800
aggccagagg ggcctggggc tcaagcaccc agctccccca gggtcacaga agcgccttgc  16860
tacccaggag caccgagcac agaagcatca ggccagactg ggcctcaaga gcccacctcc  16920
```

-continued gccagggcct agagagcctg gtgttgggtc atgctgggaa gggagcggca gcccagccag 16980
gcctggccca taaaaggctc ccatgctgag cagcccattg ctgaagccag gatgttctga 17040
cctggctggc atctggcact tgcaattttg gattttgtgg gtcagtttta cgtacatagg 17100
gcattttgca aggccttgca aatgcattta tacctgtaag tgtacagtgg gcttgcattg 17160
gggatggggg tgtgtacaga tgaagtcagt ggcttgtctg tgagctgaag agtcttgaga 17220
ggggctgtca tctgtagctg ccatcacagt gagttggcag aagtgacttg agcatttctc 17280
tgtctgattt gaggctcaga cccctccctg cccttcagag ctcaagacaa gtaatacacc 17340
caggtcttga ctgcatttgt cttgtgagca gggcttgctt ggtcagctca ggccctccta 17400
gctgctctgg aggctccttt gattctctag acctggaaaa ggtgtcccta ggcagagccc 17460
tggcagggcg ctcagagctg gggatttgct gcctggaaca agggacctgg agaatgtttt 17520
tgcgtgggat gatgtgctgg tcaggagccc cttgggcatc gcttcccctg ccctttggta 17580
gtgccaggac caggccaatg atgcttctca gtagccttat cattcacagg tgcctctcta 17640
gcctgcacaa atgattgaca agagatcacc caaaggatta tttctgaagg tgtttttttc 17700
tttatttctt tttctttttt tttttttttc tttttctttt ttttttgcac atgacagtgt 17760
ttgtattgag gaccttccaa ggaagaggga tgctgtagca gtggtgcctg ggtgcctggc 17820
ctccagtgtc ccacctcctt caccacccca cttggctcct ttgccatctt gatgctgagg 17880
tttcctgttt ggtgagatca ggttgtttgt ggtaaaagaa aggaaagggc ttctgatggc 17940
tttgccacaa gcttacctgt gggtttcagt cctgagaggc caccaccagt tcccatcagc 18000
actgtctcca tgcagcagtt gctgggtccc atgtccagct gcctctttgg cttcatgggt 18060
ttttctgctt cctgccccca cccccacatg tgcaatcctc aagatttgtc ctgattctat 18120
ttcctggcac ctccctgcct gtccttgggg attctacttc ttcctgtgtg ggagcccata 18180
gctgttgtct aacaggtaag aaatgaaatt gaactattga ctgggcccca gaaatccata 18240
aaatggctgc agacagttgt ttctgtgtcc tgttctaccc ccactccagt acataactac 18300
tatgtactgt gtagagccat tctatatgct gaatgttctg ctgttgcaaa cttgccaggg 18360
tattagccag tgtttgtgcc aagcagtttt ctgggacaac agaatgactc agaccaagat 18420
ggataggatg gttagggctt tgcttcttgc tgtttttctt tgaagctagt tcattgtcct 18480
gcaggtccct tcatcttcca tacctagccc actcttttag cccttacctt aaatctctca 18540
gataagttgg ttcacaaaga atgttaagta ctgaatcatg tgtgactgag accagagatg 18600
gcaaatgaat ggcacaccat ttctccttct cctgccccag ggcaggtacc actgatctgc 18660
atcagagttg cctgctattc tctggtgtat ccttcacatc taggtgccct caagcagctg 18720
tgtgagtgtt gagatctctg ccatctctgg ctgagatact gctgtcctgt gaagtgtttc 18780
ccatgacctt tttcttcccc tttgaatccc tctgtctgga gtagtccttg cctcttcctg 18840
ctccagtagg gccttttccc taccccagcc cctgtgccag gctaagctgg tacaagagct 18900
gccaacctca cagagtgttt gctaggcgag agaggtgcag ggaagaggca gaggtatgca 18960
ccttcccccct tgaagagagg ggaaaggcct acagtggccc acataattgc ctgactcaca 19020
cttcagctac ctcttaatgc ctgtggaggg actggagctg ctggatccca gtgtggtggt 19080
gtaggaggcc acagtgagca ggtggcccca gctgggtttc ccaggtcagg aatgtgggcc 19140
ccaggcaagg tgcagccttt gctcacagct ccatccatgt ctagaccttc aggccagtct 19200
gcagatgagg ttccctacct tttcttctc ttcattgacc aaatcaacca atcactacag 19260

-continued

```
ctgctctgct tctgctttcc aaagtagccc aggtcctggg ccagatgcag gggaggtgcc  19320
tatccatgag tgaaggccag tgtcttcctc acctgggtgg gtcccacact tgtgacctca  19380
gttttaggac caagatctgt gttggtttct tagattgcta gcttttcctc caggggacca  19440
cagcaggtga agctcaagag cgcatggctc tgctaatagt aaattgtttt cagggccttg  19500
tccagctgag agcttcatgt ccaccagatt ctgagaggtg tcagcagcac tttttttttt  19560
tatttgttgt ttgttttcca tgaggttatc ggaccatggg ctgagctcag gcactttctg  19620
taggagactg ttatttctgt aaagatggtt atttaaccct tctcacccca tcacggtggc  19680
cctgagggct gacccggagg ccagtggagc tgcctggtgt ccacggggga gggccaaggc  19740
ctgctgagct gattctccag ctgctgcccc agcctttccg ccttgcacag cacagaggtg  19800
gtcaccccag ggacagccag gcacctgctc ctcttgccct tcctggggga agggagctgc  19860
cttctgtccc tgtaactgct ttccttatgg cccagcccgg ccactcagac ttgtttgaag  19920
ctgcactggc agctttttg tctcctttgg gtattcacaa cagccaggga cttgattttg  19980
atgtatttta aaccacatta aataaagagt ctgttgcctt acttgtttct ctcctgacct  20040
gtgtattcct ttgtttctgg atctgatcca ttcagcccct tccatcatca ctgacttgtt  20100
caggtctgct gcagagcgcc catggtggtt ccctggtatc ttacatattc cacagtgtct  20160
ttgagcagtc gccacagcct caggatgctg gcatattcac ttgagctgcc tgagtggagc  20220
ccttggcaaa gttggcaaga cccttgcctc agagaggatc acacacacac aaaaaagttt  20280
tccctgacct gggggctcac aggctagtga agggaaaagg tacttttagc tatagacagg  20340
tcaatggtgc tgagagcaga gaggaggccc ctgccccctt cagcaaggtg agggggtgat  20400
acctggaatg gccttctgaa ccacagggca ggtagaagat gaacgtcatt tagtgattaa  20460
atggtacagc tgggaagcag gtccatggga ctgggagagg gggtgaggct gggcccagag  20520
tctgggtacc aggttaagga atgtgggcta gatccagagg gcaggggggg caactgaagg  20580
tgtttcaata ggaaattgat aggctccagc agtaaggcaa aaggcatgga gccaggcata  20640
ggccatttga ggcccaggtt aagaggggtg gacactcatc actgctattt gggtctgagc  20700
tgtgggtagg ctcctatagc cctggcctgc ccaagggaat tcacaggggc ctctaattgt  20760
atgcattcct taaggagagc acattctctg ttcagttttt acacccccca tttacccacc  20820
tcaagcatgg gactcctata tgggagacat gctgctggtg gcctcaccca gcaccctgtt  20880
ctctctgggt cctgggttgg tcaggcacaa aggatgatat gtgctgaatg cccaggaaat  20940
ggcagagaca acccacctgc ccttccctcc aggcctccac aaatagatgt gcccacaatg  21000
actgtgacag tcccagcaga gcctctgacc cttctagctg ggtcctgata catgttttcc  21060
atgctggcca tgttatttct agtcgcagat cctctggagg gtgtgggggg ggtgccgccc  21120
caactcttgg agattccaag caaagcagct ctgagaataa tgaggtttct gaccccccag  21180
tgaagcagct gaggatggga accacagggg tgctccctct gtcagcagca ttaccactgt  21240
ctactctagc agctccggtg gggaaggaga gggatttctg ttgtccccag tctgggcccc  21300
tggttattga aaaagttcgg aattactctt tacccttgtg gagtgttctg agtgttggaa  21360
gtacccagga agaagccctg agcaggtgcc ctcaggagca gtgcccatgg ctccccacat  21420
cagccaagag gcccaacccc aggaagccac tcctgcccgg ggatggggaa ggtgggctgg  21480
gtggctgtgt gcactgccct gggccagctc acttgagcct gctgagccgc ctggccaaac  21540
atgagcctct ctcctgttgt atcagatgct gttctgggga cctgcgccag gagcctctgc  21600
cagggcttta aatagctgcc cccattgatc tggctgcagg cagcagcagt cacactgggt  21660
```

-continued

```
cagcctccat caggtgctca ggtttccctg aggactggag tcaggtgcca gggaatcgcg  21720

tggtctacct tatgacctgg tgctccccac acctgtctcc taggcctggg gggtggggag  21780

gactcctgtc acttcatctg cggcaaaata cagcccccac cacttaccag agaaaactgt  21840

ctggcattgt agagagaggg gttttgccct caaaagactg ttgcttactt tcagtagaat  21900

ggggaatgac actggtatct tccttaaggg ttgttatggg gatgaaatgt atgtaaagtg  21960

ctcaataggg cactggactc actccattga tggctgtctt tgctcgaagt gtcttcctga  22020

tgctgctgct gttgctgctt gtgcttcttc tgtgcttaca ttctctctct ctcactcact  22080

cactctgtct ctcctctccc ccgccccacc cccttctga caaagccacc accattttgt  22140

aaggaactgt agcttctctc tgaaactgcc gggaaaggga aaatcttttt aaaatagaca  22200

tcacacaacc aacagggtcc cctaggttca ggcggggagg tgaggtcgag tgaga       22255


<210> SEQ ID NO 52
<211> LENGTH: 7
<212> TYPE: PRT
<213> ORGANISM: Artificial Sequence
<220> FEATURE:
<223> OTHER INFORMATION: Polycatonic peptide

<400> SEQUENCE: 52

Arg Arg Arg Arg Arg Arg Arg
 1               5


<210> SEQ ID NO 53
<211> LENGTH: 7
<212> TYPE: PRT
<213> ORGANISM: Artificial Sequence
<220> FEATURE:
<223> OTHER INFORMATION: Polycatonic peptide
<221> NAME/KEY: VARIANT
<222> LOCATION: (1)...(7)
<223> OTHER INFORMATION: Xaa = Any Amino Acid

<400> SEQUENCE: 53

Lys Lys Leu Lys Leu Xaa Xaa
 1               5
```

LOW DENSITY LIPOPROTEIN BINDING PROTEINS AND THEIR USE IN DIAGNOSING AND TREATING ATHEROSCLEROSIS

CROSS REFERENCE TO RELATED APPLICATIONS

This application is a divisional of U.S. patent application Ser. No. 09/616,289, filed Jul. 14, 2000, now U.S. Pat. No. 6,632,923 which is a continuation-in-part of U.S. patent application Ser. No. 09/517,849, filed Mar. 2, 2000, now U.S. Pat. No. 6,605,588 which is a continuation-in part of U.S. patent application Ser. No. 08/979,608, filed Nov. 26, 1997, now U.S. Pat. No. 6,355,451 which claimed priority from U.S. Provisional Application No. 60/031,930, filed Nov. 27, 1996, and U.S. Provisional Application No. 60/048,547, filed Jun. 3, 1997. These applications are incorporated herein by reference in their entirety.

FIELD OF THE INVENTION

This invention relates to novel polypeptides (LBPs) which bind to low density lipoprotein (LDL), polynucleotides which encode these polypeptides, and treatments, diagnoses and therapeutic agents for atherosclerosis.

BACKGROUND OF THE INVENTION

Atherosclerosis is the principal cause of heart attacks and strokes. It has been reported that about 50% of all deaths in the United States, Europe and Japan are due to atherosclerosis. Atherosclerotic lesions in the arterial wall characterize atherosclerosis. Cholesteryl esters (CE) are present in these atherosclerotic lesions. Low density lipoprotein (LDL) has been shown to be the major carrier of plasma CE, and has been implicated as the agent by which CE enter the atherosclerotic lesions.

Scattered groups of lipid-filled macrophages, called foam cells, are the first visible signs of atherosclerosis and are described as type I lesions. These macrophages are reported to contain CE derived from LDL. The macrophages recognize oxidized LDL, but not native LDL, and become foam cells by phagocytosing oxidized LDL. Larger, more organized collections of foam cells, fatty streaks, represent type II lesions. These lesions further develop into complex lesions called plaques, which can result in impeding the flow of blood in the artery.

It is widely believed that accumulation of LDL in the artery depends on the presence of functionally modified endothelial cells in the arterial wall. It has been reported in animal models of atherosclerosis that LDL, both native LDL and methylated LDL, accumulates focally and irreversibly only at the edges of regenerating endothelial islands in aortic lesions, where functionally modified endothelial cells are present, but not in the centers of these islands where endothelial regeneration is completed. Similarly, LDL accumulates in human atherosclerotic lesions. The mechanism by which the LDL accumulates focally and irreversibly in arterial lesions has not heretofore been understood.

SUMMARY OF THE INVENTION

It is an object of the invention to provide polypeptides which bind to LDL.

It is yet another object of the invention to provide a method for determining if an animal is at risk for atherosclerosis.

It is yet another object of the invention to provide a method for evaluating an agent for use in treating atherosclerosis. It is yet another object of the invention to provide a method for treating atherosclerosis.

Still another object of the invention is to utilize an LBP (low density lipoprotein binding protein) gene and/or polypeptide, or fragments, analogs and variants thereof, to aid in the treatment, diagnosis and/or identification of therapeutic agents for atherosclerosis.

In one aspect, the invention features an isolated polynucleotide comprising a polynucleotide encoding the polypeptide comprising the amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8; SEQ ID NO: 9; SEQ ID NO:43; SEQ ID NO:44; SEQ ID NO:47 or a polynucleotide capable of hybridizing to and which is at least about 95% identical to any of the above polynucleotides and wherein the encoded polypeptide is capable of binding to LDL; or a biologically active fragment of any of the above polynucleotides wherein the encoded polypeptide is capable of binding to LDL.

In certain embodiments, the polynucleotide comprises the nucleic acid sequence as set forth in SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17; SEQ ID NO: 18; SEQ ID NO:45; SEQ ID NO:46; SEQ ID NO:48.

Another aspect of the invention is an isolated polypeptide comprising a polypeptide having the amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8; SEQ ID NO: 9; SEQ ID NO: 43; SEQ ID NO:44; SEQ ID NO:47; or a polypeptide which is at least about 95% identical to any of the above polypeptides and wherein the polypeptide is capable of binding to LDL; or a biologically active fragment of any of the above polypeptides wherein the fragment is capable of binding to LDL.

Another aspect of the invention is a method for determining if an animal is at risk for atherosclerosis. An animal is provided. An aspect of LBP metabolism or structure is evaluated in the animal. An abnormality in the aspect of LBP metabolism or structure is diagnostic of being at risk for atherosclerosis. Another aspect of the invention is a method for evaluating an agent for use in treating atherosclerosis. A test cell, cell-free system or animal is provided. An agent is provided. The agent is administered to the test cell, cell-free system or animal in a therapeutically effective amount. The effect of the agent on an aspect of LBP metabolism or structure is evaluated. A change in the aspect of LBP metabolism or structure is indicative of the usefulness of the agent in treating atherosclerosis.

Another aspect of the invention is a method for evaluating an agent for the ability to alter the binding of LBP polypeptide to a binding molecule, e.g., native LDL, modified LDL, e.g., methylated LDL or oxidized LDL, or an arterial extracellular matrix structural component. An agent is provided. An LBP polypeptide is provided. A binding molecule is provided. The agent, LBP polypeptide and binding molecule are combined. The formation of a complex comprising the LBP polypeptide and binding molecule is detected. An alteration in the formation of the complex in the presence of the agent as compared to in the absence of the agent is indicative of the agent altering the binding of the LBP polypeptide to the binding molecule.

Another aspect of the invention is a method for evaluating an agent for the ability to bind to an LBP polypeptide. An agent is provided. An LBP polypeptide is provided. The agent is contacted with the LBP polypeptide. The ability of the agent to bind to the LBP polypeptide is evaluated.

Another aspect of the invention is a method for evaluating an agent for the ability to bind to a nucleic acid encoding an LBP regulatory sequence. An agent is provided. A nucleic acid encoding an LBP regulatory sequence is provided. The agent is contacted with the nucleic acid. The ability of the agent to bind to the nucleic acid is evaluated.

Another aspect of the invention is a method for treating atherosclerosis in an animal. An animal in need of treatment for atherosclerosis is provided. An agent capable of altering an aspect of LBP structure or metabolism is provided. The agent is administered to the animal in a therapeutically effective amount such that treatment of the atherosclerosis occurs. In certain embodiments, the agent is an LBP polypeptide, e.g., LBP-1, LBP-2 or LBP-3, or a biologically active fragment or analog thereof. In certain embodiments, the agent is a polypeptide of no more than about 100, 50, 30, 20, 10, 5, 4, 3 or 2 amino acid residues in length. In certain embodiments, the agent is a polypeptide having an amino acid sequence that includes at least about 20%, 40%, 60%, 80%, 90%, 95% or 98% acidic amino acid residues.

Another aspect of the invention is a method for treating an animal at risk for atherosclerosis. An animal at risk for atherosclerosis is provided. An agent capable of altering an aspect of LBP structure or metabolism is provided. The agent is administered to the animal in a therapeutically effective amount such that treatment of the animal occurs.

Another aspect of the invention is a method for treating a cell having an abnormality in structure or metabolism of LBP. A cell having an abnormality in structure or metabolism of LBP is provided. An agent capable of altering an aspect of LBP structure or metabolism is provided. The agent is administered to the cell in a therapeutically effective amount such that treatment of the cell occurs.

Another aspect of the invention is a pharmaceutical composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

Another aspect of the invention is a vaccine composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

Another aspect of the invention is a method for diagnosing atherosclerotic lesions in an animal. An animal is provided. A labeled agent capable of binding to LBP, e.g., LBP-1, LBP-2 or LBP-3, present in atherosclerotic lesions is provided. The labeled agent is administered to the animal under conditions which allow the labeled agent to interact with the LBP so as to result in labeled LBP. The localization or quantification of the labeled LBP is determined by imaging so as to diagnose the presence of atherosclerotic lesions in the animal.

Another aspect of the invention is a method for immunizing an animal against an LBP, e.g., LBP-1, LBP-2 or LBP-3, or fragment or analog thereof. An animal having LDL is provided. The LBP or fragment or analog thereof is administered to the animal so as to stimulate antibody production by the animal to the LBP or fragment or analog thereof such that binding of the LBP to the LDL is altered, e.g., decreased or increased.

Another aspect of the invention is a method of making a fragment or analog of LBP polypeptide, the fragment or analog having the ability to bind to native LDL and to modified LDL, e.g., methylated LDL, oxidized LDL, acetylated LDL, or cyclohexanedione-treated LDL. An LBP polypeptide is provided. The sequence of the LBP polypeptide is altered. The altered LBP polypeptide is tested for the ability to bind to modified LDL and native LDL.

Yet another aspect of the invention is a method for isolating a cDNA encoding an LBP. A cDNA library is provided. The cDNA library is screened for a cDNA encoding a polypeptide which binds to native LDL and modified LDL, e.g., methylated LDL or oxidized LDL. The cDNA which encodes the polypeptide is isolated, the cDNA encoding an LBP.

The above and other features, objects and advantages of the present invention will be better understood by a reading of the following specification in conjunction with the drawings.

BRIEF DESCRIPTION OF THE DRAWINGS

FIG. 1 depicts the amino acid sequence of rabbit LBP-1 (SEQ ID NO: 1). Differences in amino acids between rabbit and human LBP-1 are depicted in bold type.

FIG. 2A depicts the nucleotide sequence (SEQ ID NO: 48) and amino acid sequence (SEQ ID NO: 47) of rabbit LBP-2.

FIG. 2B depicts a portion of the amino acid sequence of rabbit LBP-2 (SEQ ID NO: 2). Differences in amino acids between rabbit and human LBP-2 are depicted in bold type. Where the sequences depicted in FIG. 2A and FIG. 2B differ, FIG. 2A represents the rabbit LBP-2 sequence.

FIG. 3 depicts the amino acid sequence of amino acids 319 to 550 of rabbit LBP-2 (SEQ ID NO: 3).

FIG. 4 depicts the amino acid sequence of amino acids 299 to 550 of rabbit LBP-2 (SEQ ID NO: 4).

FIG. 5 depicts the amino acid sequence of rabbit LBP-3 (SEQ ID NO: 5). Differences in amino acids between rabbit and human LBP-3 are depicted in bold type.

FIG. 6 depicts the amino acid sequence of human LBP-1 (SEQ ID NO: 6). Differences in amino acids between rabbit and human LBP-1 are depicted in bold type.

FIG. 7A depicts the nucleotide sequence (SEQ ID NO: 45) and amino acid sequence (SEQ ID NO: 43) of human LBP-2.

FIG. 7B depicts the amino acid sequence of amino acids 322 to 538 of human LBP-2 (SEQ ID NO: 7). Differences in amino acids between rabbit and human LBP-2 are depicted in bold type.

FIG. 8A depicts the nucleotide sequence (SEQ ID NO: 46) and amino acid sequence (SEQ ID NO: 44) of human LBP-3.

FIG. 8B depicts the amino acid sequence of amino acids 17 to 546 of human LBP-3 (SEQ ID NO: 8). Differences in amino acids between rabbit and human LBP-3 are depicted in bold type. Where the sequences depicted in FIG. 8A and FIG. 8B differ, FIG. 8A represents the human LBP-3 sequence.

FIG. 9 depicts the amino acid sequence of amino acids 14 to 33 of human or rabbit LBP-1, called BHF-1 (SEQ ID NO: 9).

FIG. 10 depicts the cDNA sequence encoding rabbit LBP-1 (SEQ ID NO: 10) and the corresponding amino acid sequence (SEQ ID NO:1). Differences in amino acids between rabbit and human LBP-1 are depicted in bold type.

FIG. 11 depicts a cDNA sequence encoding a portion of rabbit LBP-2 (SEQ ID NO: 11) and the corresponding amino acid sequence (SEQ ID NO:2). Differences in amino acids between rabbit and human LBP-2 are depicted in bold type. Where the sequences depicted in FIG. 2A and FIG. 11 differ, FIG. 2A represents the rabbit LBP-2 sequence.

FIG. 12 depicts a cDNA sequence of nucleotides 256 to 1617 (SEQ ID NO: 12) of SEQ ID NO: 11 of rabbit LBP-2 and the corresponding amino acid sequence (SEQ ID NO:3).

FIG. 13 depicts a cDNA sequence of nucleotides 196 to 1617 (SEQ LID NO: 13) of SEQ ID NO: 11 of rabbit LBP-2 and the corresponding amino acid sequence (SEQ ID NO:4).

FIG. 14 depicts the cDNA sequence encoding rabbit LBP-3 (SEQ ID NO: 14) and the corresponding amino acid sequence (SEQ ID NO:5). Differences in amino acids between rabbit and human LBP-3 are depicted in bold type.

FIG. 15 depicts the cDNA sequence encoding human LBP-1 (SEQ ID NO: 15) and the corresponding amino acid sequence (SEQ ID NO:6). Differences in amino acids between rabbit and human LBP-1 are depicted in bold type.

FIG. 16 depicts a cDNA sequence encoding a portion of human LBP-2 (SEQ ID NO: 16) and the corresponding amino acid sequence (SEQ ID NO:7). Differences in amino acids between rabbit and human LBP-2 are depicted in bold type.

FIG. 17 depicts a cDNA sequence encoding a portion of human LBP-3 (SEQ ID NO: 17) and the corresponding amino acid sequence (SEQ ID NO:8). Differences in amino acids between rabbit and human LBP-3 are depicted in bold type. Where the sequences depicted in FIG. 8A and FIG. 17 differ, FIG. 8A represents the human LBP-3 sequence.

FIG. 18 depicts the cDNA sequence encoding BHF-1 (SEQ ID NO: 18) and corresponding amino acid sequence (SEQ ID NO:9).

FIG. 19 corresponds to the amino acid sequence of rabbit LBP-1 (top sequence; SEQ ID NO:1) in alignment with the amino acid sequence of human LBP-1 (bottom sequence; SEQ ID NO:6).

FIG. 20 corresponds to the amino acid sequence of a portion of the amino acid sequence of rabbit LBP-2 (top sequence; amino acid residues 331–550 of SEQ ID NO:47) in alignment with a portion of the amino acid sequence of human LBP-2 (bottom sequence; SEQ ID NO:7).

FIG. 21 corresponds to the amino acid sequence of rabbit LBP-3 (top sequence; SEQ ID NO:5) in alignment with the amino acid sequence of a portion of human LBP-3 (bottom sequence; SEQ ID NO:44).

FIG. 22 depicts the genomic sequence of human LBP-1 (SEQ ID NO:49) and corresponding amino acid sequence (SEQ ID NO:6).

FIG. 23 depicts the genomic sequence of human LBP-2 (SEQ ID NO:50) and corresponding amino acid sequence (SEQ ID NO:43).

FIG. 24 depicts the genomic sequence of human LBP-3 (SEQ ID NO:51) and corresponding amino acid sequence (SEQ ID NO:44).

DETAILED DESCRIPTION

In accordance with aspects of the present invention, there are provided novel mature human and rabbit polypeptides, LBP-1, LBP-2 and LBP-3, and biologically active analogs and fragments thereof, and there are provided isolated polynucleotides which encode such polypeptides. LBP is an abbreviation for low density lipoprotein (LDL) binding protein. The terms polynucleotide, nucleotide and oligonucleotide are used interchangeably herein, and the terms polypeptides, proteins and peptides are used interchangeably herein.

This invention provides for an isolated polynucleotide comprising a polynucleotide encoding the polypeptide having the amino acid sequence of rabbit LBP-1 as set forth in FIG. 1 (SEQ ID NO: 1); rabbit LBP-2 as set forth in FIG. 2A (SEQ ID NO: 47); a portion of rabbit LBP-2 as set forth in FIG. 2B (SEQ ID NO: 2); 319 to 550 of rabbit LBP-2 as set forth in FIG. 3 (SEQ ID NO: 3); 299 to 550 of rabbit LBP-2 as set forth in FIG. 4 (SEQ ID NO: 4); rabbit LBP-3 as set forth in FIG. 5 (SEQ ID NO: 5); human LBP-1 as set forth in FIG. 6 (SEQ ID NO: 6); human LBP-2 as set forth in FIG. 7A (SEQ ID NO: 43); 322 to 538 of human LBP-2 as set forth in FIG. 7B (SEQ ID NO: 7); human LBP-3 as set forth in FIG. 8A (SEQ ID NO: 44); 17–546 of human LBP-3 as set forth in FIG. 8B (SEQ ID NO: 8); 14 to 33 of human (SEQ ID NO:6) or rabbit (SEQ ID NO:1) LBP-1, called BHF-1, as set forth in FIG. 9 (SEQ ID NO: 9); a polynucleotide capable of hybridizing to and which is at least about 80% identical, more preferably at least about 90% identical, more preferably yet at least about 95% identical, and most preferably at least about 98% identical to any of the above polynucleotides, and wherein the encoded polypeptide is capable of binding to LDL; or a biologically active fragment of any of the above polynucleotides wherein the encoded polypeptide is capable of binding to LDL.

This invention also includes an isolated polynucleotide comprising a polynucleotide encoding the polypeptide having amino acid residues 329–343 (SEQ ID NO: 19), 329–354 (SEQ ID NO: 20), 344–354 (SEQ ID NO: 21) or 529–538 (SEQ ID NO: 22) of human LBP-2 as set forth in FIG. 7A (SEQ ID NO: 43); amino acid residues 14–43 (SEQ ID NO: 23) or 38–43 (SEQ ID NO: 24) of rabbit or human LBP-1 as set forth in FIG. 1 (SEQ ID NO: 1) and FIG. 6 (SEQ ID NO: 6); amino acid residues 338–353 (SEQ ID NO: 25), 338–365 (SEQ ID NO: 26), 354–365 (SEQ ID NO: 27) or 444–453 (SEQ ID NO: 28) of rabbit LBP-2 as set forth in FIG. 2A (SEQ ID NO: 47); amino acid residues 96–110 (SEQ ID NO: 29) of rabbit LBP-3 as set forth in FIG. 5 (SEQ ID NO: 5); amino acid residues 69–75 (SEQ ID NO: 41) of human LBP-3 as set forth in FIG. 8A (SEQ ID NO: 44); a polynucleotide capable of hybridizing to and which is at least about 80% identical, more preferably at least about 90% identical, more preferably yet at least about 95% identical, and most preferably at least about 98% identical to any of the above polynucleotides, and wherein the encoded polypeptide is capable of binding to LDL; or a biologically active fragment of any of the above polynucleotides wherein the encoded polypeptide is capable of binding to LDL.

By a polynucleotide encoding a polypeptide is meant a polynucleotide which includes only coding sequence for the polypeptide, as well as a polynucleotide which includes additional coding and/or non-coding sequences. Thus, e.g., the polynucleotides which encode for the mature polypeptides of FIGS. 1–9 (SEQ ID NOS: 1–9, 43, 44 and 47) may include only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequences 5' and/or 3' of the coding sequence for the mature polypeptide. The polynucleotides of the invention are also meant to include polynucleotides in which the coding sequence for the mature polypeptide is fused in the same reading frame to a polynucleotide sequence which aids in expression and/or secretion of a polypeptide from a host cell, e.g., a leader sequence. The polynucleotides are also meant to include polynucleotides in which the coding sequence is fused in frame to a marker sequence which, e.g., allows for purification of the polypeptide.

The polynucleotides of the present invention may be in the form of RNA, DNA or PNA, e.g., cRNA, cDNA, genomic DNA, or synthetic DNA, RNA or PNA. The DNA may be double-stranded or single stranded, and if single stranded may be the coding strand or non-coding (anti-sense) strand.

In preferred embodiments, the polynucleotide comprises the nucleic acid of rabbit LBP-1 as set forth in FIG. 10 (SEQ ID NO: 10); rabbit LBP-2 as set forth in FIG. 2A (SEQ ID NO:48) or FIG. 11 (SEQ ID NO:11); nucleotide 256 to 1617 of SEQ ID NO: 11 of rabbit LBP-2 as set forth in FIG. 12 (SEQ ID NO: 12); nucleotide 196 to 1617 of SEQ ID NO: 11 of rabbit LBP-2 as set forth in FIG. 13 (SEQ ID NO: 13); rabbit LBP-3 as set forth in FIG. 14 (SEQ ID NO: 14); human LBP-1 as set forth in FIG. 15 (SEQ ID NO: 15); human LBP-2 as set forth in FIG. 7A (SEQ ID NO: 45) or FIG. 16 (SEQ ID NO: 16); human LBP-3 as set forth in FIG. 8A (SEQ ID NO: 46) or FIG. 17 (SEQ ID NO: 17); or nucleotide 97 to 156 of rabbit LBP-1 or nucleotide 157 to 216 of human LBP-1, (BHF-1), as set forth in FIG. 18 (SEQ ID NO: 18).

In other preferred embodiments, the polynucleotide comprises the nucleic acid as set forth in SEQ ID NO:30

This invention also includes a cell comprising such a recombinant vector. The recombinant vectors described herein can be introduced into a host cell, e.g., by transformation, transfection or infection.

This invention also includes a method for producing an LBP comprising culturing such a cell under conditions that permit expression of the LBP.

This invention also includes an isolated polypeptide comprising a polypeptide having the amino acid sequence as set forth in FIG. 1 (SEQ ID NO: 1); FIG. 2A (SEQ ID NO: 47); FIG. 2B (SEQ ID NO: 2); FIG. 3 (SEQ ID NO: 3); FIG. 4 (SEQ ID NO: 4); FIG. 5 (SEQ ID NO: 5); FIG. 6 (SEQ ID NO: 6); FIG. 7A (SEQ ID NO: 43); FIG. 7B (SEQ ID No: 7); FIG. 8A (SEQ ID NO: 44); FIG. 8B (SEQ ID NO: 8); or FIG. 9 (SEQ ID NO: 9); or a polypeptide which is at least about 80% identical, more preferably at least about 90% identical, more preferably yet at least about 95% identical, and most preferably at least about 98% identical to the above polypeptides, and wherein said polypeptide is capable of binding to LDL; or a biologically active fragment of any of the above polypeptides wherein the fragment is capable of binding to LDL. Differences in amino acids between the rabbit and human LBP-1, LBP-2 and LBP-3 genes are depicted in bold type in the figures. Differences in the amino acid sequences between rabbit and human LBP-1, LBP-2 and LBP-3 are also specifically shown in FIGS. 19, 20 and 21, respectively.

```
SEQ ID NO:30  (GAAGAGGAAGAAGATGATGATGAAGATGAAGATGAAGAAGATGAT),

SEQ ID NO:31  (GAAGAGGAAGAAGATGATGATGAAGATGAAGATGAAGAAGA
              TGAT GTGTCAGAGGGCTCTGAAGTGCCCGAGAGTGAC),

SEQ ID NO:32  (GTGTCAGAGGGCTCTGAAGTGCCCGAGAGTGAC),

SEQ ID NO:33  (GAGGATGATGACCCCGATGGCTTCTTAGGC),

SEQ ID NO:34  (GTGGACGTGGATGAATATGACGAGAACAAGTTCGTGGACGAA
              GAAGATGGGGGCGACGGCCAGGCCGGGCCCGACGAGGGCGAGGTGGAC),

SEQ ID NO:35  (GACGAGGGCGAGGTGGAC),

SEQ ID NO:36  (GAGGAGGAGGAGGAGGAGGAGGAAGACGACGAGGACGACG
              ACGACGAC),

SEQ ID NO:37  (GAGGAGGAGGAGGAGGAGGAGGAAGACGACGAGGACGACG
              ACGACGACGTCGTGTCCGAGGGCTCGGAGGTGCCCGAGAGCGAT),

SEQ ID NO:38  (GTCGTGTCCGAGGGCTCGGAGGTGCCCGAGAGCGAT),

SEQ ID NO:39  (CCCCCCGGGAAGCCAGCCCTCCCAGGAGCC),

SEQ ID NO:40  (GAGGATGGGGTCCAGGGTGAGCCCCCTGAACCTGAAGATGCA
              GAG), or

SEQ ID NO:42  (CGTGATGTCTCTGAGGAGCTG).
```

The coding sequence which encodes the mature polypeptide may be identical to the coding sequences shown in FIGS. 2A, 7A, 8A and 10–18 (SEQ ID NOS: 10–18, 45, 46, and 48) or SEQ ID NOS: 30–40 or 42, or may be a different coding sequence which coding sequence, as a result of the redundancy or degeneracy of the genetic code, encodes the same mature polypeptides as the DNA of FIGS. 2A, 7A, 8A and 10–18 (SEQ ID NOS: 10–18, 45, 46, and 48) and SEQ ID NOS: 30–40 and 42.

This invention also includes recombinant vectors comprising the polynucleotides described above. The vector can be, e.g., a plasmid, a viral particle or a phage. In certain embodiments, the recombinant vector is an expression vector. The vectors may also include various marker genes which are useful in identifying cells containing such vectors.

This invention also includes an isolated polypeptide comprising a polypeptide having amino acid residues 329–343 (SEQ ID NO: 19), 329–354 (SEQ ID NO: 20), 344–354 (SEQ ID NO: 21) or 529–538 (SEQ ID NO: 22) as set forth in FIG. 7A (SEQ ID NO: 47); amino acid residues 14–43 (SEQ ID NO: 23) or 38–43 (SEQ ID NO: 24) as set forth in FIG. 1 (SEQ ID NO: 1) and FIG. 6 (SEQ ID NO: 6); amino acid residues 338–353 (SEQ ID NO: 25), 338–365 (SEQ ID NO: 26), 354–365 (SEQ ID NO: 27) or 444–453 (SEQ ID NO: 28) as set forth in FIG. 2A (SEQ ID NO: 47); amino acid residues 96–110 (SEQ ID NO: 29) as set forth in FIG. 5 (SEQ ID NO: 5); and amino acid residues 69–75 (SEQ ID NO: 41) as set forth in FIG. 8A (SEQ ID NO:44); or a polypeptide which is at least about 80% identical, more preferably at least about 90% identical, more preferably yet at least about 95% identical, and most preferably at least about 98% identical to the above polypeptides, and wherein said polypeptide is capable of binding to LDL; or a biologically active fragment of any of the above polypeptides wherein the fragment is capable of binding to LDL.

The polypeptides of the invention are meant to include, e.g., a naturally purified product, a chemically synthesized product, and a recombinantly derived product.

The polypeptides can be used, e.g., to bind to LDL, thereby inhibiting formation of atherosclerotic plaques. The polypeptides can also be used, e.g., in gene therapy, by expression of such polypeptides in vivo. The polypeptides can also be used in pharmaceutical or vaccine compositions. The polypeptides can also be used as immunogens to produce antibodies thereto, which in turn, can be used as antagonists to the LBP polypeptides.

Without being bound by any theory, it is believed that the LBPs provide the mechanism by which atherosclerosis is promoted through LDL oxidation. The LBPs are believed to be required in order for focal, irreversible LDL binding to occur at the arterial wall, and that such binding is a critical early event in atherosclerosis because it allows the time necessary for LDL to be changed from its native state to a fully oxidized state.

Since oxidized, but not native, LDL is a foreign protein, macrophages ingest it, first becoming the foam cells of type I lesions, and subsequently forming the fatty streaks of type II lesions.

This invention also includes a method for determining if an animal is at risk for atherosclerosis. An animal is provided. An aspect of LBP metabolism or structure is evaluated in the animal. An abnormality in the aspect of LBP metabolism or structure is diagnostic of being at risk for atherosclerosis.

By atherosclerosis is meant a disease or condition which comprises several stages which blend imperceptibly into each other, including irreversible binding of LDL, LDL oxidation, macrophage recruitment, blockage of the artery and tissue death (infarction).

By animal is meant human as well as non-human animals. Nonhuman animals include, e.g., mammals, birds, reptiles, amphibians, fish, insects and protozoa. Preferably, the non-human animal is a mammal, e.g., a rabbit, a rodent, e.g., a mouse, rat or guinea pig, a primate, e.g., a monkey, or a pig. An animal also includes transgenic non-human animals. The term transgenic animal is meant to include an animal that has gained new genetic information from the introduction of foreign DNA, i.e., partly or entirely heterologous DNA, into the DNA of its cells; or introduction of a lesion, e.g., an, in vitro induced mutation, e.g., a deletion or other chromosomal rearrangement into the DNA of its cells; or introduction of homologous DNA into the DNA of its cells in such a way as to alter the genome of the cell into which the DNA is inserted, e.g., it is inserted at a location which differs from that of the natural gene or its insertion results in a knockout or replacement of the homologous host gene or results in altered and/or regulatable expression and/or metabolism of the gene. The animal may include a transgene in all of its cells including germ line cells, or in only one or some of its cells. Transgenic animals of the invention can serve as a model for studying atherosclerosis or for evaluating agents to treat atherosclerosis.

In certain embodiments, the determination for being at risk for atherosclerosis is done in a prenatal animal.

By LBP is meant a low density lipoprotein (LDL) binding protein which is capable of binding LDL and methylated LDL. By methylated LDL is meant that about 50% to about 90% of the lysine residues of LDL have a methyl group chemically attached. Methylated LDL is not recognized by previously reported cell surface receptors. See, e.g., Weisgraber et al., J. Biol. Chem. 253: 9053–9062 (1978). In certain embodiments, the LBP is also capable of binding oxidized LDL. In certain preferred embodiments, the binding of LDL to an LBP is irreversible. In certain preferred embodiments, the LBP does not transport the LDL to any intracellular compartment. Examples of LBPs are LBP-1, LBP-2 and LBP-3 described herein.

By LBP metabolism is meant any aspect of the production, release, expression, function, action, interaction or regulation of LBP. The metabolism of LBP includes modifications, e.g., covalent or non-covalent modifications, of LBP polypeptide. The metabolism of LBP includes modifications, e.g., covalent or noncovalent modifications, that LBP induces in other substances.
The metabolism of LBP also includes changes in the distribution of LBP polypeptide, and changes LBP induces in the distribution of other substances.

Any aspect of LBP metabolism can be evaluated. The methods used are standard techniques known to those skilled in the art and can be found in standard references, e.g., Auaubel et al., ed., Current Protocols in Mol. Biology, New York: John Wiley & Sons, 1990; Kriegler, M., ed., Gene Transfer and Expression, Stockton Press, New York, N.Y., 1989; pDisplay gene expression system (Invitrogen, Carlsbad, Calif.). Preferred examples of LBP metabolism that can be evaluated include the binding activity of LBP polypeptide to a binding molecule, e.g., LDL; the transactivation activity of LBP polypeptide on a target gene; the level of LBP protein; the level of LBP mRNA; the level of LBP modifications, e.g., phosphorylation, glycosylation or acylation; or the effect of LBP expression on transfected mammalian cell binding of LDL.

By binding molecule is meant any molecule to which LBP can bind, e.g., a nucleic acid, e.g., a DNA regulatory region, a protein, e.g., LDL, a metabolite, a peptide mimetic, a non-peptide mimetic, an antibody, or any other type of ligand. In certain preferred embodiments, the aspect of LBP metabolism that is evaluated is the ability of LBP to bind to native LDL and/or methylated LDL and/or oxidized LDL. Binding to LDL can be shown, e.g., by antibodies against LDL, affinity chromatography, affinity coelectrophoresis (ACE) assays, or ELISA assays. See Examples. In other embodiments, it is the ability of LBP to bind to an arterial extracellular matrix structural component that is evaluated. Examples of such components include proteoglycans, e.g., chondroitin sulfate proteoglycans and heparin sulfate proteoglycans; elastin; collagen; fibronectin; vitronectin; integrins; and related extracellular matrix molecules. Binding to arterial extracellular matrix structural components can be shown by standard methods known to those skilled in the art, e.g., by ELISA assays. Primary antibodies to the LBP are then added, followed by an enzyme-conjugated secondary antibody to the primary antibody, which produces a stable color in the presence of an appropriate substrate, and color development on the plates is measured in a microtiter plate reader.

Transactivation of a target gene by LBP can be determined, e.g., in a transient transfection assay in which the promoter of the target gene is linked to a reporter gene, e.g., β-galactosidase or luciferase, and co-transfected with an LBP expression vector. Such evaluations can be done in vitro or in vivo. Levels of LBP protein, mRNA or phosphorylation, can be measured, e.g., in a sample, e.g., a tissue sample, e.g., arterial wall, by standard methods known to those skilled in the art.

In certain embodiments, an aspect of LBP structure is evaluated, e.g., LBP gene structure or LBP protein structure. For example, primary, secondary or tertiary structures can be evaluated. For example, the DNA sequence of the gene is determined and/or the amino acid sequence of the protein is determined. Standard cloning and sequencing methods can be used as are known to those skilled in the art. In certain embodiments, the binding activity of an antisense nucleic acid with the cellular LBP mRNA and/or genomic DNA is determined using standard methods known to those skilled in the art so as to detect the presence or absence of the target mRNA or DNA sequences to which the antisense nucleic acid would normally specifically bind.

The risk for atherosclerosis that is determined can be a reduced risk or an increased risk as compared to a normal animal. For example, an abnormality which would give a reduced risk is an inactive LBP polypeptide. An abnormality which would give an increased risk would be, e.g., an LBP polypeptide that has higher activity, e.g., LDL binding activity, than native LBP polypeptide.

The invention also includes a method for evaluating an agent for use in treating atherosclerosis. A test cell, cell-free system or animal is provided. An agent is provided. The agent is administered to the test cell, cell-free system or animal in a therapeutically effective amount. The effect of the agent on an aspect of LBP metabolism or structure is evaluated. A change in the aspect of LBP metabolism or structure is indicative of the usefulness of the agent in treating atherosclerosis.

In certain embodiments, the method employs two phases for evaluating an agent for use in treating atherosclerosis, an initial in vitro phase and then an in vivo phase. The agent is administered to the test cell or cell-free system in vitro, and if a change in an aspect of LBP metabolism occurs, then the agent is further administered to a test animal in a therapeutically effective amount and evaluated in vivo for an effect of the agent on an aspect of LBP metabolism.

By cell is meant a cell or a group of cells, or a cell that is part of an animal. The cell can be a human or non-human cell. Cell is also meant to include a transgenic cell. The cell can be obtained, e.g., from a culture or from an animal. Animals are meant to include, e.g., natural animals and non-human transgenic animals. In certain embodiments, the transgenic cell or nonhuman transgenic animal has an LBP transgene, or fragment or analog thereof. In certain embodiments, the transgenic cell or non-human transgenic animal has a knockout for the LBP gene.

The test cell, cell-free system or animal can have a wild type pattern or a non-wild type pattern of LBP metabolism. A non-wild type pattern of LBP metabolism can result, e.g., from under-expression, over-expression, no expression, or a temporal, site or distribution change. Such a non-wild type pattern can result, e.g., from one or more mutations in the LBP gene, in a binding molecule gene, a regulatory gene, or in any other gene which directly or indirectly affects LBP metabolism. A mutation is meant to include, e.g., an alteration, e.g., in gross or fine structure, in a nucleic acid. Examples include single base pair alterations, e.g., missense or nonsense mutations, frameshifts, deletions, insertions and translocations. Mutations can be dominant or recessive. Mutations can be homozygous or heterozygous. Preferably, an aspect of LBP-1, LBP-2 or LBP-3 metabolism is evaluated.

An agent is meant to include, e.g., any substance, e.g., an anti-atherosclerosis drug. The agent of this invention preferably can change an aspect of LBP metabolism. Such change can be the result of any of a variety of events, including, e.g., preventing or reducing interaction between LBP and a binding molecule, e.g., LDL or an arterial extracellular matrix structural component; inactivating LBP and/or the binding molecule, e.g., by cleavage or other modification; altering the affinity of LBP and the binding molecule for each other; diluting out LBP and/or the binding molecule; preventing expression of LBP and/or the binding molecule; reducing synthesis of LBP and/or the binding molecule; synthesizing an abnormal LBP and/or binding molecule; synthesizing an alternatively spliced LBP and/or binding molecule; preventing or reducing proper conformational folding of LBP and/or the binding molecule; modulating the binding properties of LBP and/or the binding molecule; interfering with signals that are required to activate or deactivate LBP and/or the binding molecule; activating or deactivating LBP and/or the binding molecule in such a way as to prevent binding; or interfering with other receptors, ligands or other molecules which are required for the normal synthesis or functioning of LBP and/or the binding molecule. For example, the agent can block the binding site on LDL for LBPs expressed focally in the arterial wall extracellular matrix, or it could block the binding site on an LBP for LDL, or it could be bifunctional, i.e., it could block both binding sites.

Examples of agents include LBP polypeptide, e.g., LBP-1, LBP-2 or LBP-3, or a biologically active fragment or analog thereof; a nucleic acid encoding LBP polypeptide or a biologically active fragment or analog thereof; a nucleic acid encoding an LBP regulatory sequence or a biologically active fragment or analog thereof; a binding molecule for LBP polypeptide; a binding molecule for LBP nucleic acid, the LBP nucleic acid being, e.g., a nucleic acid comprising a regulatory region for LBP or a nucleic acid comprising a structural region for LBP or a biologically active fragment of LBP; an antisense nucleic acid; a mimetic of LBP or a binding molecule; an antibody for LBP or a binding molecule; a metabolite; or an inhibitory carbohydrate or glycoprotein. In certain embodiments, the agent is an antagonist, agonist or super agonist.

Knowledge of the existence of the sequence of the LBPs allows a search for natural or artificial ligands to regulate LDL levels in the treatment of atherosclerosis. In certain embodiments, the agent is a natural ligand for LBP. In certain embodiments, the agent is an artificial ligand for LBP.

By analog is meant a compound that differs from naturally occurring LBP in amino acid sequence or in ways that do not involve sequence, or both. Analogs of the invention generally exhibit at least about 80% homology, preferably at least about 90% homology, more preferably yet at least about 95% homology, and most preferably at least about 98% homology, with substantially the entire sequence of a naturally occurring LBP sequence, preferably with a segment of about 100 amino acid residues, more preferably with a segment of about 50 amino acid residues, more preferably yet with a segment of about 30 amino acid residues, more preferably yet with a segment of about 20 amino acid residues, more preferably yet with a segment of about 10 amino acid residues, more preferably yet with a segment of about 5 amino acid residues, more preferably yet with a segment of about 4 amino acid residues, more preferably yet with a segment of about 3 amino acid residues, and most preferably with a segment of about 2 amino acid residues. Non-sequence modifications include, e.g., in vivo or in vitro chemical derivatizations of LBP. Non-sequence modifications include, e.g., changes in phosphorylation, acetylation, methylation, carboxylation, or glycosylation. Methods for making such modifications are known to those skilled in the art. For example, phosphorylation can be modified by exposing LBP to phosphorylation-altering enzymes, e.g., kinases or phosphatases. Preferred analogs include LBP or biologically active fragments thereof whose sequences differ from the wild-type sequence by one or more conservative amino acid substitutions or by one or more non-conservative amino acid substitutions, deletions, or insertions which do not abolish LBP biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine tyrosine. Other examples of conservative substitutions are shown in Table 1.

(1981)). Non-random or directed mutagenesis can be used to provide specific sequences or mutations in specific regions. These techniques can be used to create variants which include, e.g., deletions, insertions, or substitutions, of residues of the known amino acid sequence of a protein. The sites for mutation can be modified individually or in series, e.g., by (i) substituting first with conserved amino acids and then with more radical choices depending upon results achieved, (ii) deleting the target residue, (iii) inserting residues of the same or a different class adjacent to the located site, or (iv) combinations of the above. For example, analogs can be made by in vitro DNA sequence modifications of the sequences of FIGS. 2A, 7A, 8A, 10–18 (SEQ ID NOS: 10–18, 45, 46, and 48). For example, in vitro mutagenesis can be used to convert any of these DNA sequences into a sequence which encodes an analog in which one or more amino acid residues has undergone a replacement, e.g., a conservative replacement as described in Table 1.

TABLE 1

CONSERVATIVE AMINO ACID SUBSTITUTIONS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn, L-NMMA, L-NAME |
| Asparagine | N | D-Asn. Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Histidine | H | D-His |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tryptophan | W | D-Trp, Phe, D-Phe, Tyr, D-Tyr |
| Tyrosine | Y | D-Tyr, Phe, D-Phe, L-Dopa, His, D-His |
| Valine | V | D-Val, Leu, D-Leu, Ile, D-Ile, Met, D-Met |

Amino acid sequence variants of a protein can be prepared by any of a variety of methods known to those skilled in the art. For example, random mutagenesis of DNA which encodes a protein or a particular domain or region of a protein can be used, e.g., PCR mutagenesis (using, e.g., reduced Taq polymerase fidelity to introduce random mutations into a cloned fragment of DNA; Leung et al., Bio Technique 1: 11–15 (1989)), or saturation mutagenesis (by, e.g., chemical treatment or irradiation of single-stranded DNA in vitro, and synthesis of a complementary DNA strand; Mayers et al., Science 229: 242 (1985)). Random mutagenesis can also be accomplished by, e.g., degenerate oligonucleotide generation (using, e.g., an automatic DNA synthesizer to chemically synthesize degenerate sequences; Narang, Tetrahedron 39: 3 (1983); Itakura et al., Recombinant DNA, Proc. 3rd Cleveland Sympos. Macromolecules, ed. A. G. Walton, Amsterdam: Elsevier, pp. 273–289

Methods for identifying desirable mutations include, e.g., alanine scanning mutagenesis (Cunningham and Wells, Science 244: 1081–1085 (1989)), oligonucleotide-mediated mutagenesis (Adelman et al., DNA, 2: 183 (1983)); cassette mutagenesis (Wells et al., Gene 34: 315 (1985)), combinatorial mutagenesis, and phage display libraries (Ladner et al., PCT International Appln. No. WO88/06630). The LBP analogs can be tested, e.g., for their ability to bind to LDL and/or to an arterial extracellular matrix component, as described herein. Other analogs within the invention include, e.g., those with modifications which increase peptide stability. Such analogs may contain, e.g., one or more non-peptide bonds (which replace the peptide bonds) in the peptide sequence. Also included are, e.g.: analogs that include residues other than naturally occurring L-amino acids, e.g., D-amino acids or nonnaturally occurring or synthetic amino acids, e.g., β or γ amino acids; and cyclic analogs.

Analogs are also meant to include peptides in which structural modifications have been introduced into the peptide backbone so as to make the peptide non-hydrolyzable. Such peptides are particularly useful for oral administration, as they are not digested. Peptide backbone modifications include, e.g., modifications of the amide nitrogen, the α-carbon, the amide carbonyl, or the amide bond, and modifications involving extensions, deletions or backbone crosslinks. For example, the backbone can be modified by substitution of a sulfoxide for the carbonyl, by reversing the peptide bond, or by substituting a methylene for the carbonyl group. Such modifications can be made by standard procedures known to those skilled in the art. See, e.g., Spatola, A. F., "Peptide Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267–357, B. Weinstein (ed.), Marcel Dekker, Inc., New York (1983).

An analog is also meant to include polypeptides in which one or more of the amino acid residues include a substituent group, or polypeptides which are fused with another compound, e.g., a compound to increase the half-life of the polypeptide, e.g., polyethylene glycol.

By fragment is meant some portion of the naturally occurring LBP polypeptide. Preferably, the fragment is at least about 100 amino acid residues, more preferably at least about 50 amino acid residues, more preferably yet at least about 30 amino acid residues, more preferably yet at least about 20 amino acid residues, more preferably yet at least about 5 amino acid residues, more preferably yet at least about 4 amino acid residues, more preferably yet at least about 3 amino acid residues, and most preferably at least about 2 amino acid residues in length. Fragments include, e.g., truncated secreted forms, proteolytic fragments, splicing fragments, other fragments, and chimeric constructs between at least a portion of the relevant gene, e.g., LBP-1, LBP-2 or LBP-3, and another molecule. Fragments of LBP can be generated by methods known to those skilled in the art. In certain embodiments, the fragment is biologically active. The ability of a candidate fragment to exhibit a biological activity of LBP can be assessed by methods known to those skilled in the art. For example, LBP fragments can be tested for their ability to bind to LDL and/or to an arterial extracellular matrix structural component, as described herein. Also included are LBP fragments containing residues that are not required for biological activity of the fragment or that result from alternative mRNA splicing or alternative protein processing events.

Fragments of a protein can be produced by any of a variety of methods known to those skilled in the art, e.g., recombinantly, by proteolytic digestion, or by chemical synthesis. Internal or terminal fragments of a polypeptide can be generated by removing one or more nucleotides from one end (for a terminal fragment) or both ends (for an internal fragment) of a nucleic acid which encodes the polypeptide. Expression of the mutagenized DNA produces polypeptide fragments. Digestion with "end-nibbling" endonucleases can thus generate DNAs which encode an array of fragments. DNAs which encode fragments of a protein can also be generated; e.g., by random shearing, restriction digestion or a combination of the above-discussed methods. For example, fragments of LBP can be made by expressing LBP DNA which has been manipulated in vitro to encode the desired fragment, e.g., by restriction digestion of any of the DNA sequences of FIGS. 2A, 7A, 8A, 10–18 (SEQ ID NOS: 10–18, 45, 46, and 48).

Fragments can also be chemically synthesized using techniques known in the art, e.g., conventional Merrifield solid phase f-Moc or t-Boc chemistry for example, peptides of the present invention can be arbitrarily divided into fragments of desired length with no overlap of the fragments, or divided into overlapping fragments of a desired length.

An LBP or a biologically active fragment or analog thereof, or a binding molecule or a biologically active fragment or analog thereof, can, e.g., compete with its cognate molecule for the binding site on the complementary molecule, and thereby reduce or eliminate binding between LBP and the cellular binding molecule. LBP or a binding molecule can be obtained, e.g., from purification or secretion of naturally occurring LBP or binding molecule, from recombinant LBP or binding molecule, or from synthesized LBP or binding molecule.

Therefore, methods for generating analogs and fragments and testing them for activity are known to those skilled in the art.

An agent can also be a nucleic acid used as an antisense molecule. Antisense therapy is meant to include, e.g., administration or in situ generation of oligonucleotides or their derivatives which specifically hybridize, e.g., bind, under cellular conditions, with the cellular mRNA and/or genomic DNA encoding an LBP polypeptide, or mutant thereof, so as to inhibit expression of the encoded protein, e.g., by inhibiting transcription and/or translation. The binding may be by conventional base pair complementarity, or, for example, in the case of binding to DNA duplexes, through specific interactions in the major groove of the double helix.

In certain embodiments, the antisense construct binds to a naturally-occurring sequence of an LBP gene which, e.g., is involved in expression of the gene. These sequences include, e.g., promoter, start codons, stop codons, and RNA polymerase binding sites. In other embodiments, the antisense construct binds to a nucleotide sequence which is not present in the wild type gene. For example, the antisense construct can bind to a region of an LBP gene which contains an insertion of an exogenous, non-wild type sequence. Alternatively, the antisense construct can bind to a region of an LBP gene which has undergone a deletion, thereby bringing two regions of the gene together which are not normally positioned together and which, together, create a non-wild type sequence. When administered in vivo to a subject, antisense constructs which bind to non-wild type sequences provide the advantage of inhibiting the expression of a mutant LBP gene, without inhibiting expression of any wild type LBP gene.

An antisense construct of the present invention can be delivered, e.g., as an expression plasmid which, when transcribed in the cell, produces RNA which is complementary to at least a unique portion of the cellular mRNA which encodes an LBP polypeptide. An alternative is that the antisense construct is an oligonucleotide which is generated ex vivo and which, when introduced into the cell causes inhibition of expression by hybridizing with the mRNA (duplexing) and/or genomic sequences (triplexing) of an LBP gene. Such oligonucleotides are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate, phosphorodithioates and methylphosphonate analogs of DNA and peptide nucleic acids (PNA). (See also U.S. Pat. Nos. 5,176,996; 5,264,564; and 5,256,775).

Additionally, general approaches to constructing oligomers useful in antisense therapy have been reviewed. (See, e.g., Van der Krol et al., Biotechniques 6: 958–976, (1988); Stein et al., Cancer Res. 48: 2659–2668 (1988)).

By mimetic is meant a molecule which resembles in shape and/or charge distribution LBP or a binding molecule. The mimetic can be a peptide or a non-peptide. Mimetics can act as therapeutic agents because they can, e.g., competitively inhibit binding of LBP to a binding molecule. By employing, e.g., scanning mutagenesis, e.g., alanine scanning mutagenesis, linker scanning mutagenesis or saturation mutagenesis, to map the amino acid residues of a particular LBP polypeptide involved in binding a binding molecule, peptide mimetics, e.g., diazepine or isoquinoline derivatives, can be generated which mimic those residues in binding to a binding molecule, and which therefore can inhibit binding of the LBP to a binding molecule and thereby interfere with the function of LBP. Non-hydrolyzable peptide analogs of such residues can be generated using, e.g., benzodiazepine (see, e.g., Freidinger et al., in Peptides: Chemistry and Biology, G. R. Marshall ed., ESCOM Publisher: Leiden, Netherlands (1988)); azepine (see, e.g., Huffman et al., in Peptides: Chemistry and Biology, G. R. Marshall ed., ESCOM Publisher: Leiden, Netherlands (1988)); substituted gamma lactam rings (see, e.g., Garvey et al., in Peptides: Chemistry and Biology, G. R. Marshall ed., ESCOM Publisher: Leiden, Netherlands (1988)); keto-methylene pseudopeptides (see, e.g., Ewenson et al., J. Med. Chem. 29: 295 (1986); Ewenson et al., in Peptides: Structure and Function (Proceedings of the 9th American Peptide Symposium) Pierce Chemical Co. Rockland, Ill. (1985)); β-turn dipeptide cores (see, e.g., Nagai et al., Tetrahedron Lett. 26: 647 (1985); Sato et al., J. Chem. Soc. Perkin Trans. 1: 1231 (1986)); or β-aminoalcohols (see, e.g., Gordon et al., Biochem. Biophys. Res. Commun. 126:419 (1985); Dann et al., Biochem. Biophys. Res. Commun. 134:71 (1986)).

Antibodies are meant to include antibodies against any moiety that directly or indirectly affects LBP metabolism. The antibodies can be directed against, e.g., LBP or a binding molecule, or a subunit or fragment thereof. For example, antibodies include anti-LBP-1, LBP-2 or LBP-3 antibodies; and anti-binding molecule antibodies. Antibody fragments are meant to include, e.g., Fab fragments, Fab' fragments, $F(ab')_2$ fragments, F(v) fragments, heavy chain monomers, heavy chain dimers, heavy chain trimers, light chain monomers, light chain dimers, light chain trimers, dimers consisting of one heavy and one light chain, and peptides that mimic the activity of the anti-LBP or anti-binding molecule antibodies. For example, $Fab_2'$ fragments of the inhibitory antibody can be generated through, e.g., enzymatic cleavage. Both polyclonal and monoclonal antibodies can be used in this invention. Preferably, monoclonal antibodies are used. Natural antibodies, recombinant antibodies or chimeric-antibodies, e.g., humanized antibodies, are included in this invention. Preferably, humanized antibodies are used when the subject is a human. Most preferably, the antibodies have a constant region derived from a human antibody and a variable region derived from an inhibitory mouse monoclonal antibody. Production of polyclonal antibodies to LBP is described in Example 6. Monoclonal and humanized antibodies are generated by standard methods known to those skilled in the art. Monoclonal antibodies can be produced, e.g., by any technique which provides antibodies produced by continuous cell lines cultures. Examples include the hybridoma technique (Kohler and Milstein, Nature 256: 495–497 (1975), the trioma technique, the human B-cell hybridoma technique (Kozbor et al., Immunology Today 4:72 (1983)), and the EBV-hybridoma technique to produce human monoclonal antibodies (Cole et al., in Monoclonal Antibodies and Cancer Therapy, A. R. Lisa, Inc., pp. 77–96 (1985)). Preferably, humanized antibodies are raised through conventional production and harvesting techniques (Berkower, I., Curr. Opin. Biotechnol. 7:622–628 (1996); Ramharayan and Skaletsky, Am. Biotechnol. Lab 13:26–28 (1995)). In certain preferred embodiments, the antibodies are raised against the LBP, preferably the LDL-binding site, and the Fab fragments produced. These antibodies, or fragments derived therefrom, can be used, e.g., to block the LDL-binding sites on the LBP molecules.

Agents also include inhibitors of a molecule that are required for synthesis, post-translational modification, or functioning of LBP and/or a binding molecule, or activators of a molecule that inhibits the synthesis or functioning of LBP and/or the binding molecule. Agents include, e.g., cytokines, chemokines, growth factors, hormones, signaling components, kinases, phosphatases, homeobox proteins, transcription factors, editing factors, translation factors and post-translation factors or enzymes. Agents are also meant to include ionizing radiation, non-ionizing radiation, ultrasound and toxic agents which can, e.g., at least partially inactivate or destroy LBP and/or the binding molecule.

An agent is also meant to include an agent which is not entirely LBP specific. For example, an agent may alter other genes or proteins related to arterial plaque formation. Such overlapping specificity may provide additional therapeutic advantage.

The invention also includes the agent so identified as being useful in treating atherosclerosis.

The invention also includes a method for evaluating an agent for the ability to alter the binding of LBP polypeptide to a binding molecule. An agent is provided. An LBP polypeptide is provided. A binding molecule is provided. The agent, LBP polypeptide and binding molecule are combined. The formation of a complex comprising the LBP polypeptide and binding molecule is detected. An alteration in the formation of the complex in the presence of the agent as compared to in the absence of the agent is indicative of the agent altering the binding of the LBP polypeptide to the binding molecule.

In preferred embodiments, the LBP polypeptide is LBP-1, LBP-2 or LBP-3. Examples of a binding molecule include native LDL, modified LDL, e.g., methylated LDL or oxidized LDL, and arterial extracellular matrix structural components.

Altering the binding includes, e.g., inhibiting or promoting the binding. The efficacy of the agent can be assessed, e.g., by generating dose response curves from data obtained using various concentrations of the agent. Methods for determining formation of a complex are standard and are known to those skilled in the art, e.g., affinity coelectrophoresis (ACE) assays or ELISA assays as described herein.

The invention also includes the agent so identified as being able to alter the binding of an LBP polypeptide to a binding molecule.

The invention also includes a method for evaluating an agent for the ability to bind to an LBP polypeptide. An agent is provided. An LBP polypeptide is provided. The agent is contacted with the LBP polypeptide. The ability of the agent to bind to the LBP polypeptide is evaluated. Preferably, the LBP polypeptide is LBP-1, LBP-2 or LBP-3. Binding can be determined, e.g., by measuring formation of a complex by standard methods known to those skilled in the art, e.g., affinity coelectrophoresis (ACE) assays or ELISA assays as described herein.

The invention also includes the agent so identified as being able to bind to LBP polypeptide.

The invention also includes a method for evaluating an agent for the ability to bind to a nucleic acid encoding an LBP regulatory sequence. An agent is provided. A nucleic acid encoding an LBP regulatory sequence is provided. The agent is contacted with the nucleic acid. The ability of the agent to bind to the nucleic acid is evaluated. Preferably, the LBP regulatory sequence is an LBP-1, LBP-2 or LBP-3 regulatory sequence. Binding can be determined, e.g., by measuring formation of a complex by standard methods known to those skilled in the art, e.g., DNA mobility shift assays, DNase I footprint analysis Molecular Biology, The invention being able to bind sequence. (Ausubel et al., ed., Current Protocols in John Wiley & Sons, New York, N.Y., (1989)).

The invention also includes the agent so identified as to a nucleic acid encoding an LBP regulatory sequence.

The invention also includes a method for treating atherosclerosis in an animal. An animal in need of treatment for atherosclerosis is provided. An agent capable of altering an aspect of LBP structure or metabolism is provided. The agent is administered to the animal in a therapeutically effective amount such that treatment of the atherosclerosis occurs.

In certain preferred embodiments, the agent is an LBP polypeptide, e.g., LBP-1, LBP-2 or LBP-3, or a biologically active fragment or analog thereof. The agent can be, e.g., the polypeptide as set forth in SEQ ID NOS: 1–9, 43, 44, and 47. Preferably, the agent is a polypeptide of no more than about 100 amino acid residues in length, more preferably of no more than about 50 amino acid residues, more preferably yet of no more than about 30 amino acid residues, more preferably yet of no more than about 20 amino acid residues, more preferably yet of no more than about 10 amino acid residues, more preferably yet of no more than about 5 amino acid residues, more preferably yet of no more than about 4 amino acid residues, more preferably yet of no more than about 3 amino acid residues, and most preferably of no more than about 2 amino acid residues. Preferably, the polypeptide includes at least about 20% acidic amino acid residues, more preferably yet at least about 40% acidic amino acid residues, more preferably yet at least about 60% acidic amino acid residues, more preferably yet at least about 80% acidic amino acid residues, more preferably yet at least about 90% acidic amino acid residues, more preferably yet at least about 95% acidic amino acid residues, and most preferably at least about 98% acidic amino acid residues. Acidic amino acid residues include aspartic acid and glutamic acid. An example of such an LBP poly-peptide is BHF-1, which is a 20 amino acid length fragment of human or rabbit LBP-1 which contains amino acid residues 14 through 33. See FIG. 9 (SEQ ID NO: 9). 45% of the amino acid residues of BHF-1 are acidic. The invention also includes biologically active fragments and analogs of BHF-1.

Other preferred acidic regions from the LBPs are amino acid residues 329 through 343 (SEQ ID NO: 19), 329 through 354 (SEQ ID NO: 20), 344 through 354 (SEQ ID NO: 21), and 529 through 538 (SEQ ID NO: 22) of human LBP-2 as depicted in FIG. 7A (SEQ. ID NO: 43); amino acid residues 14 through 43 (SEQ ID NO: 23) and 38 through 43 (SEQ ID NO: 24) of rabbit or human LBP-1 as depicted in FIG. 1 (SEQ ID NO: 1) and FIG. 6 (SEQ ID NO: 6); amino acid residues 338 through 353 (SEQ ID NO: 25), 338 through 365 (SEQ ID NO: 26), 354 through 365 (SEQ ID NO: 27), and 444 through 453 (SEQ ID NO: 28) of rabbit LBP-2 as depicted in FIG. 2A (SEQ ID NO: 47); amino acid residues 96 through 110 (SEQ ID NO: 29) of rabbit LBP-3 as depicted in FIG. 5 (SEQ ID NO: 5); and amino acid residues 69–75 (SEQ ID NO: 41) of human LBP-3 as depicted in FIG. 8A (SEQ ID NO: 44). The invention is also meant to include biologically active fragments and analogs of any of these polypeptides.

Other examples of agents include homopolymers and heteropolymers of any amino acid or amino acid analog. In certain preferred embodiments, the agent is a homopolymer of an acidic amino acid or analog thereof. In certain embodiments, the agent is a heteropolymer of one or more acidic amino acids and one or more other amino acids, or analogs thereof. For example, agents include poly(glu), poly(asp), poly(glu asp), poly(glu N), poly (asp N) and poly(glu asp N). By N is meant any amino acid, or analog thereof, other than glu or asp. By poly(glu asp) is meant all permutations of glu and asp for a given length peptide. A preferred peptide is poly(glu) of no more than about 10 amino acids in length, preferably about 7 amino acids in length.

In certain preferred embodiments, the agent is an LBP nucleic acid or a biologically active fragment or analog thereof, e.g., a nucleic acid encoding LBP-1, LBP-2 or LBP-3 polypeptide, or a biologically active fragment or analog thereof. The agent can be, e.g., a nucleic acid comprising a nucleotide sequence as set forth in SEQ ID NOS: 10–18, 45, 46, and 48. In other embodiments, the agent is an antisense molecule, e.g., one which can bind to an LBP gene sequence.

Treating is meant to include, e.g., preventing, treating, reducing the symptoms of, or curing the atherosclerosis. Administration of the agent can be accomplished by any method which allows the agent to reach the target area, e.g., a target cell or the extracellular matrix. These methods include, e.g., injection, deposition, implantation, suppositories, oral ingestion, inhalation, topical administration, or any other method of administration where access to the target area by the agent is obtained. Injections can be, e.g., intravenous, intradermal, subcutaneous, intramuscular or intraperitoneal. Implantation includes inserting implantable drug delivery systems, e.g., microspheres, hydrogels, polymeric reservoirs, cholesterol matrices, polymeric systems, e.g., matrix erosion and/or diffusion systems and non-polymeric systems, e.g., compressed, fused or partially fused pellets. Suppositories include glycerin suppositories. Oral ingestion doses can be enterically coated. Inhalation includes administering the agent with an aerosol in an inhalator, either alone or attached to a carrier that can be absorbed.

Administration of the agent can be alone or in combination with other therapeutic agents. In certain embodiments, the agent can be combined with a suitable carrier, incorporated into a liposome, or incorporated into a polymer release system.

In certain embodiments of the invention, the administration can be designed so as to result in sequential exposures to the agent over some time period, e.g., hours, days, weeks, months or years. This can be accomplished by repeated administrations of the agent by one of the methods described above, or alternatively, by a controlled release delivery system in which the agent is delivered to the animal over a prolonged period without repeated administrations. By a controlled release delivery system is meant that total release of the agent does not occur immediately upon administration, but rather is delayed for some time. Release can occur in bursts or it can occur gradually and continuously. Administration of such a system can be, e.g., by long acting oral dosage forms, bolus injections, transdermal patches or subcutaneous implants.

Examples of systems in which release occurs in bursts include, e.g., systems in which the agent is entrapped in liposomes which are encapsulated in a polymer matrix, the liposomes being sensitive to a specific stimulus, e.g., temperature, pH, light, magnetic field, or a degrading enzyme, and systems in which the agent is encapsulated by an ionically-coated microcapsule with a microcapsule core-degrading enzyme. Examples of systems in which release of the agent is gradual and continuous include, e.g., erosional systems in which the agent is contained in a form within a matrix, and diffusional systems in which the agent permeates at a controlled rate, e.g., through a polymer. Such sustained release systems can be, e.g., in the form of pellets or capsules.

The agent can be suspended in a liquid, e.g., in dissolved form or colloidal form. The liquid can be a solvent, partial solvent or non-solvent. In many cases water or an organic liquid can be used.

The agent can be administered prior to or subsequent to the appearance of atherosclerosis symptoms. In certain embodiments, the agent is administered to patients with familial histories of atherosclerosis, or who have phenotypes that may indicate a predisposition to atherosclerosis, or who have been diagnosed as having a genotype which predisposes the patient to atherosclerosis, or who have other risk factors, e.g., hypercholesterolemia, hypertension or smoking.

The agent is administered to the animal in a therapeutically effective amount. By therapeutically effective amount is meant that amount which is capable of at least partially preventing or reversing atherosclerosis. A therapeutically effective amount can be determined on an individual basis and will be based, at least in part, on consideration of the species of animal, the animal's size, the animal's age, the agent used, the type of delivery system used, the time of administration relative to the onset of atherosclerosis symptoms, and whether a single, multiple, or controlled release dose regimen is employed. A therapeutically effective amount can be determined by one of ordinary skill in the art employing such factors and using no more than routine experimentation.

Preferably, the concentration of the agent is at a dose of about 0.1 to about 1000 mg/kg body weight/day, more preferably at about 0.1 to about 500 mg/kg/day, more preferably yet at about 0.1 to about 100 mg/kg/day, and most preferably at about 0.1 to about 5 mg/kg/day. The specific concentration partially depends upon the particular agent used, as some are more effective than others. The dosage concentration of the agent that is actually administered is dependent at least in part upon the final concentration that is desired at the site of action, the method of administration, the efficacy of the particular agent, the longevity of the particular agent, and the timing of administration relative to the onset of the atherosclerosis symptoms. Preferably, the dosage form is such that it does not substantially deleteriously affect the animal. The dosage can be determined by one of ordinary skill in the art employing such factors and using no more than routine experimentation.

In certain embodiments, various gene constructs can be used as part of a gene therapy protocol to deliver nucleic acids encoding an agent, e.g., either an agonistic or antagonistic form of an LBP polypeptide. For example, expression vectors can be used for in vivo transfection and expression of an LBP polypeptide in particular cell types so as to reconstitute the function of, or alternatively, abrogate the function of, LBP polypeptide in a cell in which non-wild type LBP is expressed. Expression constructs of the LBP polypeptide, and mutants thereof, may be administered in any biologically effective carrier, e.g., any formulation or composition capable of effectively delivering the LBP gene to cells in vivo. Approaches include, e.g., insertion of the subject gene in viral vectors including, e.g., recombinant retroviruses, adenovirus, adeno-associated virus, and herpes simplex virus-1, or recombinant bacterial or eukaryotic plasmids. Viral vectors infect or transduce cells directly; plasmid DNA can be delivered with the help of, for example, cationic liposomes (lipofectin™ (Life Technologies, Inc., Gaithersburg, Md.) or derivatized (e.g. antibody conjugated), polylysine conjugates, gramacidin S, artificial viral envelopes or other such intracellular carriers, as well as direct injection of the gene construct or $Ca_3,(PO_4)_2$ precipitation carried out in vivo. The above-described methods are known to those skilled in the art and can be performed without undue experimentation. Since transduction of appropriate target cells represents the critical first step in gene therapy, choice of the particular gene delivery system will depend on such factors as the phenotype of the intended target and the route of administration, e.g., locally or systemically. Administration can be directed to one or more cell types, and to one or more cells within a cell type, so as to be therapeutically effective, by methods that are known to those skilled in the art. In a preferred embodiment, the agent is administered to arterial wall cells of the animal. For example, a genetically engineered LBP gene is administered to arterial wall cells. In certain embodiments, administration is done in a prenatal animal or embryonic cell. It will be recognized that the particular gene construct provided for in vivo transduction of LBP expression is also useful for in vitro transduction of cells, such as for use in the diagnostic assays described herein.

In certain embodiments, therapy of atherosclerosis is performed with antisense nucleotide analogs of the genes which code for the LBPs. Preferably, the antisense nucleotides have non-hydrolyzable "backbones," e.g., phosphorothioates, phosphorodithioates or methylphosphonates. The nucleoside base sequence is complementary to the sequence of a portion of the gene coding for, e.g., LBP-1, 2 or 3. Such a sequence might be, e.g., ATTGGC if the gene sequence for the LBP is TAACCG. One embodiment of such therapy would be incorporation of an antisense analog of a portion of one of the LBP genes in a slowrelease medium, e.g., polyvinyl alcohol, which is administered, e.g., by subcutaneous injection, so as to release the antisense nucleotide analog over a period of weeks or months. In another embodiment, the antisense analog is incorporated into a polymeric matrix, e.g., polyvinyl alcohol, such that the gel can be applied locally to an injured arterial wall to inhibit LBP synthesis and prevent LDL accumulation, e.g., after angioplasty or atherectomy.

The invention also includes a method for treating an animal at risk for atherosclerosis. An animal at risk for atherosclerosis is provided. An agent capable of altering an aspect of LBP structure or metabolism is provided. The agent is administered to the animal in a therapeutically effective amount such that treatment of the animal occurs. Being at risk for atherosclerosis can result from, e.g., a family history of atherosclerosis, or phenotypic symptoms which predispose to atherosclerosis, e.g., having hypercholesterolemia, hypertension or smoking.

The invention also includes a method for treating a cell having an abnormality in structure or metabolism of LBP. A cell having an abnormality in structure or metabolism of LBP is provided. An agent capable of altering an aspect of LBP structure or metabolism is provided. The agent is administered to the cell in a therapeutically effective amount such that treatment of the cell occurs.

In certain embodiments, the cell is obtained from a cell culture or tissue culture or an embryo fibroblast. The cell can be, e.g., part of an animal, e.g., a natural animal or a nonhuman transgenic animal. Preferably, the LBP is LBP-1, LBP-2 or LBP-3.

The invention also includes a pharmaceutical composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier. Pharmaceutically acceptable carriers include, e.g., saline, liposomes and lipid emulsions.

In certain preferred embodiments, the agent of the pharmaceutical composition is an LBP polypeptide, e.g., LBP-1, LBP-2 or LBP-3, or a biologically active fragment or analog thereof. The agent can be, e.g., the polypeptide as set forth in SEQ ID NOS: 1–9, 43, 44, and 47. Preferably, the agent is a polypeptide of no more than about 100 amino acid residues in length, more preferably of no more than about 50 amino acid residues, more preferably yet of no more than about 30 amino acid residues, more preferably yet of no more than about 20 amino acid residues, more preferably yet of no more than about 10 amino acid residues, more preferably yet of no more than about 5 amino acid residues, more preferably yet of no more than about 4 amino acid residues, more preferably yet of no more than about 3 amino acid residues, and most preferably of no more than about 2 amino acid residues. Preferably, the polypeptide includes at least about 20% acidic amino acid residues, more preferably yet at least about 40% acidic amino acid residues, more preferably yet at least about 60% acidic amino acid residues, more preferably yet at least about 80% acidic amino acid residues, more preferably yet at least about 90% acidic amino acid residues, more preferably yet at least about 95% acidic amino acid residues, and most preferably at least about 98% acidic amino acid residues.

In certain preferred embodiments, the agent is an LBP nucleic acid, e.g., a nucleic acid encoding LBP-1, LBP-2 or LBP-3 polypeptide, or a biologically active fragment or analog thereof. The agent can be, e.g., a nucleic acid comprising a nucleotide sequence as set forth in SEQ ID NOS: 10–18, 45, 46, and 48.

The invention also includes a vaccine composition for treating atherosclerosis in an animal comprising a therapeutically effective amount of an agent, the agent being capable of altering an aspect of LBP metabolism or structure in the animal so as to result in treatment of the atherosclerosis, and a pharmaceutically acceptable carrier.

The invention also includes a method for diagnosing atherosclerotic lesions in an animal. An animal is provided. A labeled agent capable of binding to LBP present in atherosclerotic lesions is provided. The labeled agent is administered to the animal under conditions which allow the labeled agent to interact with the LBP so as to result in labeled LBP. The localization or quantification of the labeled LBP is determined by imaging so as to diagnose the presence of atherosclerotic lesions in the animal.

Preferably, the LBP is LBP-1, LBP-2 or LBP-3. The imaging can be performed by standard methods known to those skilled in the art, including, e.g., magnetic resonance imaging, gamma camera imaging, single photon emission computed tomographic (SPECT) imaging, or positron emission tomography (PET).

Preferably, agents that bind tightly to LBPs in atherosclerotic lesions are used for atherosclerotic imaging and diagnosis. The agent is radiolabeled with, e.g., $^{99m}$Tc or another isotope suitable for clinical imaging by gamma camera, SPECT, PET scanning or other similar technology. Since LBPs occur in very early lesions, such imaging is more sensitive than angiography or ultrasound for locating very early lesions which do not yet impinge on the arterial lumen to cause a visible bulge or disturbed flow. In addition to locating both early and more developed lesions, the imaging agents which bind to LBPs can also be used to follow the progress of atherosclerosis, as a means of evaluating the effectiveness of both dietary and pharmacological treatments.

Thus, a diagnostic embodiment of the invention is the adaptation of, e.g., a peptide complementary to one of the LBPs, by radiolabeling it and using it as an injectable imaging agent for detection of occult atherosclerosis. The peptide is selected from those known to bind to LBPs, e.g., RRRRRRR (SEQ ID NO:52) or KKLKLXX (SEQ ID NO:53), or any other polycationic peptide which binds to the highly electronegative domains of the LBPs. For extracorporeal detection with a gamma scintillation (Anger) camera, technetium-binding ligands, e.g., CGC, GGCGC, or GGCGCF, can be incorporated into the peptides at the N-terminus or C-terminus for $^{99m}$Tc labeling. For external imaging by magnetic resonance imaging (MRI), e.g., the gadolinium-binding chelator, diethylene triamine pentaacetic acid (DTPA), is covalently bound to the N- or C-terminus of the peptides. In yet other embodiments, the LBP-binding peptides are covalently bound, e.g., to magnetic ion oxide particles by standard methods known to those skilled in the art, e.g., conjugating the peptides with activated polystyrene resin beads containing magnetic ion oxide.

The invention also includes a method for immunizing an animal against an LBP, e.g., LBP-1, LBP-2 or LBP-3, or fragment or analog thereof. An animal having LDL is provided. An LBP or fragment or analog thereof is provided. The LBP or fragment or analog thereof is administered to the animal so as to stimulate antibody production by the animal to the LBP or fragment or analog thereof such that binding of the LBP to the LDL is altered, e.g., decreased or increased.

The invention also includes a method of making a fragment or analog of LBP polypeptide, the fragment or analog having the ability to bind to modified LDL and native LDL. An LBP polypeptide is provided. The sequence of the LBP polypeptide is altered. The altered LBP polypeptide is tested for the ability to bind to modified LDL, e.g., methylated LDL, oxidized LDL, acetylated LDL, cyclohexanedione-treated LDL (CHD-LDL), and to native LDL.

The fragments or analogs can be generated and tested for their ability to bind to these modified LDLs and to native LDL, by methods known to those skilled in the art, e.g., as described herein. Preferably, they are tested for their ability to bind to methylated LDL and native LDL. The binding activity of the fragment or analog can be greater or less than the binding activity of the native LBP. Preferably, it is greater. In preferred embodiments, the LBP is LBP-1, LBP-2 or LBP-3.

The invention also includes a method for isolating a cDNA encoding an LBP. A cDNA library is provided. The cDNA library is screened for a cDNA encoding a polypeptide which binds to native LDL and modified LDL, e.g., methylated LDL or oxidized LDL. The cDNA which encodes this polypeptide is isolated, the cDNA encoding an LBP.

Atherosclerosis in a hyperlipidemic subject can be reduced following the generation of an immune response in the subject by immunization with LBPs. Numerous immunotherapeutic products can be used to generate antibodies that will block the binding between LDL and LBPs.

The injection of one or more LBPs can result in the production of anti-LBP antibodies, resulting in a reduction in, e.g., aortic atherosclerosis. This effect is thought to be mediated by an inhibition of LBP binding to LDL. LBP immunogens that can be used in the invention include human LBPs, non-human LBPs, recombinant LBPs, and proteins structurally related to the LBPs described herein, e.g. non-naturally occurring proteins that differ from a naturally occurring LBP at one or more amino acid residues. In addition to full length proteins, injecting one or more peptides that include an LBP domain can generate an effective immune response. For example, the injection of a peptide comprising an LBP domain having LDL-binding activity can cause an organism to make antibodies to the LBP binding sites for LDL. These peptide immunogens can include sequences derived from human LBPs, non-human LBPs, recombinant LBPs, and proteins structurally related to the LBPs described herein.

Modifications can be made to a protein or peptide immunogen of the invention to increase its immunogenicity. The immunogen can be conjugated or coupled with a carrier, e.g. a Cholera toxin B chain or monoclonal antibodies. The immunogen can be precipitated with aluminum salts or cross-linked with formaldehyde or other aldehydes. The protein may be mixed with a physiologically acceptable diluent such as water, phosphate buffered saline, or saline. The composition may further include an adjuvant. In addition to RIBI adjuvant, adjuvants such as incomplete Freund's adjuvant, aluminum phosphate, aluminum hydroxide are all well known in the art. Adjustments in the adjuvant of the invention can be made to affect the immunogenicity of the peptide or protein. Examples of such modifications include using: aluminum salts; cytokines; MF59 (microfluidized emulsion of oil and surfactants); SAF-1 (oil-based emulsion); saponin derivatives; polymers (such as polyphosphazene); and bacterial toxins. Additional descriptions of antigenic protein-adjuvant combinations are described in WO 99/54452 (herein incorporated by reference) and WO 99/49890 (herein incorporated by reference).

In addition to delivery of the proteins and peptides described above, numerous other delivery systems can be used to generate the anti-atherosclerotic immunity of the invention. The LBP immunogen can be delivered either directly as a protein antigen or alternatively as a nucleic acid that encodes the protein antigen. The immunotherapeutic products of the invention, either protein or nucleic acid, can be delivered by numerous delivery routes. These include injection, deposition, implantation, suppositories, oral ingestion, inhalation (e.g., delivery via a nasal spray), and topical administration (e.g., delivery via a skin patch).

A nucleic acid encoding an immunogen of the invention can be directly administered, for example by injection, to tissues and expressed as a protein. The DNA or RNA can be either associated with a delivery vehicle (e.g., viruses, bacteria, liposomes, and gold beads) or naked (free from association with transfection-facilitating proteins, viral particles, liposomal formulations, charged lipids and calcium phosphate precipitating). The nucleic acid can optionally include a promoter, e.g. a viral promoter. The immunogen encoded by the nucleic acid is produced in the host, resulting in the generation of an immune response. Methods for the delivery of nucleic acid sequences encoding therapeutic proteins and peptides are described in detail by Felgner et al. (U.S. Pat. No. 5,580,859; herein incorporated by reference) and Barbet et al. (U.S. Pat. No. 6,025,338; herein incorporated by reference). Vaccine compositions of viral liposomes comprising a nucleic acid, e.g. an RNA, encoding a protein antigen are described in WO 99/52503 (herein incorporated by reference). Proteins and nucleic acids encoding peptides can also be delivered to an individual by their encapsulation in liposomes, microparticles, and ISCOMS, all of which are well known in the art (see, e.g., U.S. Pat. No. 6,013,258, herein incorporated by reference).

A nucleic acid encoding an immunogen of the invention can also be included in the genome of a plant, so as to result in the production of the immunogen by plant tissues. The genetically modified plant may then consumed by an individual, resulting in the ingestion of the immunogen and the generation of an anti-LBP immune response. Methodology for the generation and usage of edible plant vaccines is described in WO 99/54452 (herein incorporated by reference).

Numerous plants may be useful for the production of an edible vaccine, including: tobacco, tomato, potato, eggplant, pepino, yam, soybean, pea, sugar beet, lettuce, bell pepper, celery, carrot, asparagus, onion, grapevine, muskmelon, strawberry, rice, sunflower, rapeseed/canola, wheat, oats, maize, cotton, walnut, spruce/conifer, poplar and apple. The edible vaccine can include a plant cell transformed with a nucleic acid construct comprising a promoter and a sequence encoding an LBP. The sequence may optionally encode a chimeric protein, comprising a cholera toxin subunit B peptide fused to the LBP peptide. Preferred plant promoters of the invention include CaMV 35S, patatin, mas, and granule-bound starch synthase promoters. Additional useful promoters and enhancers are described in WO 99/54452.

The edible vaccine of the invention can be administered to a mammal suffering from or at risk of atherosclerosis. Preferably, an edible vaccine is administered orally, e.g. consuming a transgenic plant of the invention. The transgenic plant can be in the form of a plant part, extract, juice, liquid, powder, or tablet. The edible vaccine can also be administered via an intranasal route.

Microorganisms, e.g., attenuated viruses or bacteria, can be used in the invention by including a nucleic acid encoding an LBP immunogen in the genome of the microorganism. This modified vector can then be delivered to a host, resulting in the in vivo production of the immunogen. The immune response generated by these vectors is expected to result in anti-atherosclerotic immunity. Nucleic acid molecules are inserted into microorganism genomes by standard methods known in the art (U.S. Pat. No. 5,866,136 and U.S. Pat. No. 6,025,164, both of which are herein incorporated by reference).

The anti-atherosclerotic methods of the invention are directed to treating a subject, e.g., a human, primate, horse, dog, cat, or goat, at risk for atherosclerosis by stimulating an anti-LBP response in the subject by immunotherapy. The LBP proteins and peptides of the invention may be delivered to the subject by the numerous delivery systems described herein. The immunotherapy may comprise an initial immunization followed by additional, e.g. one, two, or three, boosters.

The invention also includes a method of treating a subject at risk for atherosclerosis by (1) providing a subject at risk for atherosclerosis and (2) administering to the subject one or more of the following: (a) an LBP protein or fragment or analog thereof and an adjuvant; (b) a nucleic acid encoding an LBP protein; (c) a virus or bacteria comprising a nucleic acid encoding an LBP protein; and (d) an edible plant comprising a nucleic acid encoding an LBP protein. The LBP protein used in this method can be any LBP described herein, e.g., LBP-1, LBP-2, or LBP-3. A combination of more than one nucleic acid or LBP protein or fragment or analog thereof can be administered to the subject. For example, combinations of LBP proteins, or nucleic acids encoding LBP proteins, include: (1) LBP-1 and LBP-2; (2) LBP-1 and LBP-3; (3) LBP-2 and LBP-3; and (4) LBP-1, LBP-2, and LBP-3. This method optionally includes a step of diagnosing the subject as being at risk for atherosclerosis.

Also provided by the invention is a method of treating a subject at risk for atherosclerosis whereby a non-autologous LBP protein or a nucleic acid encoding a non-autologous LBP protein is delivered to the subject to generate an immune response to an autologous LBP. Specifically, this method entails identifying one or more autologous LBP proteins, e.g., LBP-1, LBP-2, or LBP-3, produced by the subject. The identification can by, e.g., DNA sequence analysis, protein sequence analysis, antibody reactivity, hybridization analysis, or nucleic acid amplification. Next, a non-autologous LBP protein, e.g., allogeneic, xenogeneic, or a genetically modified, non-naturally occurring protein that differs at one or more amino acid residues from the one or more LBP proteins, is administered to the subject. Alternatively, a nucleic acid encoding a non-autologous LBP protein is administered to the subject. The anti-atherosclerotic effectiveness of this immunotherapeutic product is determined by its ability to induce an immune response against one or more autologous LBP proteins when administered to the subject. It is therefore expected that extensive differences between a non-autologous and autologous LBP protein will not result in cross immunoreactivity. This method optionally includes a step of diagnosing the subject as being at risk for atherosclerosis.

Another method of the invention is a method of treating a subject at risk for atherosclerosis by increasing the levels of one or more LBP proteins circulating in the plasma. According to this method, either autologous or non-autologous LBP levels may be increased. Non-autologous LBP proteins include, e.g., allogeneic LBP, xenogeneic LBP, and genetically modified LBP. The plasma levels of one or more LBP proteins can be increased by the delivery of a nucleic acid encoding an LBP protein. Because LBP generally does not normally occur as a circulating protein, the endogenous molecule is expected to be susceptible to immune recognition when delivered in a soluble form. This method optionally includes a step of diagnosing the subject as being at risk for atherosclerosis.

Also included in the invention is a pharmaceutical composition containing one or more LBP proteins, e.g., LBP-1, LBP-2, or LBP-3, mixed with an adjuvant, suitable for use in humans. The pharmaceutical composition can contain a combination of more than one LBP protein. For example, compositions can include any of the following: (1) LBP-1 and LBP-2; (2) LBP-1 and LBP-3; (3) LBP-2 and LBP-3; and (4) LBP-1, LBP-2, and LBP-3.

Also included in the invention is a cell therapy system, whereby a cell expressing an LBP is delivered to a subject at risk for atherosclerosis. This cell can be engineered to express either an autologous or non-autologous LBP protein or peptide of the invention. Delivery of this engineered cell to a subject results in the in vivo production of an LBP protein and the associated immunotherapy produced when either the protein or a nucleic acid encoding the protein is provided to an individual. Cell therapy methods are described in U.S. Pat. No. 5,955,095 (herein incorporated by reference).

The following non-limiting examples further illustrate the present invention.

EXAMPLES

Example 1

Construction of a Rabbit cDNA Library

This example illustrates the construction of a rabbit cDNA library using mRNA from balloon-deendothelialized healing rabbit abdominal aorta. Balloon-catheter deendothelialized rabbit aorta has been shown to be a valid model for atherosclerosis (Minick et al., Am. J. Pathol. 95:131–158 (1979).

The mRNA was obtained four weeks after ballooning to maximize focal LDL binding in the ballooned rabbit aorta. First strand cDNA synthesis was carried out in a 50 $\mu$l reaction mixture containing 4 $\mu$g mRNA; 2 $\mu$g oligo d(T) primer; methylation dNTP mix (10 mM each); 10 mM DTT; 800 units superscript II RT (Life Technologies, Gaithersburg, Md.); 1×first strand cDNA synthesis buffer (50 mM Tris-HCl, pH 8.3; 75 mM KCl; 5 mM $MgCl_2$), which was incubated for 1 hr at 37° C. The reaction mixture was then adjusted to 250 $\mu$l through the addition of 1×second strand buffer (30 mM Tris-HCl, pH 7.5; 105 mM $_{KCl;}$ 5.2 mM $MgCl_2$); 0.1 mM DTT; methylation dNTP mix (10 mM each); 50 units *E. coli* DNA polymerase I, 3 units RNase H; 15 units *E. coli* DNA ligase (all enzymes from Life Technologies), which was incubated for an additional 2.5 hr at 15° C. The resulting double-stranded cDNAs (dscDNA) were then treated with 1.5 units T4 DNA polymerase (Novagen Inc., Madison, Wis.) for 20 min at 11° C. to make blunt-ended dscDNA. These were then concentrated by ethanol precipitation and EcoR1/Hind III linkers were attached to the ends by T4 DNA ligase (Novagen Inc.). The inker-ligated cDNAs were treated with EcoR1 and Hind111 restriction enzymes to produce EcoR1 and Hind III recognition sequences at their 5' and 3' ends, respectively. After the removal of linker DNA by gel exclusion chromatography, the dscDNAs were inserted into λEXlox phage arms (Novagen Inc.) in a unidirectional manner by T4 DNA ligase and packaged into phage particles according to the manufacturer's protocol (Novagen Inc.). A phage library of cDNAs containing $2\times10^6$ independent clones was established from 4 $\mu$g of mRNA.

Example 2

Identification of Rabbit cDNAs Encoding LDL Binding Proteins (LBPs)

This example illustrates a method of functionally screening a rabbit cDNA library so as to identify cDNAs encoding LBPs which bind to both native LDL and methyl LDL. Methyl LDL is not recognized by previously reported cell surface receptors. See, e.g., Weisgraber et al., J. Biol. Chem. 253:9053–9062 (1978).

A fresh overnight culture of *E. coli* ER1647 cells (Novagen Inc.) was infected with the cDNA phage obtained from Example 1, and plated at a density of $2\times10^4$ plaque-forming units (pfu) in 150 mm diameter plates containing 2×YT agar. A total of 50 plates, equivalent to $1\times10^6$ phage, were plated and incubated at 37° C. until the plaques reached 1 mm in diameter (5–6 hr). A dry nitrocellulose membrane, which had previously been saturated with 10 mM IPTG solution, was layered on top of each plate to induce the production of recombinant protein, as well as to immobilize the proteins on the membranes. The plates were incubated at 37° C. for an additional 3–4 hr, and then overnight at 4° C.

The next day, the membranes were lifted from each plate and processed as follows. Several brief rinses in TBST solution (10 mM Tris-HCl, pH 8.0; 150 mM NaCl, 0.05% Tween 20); two 10-min rinses with 6M guanidine-HCl in HBB (20 mM HEPES, pH 7.5; 5 mM $MgCl_2$, 1 mM DTT, and 5 mM KCl); two 5-min rinses in 3M guanidine-HCl in HBB; a final brief rinse in TBSEN (TBS, 1 mM EDTA, 0.02% $NaN_3$).

The membranes were then blocked for 30 min at room temperature in a solution of TBSEN with 5% non-fat dry milk, followed by 10 min in TBSEN with 1% non-fat dry milk. Following blocking, the membranes were incubated with native human LDL (obtained as described in Example 11 or methylated human LDL (meLDL) (see Weisgraber et al., J. Biol. Chem. 253:9053–9062 (1978)), at a concentration of 4 μg/ml, in a solution containing 1×TBSEN, 1% non-fat dry milk, 1 mM PMSF, 0.5×protease inhibitor solution (1 mM ε-amino caproic acid/1 mM benzamidine). Incubation was for 4 hr at room temperature in a glass Petri dish with gentle stirring on a stirring table, followed by overnight at 4° C. with no stirring.

Specifically bound meLDL and native LDL were detected on the nitrocellulose membranes by antibodies against human LDL. Sheep anti-human LDL polyclonal antibodies (Boehringer Mannheim, Indianapolis, Ind.) were adsorbed with *E. coli* plys E cell extracts to abolish background. For adsorption, *E. coli* plys E cells were grown to log phase, spun down and resuspended in PBS containing 1 mM PMSF, 2 mM ε-amino caproic acid, and 1 mM benzamidine. The cell suspension then underwent 8 freeze-thaw cycles via immersion in liquid nitrogen and cold running tap water, respectively. The anti LDL antibodies/cell extract solution were incubated with gentle stirring for 1 hr at 4° C. (1 ml of antibody solution/3 mg crude cell extract). Following incubation, the mixture was centrifuged (10,000×g; 10 min; 4° C.) and the supernatant was stored at 4° C. in the presence of 0.02% $NaN_3$, until use. The membranes were processed for immunoscreening as follows: (i) three 5-min washes at room temperature in TBSEN containing 1% gelatin; (ii) 30 min incubation in PBS, pH 7.4 with 1% gelatin; (iii) two-hr room temperature incubation with gentle stirring in fresh PBS/gelatin solution containing adsorbed sheep anti-human LDL antibodies (Boehringer Manheim, Indianapolis, Ind.) (1:1000 dilution); (iv) three brief washes in TBS, pH 7.4; (v) one-hr room temperature incubation with gentle stirring in PBS/gelatin solution containing donkey anti-sheep alkaline phosphatase-conjugated antibodies (Sigma, St. Louis, Mo.) (1:10,000 dilution); (vi) three brief washes with TBS, PH 7.4.; and (vii) development according to the manufacturer's instructions, using an alkaline phosphatase substrate development kit (Novagen Inc.). Phage plaques which produced LBPs appeared as blue-colored "donuts" on the membranes.

The phage from Example 1 containing the LBP cDNAs were plaque-purified and converted into plasmid subclones by following a protocol called "Autosubcloning by Cre-mediated Plasmid Excision" provided by Novagen Inc. DNA sequences were obtained by the dideoxynucleotide chain-termination method (Sanger et al., Proc. Natl. Acad. Sci., USA 74: 5463–5467 (1977), and analyzed by an Applied Biosystems automated sequencer. The open reading frame (ORF) of each cDNA was determined from consensus sequences obtained from both the sense and antisense strands of the cDNAs. Sequencing confirmed that three previously unknown genes had been isolated. Since the genes were selected by functional screening for LDL binding, the proteins coded by these genes were termed LDL binding proteins (LBPs), specifically, LBP-1, LBP-2 and LBP-3. The cDNA sequences for rabbit LBP-1, LBP-2 and LBP-3 and the corresponding proteins are set forth in SEQ ID NOS: 10–14 and 48.

Based on their respective cDNA coding sequences, the sizes of the recombinant proteins were determined to be 16.2 kDa for LBP-1, 40 kDa for LBP-2, and 62.7 kDa for LBP-3.

Example 3

Northern Blot Analysis of Rabbit RNA Using LBP cDNA or cRNA

This example illustrates the size and tissue distribution of LBP mRNAs. Total RNA was isolated from different rabbit tissues: adrenals, thoracic aorta, abdominal aorta, ballooned and reendothelialized abdominal aorta, heart, kidney, smooth muscle cells, lung and liver, by Trizol reagent (Life Technologies) and concentrated by ethanol precipitation. Gel electrophoresis of RNA was carried out in 1.2% agarose gel containing 1×MOPS buffer (0.2M MOPS, pH 7.0; 50 mM sodium acetate; 5 mM EDTA, pH 8.0) and 0.37M formaldehyde. Gels were loaded with 20 μg total RNA from each tissue examined and electrophoresed at 100 volts for 2 hr in 1×MOPS buffer. RNAs were blotted onto supported nitrocellulose membranes (Schleicher & Schuell, Keene, N.H.) and immobilized by baking at 80° C. for 2 hr. Hybridization to radiolabeled LBP-1, LBP-2 and LBP-3 cDNA or cRNA probes was carried out by standard procedures known to those skilled in the art (see, e.g., Ausubel et al., Current Protocols in Molecular Biology; John Wiley & Sons (1989)); signals were detected by autoradiography.

The results were as follows: the sizes of the mRNAs were about 1.3 kb for LBP-1, about 2.3–2.5 kb for LBP-2, and about 4.7 kb for LBP-3. LBP-1, LBP-2 and LBP-3 mRNA were found in all tissues tested, but the highest amount was in ballooned abdominal aorta.

Example 4

Isolation of Human LBP cDNAs and Genomic Clones

This example illustrates isolation of human LBP cDNAs. Human LBP cDNA clones were isolated from three cDNA libraries. A human fetal brain cDNA library was obtained from Stratagene, LaJolla, Calif., a human liver and a human aorta cDNA library were obtained from Clontech, Palo Alto, Calif., and screened with a radiolabeled cDNA probe derived from rabbit LBP-1, LBP-2 or LBP-3, according to the method described in Law et al., Gene Expression 4:77–84 (1994). Several strongly hybridizing clones were identified and plaque-purified. Clones were confirmed to be human LBP-1, LBP-2 and LBP-3, by DNA sequencing using the dideoxynucleotide chain-termination method and analysis by an Applied Biosystems automated sequencer. The cDNA sequences and the corresponding proteins for human LBP-1, LBP-2 and LBP-3 are set forth in SEQ ID NOS: 15, 16 and 17, respectively.

A human genomic library was screened with each of the LBP-1, LBP-2, and LBP-3 clones obtained from the cDNA library screening. Clones hybridizing to each of the three cDNAs were isolated and sequenced. The genomic sequence for LBP-1, LBP-2, and LBP-3 are set forth in FIGS. 22–24, respectively. The LBP-1 open reading frame spans four exons of the LBP-1 gene (FIG. 22; SEQ ID NO:49). The LBP-1 protein predicted by the genomic sequence is identical to that predicted by the cDNA clone described above. The LBP-2 open reading frame spans five exons of the LBP-2 gene (FIG. 23; SEQ ID NO:50). The LBP-2 protein predicted by the genomic sequence differs from that predicted by the cDNA clone in that it contains an additional 321 amino acids at its amino terminus (the LBP-2 cDNA is a 5' truncation). The LBP-3 open reading frame spans ten exons of the LBP-3 gene (FIG. 24; SEQ ID NO:51). The LBP-3 protein predicted by the genomic sequence differs from that predicted by the cDNA clone in that it contains an additional 16 amino acids at its amino terminus (the LBP-3 cDNA is a 5' truncation) and an Asn at amino acid position 130 (the cDNA predicts a Tyr at this position). A comparison between the corresponding LBP-1, LBP-2 and LBP-3 protein sequences for rabbit and human are shown in FIGS. 19, 20 and 21.

Example 5

Isolation of Recombinant LBP-1, LBP-2 and LBP-3 Rabbit Proteins from *E. coli*

LBP cDNA was isolated from the original pEXlox plasmids obtained as described in Examples 1 and 2, and subcloned into the pPROEX-HT vector (Life Technologies) for recombinant protein expression. Induction of the recombinant protein by IPTG addition to transformed *E. coli* DH10B cultures resulted in the expression of recombinant protein containing a 6-histidine tag (N-terminal). This tagged protein was then purified from whole cell proteins by binding to Ni-NTA (nickel nitrilo-triacetic acid) as described in the protocol provided by the manufacturer (Qiagen, Inc., Santa Clara, Calif.). The preparation obtained after the chromatography step was approximately 90% pure; preparative SDS-PAGE was performed as the final purification step.

When required by the characterization procedure, iodination of LBPs was carried out using Iodobeads (Pierce, Rockford, Ill.). The Iodobeads were incubated with 500 μCi of $Na^{125}I$ solution (17 Ci/mg) (New England Nuclear, Boston, Mass.) in a capped microfuge tube for 5 min at room temperature. The protein solution was added to the Iodobeads-$Na^{125}I$ microfuge tube and incubated for 15 min at room temperature. At the end of this incubation, aliquots were removed for the determination of total soluble and TCA precipitable counts. The radiolabeled protein was then precipitated with cold acetone (2.5 vol; −20° C.; 2.5 hr). Following this incubation, precipitated protein was collected by centrifugation (14,000 g; 1 hr; room temperature) and resuspended in sample buffer (6 M urea/50 mM Tris, pH 8.0/2 mM EDTA). Integrity of the protein preparation was assessed by SDS-PAGE.

The identities of the recombinant LBPs were confirmed using standard protein sequencing protocols known to those skilled in the art. (A Practical Guide for Protein and Peptide Purification for Microsequencing, Matsudaira, ed., Academic Press, Inc., 2d edition (1993)). Analysis was performed using an Applied Biosystems Model 477A Protein Sequencer with on-line Model 120 PTH amino acid analyzer.

Example 6

Production of Antibodies to LBP-1, LBP-2 and LBP-3

This example illustrates the production of polyclonal antibodies to LBP-1, LBP-2 and LBP-3. A mixture of purified recombinant LBP protein (0.5 ml; 200 μg) and RIBI adjuvant (RIB1 ImmunoChem. Research, Inc., Hamilton, Mont.) was injected subcutaneously into male guinea pigs (Dunkin Hartley; Hazelton Research Products, Inc., Denver, Pa.) at 3–5 sites along the dorsal thoracic and abdominal regions of the guinea pig. Blood was collected by venipuncture on days 1 (pre-immune bleeding), 28, 49 and 70. Booster injections were administered on days 21 (100 μg; SC), 42 (50 μg; SC), and 63 (25 μg; SC). The titer of the guinea pig antiserum was evaluated by serial dilution "dot blotting." Preimmune antiserum was evaluated at the same time. After the third booster of LBP protein, the titer against the recombinant protein reached a maximal level with a detectable calorimetric response on a dot blot assay of 156 pg.

Specificity of the polyclonal antibody for recombinant LBP-1, LBP-2 or LBP-3 was demonstrated using Western blot analysis. (Towbin et al., Proc. Natl. Acad. Sci. USA 76: 4350 (1979)). The protein-antibody complex was visualized immunochemically with alkaline phosphatase-conjugated goat antiguinea pig IgG, followed by staining with nitro blue tetrazolium (BioRad Laboratories, Hercules, Calif.). Non-specific binding was blocked using 3% non-fat dry milk in Tris buffered saline (100 mM Tris; 0.9% NaCl, pH 7.4).

Example 7

Immunohistochemical Characterization

This example illustrates the presence of LBPs in or on endothelial cells covering plaques, in or on adjacent smooth muscle cells, and in the extracellular matrix. In addition, co-localization of LDL and LBPs was demonstrated. These results were obtained by examining ballooned rabbit arterial lesions and human atherosclerotic plaques by immunohistochemical methods.

Ballooned deendothelialized aorta was obtained from rabbits which had received a bolus injection of human LDL (3 mg; i.v.) 24 hr prior to tissue collection. Human aortas containing atherosclerotic plaques were obtained from routine autopsy specimens. Tissues were fixed in 10% buffered formalin (≦24 hr) and imbedded in paraffin using an automated tissue-imbedding machine. Tissue sections were cut (5–7μ) and mounted onto glass slides by incubating for 1 hr at 60° C. Sections were deparaffinized. After a final wash with deionized $H_2O$, endogenous peroxidase activity was eliminated by incubating the sections with 1% $H_2O_2/H_2O$ buffer for 5 min at room temperature. Sections were rinsed with phosphate buffered saline (PBS) for 5 min at room temperature and nonspecific binding was blocked with 5% normal goat serum or 5% normal rabbit serum depending on the source of the secondary antibody (Sigma, St. Louis, Mo.) (1 hr; room temperature). Sections were then incubated with a 1:50 dilution (in 5% normal goat serum/PBS) of a guinea pig polyclonal antibody against the rabbit form of recombinant LBP-1, LBP-2 or LBP-3. Controls included preimmune serum as well as specific antisera to LBP-1, LBP-2, or LBP-3 in which the primary antibody was completely adsorbed and removed by incubation with recombinant LBP-1, LBP-2 or LBP-3 followed by centrifugation prior to incubation with the tissue sections. An affinity purified rabbit polyclonal antibody against human apolipoprotein B (Polysciences Inc.; Warrington, Pa.) was used at a dilution of 1:100 (in 5% normal rabbit serum/PBS). Sections were incubated for 2 hr at room temperature in a humidified chamber. At the end of incubation, sections were rinsed with PBS and incubated with a 1:200 dilution (in 5% normal goat serum/PBS) of goat anti-guinea pig biotinylated IgG conjugate (Vector Laboratories, Burlingame, Calif.) or a 1:250 dilution (in 5% normal rabbit serum/PBS)of rabbit anti-goat biotinylated IgG conjugate (Vector Laboratories, Burlingame, Calif.) for 1 hr at room temperature in a humidified chamber. Sections were then rinsed with PBS and antigen-antibody signal amplified using avidin/biotin HRP conjugate (Vectastain ABC kit; Vector Laboratories, Burlingame, Calif.). Sections were developed using DAB substrate (4–6 min; room temperature) and counterstained with hematoxylin. In the ballooned rabbit artery, immunohistochemistry with the anti-LBP-1, LBP-2 and LBP-3 antibodies showed that LBP-1, LBP-2 and LBP-3 were located in or on functionally modified endothelial cells at the edges of regenerating endothelial islands, the same location in which irreversible LDL binding has been demonstrated (Chang et al., Arteriosclerosis and Thrombosis 12:1088–1098 (1992)). LBP-1, LBP-2 and LBP-3 were also found in or on intimal smooth muscle cells underneath the functionally modified endothelial cells, and to a lesser extent, in extracellular matrix. No LBP-1, LBP-2 or LBP-3 was detected in still deendothelialized areas, where LDL binding had been shown to be reversible (Chang et al., Arteriosclerosis and Thrombosis 12:1088–1098 (1992)). Immunohistochemistry of ballooned rabbit aorta with anti-human apolipoprotein B antibodies showed the presence of LDL at the same locations as that found for LBP-1, LBP-2 and LBP-3.

In the human atherosclerotic plaques taken at routine autopsies, immunohistochemistry with the anti-LBP-1, anti-LBP-2 and anti-LBP-3 antibodies showed that LBP-1, LBP-2, and LBP-3 were also found in or on endothelial cells covering plaques and in or on adjacent smooth muscle cells. In the human tissue, there was greater evidence of LBP-1, LBP-2 and LBP-3 in extracellular matrix.

The results obtained with paraffin sections were identical to those of frozen sections.

Example 8

Affinity Coelectrophoresis (ACE) Assays of LBPs and LDL or HDL

This example illustrates that binding occurs between LBP-1, LBP-2 or LBP-3 and LDL, and that this binding is specific, as illustrated by the fact that binding does not occur between LBP-1, LBP-2 or LBP-3 and HDL (high density lipoprotein). Analysis of the affinity and specificity of recombinant rabbit LBP-1, LBP-2 or LBP-3 binding to LDL was carried out using the principle of affinity electrophoresis (Lee and Lander, Proc. Natl. Acad. Sci. USA 88:2768–2772 (1991)). Melted agarose (1%; 65° C.) was prepared in 50 mM sodium MOPS, pH 7.0; 125 mM sodium acetate, 0.5% CHAPS. A teflon comb consisting of nine parallel bars (45×4×4 mm/3 mm spacing between bars) was placed onto GelBond film (FMC Bioproducts, Rockland, Me.) fitted to a plexiglass casting tray with the long axis of the bars parallel to the long axis of the casting tray. A teflon strip (66×1×1 mm) was placed on edge with the long axis parallel to the short axis of the casting tray, at a distance of 4 mm from the edge of the teflon comb. Melted agarose (>65° C.) was then poured to achieve a height of approximately 4 mm. Removal of the comb and strip resulted in a gel containing nine 45×4×4 mm rectangular wells adjacent to a 66×1 mm slot. LDL or HDL samples were prepared in gel buffer (50 mM sodium MOPS, pH 7.0, 125 mM sodium acetate) at twice the desired concentration. Samples were then mixed with an equal volume of melted agarose (in 50 mM MOPS, pH 7.0; 125 mM sodium acetate; 50° C.), pipetted into the appropriate rectangular wells and allowed to gel. The binding affinity and specificity of LBP-1 and LBP-3 was tested using several concentrations of LDL (540 to 14 nM) and HDL (2840177 nM). A constant amount (0.003 nM–0.016 nM) of $^{125}$I-labeled LBP-1, LBP-2 or LBP-3 (suspended in 50 mM sodium MOPS, pH 7.0; 125 mM sodium acetate; 0.5% bromphenol blue; 6% (wt/vol) sucrose) was loaded into the slot. Gels were electrophoresed at 70 v/2 hr/20° C. At the end of the run, the gels were air dried and retardation profiles were visualized by exposure of X-ray films to the gels overnight at −70° C., with intensifying screens.

LDL retarded LBP-1, LBP-2 and LBP-3 migration through the gel in a concentration-dependent, saturable manner, indicating that LBP-1, LBP-2 and LBP-3 binding to LDL was highly specific. This conclusion is supported by the fact that HDL did not retard LBP-1, LBP-2 or LBP-3. A binding curve generated from the affinity coelectrophoresis assay indicated that LBP-1 binds to LDL with a $K_d$ of 25.6 nM, that LBP-2 (rabbit clone 26) binds to LDL with a $K_d$ of 100 nM, and that LBP-3 (80 kDa fragment) binds to LDL with a $K_d$ of 333 nM.

In addition to testing affinity and specificity of LBP-1, LBP-2 and LBP-3 binding to LDL, the ability of "cold" (i.e., non-radiolabeled) LBP-1, LBP-2 or LBP-3 to competitively inhibit radiolabeled LBP-1, LBP-2 or LBP-3 binding to LDL, respectively, was tested. Competition studies were carried out using fixed concentrations of cold LDL and radiolabeled LBP-1 and increasing amounts of cold recombinant LBP-1 (6–31 μM). The ACE assay samples and gel were prepared as described herein. Cold LBP-1 inhibited binding of radiolabeled LBP-1 to LDL in a concentration-dependent manner, cold LBP-2 inhibited binding of radiolabeled LBP-2 to LDL in a concentration-dependent manner, and cold LBP-3 inhibited binding of radiolabeled LBP-3 to LDL in a concentration-dependent manner.

Rabbit and human LBP-2 contain a long stretch of acidic amino acids at the amino terminal (rabbit LBP-2 amino acid residues 338 through 365 and human LBP-2 amino acid residues 329 through 354). The possibility that this segment of LBP-2 was the LDL binding domain was tested by subcloning two rabbit LBP-2 clones which differ from each other by the presence or absence of this acidic region (clone 26 and clone 45, respectively) into expression vectors, by standard methods known to those skilled in the art. ACE assays were then conducted in order to assess the affinity and specificity of the binding of these two clones to LDL. LDL retarded clone 26 derived radiolabeled LBP-2 migration through the gel in a concentration-dependent, saturable, manner while clone 45 derived radiolabeled LBP-2 migration was not retarded.

Competition studies using fixed concentrations of cold LDL and clone 26 derived radiolabeled LBP-2 and increasing concentrations of cold recombinant LBP-2/clone 26 and LBP-a/clone 45 were carried out. Cold clone 26 derived LBP-2 inhibited binding of clone 26 derived radiolabeled LBP-2 to LDL in a concentration-dependent manner. Clone 45 derived LBP-2, on the other hand, did not affect the binding of clone 26 derived radiolabeled LBP-2 to LDL. These results indicate that the long stretch of acidic amino acids contain a binding domain of LBP-2 to LDL.

Example 9

Affinity Coelectrophoreses (ACE) Assays of LBP-1 or LBP-2 and LDL in the Presence of Inhibitors This example illustrates that binding between LBP-1 or LBP-2 and LDL is inhibited by polyglutamine acid or BHF-1. The ability of a third compound to inhibit binding between two proteins previously shown to interact was tested by a modification of the ACE assays described in Example 8. The third compound was added to the top or wells together with the radiolabeled protein. If the third compound inhibited binding, the radiolabeled protein would run through the gel. If the third compound did not inhibit binding, migration of the radiolabeled protein was retarded by the protein cast into the gel.

Inhibition of LBP-1/LDL or LBP-2/LDL binding by polyglutamic acid (average MW about 7500, corresponding to about 7 monomers) was shown by casting a constant amount of LDL (148 nM) in all the rectangular lanes. A constant amount (1 $\mu$l) of $^{125}$I-labeled LBP-1 or LBP-2 (0.003 nM –0.016 nM) was loaded in the wells at the top of the gel, together with increasing concentrations of polyglutamic acid (obtained from Sigma) (0–0.4 nM). The gel was electrophoresed at 70 volts for 2 hr, dried and placed on X-ray film, with intensifying screens, overnight at –70° C. before the film was developed to determine the retardation profile of LBP-1 and LBP-2. As the concentration of polyglutamic acid increased, retardation of radiolabeled LBP-1 and LBP-2 migration by LDL decreased in a concentration-dependent manner, which showed that polyglutamic acid inhibited binding between LBP-1, LBP-2 and LDL.

Inhibition of LBP-1/LDL binding by BHF-1 was shown by casting a constant amount of LDL (148 nM) in all the rectangular lanes. A constant amount of $^{125}$I-labeled LBP-1 (0.003 nM –0.016 nM) was loaded in the wells at the top of the gel, together with increasing concentrations of BHF-1 (0–10 nM), obtained as described in Example 15. The gel was electrophoresed at 70 volts for 2 hr, dried and placed on X-ray film, with intensifying screens, overnight at –70° C. The film was then developed to determine the retardation profile of $^{125}$I-LBP-1. As the concentration of BHF-1 increased, retardation of LBP-1 by LDL decreased in a concentration-dependent manner, which demonstrated that BHF-1 inhibited binding between LBP-1 and LDL.

Example 10

Affinity Coelectrophoreses (ACE) Assays for Identifying Fragments, Analogs and Mimetics of LBPs Which Bind to LDL This example illustrates a method for identifying fragments, analogs or mimetics of LBPs which bind to LDL, and which thus can be used as inhibitors of LDL binding to LBP in the arterial walls, by occupying binding sites on LDL molecules, thereby rendering these sites unavailable for binding to LBP in the arterial wall.

Fragments of LBPs are generated by chemical cleavage or synthesized from the known amino acid sequences. Samples of these fragments are individually added (cold) to radiolabeled LBP as described in Example 8, to assess the inhibitory potency of the various fragments. By iterative application of this procedure on progressively smaller portions of fragments identified as inhibitory, the smallest active polypeptide fragment or fragments are identified. In a similar manner, analogs of the LBPs are tested to identify analogs which can act as inhibitors by binding to LDL. And, similarly, mimetics of LBP (molecules which resemble the conformation and/or charge distributions of the LDL-binding sites on LBP molecules) are tested in a similar fashion to identify molecules exhibiting affinities for the LDL-binding sites on LBP.

The affinities of the inhibitors so identified are at least as strong as the affinity of LDL itself for the LDL-binding sites on LBP. The inhibitors bind at least competitively, and some irreversibly and preferentially as well, to the LDL-binding sites, thereby rendering such sites unavailable for binding to humoral LDL.

Example 11

ELISA Assays

This example illustrates the use of ELISA plate assays for the quantification of a test compound's capacity to inhibit the binding of LDL to a specific LBP.

In one example, the ELISA assay was carried out as follows: LDL was diluted in 50 mM $Na_2HCO_3$, pH 9.6/0.02% $NaN_3$ and added to the wells of a 96-well plate (ImmunoWare 96-Well Reacti-Bind EIA Polystyrene Plates; Pierce (Rockford, Ill.)) to achieve a final concentration ranging from 0.1 to 1 $\mu$g/well. The plates were incubated for 6 hr at room temperature. At the end of the incubation period, the wells were washed 3 times with Tris-buffered saline, pH 7.4 (TBS), and blocked overnight with 200 $\mu$l of 1% bovine serum albumin (BSA) in TBS/0.02% $NaN_3$ (Sigma; St. Louis Mo.) at room temperature. The wells were then incubated with 200 $\mu$l of LBP protein (5–10 $\mu$g/well) in TBS and varying concentrations of the test compound. Plates were incubated for 1 hr at room temperature. The wells were then washed three times with TBS and blocked for 2 hr with 200 $\mu$l of 1% BSA in TBS/0.02% $NaN_3$ at room temperature. At the end of the incubation period, the wells were washed 3 times with TBS and a 1:1000 dilution (in TBS/0.05% Tween 20) of the appropriate guinea pig anti-LBP protein polyclonal antibody was added to the wells and incubated for 1 hr at room temperature. The wells were then washed 3 times with TBS/0.05% Tween 20; a 1:30,000 dilution of goat anti-guinea pig IgG alkaline phophatase conjugate (Sigma) was added to each well. Plates were incubated for 1 hr at room temperature. The wells were washed 3 times with TBS/0.05% Tween 20 and a calorimetric reaction was carried out by adding 200 ml of p-nitrophenyl phosphate substrate (Sigma; St. Louis Mo.) to the wells. The reaction was allowed to proceed for 30 min at room temperature and stopped with 50 $\mu$l of 3N NaOH. The absorbance was determined at 405 nm using an ELISA plate reader. The test compound's effectiveness in blocking the binding of LDL to the recombinant protein was assessed by comparing the absorbance values of control and treated groups.

In a second example, the ELISA assay was carried out as follows: LDL was diluted in Tris-buffered saline, pH 7.4 (TBS) and added to the wells of a 96-well plate (ImmunoWare 96-Well Reacti-Bind EIA Polystyrene Plates; Pierce (Rockford, Ill.)) to give a plate-saturating concentration of 0.2 $\mu$g/well. The plate was incubated for 1 hr at room temperature, after which the wells were washed three times with TBS, before being blocked for 1 hr at room temperature with 1% bovine serum albumin (BSA in TBS). The wells were then washed twice with TBS before LBP-1 or LBP-2 (0.025 $\mu$g/well), or LBP-3 (0.01 $\mu$g/well) were added, without and with varying concentrations of the test inhibitor compound. Each condition was set up in quadruplicate. The plate was incubated for 1 hr at room temperature, then washed three times with TBS/0.02% Tween 20 (TBS/Tween). An appropriate dilution of guinea pig anti-LBP polyclonal antibody (1:750 to 1:1500, depending on the antibody) was added to three wells for each condition and incubated for 1 hr. Anti-LBP antibody was replaced by buffer for the fourth well of each condition, as a negative control. After 1 hr, the plate was again washed three times with TBS/Tween before a 1:10,000 dilution (in TBS/Tween) of goat anti-guinea pig IgG alkaline phosphatase-conjugated antibody (Sigma) was added to each well. The plate was incubated for 1 hr at room temperature, then washed three times with TBS/Tween. A fresh solution of substrate was prepared from an Alkaline Phosphatase Substrate Kit (Bio-Rad, Hercules, Calif.) as follows: Mix 1 ml 5× concentrated diethanolamine buffer with 4 ml distilled water. Add one tablet of p-nitrophenylphosphate (5 mg) and vortex until tablet is completely dissolved. Subtrate solution was added to wells immediately. Increasing concentrations of diluted alkaline phosphatase-conjugated goat anti-guinea pig IgG (1:100,000 dilution in TBS/Tween) were added to five empty wells, followed by substrate, as a positive control. Following addition of substrate, the plate was immediately placed in an ELISA plate reader, allowed to stand at 37° C., generally for 75 min, before absorbance was measured at 405 nm. Incubation in the ELISA reader at 37° C. was sometimes adjusted to optimize absorbance (60–90 min). The effectiveness of the test inhibitor was determined, after subtracting absorbance of negative controls, by comparing absorbance in wells where an LBP was mixed with test inhibitor to absorbance in wells containing LBP with no inhibitor.

Alternatively, LBPs, rather than LDL, were bound to the plate. Recombinant LBP protein binding to LDL and the effect of varying concentration of the inhibitor on LBP-LDL binding was determined through the use of antibodies against LDL. This interaction was visualized through the use of a secondary antibody conjugated to a reporter enzyme (e.g. alkaline phosphatase).

ELISA plate assays were used to screen agents which can affect the binding of LBP proteins to LDL. For example peptides derived from LBP-1 and human LBP-3 protein sequences (BHF-1 and BHF-2, respectively) were synthesized and have been shown to reduce the binding of LDL to recombinant LBP-1 and LBP-2 in this format. These results were in agreement with those obtained with the ACE assays.

Example 12

Administration of Humanized Antibodies Against LBPs so as to Block LDL-Binding Sites on the LBPs This example illustrates administration to patients of humanized antibodies against LBP-1, LBP-2 or LBP-3 so as to block LDL-binding sites on arterial LBP molecules. Mouse monoclonal antibodies are humanized by recombinant DNA techniques and produced by standard procedures known to those skilled in the art (Berkower, I., Curr. Opin. Biotechnol. 7:622–628 (1996); Ramharayan and Skaletsky, Am. Biotechnol. Lab 13: 26–28 (1995)) against LBPs and/or the LDL-binding sites on the LBPs. The corresponding Fab fragments are also produced, as described in Goding, J. W., Monoclonal Antibodies: Principles and Practice, Academic Press, New York, N.Y. (1986). These antibodies are administered parenterally in sufficient quantity so as to block LDL-binding sites on the LBP molecules, i.e., 1–10 mg/kg daily. This prevents the irreversible arterial uptake of LDL that is required to facilitate oxidation of the LDL.

Example 13

Preparation of LDL

This example illustrates the preparation of LDL. LDL was prepared from the plasma of normolipemic donors (Chang et al., Arterioscler. Thromb. 12:1088–1098 (1992)). 100 ml of whole blood was placed into tubes containing 100 mM disodium EDTA. Plasma was separated from red blood cells by low-speed centrifugation (2,000 g; 30 min; 4° C.). Plasma density was adjusted to 1.025 gm/ml with a solution of KBr and centrifuged for 18–20 hr, 100,000×g, 12° C. Very low density lipoproteins (VLDL) were removed from the tops of the centrifuge tubes with a Pasteur pipette. The density of the infranate was raised to 1.050 gm/ml with KBr solution and centrifuged for 22–24 hr, 100,000×g, 12° C. LDL was removed from the tops of the centrifuge tubes with a drawn out Pasteur pipette tip. Purity of the LDL preparation was checked by Ouchterlony double immunodiffusion against antibodies to human LDL, human HDL, human immunoglobulins, and human albumin. KBr was removed from the LDL solution by dialysis (1 L, ×2, approximately 16 hr) against 0.9% saline, pH 9.0, containing 1 mM EDTA and 10 $\mu$M butylated hydroxytoluene (BHT), the latter to prevent oxidation of LDL. Following dialysis, LDL protein was measured by the method of Lowry (Lowry et al., J. Biol. Chem. 193:265–275 (1951)), and the LDL was stored at 4° C. until use. LDL preparations were kept for no more than 4–6 weeks.

Example 14

Preparation of HDL

This example illustrates the preparation of HDL. HDL was prepared from plasma of normolipemic donors. 100 ml of whole blood was placed into tubes containing 100 mM disodium EDTA and plasma was collected by centrifugation (2000 g; 30 min; 4° C.). Apolipoprotein B containing lipoproteins present in plasma were then precipitated by the sequential addition of sodium heparin (5,000 units/ml) and $MnCl_2$ (1M) to achieve a final concentration of 200 units/ml and 0.46 M, respectively (Warnick and Albers, J. Lipid Res. 19:65–76 (1978)). Samples were then centrifuged, (2000 g; 1 hr; 4° C.). The supernatant was collected and density adjusted to 1.21 g/ml by the slow addition of solid KBr. HDL was separated by ultracentrifugation (100,000 g; >46 hr; 12° C.). Purity of the HDL preparation was assessed via Ouchterlony double immunodiffusion test using antibodies against human HDL, human LDL, human immunoglobulins, and human albumin. HDL samples were dialyzed against saline pH 9.0/1 mM EDTA/10 $\mu$M BHT (4 L; 24 hr/4° C.) and total protein was determined by the Lowry protein assay (Lowry et al., J. Biol. Chem. 193:265–275 (1951)). HDL was stored at 4° C. until use. HDL preparations were kept for no longer than 2 weeks.

Example 15

Synthesis of BHF-1

This example illustrates the synthesis of BHF-1, a fragment of human or rabbit LBP-1 which contains amino acid residues 14 through 33. BHF-1 was synthesized using an Applied Biosystems Model 430A peptide synthesizer with standard T-Boc NMP chemistry cycles. The sequence of BHF-1 is as follows:

val-asp-val-asp-glu-tyr-asp-glu-asn-lys-phe-val-asp-glu-glu-asp-gly-gly-asp-gly (SEQ ID NO: 9).

After synthesis, the peptide was cleaved with hydrofluoric acid/anisole (10/1 v/v) for 30 min at −10° C. and then incubated for 30 min at 0° C. BHF-1 was then precipitated and washed three times with cold diethyl ether. Amino acid coupling was monitored with the ninhydrin test (>99%).

The BHF-1 peptide was purified to homogeneity by high performance liquid chromatography on a reverse phase Vydac $C_4$ column (2.24×25 cm) using a linear gradient separation (2–98% B in 60 min) with a flow rate of 9 ml/min. Buffer A consisted of 0.1% trifluoroacetic acid (TFA)/Milli Q water and Buffer B consisted of 0.085% TFA/80% acetonitrile. The gradient was run at room temperature and absorbance monitored at 210 and 277 nm.

Fast atom bombardment-mass spectrometry gave a protonated molecular ion peak $(M+H)^+$ at m/z=2290.2, in good agreement with the calculated value. On amino acid analysis, experimental values for the relative abundance of each amino acid in the peptide were in good agreement with theoretical values. The lyophilized peptide was stored at −20° C.

Example 16

In Vitro Screening for Agents Which Inhibit Binding between LDL and LBPs

This example illustrates in vitro screening for agents which inhibit binding between LDL and LBPs.

A candidate polypeptide for being an agent is chosen, e.g., LBP-1, LBP-2, LBP-3, BHF-1 or any other polypeptide. The shortest fragment of the polypeptide that inhibits LDL binding to LBPs in vitro is determined. Peptides are synthesized by standard techniques described herein. Inhibition assays are performed using standard ELISA techniques for screening, and affinity coelectrophoresis (ACE) assays to confirm the ELISA results, as described herein. Additional assays that can be used in this screening method include, e.g., fluorescence polarization and pulsed ultra-filtration electrospray mass spectrometry. Short peptides ranging, e.g., from dimers to 20-mers are constructed across sequences of the candidate polypeptide whose chemical characteristics make them likely LDL binding sites, e.g., acidic regions. The ability of shorter and shorter lengths of the peptides to inhibit LDL binding in vitro and to mammalian cells in culture is tested. For example, the effect of the peptide on inhibiting LDL binding in mammalian cells transfected to express an LBP gene is tested. Each of the peptides so identified as an inhibitor is tested with each of LBP-1, LBP-2 and LBP-3, to determine whether a single inhibitor works against all three LBPs.

Once the minimum active sequence is determined, the peptide backbone is modified so as to inhibit proteolysis, as discussed herein. For example, modification is accomplished by substitution of a sulfoxide for the carbonyl, by reversing the peptide bond, by substituting a methylene for the carbonyl group, or other similar standard methodology. See Spatola, A. F., "Peptide Backbone Modifications: A Structure-Activity Analysis of Peptides Containing Amide Bond Surrogates, Conformational Constraints, and Related Backbone Replacements," in Chemistry and Biochemistry of Amino Acids, Peptides and Proteins, Vol. 7, pp. 267–357, B. Weinstein (ed.), Marcel Dekker, Inc., New York (1983). The ability of these analogs to inhibit LDL binding to the LBPs in vitro is tested in a similar manner as for the natural peptides described above, e.g., by ELISA, ACE, fluorescence polarization, and/or pulsed ultra-filtration electrospray mass spectrometry.

Example 17

In Vitro Screening with Cultured Mammalian Cells for Agents Which Inhibit Binding between LDL and LBPs This example illustrates cell-based in vitro screening of agents which have been shown by in vitro tests such as ACE assay and ELISA to be potential inhibitors of binding between LDL and LBPs.

Mammalian cells, such as 293 cells, which are commonly used for expression of recombinant gene constructs, are used to develop cell lines which express LBPs on the cell surface. This is done by subcloning LBP open reading frames (ORFS) into a mammalian expression plasmid vector, pDisplay (Invitrogen, Carlsbad, Calif.), which is designed to express the gene of interest on the cell surface. The use of mammalian cells to produce LBPs allows for their expression in a functionally active, native conformation. Therefore, stably transfected mammalian cell lines with surface expression of LBPs individually, or in combination, are particularly suitable for assaying and screening inhibitors that block LDL binding in cell culture, as well as to evaluate the cytotoxicity of these compounds.

Specifically, LBP ORFs are amplified by PCR (Perkin Elmer, Foster City, Calif.) from cDNA templates using Taq polymerase (Perkin Elmer) and appropriate primers. The amplified LBP ORFs are purified by agarose gel electrophoresis and extracted from gel slices with the Bio-Rad DNA Purification kit (Bio-Rad, Hercules, Calif.). The purified DNAs are then cut with the restriction enzymes Bgl II and Sal I (New England Biolabs, Beverly, Mass.) to generate cohesive ends, and purified again by agarose gel electrophoresis and DNA extraction as described above. The LBP ORFs are then subcloned into the Bgl II/Sal I sites in the mammalian expression vector, pDisplay (Invitrogen) by ligation. Recombinant plasmids are established by transformation in *E. coli* strains TOP10 (Invitrogen) or DH5α (Life Technologies, Grand Island, N.Y.). Recombinant pDisplay/LBP plasmid DNA is isolated from overnight *E. coli* cultures with the Bio-Rad Plasmid Miniprep kit, cut with Bgl II/Sal I, and analyzed by agarose gel electrophoresis. LBP ORFs in successfully transformed clones are verified by automated dideoxy DNA sequencing. To transfect human kidney 293 cells, 1–2 μg of DNA is mixed with 6 μl lipofectamine reagent (Life Technologies) and incubated with the cells as described in the Life Technologies protocol. LBP expression in transfected cells is confirmed by Western blot analysis of cell extracts obtained 48 hr after transfection. To select for stably transfected 293 cells, the antibiotic G418 (Life Technologies) is added to the growth medium at a concentration of 800 μg/ml. Colonies resistant to G418 are tested for recombinant LBP expression by Western blot, and recombinant clones expressing LBPs are expanded, assayed for LDL binding and used to test compounds for their ability to inhibit LDL binding.

Example 18

In Vivo Screening for Agents Which Inhibit Binding between LDL and LBPs

This example illustrates in vivo screening of agents which have been shown by in vitro tests to be promising candidate inhibitors of binding between LDL and LBPs.

In vivo inhibitory activity is first tested in the healing balloon-catheter deendothelialized rabbit aorta model of arterial injury (Roberts et al., J. Lipid Res. 24:1160–1167 (1983); Chang et al., Arterioscler. Thromb. 12:1088–1098 (1992)). This model was shown to be an excellent analog for human atherosclerotic lesions. Other useful animal models for human atherosclerosis include Apo E knockout mice and LDL receptor knockout mice. Both of these mouse models are characterized by high levels of plasma cholesterol and the development of naturally-occurring atherosclerotic-like lesions.

Each candidate inhibitor is tested in five to ten ballooned rabbits, while an equal number of rabbits receive a control peptide, or placebo. Four weeks following aortic deendothelialization, when reendothelialization (healing) is partially complete, daily parenteral (intravenous or subcutaneous) or intragastric administration of the peptides and the analogs begins at an initial concentration of 10 mg/kg body weight, which is varied down, or up to 100 mg/kg depending on results. 30 min later, a bolus of intravenously injected $^{125}$I (or $^{99m}$Tc-) labeled LDL is given to test the candidate inhibitor's ability in short term studies to inhibit LDL sequestration in healing arterial lesions. If $^{125}$I-LDL is used, the animals are sacrificed 8–24 hr later, the aortas excised, washed and subjected to quantitative autoradiography of excised aortas, as previously described (Roberts et al., J. Lipid Res. 24:1160–1167 (1983); Chang et al., Arterioscler. Thromb. 12:1088–1098 (1992)). If $^{99m}$Tc-LDL is used, analysis is by external gamma camera imaging of the live anesthetized animal at 2–24 hr, as previously described (Lees and Lees, Syndromes of Atherosclerosis, in Fuster, ed., Futura Publishing Co., Armonk, N.Y., pp. 385–401(1996)), followed by sacrifice, excision and imaging of the excised aorta. Immediately before the end of testing, the animals have standard toxicity tests, including CBC, liver enzymes, and urinalysis.

The compounds which are most effective and least toxic are then tested in short term studies of rabbits fed a 2% cholesterol diet (Schwenke and Carew, Arteriosclerosis 9:895–907 (1989)). Each candidate inhibitor is tested in five to ten rabbits, while an equal number of rabbits receive a control peptide, or placebo. Animals receive one or more doses per day of the candidate inhibitor, or placebo, for up to two weeks. Daily frequency of doses is determined by route of administration. If active drug or placebo are administered parenterally, they are given 1–3 times daily and the 2% cholesterol diet is continued. If drug or placebo are given orally, they are mixed with the 2% cholesterol diet. Schwenke and Carew (Arteriosclerosis 9:895–907 (1989)) have shown that the LDL concentration in lesion-prone areas of the rabbit aorta is increased 22-fold above normal in rabbits fed a 2% cholesterol diet for 16 days, and that the increased LDL content precedes the histological evidence of early atherosclerosis. Therefore, analysis of the effect of the candidate inhibitors is tested two weeks after the start of cholesterol feeding by injecting $^{125}$I-LDL, allowing it to circulate for 8–24 hr, and then performing quantitative autoradiography on the excised aortas of both test and control animals. If appropriate, quantitation of aortic cholesterol content is also carried out (Schwenke and Carew, Arteriosclerosis 9:895–907 (1989); Schwenke and Carew, Arteriosclerosis 9:908–918 (1989).

The above procedures identify the most promising candidate inhibitors, as well as the best route and frequency of their administration. Inhibitors so identified are then tested in long-term studies of cholesterol-fed rabbits. These tests are carried out in the same way as the short-term cholesterol feeding studies, except that inhibitor effectiveness is tested by injection of $^{125}$I-LDL at longer intervals following the initiation of cholesterol feeding, and lesion-prone areas of the aorta are examined histologically for evidence of atherosclerosis. Testing times are at two, four, and six months. Major arteries are examined grossly and histologically or evidence and extent of atherosclerosis. If necessary, other accepted animal models, such as atherosclerosis-susceptible primates (Williams et al., Arterioscler. Thromb. Vast. Biol. 15:827–836 (1995)), genetically altered mice, and/or Watanabe rabbits are tested with short- and long-term cholesterol feeding.

Example 19

In Vivo Inhibition of Radiolabeled LDL Accumulation in the Ballooned Deendothelialized Rabbit Aorta via Induction of Active Immunity Against LBP Protein This example illustrates the effect that induction of immunity against LBP protein has on the accumulation of radiolabeled LDL in the ballooned deendothelialized rabbit aorta model of atherosclerosis.

Immunity was induced in male New Zealand White rabbits (Hazelton Research Products, Denver, Pa.) as follows: A mixture of purified human recombinant LBP-2 or BHF-1 peptide (1 ml; 1 mg) and RIBI adjuvant (RIBI ImmunoChem Research, Inc., Hamilton, Mont.) was injected subcutaneously at 2–5 sites along the dorsal thoracic and abdominal regions of the rabbits. Blood was collected by venipuncture on days 1 (preimmune bleeding), 35, 63, and 91. Booster injections were administered on days 28 (500 $\mu$g; SC), 56 (250 $\mu$g; SC), and 84 (125 $\mu$g; SC).

The titer of the rabbits was evaluated by serial dilution using an ELISA plate format. Preimmune serum was evaluated at the same time. After the third booster of LBP protein or peptide, the titer reached a maximal level with a detectable calorimetric response on an ELISA plate of 156 $\mu$g. Titer is defined as the maximum dilution of antibody which generates an absorbance reading of 0.5 above control in 30 min. Specificity of the polyclonal antibodies was demonstrated using Western blot analysis as described in Example 6.

On day 93, the abdominal aorta of immunized and control rabbits was deendothelialized using a Fogarty number 4 embolectomy catheter (Chang et al., Arteriosclerosis and Thrombosis 12:1088–1098 (1992)). Four weeks after ballooning, rabbits received a bolus injection of $^{125}$I-labeled LDL (1 ml; i.v.). Blood samples were collected at 1 hr intervals for 8 hr, and 24 hr post injection. Blood samples were centrifuged for 30 min at 2000 rpm (40° C.)and total activity present in the serum was determined using a Gamma counter. Total TCA precipitable counts were determined by addition of TCA to the serum to a final concentration of 10% followed by incubation for 10 min at 4° C. Serum samples were then centrifuged (2000 rpm; 30 min; 40° C.) and total activity present in the supernate was determined. TCA precipitable counts were calculated by substration: total soluble counts minus counts present in the supernate after TCA precipitation. Blood samples for the determination of antibody titers were collected prior to the injection of the radiolabeled LDL.

After 24 hr, the rabbits were injected intravenously with 5% Evan's blue dye which was allowed to circulate for 15 min. Areas of the aorta in which the endothelial covering is absent stain blue while those areas covered by endothelium remain unstained. At the end of the incubation period, the rabbits were euthanized and the abdominal and thoracic aorta were dissected out, rinsed, and fixed overnight in 10% TCA at room temperature. The aortas were then rinsed exhaustively with physiological saline, weighed, counted, blotted dry and placed onto X-ray film in order to visualize the pattern of radiolabeled LDL accumulation in the deendothelialized rabbit abdominal aorta.

Immunization of rabbits against recombinant human LBP-2 or BHF-1 peptide altered the pattern of radiolabeled LDL accumulation in the ballooned deendothelialized abdominal aorta. When corrected for dosage, and percent reendothelialization, immunized-ballooned rabbits had lower accumulation of radiolabeled LDL compared to nonimmune-ballooned rabbits. These results indicate that active immunization against LBP provides an effective means by which the accumulation of LDL in the injured arterial wall can be modified.

Example 20

Screening Agents in Humans Which Inhibit Binding between LDL and LBPs

Human studies are carried out according to standard FDA protocols for testing of new drugs for safety (Phase I), efficacy (Phase II), and efficacy compared to other treatments (Phase III). Subjects, who are enrolled into studies after giving informed consent, are between the ages of 18 and 70. Women who are pregnant, or likely to become pregnant, or subjects with diseases other than primary atherosclerosis, such as cancer, liver disease, or diabetes, are excluded. Subjects selected for study in FDA Phase II and Phase III trials have atherosclerotic disease previously documented by standard techniques, such as ultrasound and/or angiography, or are known to be at high risk of atherosclerosis by virtue of having at least one first degree relative with documented atherosclerosis. Subjects themselves have normal or abnormal plasma lipids. Initial testing includes 20–50 subjects on active drug and 20–50 subjects, matched for age, sex, and atherosclerotic status, on placebo. The number of subjects is pre-determined by the number needed for statistical significance. Endpoints for inhibitor efficacy includes ultrasound measurements of carotid artery thickness in high risk subjects, as well as in subjects with known carotid or coronary disease; atherosclerotic events; atherosclerotic deaths; and all-cause deaths in all subjects. Non-invasive analysis (carotid artery thickness by ultrasound) as per Stadler (Med. and Biol. 22:25–34 (1996)) are carried out at 6- to 12-month intervals for 3 years. Atherosclerotic events and deaths, as well as all-cause deaths are tabulated at 3 years.

Oral dosage of drug in FDA Phase I trials ranges from 0.01 to 10 gm/day, and is determined by results of animal studies, extrapolated on a per kg basis. Based on data obtained from Phase I studies, the dose range and frequency are narrowed in Phase II and III trials. If parenteral administration of drug is determined by animal studies to be the only effective method, parenteral administration in human subjects is tested by injection, as well as by the transdermal and nasal insufflation routes. Testing of parenteral drug follows the same outline as that for oral administration.

The optimal treatment schedule and dosage for humans is thus established.

Example 21

Treating an Individual Having Atherosclerosis with BHF-1

This example illustrates a method for treating an individual having atherosclerosis with an LBP fragment, e.g., BHF-1, so as to decrease the levels of arterially bound LDL in the individual. BHF-1 is obtained as described herein. The BHF-1 is administered to the mammal intravenously as a bolus or as an injection at a concentration of 0.5–10 mg/kg body weight. Such administrations are repeated indefinitely in order to prevent the development or progression of symptomatic atherosclerosis, just as is done currently with cholesterol lowering drugs. Stable subjects are examined twice yearly to evaluate the extent of any atherosclerotic disease by physical exam and non-invasive studies, such as carotid artery thickness, ultrasound, and/or gamma camera imaging of the major arteries, to determine if atherosclerotic lesions are present, and, if previously present, have regressed or progressed. Such a regimen results in treatment of the atherosclerosis.

Example 22

In Vivo Reduction of Atherosclerosis in Apo E Knockout Mice by Immunization with LBPs Separate immunization experiments were performed with each of LBP-1, LBP-2, and LBP-3. Immunity was induced by injecting apo E knockout mice with the LBP protein (LBP-1, LBP-2, or LBP-3) together with an RIBI adjuvant (RIBI ImmunoChem Research, Inc., Hamilton, Mont.). Apo E knockout mice (Jackson Laboratories, Bar Harbor, Me.) are hyperlipidemic and thus a model for human atherosclerosis. Apo E knockout mice have high levels of plasma cholesterol and develop naturally-occurring atherosclerotic-like lesions.

Four week old apo E knockout mice (Jackson Laboratories, Bar Harbor, Me.) were ear tagged, randomly assigned to different cages and weighed. Body weights were determined weekly. Animals were allowed to habituate for 1 week. Normal rodent chow was provided ad libitum and animals were maintained in a 12:12 light:dark cycle. The following four groups of mice were treated with either recombinant LBP proteins (40 $\mu$g of recombinant protein/mouse) plus RIBI adjuvant or RIBI adjuvant alone (control group).

LBP-1: Immunized with rabbit recombinant LBP-1 (6-His tag).

LBP-2: Immunized with rabbit recombinant LBP-2 clone 26 (6-His tag).

LBP-3: Immunized with rabbit recombinant LBP-3 (6-His tag).

Control: Received adjuvant.

Blood samples (pre-immune serum) were collected prior to the initial injection of recombinant protein and RIBI adjuvant (as described in the manufacturer's manual). After 21 days, mice received a booster injection (half-initial dose) and were then bled seven days later. Titer was defined as the maximum dilution of serum that yielded a change in absorbance equivalent to 2× that of control serum (60 min; 37° C.). The amount of recombinant protein per well was 100 ng.

Booster injections took place at 21 day intervals until an average titer value of 1:10,000 was reached. At this time, mice were switched to western type diet (Harland Teklad, Madison, Wis.) and fed ad libitum. Blood samples were collected at this time (retro-orbital sinus bleeding technique) and monthly thereafter.

Blood samples were analyzed for total cholesterol, HDL cholesterol, and triglyceride concentration with a commercially available total cholesterol and triglycerides assay kits (Sigma; St. Louis Mo.) using an ELISA format. HDL concentration was determined after Apo B containing lipoproteins were precipitated using heparin/$MnCl_2$.

Apo E knockout mice were sacrificed at 26 weeks of age. The mice were anesthetized with methoxyfluorane and exanguinated via cardiac puncture. A midline thoracotomy was performed, a cannula inserted into the right ventricle and perfusate allowed unrestricted flow via an incision into the right atrium. The mice were perfused with saline, followed by 10% phosphate buffered formalin until fasciculations stopped. At this time, the aorta was exposed and adventitial fat removed in situ. The aorta was then removed from the heart down to the iliac bifurcation and placed in 10% phosphate buffered formalin overnight.

The aorta was stained as follows: after a brief 70% ethanol rinse, it was immersed in a filtered solution of 0.5% (weight/volume) Sudan IV in 35% ethanol/50% acetone with continuous shaking for 10 minutes at room temperature. Unbound dye was removed by incubating the aorta in an 80% ethanol solution with shaking until the background color was clear. The vessel was then rinsed in distilled water, placed in physiological saline and opened longitudinally from the aortic arch down to the iliac bifurcation. The vessel was pinned out and photographed. Photographs were then digitized using an Astra 1200S scanner (UMAX Technologies Inc., Freemont, Calif.) and a commercially available graphics program (Canvas; Deneba Software, Miami Fla.). Total and lesion areas were determined using the signal processing toolbox of MATLAB (The Mathworks Inc., Natick, Mass.). Percent involvement was calculated by dividing lesion area by total area.

A second analysis was done to measure aortic atherosclerosis by a cholesterol extraction method whereby cholesterol is determined as a unit weight of artery. This method may be more accurate in measuring lesion size than attempting to measure the thickness of many sections. Specifically, the weight of an artery was measured, then the cholesterol was extracted. Aortic cholesterol content was then measured by gas-liquid chromatography. The amount of cholesterol per unit weight of artery was then determined.

After the first booster injection, some of the apo E knockout mice immunized against LBP-1 had relatively high anti-LBP-1 titers (≦1:5000) while others in the same group exhibited moderate levels (>1:500 to <1:1000). LBP-2/26 titers were low in the apoE knockout mice (<1:500) at this time. LBP-3 titers ranged from moderate to low (≧1:500 to <1:1000) to low (<1:500) in the apoE knockout mice.

After the second booster injection, Apo E knockout mice immunized against LBP-1 had moderate to high titers (>1:1000 to ≦1:8000). Apo E knockout mice immunized against LBP-2/26 had moderate titer levels (>1:2000). LBP-3 titers range from moderate to high (>1:1000 to >1:8000) in the Apo knockout mice.

After the third booster injection, most of the mice immunized against LBP-1 had relatively high titers (>1:10,000) while others had moderate to high titers (>1000 to <1:10,000). Some of the Apo E knockout mice had moderate (<1:5000) to low (<1:1000) titers. LBP-3 titers ranged from high (>1:5000 to ≦1:10,000) to moderate (>1:1000 to <1:5000).

Data were analyzed using T-tests and Wilcoxons. Immunization against LBP-1, LBP-2/26 or LBP-3 did not have a significant effect (P>0.05) on body weight of Apo E knockout mice. Due to the small sample size and the large variability present in the Apo E knockout mice, it was not possible to determine whether immunization against LBP-1, LBP-2/26 or LBP-3 had an effect on total cholesterol, HDL cholesterol or triglycerides concentration, but it did not appear to.

Immunization against LBP-1 or LBP-3 did not have a significant effect (P>0.05) on lesions of the apo E knockout mice or LDL receptor negative knockout mice. However, immunization of the apo E knockout mice against LBP-2 had a significant effect on lesion area (Table 2), and, once outliers were deleted, a significant effect on arterial wall cholesterol content (Table 3). The LBP-2 immunized apo E knockout mice had significantly reduced aortic atherosclerosis as compared to the control, non-immunized mice. Without being bound to any particular theory, the circulating antibodies generated against LBP-2 proteins are thought to block LDL binding to the artery wall.

TABLE 2

Lesion Area in LBP-Immunized Apo E Mice

| Apo E Mice | Lesion Area % Coverage | Treated Area Change | P-Value Wilcoxon |
|---|---|---|---|
| Control | 9.40 | | |
| LBP-1 | 6.05 | −0.36% | 0.07 |
| LBP-2 | 6.01 | −0.36% | 0.01 |
| LBP-3 | 7.14 | −0.24% | 0.36 |

TABLE 3

Arterial Cholesterol Content in LBP-Immunized Apo E Mice

| Apo E Mice | Arterial Wall Cholesterol (ug cholesterol/mg aorta) | Treated Area Cholesterol Change | P-Value Wilcoxon |
|---|---|---|---|
| Control | 6.33 | | |
| LBP-1 | 3.82 | −0.40% | 0.14 |
| LBP-2 | 3.28 | −0.48% | 0.07 |
| LBP-2 (outliers deleted) | 1.83 | −0.71% | 0.01 |
| LBP-3 | 4.48 | −0.29% | 0.20 |

Example 23

In Vivo Reduction of Atherosclerosis in LDL Receptor Knockout Mice by Immunization with BHF-1

An immunization experiment was performed with the BHF-1 peptide. LDL receptor (LDLR) knockout mice (B6, 129S-Ldlr$^{tmlHer}$, Jackson Laboratories, Bar Harbor, Me.) were injected with the BHF-1 peptide (see Example 15 for methods of synthesizing the BHF-1 peptide) together with an RIBI adjuvant (RIBI ImmunoChem Research, Inc., Hamilton, Mont.). LDLR knockout mice are hyperlipidemic and thus a model for human atherosclerosis. LDLR knockout mice have high levels of plasma cholesterol and develop naturally-occurring atherosclerotic-like lesions.

Four week old LDLR knockout mice were ear tagged, randomly assigned to different cages and weighed. Body weights were subsequently determined weekly. Animals were allowed to habituate for one week prior to experimentation. Normal rodent chow was provided ad libitum and animals were maintained in a 12:12 light:dark cycle. Animals were divided into experimental and control groups, as follows: (1) experimental, 16 mice were immunized with the BHF-1.20.L peptide; (2) control, 8 mice were immunized against bovine serum albumin.

Mice in the experimental group received subcutaneous injections (9.99 μg/g body weight; 200 μl final volume) of the BHF-1.20.L peptide daily for 2 weeks, from 5 to 7 weeks of age, prior to the initial injection with the peptide and adjuvant. Blood samples (pre-immune serum) were collected prior to the initial injection of BHF-1.20.L and RIBI adjuvant (50 μg of peptide/mouse) (as described in the manufacturer's manual) at 7 weeks of age. After 21 days, mice received a booster injection (half-initial dose) and were then bled 7 days later. Titer was defined as the maximum dilution of serum that yielded a change in absorbance equivalent to 2× that of control serum (60 min; 37° C.). The amount of peptide per well was 100 ng. Booster injections took place at 21 days interval.

Blood samples were analyzed for total cholesterol, HDL cholesterol, and triglyceride concentration, using commercially available total cholesterol and triglycerides assay kits (Sigma; St. Louis Mo.) (ELISA). HDL concentration was determined after Apo B containing lipoproteins were precipitated using heparin/$MnCl_2$.

When fed a normal rodent chow, total serum cholesterol concentration in LDLR knockout mice remains relatively low. A high fat diet, on the other hand, results in an increase in total serum cholesterol concentration in these mice. The animals were thus switched at 16 weeks of age to a modified "Western Type" diet (0.1% cholesterol content) (Harland Teklad, Madison, Wis.) and fed ad libitum. This diet was expected to increase the total serum cholesterol concentration to a range of 600–800 mg/dl, thereby increasing the rate of lesion formation. Blood samples were collected at 18 weeks of age (retro-orbital sinus bleeding technique) and monthly thereafter.

At 30 weeks of age, the mice were sacrificed and aorta were removed as described in Example 22. Aortic atherosclerosis was measured by the cholesterol extraction method described in Example 22, whereby cholesterol is determined as a unit weight of artery.

Immunization against BHF-1.20.L had no effect on body weight of LDLR knockout mice. Consumption of the modified "Western Type" diet for 12 weeks significantly ($P<0.05$) increased total serum cholesterol, HDL cholesterol and triglycerides in both experimental and control animals. Levels of total serum cholesterol, HDL serum cholesterol and serum triglyceride concentration were not significantly different ($P>0.05$) between experimental and control animals.

Mice that were immunized with the BHF-1 peptide had 24% less aortic cholesterol content ($P>0.037$) as compared to the control, non-immunized mice. Without being bound to any particular theory, the immunization is thought to generate circulating antibodies against the BHF-1 peptide. These antibodies are thought to block LDL binding to the artery wall, thereby reducing aortic cholesterol content.

Those skilled in the art will be able to ascertain using no more than routine experimentation, many equivalents of the specific embodiments of the invention described herein. These and all other equivalents are intended to be encompassed by the following claims.

What is claimed is:

1. An isolated nucleic acid comprising a nucleotide sequence that encodes a polypeptide comprising an amino acid sequence that binds to low density lipoprotein (LDL) and has at least 80% sequence identity to the sequence of SEQ ID NO:7.

2. The nucleic acid of claim 1, wherein the amino acid sequence has at least 90% sequence identity to the sequence of SEQ ID NO:7.

3. The nucleic acid of claim 1, wherein the amino acid sequence has at least 95% sequence identity to the sequence of SEQ ID NO:7.

4. An isolated nucleic acid comprising a nucleotide sequence that encodes a polypeptide comprising the sequence of SEQ ID NO:7.

5. An isolated nucleic acid comprising a nucleotide sequence that encodes a polypeptide comprising an amino acid sequence that binds to LDL and has at least 80% sequence identity to the sequence of SEQ ID NO:43.

6. The nucleic acid of claim 5, wherein the amino acid sequence has at least 90% sequence identity to the sequence of SEQ ID NO:43.

7. The nucleic acid of claim 5, wherein the amino acid sequence has at least 95% sequence identity to the sequence of SEQ ID NO:43.

8. An isolated nucleic acid comprising a nucleotide sequence that encodes a polypeptide comprising the sequence of SEQ ID NO:43.

9. The nucleic acid of claim 8, wherein the polypeptide consists of the sequence of SEQ ID NO:43.

10. An isolated nucleic acid comprising a nucleotide sequence that encodes a polypeptide comprising an amino acid sequence that (i) binds to LDL and (ii) is identical to a fragment of at least ten amino acid residues of SEQ ID NO:7.

11. The nucleic acid of claim 10, wherein the amino acid sequence is identical to a fragment of at least 20 amino acid residues of SEQ ID NO:7.

12. The nucleic acid of claim 10, wherein the amino acid sequence is identical to a fragment of at least 30 amino acid residues of SEQ ID NO:7.

13. The nucleic acid of claim 10, wherein the amino acid sequence comprises SEQ ID NO:19, SEQ ID NO:20, SEQ ID NO:21, or SEQ ID NO:22.

14. An isolated nucleic acid comprising a nucleotide sequence that encodes a polypeptide comprising an amino acid sequence that (i) binds to LDL and (ii) is identical to a fragment of at least ten amino acid residues of SEQ ID NO:43.

15. The nucleic acid of claim 14, wherein the amino acid sequence is identical to a fragment of at least 20 amino acid residues of SEQ ID NO:43.

16. The nucleic acid of claim 14, wherein the amino acid sequence is identical to a fragment of at least 30 amino acid residues of SEQ ID NO:43.

17. An isolated nucleic acid comprising a nucleotide sequence that encodes a polypeptide comprising an amino acid sequence, wherein the amino acid sequence binds to LDL and differs by one or more conservative amino acid substitutions from the sequence of SEQ ID NO:7.

18. An isolated nucleic acid comprising a nucleotide sequence that encodes a polypeptide comprising an amino acid sequence, wherein the amino acid sequence binds to LDL and differs by one or more conservative amino acid substitutions from the sequence of SEQ ID NO:43.

19. A recombinant vector comprising the nucleic acid of claim 8.

20. A recombinant vector comprising the nucleic acid of claim 1.

21. A cell comprising the recombinant vector of claim 19.

22. A cell comprising the recombinant vector of claim 20.

23. A method of producing a polypeptide, the method comprising culturing the cell of claim 21 under conditions that permit expression of the polypeptide.

24. A method of producing a polypeptide, the method comprising culturing the cell of claim 22 under conditions that permit expression of the polypeptide.

* * * * *